US011426452B2

(12) United States Patent
Lisziewicz et al.

(10) Patent No.: US 11,426,452 B2
(45) Date of Patent: Aug. 30, 2022

(54) VACCINE

(71) Applicant: Treos Bio Limited, London (GB)

(72) Inventors: Julianna Lisziewicz, Balatonalmádi (HU); Levente Molnár, Felsopakony (HU); Eniko R. Toke, Felsopakony (HU); József Toth, Gyor (HU); Orsolya Lorincz, Budapest (HU); Zsolt Csiszovszki, Budapest (HU); Eszter Somogyi, Balatonalmádi (HU); Katalin Pántya, Budapest (HU); Mónika Megyesi, Mezokeresztes (HU)

(73) Assignee: Treos Bio Limited, London (GB)

( * ) Notice: Subject to any disclaimer, the term of this patent is extended or adjusted under 35 U.S.C. 154(b) by 0 days.

(21) Appl. No.: 17/645,737

(22) Filed: Dec. 22, 2021

(65) Prior Publication Data

US 2022/0111024 A1    Apr. 14, 2022

Related U.S. Application Data

(63) Continuation of application No. 16/244,497, filed on Jan. 10, 2019, now Pat. No. 11,213,578, which is a continuation of application No. 15/910,988, filed on Mar. 2, 2018, now Pat. No. 10,213,497.

(30) Foreign Application Priority Data

Mar. 3, 2017  (EP) .................................... 17159242
Mar. 3, 2017  (EP) .................................... 17159243
Mar. 9, 2017  (GB) .................................... 1703809

(51) Int. Cl.
*A61K 39/00*    (2006.01)
*A61K 39/395*   (2006.01)
*A61K 39/39*    (2006.01)
*A61P 35/00*    (2006.01)
*A61K 47/64*    (2017.01)
*G01N 33/50*    (2006.01)
*G01N 33/569*   (2006.01)
*G16B 40/00*    (2019.01)
*G16B 15/30*    (2019.01)
*C12Q 1/6869*   (2018.01)
*G01N 33/574*   (2006.01)

(52) U.S. Cl.
CPC .. *A61K 39/0011* (2013.01); *A61K 39/001184* (2018.08); *A61K 39/39* (2013.01); *A61K 39/39558* (2013.01); *A61K 47/646* (2017.08); *A61K 47/6415* (2017.08); *A61P 35/00* (2018.01); *C12Q 1/6869* (2013.01); *G01N 33/505* (2013.01); *G01N 33/56977* (2013.01); *G01N 33/574* (2013.01); *G16B 15/30* (2019.02); *G16B 40/00* (2019.02); *A61K 39/0002* (2013.01); *A61K 39/0008* (2013.01); *A61K 2039/53* (2013.01); *A61K 2039/55505* (2013.01); *A61K 2039/55511* (2013.01); *A61K 2039/55544* (2013.01); *A61K 2039/55566* (2013.01); *A61K 2039/55594* (2013.01); *A61K 2039/585* (2013.01); *A61K 2039/605* (2013.01); *A61K 2039/6075* (2013.01); *A61K 2039/70* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,235,877 A | 11/1980 | Fullerton | |
| 7,227,002 B1 | 6/2007 | Kufer et al. | |
| 7,632,925 B2 | 12/2009 | Kufer et al. | |
| 7,820,786 B2 | 10/2010 | Thomson et al. | |
| 7,846,651 B2 | 12/2010 | Kuzushima | |
| 7,892,559 B2 | 2/2011 | Straten et al. | |
| 8,129,184 B2 | 3/2012 | Yu | |
| 8,268,964 B2 | 9/2012 | Scholler et al. | |
| 8,487,076 B1 | 7/2013 | Miyakawa et al. | |
| 9,498,512 B2 | 11/2016 | Rammensee et al. | |
| 9,687,539 B2 | 6/2017 | Wang et al. | |
| 10,172,925 B2 | 1/2019 | Nishimura | |
| 10,213,497 B2 | 2/2019 | Lisziewicz et al. | |
| 10,973,909 B1 | 4/2021 | Csiszovszki et al. | |

(Continued)

FOREIGN PATENT DOCUMENTS

CN    1824678 A     8/2006
EP    2042600 A1    4/2009

(Continued)

OTHER PUBLICATIONS

Ahmed, S.F., et al., Preliminary identification of potential vaccine targets for the COVID-19 coronavirus (SARS-CoV-2) based on SARS-CoV Immunological studies, Viruses, 12: 254 (2020).

(Continued)

*Primary Examiner* — Brad Duffy
(74) *Attorney, Agent, or Firm* — Goodwin Procter LLP

(57) ABSTRACT

The disclosure relates to polypeptides and pharmaceutical compositions comprising polypeptides that find use in the prevention or treatment of cancer, in particular breast cancer, ovarian cancer and colorectal cancer. The disclosure also relates to methods of inducing a cytotoxic T cell response in a subject or treating cancer by administering pharmaceutical compositions comprising the peptides, and companion diagnostic methods of identifying subjects for treatment. The peptides comprise T cell epitopes that are immunogenic in a high percentage of patients.

7 Claims, 27 Drawing Sheets
Specification includes a Sequence Listing.

(56) References Cited

U.S. PATENT DOCUMENTS

| | | |
|---|---|---|
| 2004/0209324 A1 | 10/2004 | Koren et al. |
| 2005/0100883 A1 | 5/2005 | Wang et al. |
| 2006/0127408 A1 | 6/2006 | Young et al. |
| 2006/0257852 A1 | 11/2006 | Rappuoli et al. |
| 2009/0285843 A1 | 11/2009 | Simard et al. |
| 2010/0074925 A1 | 3/2010 | Carmon |
| 2010/0099613 A1 | 4/2010 | Buyse et al. |
| 2013/0189291 A1* | 7/2013 | Tsunoda ............ A61K 31/7088 514/19.5 |
| 2016/0199469 A1 | 7/2016 | Georges et al. |
| 2017/0096455 A1 | 4/2017 | Baric et al. |
| 2018/0264094 A1 | 9/2018 | Lisziewicz et al. |
| 2018/0264095 A1 | 9/2018 | Lisziewicz et al. |
| 2019/0240302 A1 | 8/2019 | Lisziewicz et al. |
| 2020/0069786 A1 | 3/2020 | Molnar et al. |
| 2021/0236611 A1 | 8/2021 | Moln r et al. |
| 2022/0031823 A1 | 2/2022 | Lisziewicz et al. |
| 2022/0072114 A1 | 3/2022 | Lisziewicz et al. |

FOREIGN PATENT DOCUMENTS

| | | |
|---|---|---|
| EP | 2745845 A1 | 6/2014 |
| EP | 3369431 A1 | 9/2018 |
| EP | 3370065 A1 | 9/2018 |
| JP | 2016521128 A | 7/2016 |
| WO | WO-9733602 A1 | 9/1997 |
| WO | WO-0018238 A1 | 4/2000 |
| WO | WO-0056365 A1 | 9/2000 |
| WO | WO-0190197 A1 | 11/2001 |
| WO | WO-2006081826 A2 | 8/2006 |
| WO | WO-2007039716 A1 | 4/2007 |
| WO | WO-2008035350 A1 | 3/2008 |
| WO | WO-2009040674 A2 | 4/2009 |
| WO | WO-2010037395 A2 | 4/2010 |
| WO | WO-2012051282 A2 | 4/2012 |
| WO | WO-2014180490 A1 | 11/2014 |
| WO | WO-2015033140 A1 | 3/2015 |
| WO | WO-2015164798 A1 | 10/2015 |
| WO | WO-2016040900 A1 | 3/2016 |
| WO | WO-2016090177 A1 | 6/2016 |
| WO | WO-2016172722 A1 | 10/2016 |
| WO | WO-2017162501 A1 | 9/2017 |
| WO | WO-2018067869 A1 | 4/2018 |
| WO | WO-2018138257 A1 | 8/2018 |
| WO | WO-2018158455 A1 | 9/2018 |
| WO | WO-2018158456 A1 | 9/2018 |
| WO | WO-2018158457 A1 | 9/2018 |
| WO | WO-2019/133853 A1 | 7/2019 |
| WO | WO-2019222760 A1 | 11/2019 |
| WO | WO-2019222762 A1 | 11/2019 |
| WO | WO-2020048990 A1 | 3/2020 |
| WO | WO-2020048992 A1 | 3/2020 |
| WO | WO-2020048995 A1 | 3/2020 |
| WO | WO-2020146431 A1 | 7/2020 |
| WO | WO-2020146434 A2 | 7/2020 |

OTHER PUBLICATIONS

Ali-Khan, N., et al., Overview of proteome analysis, Curr Protoc Protein Sci, Chapter 22: Unit 22.1.1-22.1.19 (2002).

Antigenic peptides search results for EpCAM, 1 page, retrieved on Apr. 16, 2021 from <caped.icp.ucl.ac.be/Peptide/search>.

Asahara, S., et al., Phase I/II clinical trial using HLA-A24-restricted peptide vaccine derived from KIF20A for patients with advanced pancreatic cancer, J Transl Med, 11: 291 (2013).

Bagarazzi, M., et al., Immunotherapy Against HPV16/18 Generates Potent $T_H1$ and Cytotoxic Cellular Immune Responses, Sci Transl Med, 4(155): 155ra138 (2012).

Batra, S.K., et al., Epidermal Growth Factor Ligand-independent, Unregulated, Cell-transforming Potential of a Naturally Occurring Human Mutant EGFRvIII Gene, Cell Growth Differ, 6:1251-1259 (1995).

Beatty, G.L., et al., Immune escape mechanisms as a guide for cancer immunotherapy, Clin Cancer Res, 21(4): 687-692 (2014).

Berger, T.G., et al., Circulation and homing of melanoma-reactive T cells to both cutaneous and visceral metastases after vaccination with monocyte-derived dendritic cells, Int J Cancer, 111: 229-237 (2004).

Bigner, S.H., et al., Characterization of the Epidermal Growth Factor Receptor in Human Glioma Cell Lines and Xenografts, Cancer Res, 50: 8017-8022 (1990).

Bioley, G., et al., HLA Class I-Associated Immunodominance Affects CTL Responsiveness to an ESO Recombinant Protein Tumor Antigen Vaccine, Clin Cancer Res, 15(1): 299-306 (2009).

Buonaguro, L., et al., Translating tumor antigens into cancer vaccines, Clin Vaccine Immunol, 18(1): 23-34 (2011).

Butts, C., et al., Randomized Phase IIB Trial of BLP25 Liposome Vaccine in Stage IIIB and IV Non-Small-Cell Lung Cancer, J Clin Oncol, 23(27): 6674-6681 (2005).

Carmon, L., et al., Phase I/II study exploring ImMucin, a pan-major histocompatibility complex, anti-MUC1 signal peptide vaccine, in multiple myeloma patients, Br J Hematol, 169(1):44-56 (2014).

Cathcart, K., et al., A multivalent bcr-abl fusion peptide vaccination trial in patients with chronic Myeloid Leukemia, Blood, 103:1037-1042 (2004).

Celis, E., et al., Identification of potential CTL epitopes of tumor-associated antigen MAGE-1 for five common HLA-A alleles, Mol Immunol, 31(18): 1423-1430 (1994).

Celis, E., et al., Induction of anti-tumor cytotoxic T lymphocytes in normal humans using primary cultures and synthetic peptide epitopes, PNAS USA, 91: 2105-2109 (1994).

Chapuis, A.G., et al., Transferred WT1-reactive CD8+ T cells can mediate antileukemic activity and persist in post-transplant patients, Sci Transl Med, 5(174): 174ra27 (2013).

Chen, Y., et al., Multiple Cancer/Testis Antigens Are Preferentially Expressed in Hormone-Receptor Negative and High-Grade Breast Cancers, PLoS One, 6(3):e17876 (2011).

Chiriva-Internati, M., et al., Identification of AKAP-4 as a New Cancer/Testis Antigen for Detection and Immunotherapy of Prostate Cancer, Prostate, 72(1):12-23 (2012).

Choi, J., et al., The Expression of MAGE and SSX, and Correlation of COX2, VEGF, and Survivin in Colorectal Cancer, Anticancer Res, 32(2): 559-564 (2012).

Chowell, D., et al., Patient HLA class 1 genotype influences cancer response to checkpoint blockade immunotherapy, Science, 359(6375): 582-587 (2018).

Chu, C.T., et al., Receptor dimerization is not a factor in the signalling activity of a transforming variant epidermal growth factor receptor (EGFRvIII), Biochem J, 324: 855-861 (1997).

Cusi, M.G., et al., Phase I trial of the thymidylate synthase poly-epitope (TSPP) vaccine in advance cancer patients, Cancer Immunol Immunother, 64:1159-1173 (2015).

Durie, BGM, et al., International uniform response criteria for multiple myeloma, Leukemia, 20:1467-1473 (2006).

Eisenhauer, E.A., et al., New response evaluation criteria in solid tumours: Revised RECIST guideline (version 1.1), Euro J Cancer, 45: 228-247 (2009).

Engelhard, V.H., Structure of peptides associated with MHC class I molecules, Curr Opin Immunol, 6(1): 13-23 (1994).

Fenoglio, D., et al., A multi-peptide, dual-adjuvant telomerase vaccine (GX301) is highly immunogenic in patients with prostate and renal cancer, Cancer Immunol Immunother, 62:1041-1052 (2013).

Gerdts, V., et al., Vaccines for porcine epidemic diarrhea virus and other swine coronaviruses, Vet Microbiol, 206: 45-51 (2017).

Goel, S., et al., CDK4/6 inhibition triggers anti-tumor immunity, Nature, 548(7668): 471-475 (2017).

Goossens-Beumer, J., et al., Clinical prognostic value of combined analysis of Aldh1, Survivin, and EpCAM expression in colorectal cancer, Br J Cancer, 110(12): 2935-2944 (2014).

Greenfield, W.W., et al., A phase I dose-escalation clinical trial of a peptide-based human papillomavirus therapeutic vaccine adjuvant for treating with women with biopsy-proven cervical intraepithelial neoplasia 2/3, Oncoimmunol, 10:e1031439 (2015).

(56) References Cited

OTHER PUBLICATIONS

Gudmundsdotter, L., et al., Amplified antigen-specific immune responses in HIV-1 infected individuals in a double blind DNA immunization and therapy interruption trial, Vaccine, 29(33):5558-5566 (2011).
Guo, H., et al., Different length peptides bind to HLA-Aw68 similarity at their ends but bulge out in the middle, Nature, 360: 364-366 (1992).
Hartmaier, R.J., et al., Genomic analysis of 63,220 tumors reveals insights into tumor uniqueness and targeted cancer immunotherapy strategies, Genome Med, 9:16 (2017).
HLA Genetics and Nomenclature, 10th International Summer School on Immunogenetics, Stintino, Sardinia: 34 pages (2013).
HLA Nomenclature, (2015) retrieved from http://hla.alleles.org/nomenclature/stats.html on Mar. 17, 2015.
Hodi, F.S., et al., Improved Survival with Ipilimumab in Patients with Metastatic Melanoma, N Engl J Med, 363(8): 711-723 (2010).
Hou. S., et al., Expressions of MAGE-A9 and MAGE-A11 in breast cancer and their expression mechanism, Arch Med Res, 45(1): 44-51 (2014).
Humphrey, P.A., et al., Anti-synthetic peptide antibody reacting at the fusion junction of deletion-mutant epidermal growth factor receptors in human glioblastoma, PNAS, 87: 4207-4211 (1990).
Kaida, M., et al., Phase 1 Trial of Wilms Tumor 1 (WT1) Peptide Vaccine and Gemcitabine Combination Therapy in Patients With Advanced Pancreatic or Biliary Tract Cancer, J Immunother, 34: 92-99 (2011).
Kakimi, K., et al., A phase I study of vaccination with NY-ESO-1f peptide mixed with Picibanil OK-432 and Montanide ISA-51 in patients with cancers expressing the NY-ESO-1 antigen, Int J Cancer, 129(12): 2836-2846 (2011).
Kalos, M., et al., Adoptive T cell transfer for cancer immunotherapy in the era of synthetic biology, Immunity, 39:49-60 (2013).
Kanojia, D., et al., Sperm-Associated Antigen 9, a Novel Biomarker for Early Detection of Breast Cancer, Cancer Epidemiol Biomarkers Prev, 18(2): 630-639 (2009).
Kantoff, P.W., et al., Overall Survival Analysis of a Phase II Randomized Controlled Trial of a Poxviral-Based PSA-Targeted Immunotherapy in Metastatic Castration-Resistant Prostate Cancer, J Clin Oncol, 28(7): 1099-1105 (2010).
Karkada, M., et al., Therapeutic vaccines and cancer: focus on DPX-0907, Biologies, 8: 27-38 (2014).
Keilholz, U., et al., A clinical and immunologic phase 2 trial of Wilms tumor gene product 1 (WT1) peptide vaccination in patients with AML and MDS, Blood, 113(26): 6541-6548 (2009).
Kenter, G.G., et al., Vaccination against HPV-16 Oncoproteins for Vulvar Intraepithelial Neoplasia, N Engl J Med, 361(19): 1838-1847 (2009).
Kenter, G.K., et al., Phase I immunotherapeutic trial with long peptides spanning the E6 and E7 sequences of high-risk human papillomavirus 16 in end-stage cervical cancer patients shows low toxicity and robust immunogenicity, Clin Cancer Res, 14(1): 169-177 (2008).
Kerkar, S.P., et al., Cellular constituents of immune escape within the tumor microenvironment, Cancer Res, 72(13): 3125-3130 (2012).
Khallouf, H., et al., Therapeutic vaccine strategies against human papillomavirus, Vaccines (Basel), 2(2): 422-462 (2014).
Kissler, S.M., et al. Projecting the transmission dynamics of SARS-CoV-2 through the post-pandemic period, Available at http://nrs.harvard.edu/um-3:HUL.InstRepos:42639308 (31 pgs) (2020).
Kovjazin, R., et al., ImMucin: A novel therapeutic vaccine with promiscuous MHC binding for the treatment of MUC1-expressing tumors, Vaccine, 29(29-30): 4676-4686 (2011).
Krug, L.M., et al., WT1 peptide vaccinations induce CD4 and CD8 T cell Immune responses in patients with mesothelioma and non-small cell lung cancer, Cancer Immunol Immunother, 59(10): 1467-1479 (2010).
Krüger, T., et al., Lessons to be learned from primary renal cell carcinomas: novel tumor antigens and HLA ligands for immunotherapy, Cancer Immunol Immunother, 54: 826-836 (2005).

Lammering, G., et al., Inhibition of the Type III epidermal growth factor receptor variant mutant receptor by dominant-negative EGFR-CD533 enhances malignant glioma cell radiosensitivity, Clin Cancer Res, 10: 6732-6743 (2004).
Lammering, G., et al., Radiation-induced activation of a common variant of EGFR confers enhanced radioresistance, Radiother Oncol, 72: 267-273 (2004).
Lee, et al., In silico identification of vaccine targets for2019-nCoV, F1000Res, 9:145, pp. 1-14 (2020).
Lee, S., et al., Immunomic analysis of human sarcoma, PNAS, 100(5): 2651-2656 (2003).
Li, J., et al., Thrombocytopenia caused by the development of antibodies to thrombopoietin, Blood, 96(12): 3241-3248 (2001).
Li, M., et al., Expression profile of cancer-testis genes in 121 human colorectal cancer tissue and adjacent normal tissue, Clin Cancer Res, 11(5): 1809-1814 (2005).
Libermann, T.A., et al., Amplification, enhanced expression and possible rearrangement of EGF receptor gene in primary human brain tumors of glial origin, Nature, 313: 144-147 (1985).
Liu, J., et al., Major histocompatibility complex: interaction with peptides, in: eLS, John Wiley & Sons, Ltd: Chichester, a0000922.pub2, pp. 1-12 (2011).
MHC-I binding prediction results, IEDB Analysis Resource, pp. 1/1-1/3 retrieved on Apr. 22, 2021 from <tools.iedb.org/mhci/result/>.
Montgomery, R.B., et al., Expression of oncogenic epidermal growth factor receptor family kinases induces paclitaxel resistance and alters β-tubulin isotype expression, J Biol Chem, 275(23): 17358-17363 (2000).
Nagane, M., et al., A common mutant epidermal growth factor receptor confers enhanced tumorigenicity on human glioblastoma cells by increasing proliferation and reducing apoptosis, Cancer Res, 56: 5079-5086 (1996).
Nicosia, G., et al., Artificial Immune Systems, Third International Conference, ICARIS 2004, Catania, Sicily, Italy, Sep. 13-16, 2004. Lecture Notes in Computer Science, New York: Springer, 3236:189-196 (2004).
Nishikawa, R., et al., A mutant epidermal growth factor receptor common in human glioma confers enhanced tumorgenicity, PNAS USA, 91: 7727-7731 (1994).
Ochoa-Garay, J., et al., The ability of peptides to induce cytotoxic T cells in vitro does not strongly correlate with their affinity for the $H-2L^d$ molecule: implications for vaccine design and immunotherapy, Mol Immunol, 34(3): 273-281 (1997).
Okuno, K., et al., Clinical trial of a 7-peptide cocktail vaccine with oral chemotherapy for patients with metastatic colorectal cancer, Anticancer Res, 34: 3045-3052 (2014).
Padron-Regalado, E., et al., Vaccines for SARS-CoV-2: lessons from other coronavirus strains, Infect Dis Ther, 9: 255-274 (2020).
Paoletti, L.C., Potency of clinical group B streptococcal conjugate vaccines, Vaccine, 19: 2118-2126 (2001).
Pardi, N., et al., mRNA vaccines—a new era in vaccinology, Nat Rev Drug Discov, 19 pages (2018).
Pasini, E., et al., Undifferentiated nasopharyngeal carcinoma from a nonendemic area: Protective role of HLA allele products presenting conserved EBV epitopes, Int J Cancer, 125(6): 1358-1364 (2009).
PCT/EP2018/055230 International Search Report and Written Opinion dated Jun. 8, 2018.
PCT/EP2018/055231 International Search Report and Written Opinion dated Apr. 5, 2018.
PCT/EP2018/055232 International Search Report and Written Opinion dated May 9, 2018.
PCT/EP2019/073476 International Search Report and Written Opinion dated Jan. 23, 2020.
PCT/EP2019/073478 International Search Report and Written Opinion dated Sep. 20, 2019.
PCT/EP2019/073481 International Search Report and Written Opinion dated Dec. 20, 2019.
Phuphanich, S., et al., Phase I trial of a multi-epitope-pulsed dendritic call vaccine for patients with newly diagnosed glioblastoma, Cancer Immunol Immunother, 62(1): 125-135 (2013).

(56) References Cited

OTHER PUBLICATIONS

Rahman Oany, et al., Design of an epitope-based peptide vaccine against spike protein of human coronavirus: an in silico approach, Drug Des Devel Ther, 8: 1139-1149 (2014).
Rajasagi, et al., Systematic identification of personal tumor-specific neoantigens in chronic lymphocytic leukemia, Blood, 124(3): 456-462 (2014).
Ramakrishnan, R., et al., Chemotherapy enhances tumor cell susceptibility to CTL-mediated killing during cancer immunotherapy in mice, J Clin Invest, 120(4): 1111-1124 (2010).
Rapoport, A.P., et al., Combination immunotherapy after ASCT for multiple myeloma using MAGE-A3/Poly-ICLC immunizations followed by adoptive transfer of vaccine-primed and costimulated autologous T cells, Clin Cancer Res, 20(5): 1355-1365 (2014).
Reche, P.A., et al., Definition of MHC supertypes through clustering of MHC peptide binding repertoires, in Nicosia, G., et al., Eds. ICARIS 2004, LNCS 3239: 189-196( (2004).
Repana, D., et al., The network of cancer genes (NCG): a comprehensive catalogue of known and candidate cancer genes from cancer sequencing screens, Genome Biol, 20(1): 1-12 (2019).
Rosa, D.S., et al., Multiple approaches for increasing the immunogenicity of an epitope-based anti-HIV vaccine, AIDS Res Hum Retroviruses, 31(11): 1077-1088 (2015).
Saini, S., et al., A novel cancer testis antigen, a-kinase anchor protein 4 (AKAP4) is a potential biomarker for breast cancer, PLoS One, 8(2): e57095 (2013).
Sampson, J.H., et al., Immunologic escape after prolonged progression-free survival with epidermal growth factor receptor variant III peptide vaccination in patients with newly diagnosed glioblastoma, J Clin Oncol, 28(31): 4722-4729 (2010).
Schumacher, T.N., et al., Neoantigens in cancer immunotherapy, Science, 348(6230): 69-74 (2015).
Seliger, B., et al., Molecular mechanisms of HLA class I antigen abnormalities following viral infection and transformation, Int J Cancer, 118(1): 129-138 (2006).
Singh, S.P., et al., Major histocompatibility complex linked databases and prediction tools for designing vaccines, Hum Immunol, 77(3): 295-306 (2015).
Slingluff, C.L., et al., Clinical and Immunologic results of a randomized phase II trial of vaccination using four melanoma peptides either administered in granulocyte-macrophage colony-stimulating factor in adjuvant of pulsed on dendritic cells, J Clin Oncol, 21(21): 4016-4026 (2003).
Slingluff, C.L., et al., Randomized multicenter trial of the effects of melanoma-associated helper peptides and cyclophosphamide on the immunogenicity of a multipeptide melanoma vaccine, J Clin Oncol, 29(21): 2924-2932 (2011).
Snyder, A.S., et al., Genetic basis for clinical response to CTLA-4 blockade in melanoma, N Engl J Med, 371(23): 2189-2199 (2014).
Somogyi, E., et al., Peptide vaccine candidate mimics the heterogeneity of natural SARS-CoV-2 immunity in convalescent humans and induces broad T cell responses in mice models, bioRxiv, pp. 1-39, Oct. 2020.
Song, M., et al., Cancer/testis antigen NT-SAR-35 enhances cell proliferation, migration, and invasion, Int J Oncol, 48(2):569-576 (2016).
Spranger, S., Mechanisms of tumor escape in the context of the T-cell-inflamed and the non-T-cell-inflamed tumor microenvironment, Int Immunol, 28(8): 383-391 (2016).
Tagawa, S.T., et al., Phase I study of intranodal delivery of a plasmid DNA vaccine for patients with stage IV melanoma, Cancer, 98(1):144-154 (2003).
Takedatsu, H., et al., Determination of thrombopoietin-derived peptides recognized by both cellular and humoral immunities in healthy donors and patients with thrombocytopenia, Stem Cells, 23(7): 975-982 (2005).
TANTIGEN search results for EpCAM T cell epitopes, 1 page, retrieved on Apr. 19, 2021 from <http://projects.met-hilab.org/tadb/cgi/searchT.pl>.
TANTIGEN search results for HILI/PIWIL-2, 1 page, retrieved on Apr. 16, 2021 from <http://projects.met-hilab.org/tadb/cgi/searchT.pl>.
The UniProt Consortium, UniProt: the universal protein knowledgebase, UniProtKB-Q8N0W7, Nucleic Acids Res. 46:2699 (2018).
Therasse, P., et al., New guidelines to evaluate the response to treatment in solid tumors, J Natl Cancer Inst, 92(3): 205-216 (2000).
Trimble, C.L., et al., Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial, Lancet, 386(10008): 2078-2088 (2015).
Tsuchida, Y., et al., Response evaluation criteria in solid tumors (RECIST): new guidelines, Med Pediatr Oncol, 37:1-3 (2001).
U.S. Appl. No. 17/448,020, filed Sep. 17, 2021.
U.S. Appl. No. 17/454,225, filed Nov. 9, 2021.
U.S. Appl. No. 15/910,930 Office Action dated Mar. 25, 2021.
U.S. Appl. No. 15/910,965 Office Action dated May 12, 2021.
U.S. Appl. No. 15/910,988 Office Action dated May 18, 2018.
U.S. Appl. No. 16/244,497 Office Action dated Aug. 18, 2021.
U.S. Appl. No. 16/559,430 Office Action dated Apr. 27, 2020.
U.S. Appl. No. 16/559,430 Office Action dated Aug. 27, 2020.
U.S. Appl. No. 17/249,362 Office Action dated Apr. 27, 2021.
U.S. Appl. No. 17/249,362 Office Action dated Sep. 8, 2021.
Valmori, D., et al., Epitope clustering in regions undergoing efficient proteasomal processing defines immunodominant CTL regions of a tumor antigen, Clin Immunol, 122: 163-172 (2007).
Valmori, D., et al., Vaccination with NY-ESO-1 protein and CpG in montanide induces integrated antibody/Th1 responses and CD8 T cells through cross-priming, PNAS USA, 104(21): 8947-8952 (2007).
Van Allen, E.M., et al., Genomic correlates of response to CTLA-4 blockade in metastatic melanoma, Science, 350(6257): 207-211 (2015).
Vitale, M., et al., Effect oftumor cells and tumor microenvironment on NK-cell function, EurJ Immunol, 44: 1582-1592 (2014).
Wada, H., et al., Vaccination with NY-ESO-1 overlapping peptides mixed with picibanil OK-432 and montanide ISA-51 in patients with cancers expressing the NY-ESO-1 antigen, J Immunother, 37(2): 84-92 (2014).
Walter, S., et al., Multipeptide immune response to cancer vaccine IMA901 after single-dose cyclophosphamide associates with longer patient survival, Nat Med, 18(8): 1254-1261 (2012).
Wei, J., et al., Screening of Single-Chain Variable Fragments against TSP50 from a Phage Display Antibody Library and Their Expression as Soluble Proteins, J Biol Med Screen, 11(5): 546-552, (2006).
Weller, M., et al., Rindopepimut with temozolomide for patients with newly diagnosed, EGFRvIII-expressing glioblastoma (ACT IV): a randomised, double-blind, international phase 2 trial, Lancet Oncol, 18(10): 1373-1385 (2017).
Welters, M.J.P., et al., Induction of tumor-specific CD4+ and CD8+ T-cell immunity in cervical cancer patients by a human papillomavirus type 16 E6 and E7 long peptides vaccine, Clin Cancer Res, 14(1): 178-187 (2008).
Welters, M.J.P., et al., Success or failure of vaccination for HPV16-positive vulvar lesions correlates with kinetics and phenotype of induced T-cell responses, PNAS USA, 107(25): 11895-11899 (2010).
Wieczorek, M., et al., Major histocompatibility complex (MHC) class I and MHC class II proteins: conformational plasticity in antigen presentation, Front Immunol, 8: 292 (2017).
Woolhouse, M., et al., Human viruses: discovery and emergence, Philos Trans R Soc London B Biol Sci, 367(1604): 2864-71 (2012).
Wu, F., et al., Severe acute respiratory syndrome coronavirus 2 isolate Wuhan-Hu-1, complete genome, NCBI Reference Sequence: NC_045512.2, (2020).
Yamada, A., et al., Phase I clinical study of a personalized peptide vaccination available for six different human Leukocyte antigen (HLA-A2, -A3, -A11, -A24, -A31 and -A33)-positive patients with advanced cancer, Experimental and Therapeutic Medicine, 2(1): 109-117 (2011).
Yoshitake, Y., et al., Phase II clinical trial of multiple peptide vaccination for advanced head and neck cancer patients revealed induction of immune responses and improved OS, Clin Cancer Res, 21(2): 312-321 (2015).

(56) References Cited

OTHER PUBLICATIONS

Yuan, J., et al., Integrated NY-ESO-1 antibody and CD8+ T-cell responses correlate with clinical benefit in advanced melanoma patients treated with ipilimumab, PNAS USA, 108(40): 16723-16728 (2011).

Yuan, J., et al., Safety and immunogenicity of a human and mouse gp100 DNA vaccine in a phase I trial of patients with melanoma, Cancer Immunity, 9:5 (2009).

Zajac, P., et al., MAGE-A antigens and cancer immunotherapy, Front Immunol, 4: 18 (2017).

Zhang. X.W., A combination of epitope prediction and molecular docking allows for good identification of MHC class I restricted T-cell epitopes, Comput Biol Chem, 45: 30-35 (2013).

Zheng, L., et al., High Expression of Testes-Specific Protease 50 is Associated with Poor Prognosis in Colorectal Carcinoma, PLoS One, 6(7):e22203 (2011).

U.S. Appl. No. 15/910,965, filed Mar. 2, 2018, Abandoned.
U.S. Appl. No. 17/454,225, filed Nov. 9, 2021, Pending.
U.S. Appl. No. 15/910,930, filed Mar. 2, 2018, Abandoned.
U.S. Appl. No. 17/448,020, filed Sep. 17, 2021, Pending.
U.S. Appl. No. 15/910,988, filed Mar. 2, 2018, U.S. Pat. No. 10,213,497, Feb. 26, 2019, Issued.
U.S. Appl. No. 16/244,497, filed Jan. 10, 2019, Projected to issue as U.S. Pat. No. 11,213,578, Projected to issue on Jan. 4, 2022, Allowed.
U.S. Appl. No. 16/559,430, filed Sep. 3, 2019, Abandoned.
U.S. Appl. No. 17/249,362, filed Feb. 26, 2021, Pending.

Shi, R., et al., The immunogenicity of a novel cytotoxic T lymphocyte epitope from tumor antigen PL2L60 could be enhanced by 4-chlorophenylalanine substitution at position 1, Cancer Immunol Immunother, 62(11): 1723-1732 (2013).

U.S. Appl. No. 17/645,741 Office Action dated Mar. 2, 2022.

Andersen, M.H., et al., HLA-A24 and survivin: possibilities in therapeutic vaccination against cancer, J Transl Med, 4:38, 2 pages (2006).

Bachinsky, M.M., et al., Mapping and binding analysis of peptides derived from the tumor-associated antigen survivin for eight HLA alleles, Cancer Immun, 5:6, pp. 1-9 (2005).

Hondowicz, B.D., et al., Discovery of T cell antigens by high-throughput screening of synthetic minigene libraries, PLoS One, 7(1): e29949 (2012).

Schmitz, M., et al., Generation of survivin-specific CD8+ T effector cells by dendritic cells pulsed with protein or selected peptides, Cancer Res, 60(17): 4845-4849 (2000).

Somogyi, E., et al., HIV vaccine to induce cytotoxic T cells recognizing conserved HIV-1 /2-epitopes derived from the most frequent HLA types of the human population, Immunotherapy, 5(8): 825-828 (2013).

\* cited by examiner

| Pat ID | #PEPI / HPV-16 E6 | | | | E7 | |
|---|---|---|---|---|---|---|
| | E6.1 | E6.2 | E6.3 | E6.4 | E7.1 | E7.2 |
| 1 | FP | TP | TP | FN | TN | FN |
| 2 | FP | TP | TP | TN | TN | TP |
| 3 | TP | TP | TP | TP | TN | TP |
| 6 | TP | TP | TP | FN | FP | TP |
| 7 | TP | TP | TP | TP | TN | TP |
| 8 | TP | TP | TP | FN | FP | TP |
| 9 | TP | TP | TP | FN | FP | TP |
| 10 | FP | TP | TP | FN | TN | TP |
| 11 | TP | TP | FN | FN | TN | TP |
| 13 | TP | TP | FN | FN | TN | FN |
| 16 | TP | TP | TP | FN | FP | TP |
| 18 | FP | TP | FN | FN | FN | TP |
| 22 | TP | TP | TP | FN | FN | FN |
| 23 | FP | TP | TP | FN | TN | TN |
| 27 | TP | TP | TP | FN | FN | FN |
| 28 | TP | TP | TP | FN | TN | FN |
| 29 | FP | TP | TP | FN | FP | TP |
| 30 | FP | FP | TN | TN | FN | FN |
| 100 | TP | TP | TP | FN | TN | TP |
| 102 | TP | TP | TP | FN | FN | TP |
| 103 | TP | TP | TP | FN | TN | TN |
| 105 | TP | TP | TP | TP | TN | TN |
| 107 | TP | TP | FN | FN | TN | FN |

FIG. 4A

| Patient ID | \# epitope / HPV-16 E6&E7 pools | | | | | |
|---|---|---|---|---|---|---|
| | E6.1 | E6.2 | E6.3 | E6.4 | E7.1 | E7.2 |
| 1 | FP | TP | TP | FN | FP | TP |
| 2 | FP | TP | TP | TN | TN | TP |
| 3 | TP | TP | TP | FN | FP | TP |
| 6 | TP | TP | TP | FN | TP | TP |
| 7 | TP | TP | TP | FN | FP | TP |
| 8 | TP | TP | TP | FN | FP | TP |
| 9 | TP | TP | TP | FN | FP | TP |
| 10 | FP | TP | TP | FN | FP | TP |
| 11 | TP | TP | TP | FN | FP | TP |
| 13 | TP | TP | TP | FN | TN | TP |
| 16 | TP | TP | TP | FN | TN | TP |
| 18 | FP | TP | TP | FN | FN | TP |
| 22 | TP | TP | TP | FN | TP | TP |
| 23 | FP | TP | TP | FN | FP | FP |
| 27 | TP | TP | TP | FN | TP | TP |
| 28 | TP | TP | TP | FN | FP | TP |
| 29 | FP | TP | TP | FN | FP | TP |
| 30 | FP | FP | FP | TN | FN | TP |
| 100 | TP | TP | TP | FN | FP | TP |
| 102 | TP | TP | TP | FN | TP | TP |
| 103 | TP | TP | TP | FN | TN | FP |
| 105 | TP | TP | TP | FN | TN | FP |
| 107 | TP | TP | TP | FN | FP | TP |

FIG. 4B

VACCINE

CROSS-REFERENCE

This application is a continuation of U.S. application Ser. No. 16/244,497, filed on Jan. 10, 2019, now issued as U.S. Pat. No. 11,213,578 on Jan. 4, 2022, which is a continuation of U.S. application Ser. No. 15/910,988, filed on Mar. 2, 2018, now issued as U.S. Pat. No. 10,213,497 on Feb. 26, 2019, which claims the benefit of priority to European Application No. 17159242.1, filed on Mar. 3, 2017, European Application No. 17159243.9, filed on Mar. 3, 2017, and Great Britain Application No. 1703809.2, filed on Mar. 9, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created Dec. 18, 2021, is named "TBL_004C2_SL.txt" and is 269,433 bytes in size.

FIELD

The disclosure relates to polypeptides and vaccines that find use in the prevention or treatment of cancer, in particular most breast cancers, ovarian cancers and colorectal cancers.

BACKGROUND

Cancer is killing millions of people worldwide, because existing drugs do not enable effective prevention or treatment. Current checkpoint inhibitor immunotherapies that re-activate existing immune responses can provide clinical benefit for a fraction of cancer patients. Current cancer vaccines that induce new immune responses are poorly immunogenic and fail to benefit most patients.

Recent analyses of 63,220 unique tumors revealed that cancer vaccines need to be generated specifically for each patient because extensive inter-individual tumor genomic heterogeneity (Hartmaier et al. *Genome Medicine* 2017 9:16). Using state of art technologies it is currently not feasible to scale HLA-specific cancer vaccines to large populations.

SUMMARY

In antigen presenting cells (APC) protein antigens are processed into peptides. These peptides bind to human leukocyte antigen molecules (HLAs) and are presented on the cell surface as peptide-HLA complexes to T cells. Different individuals express different HLA molecules and different HLA molecules present different peptides. Therefore, according to the state of the art, a peptide, or a fragment of a larger polypeptide, is identified as immunogenic for a specific human subject if it is presented by a HLA molecule that is expressed by the subject. In other words, the state of the art describes immunogenic peptides as HLA-restricted epitopes. However, HLA restricted epitopes induce T cell responses in only a fraction of individuals who express the HLA molecule. Peptides that activate a T cell response in one individual are inactive in others despite HLA allele matching. Therefore, it was previously unknown how an individual's HLA molecules present the antigen-derived epitopes that positively activate T cell responses.

As provided herein multiple HLAs expressed by an individual need to present the same peptide in order to trigger a T cell response. The fragments of a polypeptide antigen that are immunogenic for a specific individual are those that can bind to multiple class I (activate cytotoxic T cells) or class II (activate helper T cells) HLAs expressed by that individual. For example, the inventors have discovered that the presence of a T cell epitope that binds to at least three HLA type I of a subject predicts an immune response in the subject to a polypeptide.

Based on this discovery the inventors have identified the T cell epitopes from certain breast, ovarian and/or colorectal cancer associated-polypeptide antigens (cancer testis antigens (CTA)) that are capable of binding to at least three class I HLA in a high proportion of individuals. These T cell epitopes, or fragments of the antigens comprising the T cell epitopes, are useful for inducing specific immune responses against tumor cells expressing these antigens and for treating or preventing cancer.

In a first aspect the disclosure provides a polypeptide that comprises a fragment of up to 50 consecutive amino acids of
(a) a colorectal cancer-associated antigen selected from TSP50, EpCAM, SPAG9, CAGE1, FBXO39, SURVIVIN, LEMD1, MAGE-A8, MAGE-A6 and MAGE-A3, wherein the fragment comprises an amino acid sequence selected from any one of SEQ ID NOs: 21 to 40 and 234 to 250;
(b) an ovarian cancer-associated antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3 wherein the fragment comprises the amino acid sequence of any one of SEQ ID NOs: 272 to 301; and/or
(c) a breast cancer associated antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1 wherein the fragment comprises an amino acid sequence selected from any one of SEQ ID NOs: 1 to 20, 24 and 172 to 194.

In some specific cases the disclosure provides a polypeptide that
(a) is a fragment of a colorectal cancer-associated antigen selected from TSP50, EpCAM, SPAG9, CAGE1, FBXO39, SURVIVIN, MAGE-A8, MAGE-A6, MAGE-A3 and LEMD1, wherein the fragment comprises an amino acid sequence selected from any one of SEQ ID NOs: 21 to 40 and 234 to 250; or
(b) comprises or consists of two or more fragments of one or more colorectal cancer associated antigens selected from TSP50, EpCAM, SPAG9, CAGE1, FBXO39, SURVIVIN, MAGE-A8, MAGE-A6, MAGE-A3 and LEMD1, wherein each fragment comprises a different amino acid sequence selected from any one of SEQ ID NOs: 21 to 40 and 234 to 250, optionally wherein the fragments overlap or are arranged end to end in the polypeptide; or
(c) is a fragment of a ovarian cancer-associated antigen selected from PIWIL-4, WT1, EpCAM, BORIS, AKAP-4, OY-TES-1, SP17, PIWIL-2, PIWIL-3, SPAG9, PRAME, HIWI, SURVIVIN and AKAP-3, wherein the fragment comprises an amino acid sequence selected from any one of SEQ ID NOs: 272 to 301; or
(d) comprises or consists of two or more fragments of one or more ovarian cancer associated antigens selected from PIWIL-4, WT1, EpCAM, BORIS, AKAP-4, OY-TES-1, SP17, PIWIL-2, PIWIL-3, SPAG9, PRAME, HIWI, SURVIVIN and AKAP-3, wherein each fragment comprises a different amino acid sequence selected from any one of SEQ ID NOs: 272 to 301, optionally wherein the fragments overlap or are arranged end to end in the polypeptide; or (e) is a fragment of a breast cancer associated antigen selected from SPAG9, AKAP-4, BORIS, NY-SAR-35, NY-BR-1, SURVIVIN, MAGE-A11, PRAME, MAGE-A9, HOM-TES-85, PIWIL-2, EpCAM, HIWI, PLU-1, TSGA10, ODF-4, SP17, RHOXF-2, wherein the fragment comprises the amino acid sequence from any one of SEQ ID NOs: 1 to 20, 24 and 172 to 194; or (f) comprises or consists of two or more fragments of one or more breast cancer associated antigens selected from SPAG9, AKAP-4, BORIS, NY-SAR-35, NY-BR-1, SURVIVIN, MAGE-A11, PRAME, MAGE-A9, HOM-TES-8, PIWIL-2, EpCAM, HIWI, PLU-1, TSGA10, ODF-4, SP17, RHOXF-2, wherein each fragment comprises a different amino acid sequence selected from any one of SEQ ID NOs: 1 to 20, 24 and 172 to 194; optionally wherein the fragments overlap or are arranged end to end in the polypeptide and.

In some specific cases the polypeptide comprises or consists of fragments of (a) TSP50, EpCAM, SPAG9, CAGE1, FBXO39, SURVIVIN, MAGE-A8, MAGE-A6, MAGE-A3 and LEMD1;

(b) PIWIL-4, WT1, EpCAM, BORIS, AKAP-4, OY-TES-1, SP17, PIWIL-2, PIWIL-3, SPAG9, PRAME, HIWI, SURVIVIN and AKAP-3; and/or (c) SPAG9, AKAP-4, BORIS, NY-SAR-35, NY-BR-1, SURVIVIN, MAGE-A11, PRAME, MAGE-A9, HOM-TES-8, PIWIL-2, EpCAM, HIWI, PLU-1, TSGA10, ODF-4, SP17, RHOXF-2;

wherein each fragment comprises a different amino acid sequence selected from SEQ ID NOs: 21 to 40 and 234 to 250; SEQ ID NOs: 272 to 301; and/or SEQ ID NOs: 1 to 20, 24 and 172 to 194.

In some cases the polypeptide comprises or consists of one or more amino acid sequences selected from SEQ ID NOs: 41-80, 251 to 271, 302 to 331 and 196 to 233.

In some cases the polypeptide comprises or consists of one or more amino acid sequences selected from SEQ ID NOs: 41-80, 195-233, 251-271 and 302-331 or selected from SEQ ID NOs: 81-142, 332-346, and 435-449.

In a further aspect the disclosure provides a panel of two or more polypeptides as described above, wherein each peptide comprises or consists of a different amino acid sequence selected from SEQ ID NOs: 21 to 40 and 234 to 250; or selected from SEQ ID NOs: 272 to 301; or selected from SEQ ID NOs: 1 to 20, 24 and 172 to 194; or selected from SEQ ID NOs: 1 to 40, 234 to 250, 272 to 301 and 172 to 194. In some cases the panel of polypeptides comprises or consists of one or more peptides comprising or consisting of the amino acid sequences of SEQ ID NOs: 130, 121, 131, 124, 134, 126 and/or SEQ ID NOs: 435-449.

In a further aspect the disclosure provides a pharmaceutical composition or kit having one or more polypeptides or panels of peptides as described above as active ingredients, or having a polypeptide comprising at least two amino acid sequences selected from SEQ ID NOs: 21 to 40 and 234 to 250; SEQ ID NOs: 272 to 301; and/or SEQ ID NOs: 1 to 20, 24 and 172 to 194 as an active ingredient; or selected from SEQ ID NOs: 130, 121, 131, 124, 134, 126 and/or 435-449 as an active ingredient.

In a further aspect the disclosure provides a method of inducing immune responses, (e.g. vaccination, providing immunotherapy or inducing a cytotoxic T cell response in a subject), the method comprising administering to the subject a pharmaceutical composition, kit or the panel of polypeptides as described above. The method may be a method of treating cancer, such as breast cancer, ovarian cancer or colorectal cancer.

In further aspects, the disclosure provides the pharmaceutical composition, kit or panel of polypeptides described above for use in a method of inducing immune responses or for use in a method of treating cancer, optionally breast cancer, ovarian cancer or colorectal cancer; and use of a peptide or a panel of peptides as described above in the manufacture of a medicament for inducing immune responses or for treating cancer, optionally breast cancer, ovarian cancer or colorectal cancer.

In a further aspect the disclosure provides a method of identifying a human subject who will likely have a cytotoxic T cell response to administration of a pharmaceutical composition as described above, the method comprising (i) determining that the active ingredient polypeptide(s) of the pharmaceutical composition comprise a sequence that is a T cell epitope capable of binding to at least three HLA class I of the subject; and (ii) identifying the subject as likely to have a cytotoxic T cell response to administration of the pharmaceutical composition.

In a further aspect the disclosure provides a method of identifying a subject who will likely have a clinical response to a method of treatment as described above, the method comprising (i) determining that the active ingredient polypeptide(s) comprise two or more different amino acid sequences each of which is a. a T cell epitope capable of binding to at least three HLA class I of the subject; and b. a fragment of a cancer-associated antigen expressed by cancer cells of the subject; and (ii) identifying the subject as likely to have a clinical response to the method of treatment.

In a further aspect the disclosure provides a method of determining the likelihood that a specific human subject will have a clinical response to a method of treatment, wherein one or more of the following factors corresponds to a higher likelihood of a clinical response:

(a) presence in the active ingredient polypeptide(s) of a higher number of amino acid sequences and/or different amino acid sequences that are each a T cell epitope capable of binding to at least three HLA class I of the subject;

(b) a higher number of target polypeptide antigens, comprising at least one amino acid sequence that is both A. comprised in an active ingredient polypeptide; and B. a T cell epitope capable of binding to at least three HLA class I of the subject; optionally wherein the target polypeptide antigens are expressed in the subject, further optionally wherein the target polypeptides antigens are in one or more samples obtained from the subject;

(c) a higher probability that the subject expresses target polypeptide antigens, optionally a threshold number of the target polypeptide antigens and/or optionally target polypeptide antigens that have been determined to comprise at least one amino acid sequence that is both
   A. comprised in in an active ingredient polypeptide; and
   B. a T cell epitope capable of binding to at least three HLA class I of the subject; and/or
(d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
   A. comprised in in an active ingredient polypeptide; and
   B. a T cell epitope capable of binding to at least three HLA class I of the subject.

In some cases the cancer-associated antigens may be TSP50, EpCAM, SPAG9, CAGE1, FBXO39, SURVIVIN, LEMD1, MAGE-A8, MAGE-A6, MAGE-A3, PIWIL-4, WT1, BORIS, AKAP-4, OY-TES-1, SP17, PIWIL-2, PIWIL-3, PRAME, HIWI, PLU-1, TSGA10, ODF-4, RHOXF-2, NY-SAR-35, MAGE-A9, NY-BR-1, MAGE-A11, HOM-TES-85, NY-ESO-1 and AKAP-3. In some cases the methods above comprise the step of determining that one or more cancer-associated antigens is expressed by cancer cells of the subject. The cancer-associated antigen(s) may be present in one or more samples obtained from the subject In some cases administration of the pharmaceutical composition or the active ingredient polypeptides of the kit may then be selected as a method of treatment for the subject. The subject may further be treated by administration of the pharmaceutical composition or the active ingredient polypeptides.

In a further aspect the disclosure provides a method of treatment as described above, wherein the subject has been identified as likely to have a clinical response or as having above a threshold minimum likelihood of having a clinical response to the treatment by the method described above.

In a further aspect the disclosure provides a method of identifying a human subject who will likely not have a clinical response to a method of treatment as described above, the method comprising
(i) determining that the active ingredient polypeptide(s) of the pharmaceutical composition do not comprise two or more different amino acid sequences each of which is a T cell epitope capable of binding to at least three HLA class I of the subject; and
(ii) identifying the subject as likely not to have a clinical response to the method of treatment.

The methods described above may comprise the step of determining the HLA class I genotype of the subject.

Disclosed herein in certain embodiments are pharmaceutical compositions comprising one or more peptides, wherein each peptide comprises a different one of the amino acid sequence of any one of SEQ ID NOs: 112 to 142. In some embodiments, the composition comprises 2 or more peptides, 3 or more peptides, 4 or more peptides, 5 or more peptides, or 6 or more peptides. In some embodiments, the composition comprises two peptides, wherein each peptide comprises a different one of the amino acid sequences of SEQ ID NOs: 121 and 124. In some embodiments, the composition comprises four peptides, wherein each peptide comprises a different one of the amino acid sequences of SEQ ID NOs: 126, 130, 131, and 134. In some embodiments, the composition comprises six peptides, wherein each peptide comprises a different one of the amino acid sequences of SEQ ID NOs: 121, 124, 126, 130, 131, and 134. In some embodiments, the composition further comprises at least one additional peptide comprising a fragment of an antigen selected from TSP50, EpCAM, SPAG9, CAGE1, FBXO39, SURVIVIN, MAGE-A8, and MAGE-A6. In some embodiments, the composition further comprises one or more additional peptides, each of the one or more additional peptides comprising a different one of the amino acid sequence of any one of SEQ ID NOs: 112-120, 122, 123, 125, 127-129, 132, 133, and 135-142. In some embodiments, the composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

Disclosed herein in certain embodiments are pharmaceutical compositions comprising one or more nucleic acid molecules encoding one or more peptides, wherein each peptide comprises a different one of the amino acid sequence of any one of SEQ ID NOs: 112 to 142.

Disclosed herein in certain embodiments are methods of identifying and treating a human subject having cancer who will likely have a clinical response to administration of a pharmaceutical composition of the disclosure, the method comprising (i) assaying a biological sample of the subject to determine HLA genotype of the subject; (ii) determining that the pharmaceutical composition comprises two or more sequences that are a T cell epitope capable of binding to at least three HLA class I molecules of the subject; (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and (iv) administering the composition of the disclosure to the identified subject. In some embodiments, the subject has colorectal cancer. In some embodiments, the pharmaceutical composition comprises 2 or more peptides, 3 or more peptides, 4 or more peptides, 5 or more peptides, or 6 or more peptides. In some embodiments, the pharmaceutical composition comprises two peptides, wherein each peptide comprises a different one of the amino acid sequences of SEQ ID NOs: 121 and 124. In some embodiments, the pharmaceutical composition comprises four peptides, wherein each peptide comprises a different one of the amino acid sequences of SEQ ID NOs: 126, 130, 131, and 134. In some embodiments, the pharmaceutical composition comprises six peptides, wherein each peptide comprises a different one of the amino acid sequences of SEQ ID NOs: 121, 124, 126, 130, 131, and 134. In some embodiments, the pharmaceutical composition further comprises at least one additional peptide comprising a fragment of an antigen selected from TSP50, EpCAM, SPAG9, CAGE1, FBXO39, SURVIVIN, MAGE-A8, and MAGE-A6. In some embodiments, the pharmaceutical composition further comprises one or more additional peptides, each of the one or more additional peptides comprising a different one of the amino acid sequence of any one of SEQ ID NOs: 112-120, 122, 123, 125, 127-129, 132, 133, and 135-142. In some embodiments, the pharmaceutical composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof. In some embodiments, the method further comprises administering a chemotherapeutic agent, a checkpoint inhibitor, a targeted therapy, radiation therapy, another immunotherapy, or combination thereof to the identified subject. In some embodiments, the method further comprises prior to the administering step, (i) assaying a tumor sample from the subject to determine that the three or more peptides of the pharmaceutical composition comprise two or more different amino acid sequences each of which is a) a fragment of a cancer-associated antigen expressed by cancer cells of the subject as determined in step (i); and b) a T cell epitope capable of binding to at least three HLA class I molecules of the subject; and (ii) confirming the subject as likely to have a clinical response to the method of treatment.

Disclosed herein in certain embodiments are kits comprising: a first pharmaceutical composition comprising one or more peptides, wherein each peptide comprises a different one of the amino acid sequence of any one of SEQ ID NOs: 112 to 142; and a second different pharmaceutical composition comprising one or more peptides, wherein each peptide comprises a different one of the amino acid sequence of any one of SEQ ID NOs: 112 to 142.

Disclosed herein in certain embodiments are pharmaceutical compositions comprising: a nucleic acid molecule expressing two or more polypeptides, each polypeptide comprising a fragment of up to 50 consecutive amino acids of an antigen selected from TSP50, EpCAM, SPAG9, CAGE1, FBXO39, SURVIVIN, MAGE-A8, and MAGE-A6, wherein each fragment comprises a different amino acid sequence selected from any one of SEQ ID NOs: 21-40 and 234 to 250. In some embodiments, the polypeptides do not comprise amino acid sequences that are adjacent to each other in a corresponding antigen.

Disclosed herein in certain embodiments are pharmaceutical compositions comprising one or more peptides, wherein each peptide comprises a different one of the amino acid sequence of any one of SEQ ID NOs: 81 to 111 and 435 to 449. In some embodiments, the composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides. In some embodiments, the composition comprises 9 peptides, wherein each peptide comprises a different one of the amino acid sequences of SEQ ID NOs: 92, 93, 98, 99-101, and 103-105. In some embodiments, the composition further comprises at least one additional peptide comprising a fragment of an antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1. In some embodiments, the fragment of an antigen comprises an amino acid sequence selected from any one of SEQ ID NOs: 1 to 20, 24 and 172 to 194. In some embodiments, the fragment of an antigen comprises an amino acid sequence selected from any one of SEQ ID NOs:41-60 and 195-233. In some embodiments, the composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

Disclosed herein in certain embodiments are pharmaceutical compositions comprising one or more nucleic acid molecules encoding one or more peptides, wherein each peptide comprises a different one of the amino acid sequence of any one of SEQ ID NOs: 81 to 111 and 435 to 449 In some embodiments, the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides. In some embodiments, the one or more nucleic acid molecules encode 9 peptides, wherein each peptide comprises a different one of the amino acid sequences of SEQ ID NOs: 92, 93, 98, 99-101, and 103-105. In some embodiments, the one or more nucleic acid molecules encode at least one additional peptide comprising a fragment of an antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1. In some embodiments, the fragment of an antigen comprises an amino acid sequence selected from any one of SEQ ID NOs: 1 to 20, 24 and 172 to 194. In some embodiments, the fragment of an antigen comprises an amino acid sequence selected from any one of SEQ ID NOs:41-60 and 195-233. In some embodiments, the composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

Disclosed herein in certain embodiments are methods of identifying and treating a human subject having cancer who will likely have a clinical response to administration of a pharmaceutical composition of the disclosure, the method comprising (i) assaying a biological sample of the subject to determine HLA genotype of the subject; (ii) determining that the pharmaceutical composition comprises two or more sequences that are a T cell epitope capable of binding to at least three HLA class I molecules of the subject; (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and (iv) administering the composition of the disclosure to the identified subject. In some embodiments, the subject has breast cancer. In some embodiments, the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, or 12 or more peptides. In some embodiments, the pharmaceutical composition comprises 9 peptides, wherein each peptide comprises a different one of the amino acid sequences of SEQ ID NOs: 92, 93, 98, 99-101, and 103-105. In some embodiments, the pharmaceutical composition further comprises comprising at least one additional peptide comprising a fragment of an antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1. In some embodiments, the fragment of an antigen comprises an amino acid sequence selected from any one of SEQ ID NOs: 1 to 20, 24 and 172 to 194. In some embodiments, the fragment of an antigen comprises an amino acid sequence selected from any one of SEQ ID NOs:41-60 and 195-233. In some embodiments, the pharmaceutical composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynebacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof. In some embodiments, the method further comprises administering a chemotherapeutic agent, a checkpoint inhibitor, a targeted therapy, radiation therapy, another immunotherapy, or combination thereof to the identified subject. In some embodiments, the method further comprises prior to the administering step, (i) assaying a tumor sample from the subject to determine that the three or more peptides of the pharmaceutical composition comprise two or more different amino acid sequences each of which is a) a fragment of a cancer-associated antigen expressed by cancer cells of the subject as determined in step (i); and b) a T cell epitope capable of binding to at least three HLA class I molecules of the subject; and confirming the subject as likely to have a clinical response to the method of treatment.

Disclosed herein in certain embodiments are methods of identifying and treating a human subject having cancer who will likely have an immune response to administration of a pharmaceutical composition of the disclosure, the method comprising (i) assaying a biological sample of the subject to determine HLA genotype of the subject; (ii) determining that the pharmaceutical composition comprises one or more sequences that are a T cell epitope capable of binding to at least three HLA class I molecules of the subject; and (iii) administering the composition of the disclosure to the identified subject.

Disclosed herein in certain embodiments are kits comprising: a first pharmaceutical composition comprising one or more peptides, wherein each peptide comprises a different one of the amino acid sequence of any one of SEQ ID NOs: 81-111 and 435 to 449; and a second different pharmaceutical composition comprising one or more peptides, wherein each peptide comprises a different one of the amino acid sequence of any one of SEQ ID NOs: 81-111 and 435 to 449.

Disclosed herein in certain embodiments are pharmaceutical compositions comprising: a nucleic acid molecule expressing two or more polypeptides, each polypeptide comprising a fragment of up to 50 consecutive amino acids of an antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1, wherein each fragment comprises a different amino acid sequence selected from any one of SEQ ID NOs: 1 to 20, 24, and 172 to 194. In some embodiments, the polypeptides do not comprise amino acid sequences that are adjacent to each other in a corresponding antigen.

Disclosed herein in certain embodiments are pharmaceutical compositions comprising one or more peptides, wherein each peptide comprises a different one of the amino acid sequence of any one of SEQ ID NOs: 332-346. In some embodiments, the composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, 12 or more peptides, 13 or more peptides, 14 or more peptides, or 15 or more peptides. In some embodiments, the composition comprises 15 peptides, wherein each peptide comprises a different one of the amino acid sequences of SEQ ID NOs: 332-346. In some embodiments, the composition further comprises at least one additional peptide comprising a fragment of an antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3. In some embodiments, the fragment comprises an amino acid sequence selected from any one of SEQ ID NOs: 272-301. In some embodiments, the fragment comprises an amino acid sequence selected from any one of SEQ ID NOs:302-331. In some embodiments, the composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynebacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

Disclosed herein in certain embodiments are pharmaceutical compositions comprising one or more nucleic acid molecules encoding one or more peptides, wherein each peptide comprises a different one of the amino acid sequence of any one of SEQ ID NOs: 332-346. In some embodiments, the one or more nucleic acid molecules encode 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, 12 or more peptides, 13 or more peptides, 14 or more peptides, or 15 or more peptides. In some embodiments, the one or more nucleic acid molecules encode 15 peptides, wherein each peptide comprises a different one of the amino acid sequences of SEQ ID NOs: 332-346. In some embodiments, the one or more nucleic acid molecules encode at least one additional peptide comprising a fragment of an antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3. In some embodiments, the fragment comprises an amino acid sequence selected from any one of SEQ ID NOs: 272-301. In some embodiments, the fragment comprises an amino acid sequence selected from any one of SEQ ID NOs:302-331. In some embodiments, the composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof.

Disclosed herein in certain embodiments are methods of identifying and treating a human subject having cancer who will likely have a clinical response to administration of a pharmaceutical composition according of the disclosure, the method comprising (i) assaying a biological sample of the subject to determine HLA genotype of the subject; (ii) determining that the pharmaceutical composition comprises two or more sequences that are a T cell epitope capable of binding to at least three HLA class I molecules of the subject; (iii) determining the probability that a tumor of the subject expresses one or more antigen corresponding to the T cell epitopes identified in step (ii) using population expression data for each antigen, to identify the likelihood of the subject to have a clinical response to administration of the pharmaceutical composition; and (iv) administering the composition of of the disclosure to the identified subject. In some embodiments, the subject has ovarian cancer. In some embodiments, the pharmaceutical composition comprises 2 or more peptides, 3 or more peptides, 4 or more peptides, 5 or more peptides, 6 or more peptides, 7 or more peptides, 8 or more peptides, 9 or more peptides, 10 or more peptides, 11 or more peptides, 12 or more peptides, 13 or more peptides, 14 or more peptides, or 15 or more peptides. In some embodiments, the pharmaceutical composition comprises 15 peptides, wherein each peptide comprises a different one of the amino acid sequences of SEQ ID NOs: 332-346. In some embodiments, the pharmaceutical composition further comprises comprising at least one additional peptide comprising a fragment of an antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3. In some embodiments, the fragment comprises an amino acid sequence selected from any one of SEQ ID NOs: 272-301 In some embodiments, the fragment comprises an amino acid sequence selected from any one of SEQ ID NOs:302-331. In some embodiments, the pharmaceutical composition further comprises a pharmaceutically acceptable adjuvant, diluent, carrier, preservative, or combination thereof. In some embodiments, the adjuvant is selected from the group consisting of Montanide ISA-51, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete), Freunds adjuvant (incomplete), mineral gels, aluminum hydroxide (Alum), lysolecithin, pluronic polyols, polyanions, oil emulsions, dinitrophenol, diphtheria toxin (DT), and combinations thereof. In some embodiments, the method further comprises administering a chemotherapeutic agent, a checkpoint inhibitor, a targeted therapy, radiation therapy, another immunotherapy, or combination thereof to the identified subject. In some embodiments, the method further comprises prior to the administering step, (i) assaying a tumor sample from the subject to determine that the three or more peptides of the pharmaceutical composition comprise two or more different amino acid sequences each of which is a) a fragment of a cancer-associated antigen expressed by cancer cells of the subject as determined in step (i); and b) a T cell epitope capable of binding to at least three HLA class I molecules of the subject; and (ii) confirming the subject as likely to have a clinical response to the method of treatment. Disclosed herein in certain embodiments are methods of identifying and treating a human subject having cancer who will likely have an immune response to administration of a pharmaceutical composition of the disclosure, the method comprising (i) assaying a biological sample of the subject to determine HLA genotype of the subject; (ii) determining that the pharmaceutical composition comprises one or more sequences that are a T cell epitope capable of binding to at least three HLA class I molecules of the subject; and (iii) administering the composition of the disclosure to the identified subject.

Disclosed herein in certain embodiments are kits comprising: a first pharmaceutical composition comprising one or more peptides, wherein each peptide comprises a different one of the amino acid sequence of any one of SEQ ID NOs: 332-346; and a second different pharmaceutical composition comprising one or more peptides, wherein each peptide comprises a different one of the amino acid sequence of any one of SEQ ID NOs: 332-346.

Disclosed herein in certain embodiments are pharmaceutical compositions comprising: a nucleic acid molecule expressing two or more polypeptides, each polypeptide comprising a fragment of up to 50 consecutive amino acids of an antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3, wherein each fragment comprises a different amino acid sequence selected from any one of SEQ ID NOs: 272-301. In some embodiments, the polypeptides do not comprise amino acid sequences that are adjacent to each other in a corresponding antigen.

DISCLOSURE

The disclosure will now be described in more detail, by way of example and not limitation, and by reference to the accompanying drawings. Many equivalent modifications and variations will be apparent, to those skilled in the art when given this disclosure. Accordingly, the exemplary embodiments of the disclosure set forth are considered to be illustrative and not limiting. Various changes to the described embodiments may be made without departing from the scope of the disclosure. All documents cited herein, whether supra or infra, are expressly incorporated by reference in their entirety.

The present disclosure includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "a peptide" includes two or more such peptides.

Section headings are used herein for convenience only and are not to be construed as limiting in any way.

DESCRIPTION OF THE FIGURES

FIGS. 3A-B—Distribution of HLA class I PEPI3+ compared to CD8+ T cell responses measured by a state of art assay among peptide pools used in the CD8+ T cell response assays. FIG. 3A: HLA class I restricted PEPI3+s. The 90% Overall Percent of Agreement (OPA) among the T cell responses and PEPI3+ peptides demonstrate the utility of the invented peptides for prediction of vaccine induced T cell response set of individuals. FIG. 3B: Class I HLA restricted epitopes (PEPI1+). The OPA between predicted epitopes and CD8+ T cell responses was 28% (not statistically significant). Darkest grey: True positive (TP), both peptide and T cell responses were detected; Light grey: False negative (FN), only T cell responses were detected; Lightest grey: False positive (FP), only peptide were detected; Dark grey: True negative (TN): neither peptides nor T cell responses were detected.

FIGS. 4A-B—Distribution of HLA class II PEPIs compared to CD4+ T cell responses measured by a state of art assay among peptide pools used in the assays. FIG. 4A: HLA class II restricted PEPI4+s. 67% OPA between PEPI4+ and CD4+ T-cell responses (p=0.002). FIG. 4B: The class II HLA restricted epitopes. OPA between class II HLA restricted epitopes and CD4+ T cell responses was 66% (not statistically significant). Darkest grey: True positive (TP), both peptide and T cell responses were detected; Light grey: False negative (FN), only T cell responses were detected; Lightest grey: False positive (FP), only peptide were detected; Dark grey: True negative (TN): neither peptides nor T cell responses were detected.

FIG. 12A: non-cumulative distribution to calculate the expected value for the number of expressed antigens (AG50). This value shows that probably 6.14 vaccine antigens will be expressed by breast tumor cells. FIG. 12B: cumulative distribution curve of the minimum number of expressed antigens (CTA expression curve). This shows that minimum 4 vaccine antigens will be expressed with 95% probability in breast cancer cell (AG95).

FIG. 13A: non-cumulative distribution of AP where the average number of APs is: AP50=5.30, meaning that in average almost 6 CTAs will have PEPIs in the Model Population. FIG. 13B: cumulative distribution curve of the minimum number of APs in the Model Population (n=433). This shows that at least one vaccine antigen will have PEPIs in 95% of the Model Population (n=433) (AP95=1).

FIG. 14A: non-cumulative distribution of AGP where the expected value for number expressed CTAs represented by PEPI is AGP50=3.37. AGP50 is a measure of the effectiveness of the disclosed breast cancer vaccine in attacking breast tumor in an unselected patient population. AGP50=3.37 means that at least 3 CTAs from the vaccine will probably be expressed by the breast tumor cells and present PEPIs in the Model Population. FIG. 14B: cumulative distribution curve of the minimum number of AGPs in the Model Population (n=433) shows that at least 1 of the vaccine CTAs will present PEPIs in 92% of the population and the remaining 8% of the population will likely have no AGP at all (AGP95=0, AGP92=1).

FIG. 16A: non-cumulative distribution to calculate the expected vale for the number of expressed vaccine antigens in colorectal cancers (AG50). This value shows that probably 4.96 vaccine antigens will be expressed by colorectal tumor cells. FIG. 16B: cumulative distribution curve of the minimum number of expressed antigens (CTA expression curve). This shows that minimum 3 antigens will be expressed with 95% probability in the colorectal cancer cell (AG95).

FIG. 17A: non-cumulative distribution of AP where the average number of APs is: AP50=4.73, meaning that in average 5 CTAs will be represented by PEPIs in the model population FIG. 17B: cumulative distribution curve of the minimum number of APs in the model population (n=433). This shows that 2 or more antigens will be represented by PEPIs in 95% of the model population (n=433) (AP95=2).

FIG. 18A: non-cumulative distribution of AGP where the expected value for number expressed CTAs represented by PEPI is AGP50=2.54. AGP50 is a measure of the effectiveness of the disclosed colorectal cancer vaccine in attacking colorectal tumors in an unselected patient population. AGP50=2.54 means that at least 2-3 CTAs from the vaccine will probably be expressed by the colorectal tumor cells and present PEPIs in the Model Population. FIG. 18B: cumulative distribution curve of the minimum number of AGPs in the Model Population (n=433) shows that at least 1 of the vaccine CTAs will be expressed and also present PEPIs in 93% of the population (AGP93=1).

DESCRIPTION OF THE SEQUENCES

Figure 1:
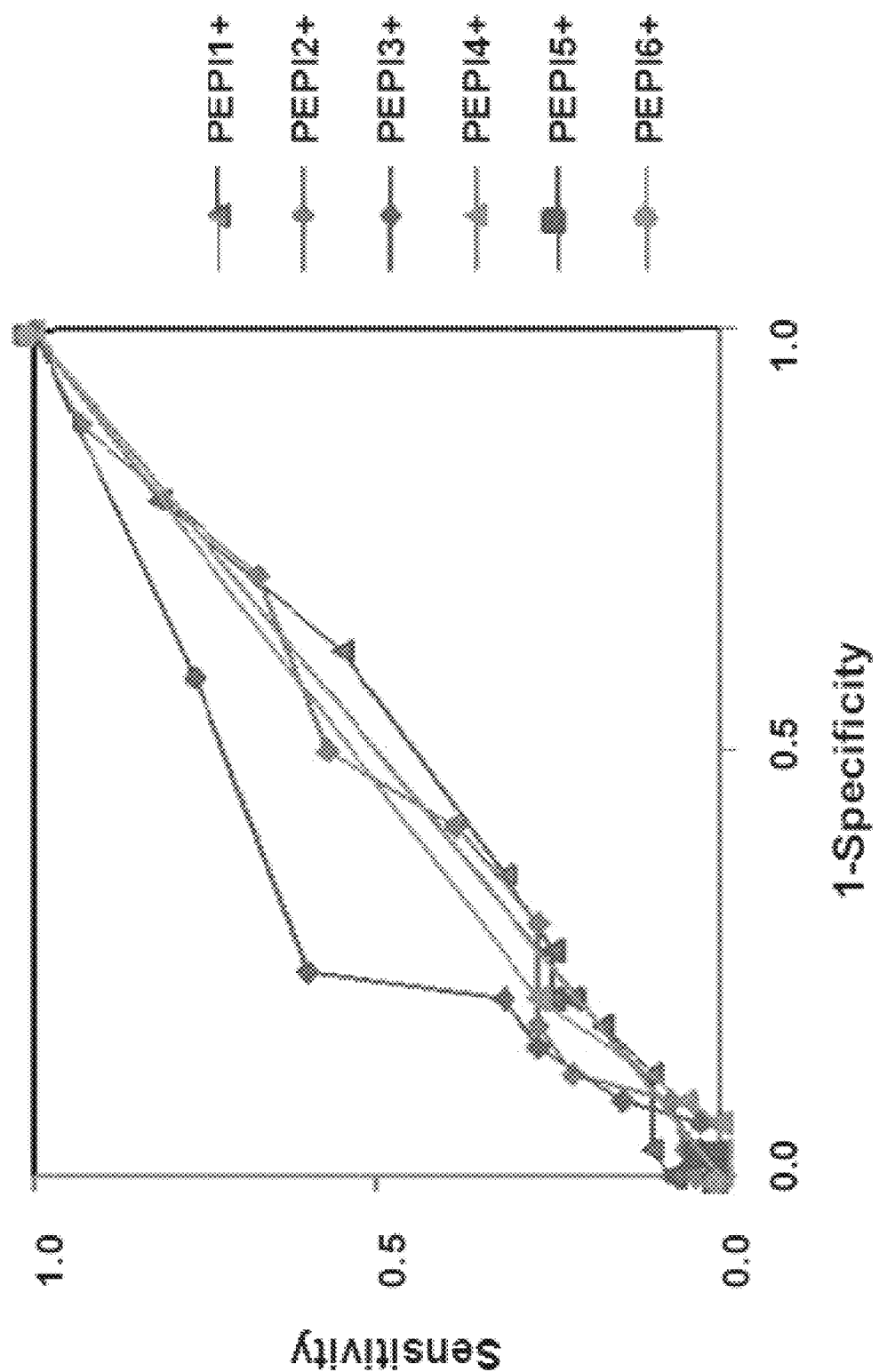
FIG. 1—ROC curve of HLA restricted PEPI biomarkers.

SEQ ID NOs: 1 to 20 set forth 9 mer T cell epitopes described in Table 17.

SEQ ID NOs: 21 to 40 set forth 9 mer T cell epitopes described in Table 20.

SEQ ID NOs 41 to 60 set forth 15 mer T cell epitopes described in Table 17.

SEQ ID NOs 61 to 80 set forth 15 mer T cell epitopes described in Table 20.

SEQ ID NOs: 81 to 111 set forth breast cancer vaccine peptides described in Table 18a.

SEQ ID NOs 112 to 142 set forth the colorectal cancer vaccine peptides described in Table 21a.

SEQ ID NOs 143 to 158 set forth breast cancer, colorectal cancer and/or ovarian cancer associated antigens.

SEQ ID NOs 159 to 171 set forth the additional peptide sequences described in Table 10.

SEQ ID NOs 172 to 194 set forth further 9 mer T cell epitopes described in Table 17.

SEQ ID NOs 195 to 233 set forth further 15 mer T cell epitopes described in Table 17.

SEQ ID NOs 234 to 250 set forth further 9 mer T cell epitopes described in Table 20.

SEQ ID NOs 251 to 271 set forth further 15 mer T cell epitopes described in Table 20.

SEQ ID NOs: 272 to 301 set forth the 9 mer T cell epitopes described in Table 23.

SEQ ID NOs: 302 to 331 set forth the 15 mer T cell epitopes described in Table 23.

SEQ ID NOs: 332 to 346 set forth the ovarian cancer vaccine peptides set forth in Table 24.

SEQ ID NOs: 347 to 361 set forth further breast cancer, colorectal cancer and/or ovarian cancer associated antigens.

SEQ ID NOs: 362 to 374 set forth personalised vaccine peptides designed for patient XYZ described in Table 38.

SEQ ID NOs: 375 to 386 set forth personalised vaccine peptides designed for patient ABC described in Table 41.

SEQ ID NOs 387 to 434 set forth further 9 mer T cell epitopes described in Table 32

SEQ ID NOs: 435 to 449 set forth further breast cancer vaccine peptides described in Table 18a.

DETAILED DESCRIPTION

HLA Genotypes

HLAs are encoded by the most polymorphic genes of the human genome. Each person has a maternal and a paternal allele for the three HLA class I molecules (HLA-A*, HLA-B*, HLA-C*) and four HLA class II molecules (HLA-DP*, HLA-DQ*, HLA-DRB1*, HLA-DRB3*/4*/5*). Practically, each person expresses a different combination of 6 HLA class I and 8 HLA class II molecules that present different epitopes from the same protein antigen. The function of HLA molecules is to regulate T cell responses. However up to date it was unknown how the HLAs of a person regulate T cell activation.

The nomenclature used to designate the amino acid sequence of the HLA molecule is as follows: gene name*allele:protein number, which, for instance, can look like: HLA-A*02:25. In this example, "02" refers to the allele. In most instances, alleles are defined by serotypes—meaning that the proteins of a given allele will not react with each other in serological assays. Protein numbers ("25" in the example above) are assigned consecutively as the protein is discovered. A new protein number is assigned for any protein with a different amino acid sequence (e.g. even a one amino acid change in sequence is considered a different protein number). Further information on the nucleic acid sequence of a given locus may be appended to the HLA nomenclature, but such information is not required for the methods described herein.

The HLA class I genotype or HLA class II genotype of an individual may refer to the actual amino acid sequence of each class I or class II HLA of an individual, or may refer to the nomenclature, as described above, that designates, minimally, the allele and protein number of each HLA gene. An HLA genotype may be determined using any suitable method. For example, the sequence may be determined via sequencing the HLA gene loci using methods and protocols known in the art. Alternatively, the HLA set of an individual may be stored in a database and accessed using methods known in the art.

Some subjects may have two HLA alleles that encode the same HLA molecule (for example, two copies for HLA-A*02:25 in case of homozygosity). The HLA molecules encoded by these alleles bind all of the same T cell epitopes. For the purposes of this disclosure "binding to at least two HLA molecules of the subject" as used herein includes binding to the HLA molecules encoded by two identical HLA alleles in a single subject. In other words, "binding to at least two HLA molecules of the subject" and the like could otherwise be expressed as "binding to the HLA molecules encoded by at least two HLA alleles of the subject".

Polypeptides

The disclosure relates to polypeptides that are derived from CTAs and that are immunogenic for a high proportion of the human population.

As used herein, the term "polypeptide" refers to a full-length protein, a portion of a protein, or a peptide characterized as a string of amino acids. As used herein, the term "peptide" refers to a short polypeptide comprising between 2, or 3, or 4, or 5, or 6, or 7, or 8, or 9, or 10, or 11, or 12, or 13, or 14, or 15 and 10, or 11, or 12, or 13, or 14, or 15, or 20, or 25, or 30, or 35, or 40, or 45, or 50 or 55 or 60 amino acids.

The terms "fragment" or "fragment of a polypeptide" as used herein refer to a string of amino acids or an amino acid sequence typically of reduced length relative to the or a reference polypeptide and comprising, over the common portion, an amino acid sequence identical to the reference polypeptide. Such a fragment according to the disclosure may be, where appropriate, included in a larger polypeptide of which it is a constituent. In some cases the fragment may comprise the full length of the polypeptide, for example where the whole polypeptide, such as a 9 amino acid peptide, is a single T cell epitope. In some cases the fragments referred to herein may be between 2, or 3, or 4, or 5 or 6 or 7 or 8 or 9 and 20, or 25, or 30, or 35, or 40, or 45, or 50 amino acids.

As used herein, the term "epitope" or "T cell epitope" refers to a sequence of contiguous amino acids contained within a protein antigen that possess a binding affinity for (is capable of binding to) one or more HLAs. An epitope is HLA- and antigen-specific (HLA-epitope pairs, predicted with known methods), but not subject specific. An epitope, a T cell epitope, a polypeptide, a fragment of a polypeptide or a composition comprising a polypeptide or a fragment thereof is "immunogenic" for a specific human subject if it is capable of inducing a T cell response (a cytotoxic T cell response or a helper T cell response) in that subject. In some cases the helper T cell response is a Th1-type helper T cell response. In some cases an epitope, a T cell epitope, a polypeptide, a fragment of a polypeptide or a composition comprising a polypeptide or a fragment thereof is "immunogenic" for a specific human subject if it is more likely to induce a T cell response or immune response in the subject than a different T cell epitope (or in some cases two different T cell epitopes each) capable of binding to just one HLA molecule of the subject.

The terms "T cell response" and "immune response" are used herein interchangeably, and refer to the activation of T cells and/or the induction of one or more effector functions following recognition of one or more HLA-epitope binding pairs. In some cases an "immune response" includes an antibody response, because HLA class II molecules stimulate helper responses that are involved in inducing both long lasting CTL responses and antibody responses. Effector functions include cytotoxicity, cytokine production and proliferation. According to the present disclosure, an epitope, a T cell epitope, or a fragment of a polypeptide is immunogenic for a specific subject if it is capable of binding to at least two, or in some cases at least three, class I or at least two, or in some cases at least three or at least four class II HLAs of the subject.

For the purposes of this disclosure we have coined the term "personal epitope", or "PEPI" to distinguish subject specific epitopes from HLA specific epitopes. A "PEPI" is a fragment of a polypeptide consisting of a sequence of contiguous amino acids of the polypeptide that is a T cell epitope capable of binding to one or more HLA class I molecules of a specific human subject. In other cases a "PEPI" is a fragment of a polypeptide consisting of a sequence of contiguous amino acids of the polypeptide that is a T cell epitope capable of binding to one or more HLA class II molecules of a specific human subject. In other words a "PEPI" is a T cell epitope that is recognised by the HLA set of a specific individual, and is consequently specific to the subject in addition to the HLA and the antigen. In contrast to an "epitope", which is specific only to HLA and the antigen, PEPIs are specific to an individual because different individuals have different HLA molecules which each bind to different T cell epitopes. This subject specificity of the PEPIs allows to make personalized cancer vaccines.

"PEPI1" as used herein refers to a peptide, or a fragment of a polypeptide, that can bind to one HLA class I molecule (or, in specific contexts, HLA class II molecule) of an individual. "PEPI1+" refers to a peptide, or a fragment of a polypeptide, that can bind to one or more HLA class I molecule of an individual.

"PEPI2" refers to a peptide, or a fragment of a polypeptide, that can bind to two HLA class I (or II) molecules of an individual. "PEPI2+" refers to a peptide, or a fragment of a polypeptide, that can bind to two or more HLA class I (or II) molecules of an individual, i.e. a fragment identified according to a method of the disclosure.

"PEPI3" refers to a peptide, or a fragment of a polypeptide, that can bind to three HLA class I (or II) molecules of an individual. "PEPI3+" refers to a peptide, or a fragment of a polypeptide, that can bind to three or more HLA class I (or II) molecules of an individual.

"PEPI4" refers to a peptide, or a fragment of a polypeptide, that can bind to four HLA class I (or II) molecules of an individual. "PEPI4+" refers to a peptide, or a fragment of a polypeptide, that can bind to four or more HLA class I (or II) molecules of an individual.

"PEPI5" refers to a peptide, or a fragment of a polypeptide, that can bind to five HLA class I (or II) molecules of an individual. "PEPI5+" refers to a peptide, or a fragment of a polypeptide, that can bind to five or more HLA class I (or II) molecules of an individual.

"PEPI6" refers to a peptide, or a fragment of a polypeptide, that can bind to all six HLA class I (or six HLA class II) molecules of an individual.

Generally speaking, epitopes presented by HLA class I molecules are about nine amino acids long and epitopes presented by HLA class II molecules are about fifteen amino acids long. For the purposes of this disclosure, however, an epitope may be more or less than nine (for HLA Class I) or fifteen (for HLA Class II) amino acids long, as long as the epitope is capable of binding HLA. For example, an epitope that is capable of binding to class I HLA may be between 7, or 8 or 9 and 9 or 10 or 11 amino acids long. An epitope that is capable of binding to a class II HLA may be between 13, or 14 or 15 and 15 or 16 or 17 amino acids long.

A given HLA of a subject will only present to T cells a limited number of different peptides produced by the processing of protein antigens in an APC. As used herein, "display" or "present", when used in relation to HLA, references the binding between a peptide (epitope) and an HLA. In this regard, to "display" or "present" a peptide is synonymous with "binding" a peptide.

Using techniques known in the art, it is possible to determine the epitopes that will bind to a known HLA. Any suitable method may be used, provided that the same method is used to determine multiple HLA-epitope binding pairs that are directly compared. For example, biochemical analysis may be used. It is also possible to use lists of epitopes known to be bound by a given HLA. It is also possible to use predictive or modelling software to determine which epitopes may be bound by a given HLA. Examples are provided in Table 1. In some cases a T cell epitope is capable of binding to a given HLA if it has an IC50 or predicted IC50 of less than 5000 nM, less than 2000 nM, less than 1000 nM, or less than 500 nM.

TABLE 1

Example software for determining epitope-HLA binding

| EPITOPE PREDICTION TOOLS | WEB ADDRESS |
| --- | --- |
| BIMAS, NIH | www-bimas.cit.nih.gov/molbio/hla_bind/ |
| PPAPROC, Tubingen Univ. | |
| MHCPred, Edward Jenner Inst. of Vaccine Res. | |
| EpiJen, Edward Jenner Inst. of Vaccine Res. | www.ddg-pharmfac.net/epijen/EpiJen/EpiJen.htm |
| NetMHC, Center for Biological Sequence Analysis | www.cbs.dtu.dk/services/NetMHC/ |
| SVMHC, Tubingen Univ. | abi.inf.uni-tuebingen.de/Services/SVMHC/ |
| SYFPEITHI, Biomedical Informatics, Heidelberg | www.syfpeithi.de/bin/MHCServer.dll/EpitopePrediction.htm |
| ETK EPITOOLKIT, Tubingen Univ. | etk.informatik.uni-tuebingen.de/epipred/ |
| PREDEP, Hebrew Univ. Jerusalem | margalit.huji.ac.il/Teppred/mhc-bind/index.html |
| RANKPEP, MIF Bioinformatics | bio.dfci.harvard.edu/RANKPEP/ |
| IEDB, Immune Epitope Database | tools.immuneepitope.org/main/html/tcell_tools.html |

| EPITOPE DATABASES | WEB ADDRESS |
| --- | --- |
| MHCBN, Institute of Microbial Technology, Chandigarh, INDIA | www.imtech.res.in/raghava/mhcbn/ |
| SYFPEITHI, Biomedical Informatics, Heidelberg | www.syfpeithi.de/ |
| AntiJen, Edward Jenner Inst. of Vaccine Res. | www.ddg-pharmfac.net/antijen/AntiJen/antijenhomepage.htm |
| EPIMHC database of MHC ligands, MIF Bioinformatics | immunax.dfci.harvard.edu/epimhc/ |
| IEDB, Immune Epitope Database | www.iedb.ord |

In some embodiments the peptides of the disclosure may comprise or consist of one or more fragments of one or more CTAs. CTAs are not typically expressed beyond embryonic development in healthy cells. In healthy adults, CTA expression is limited to male germ cells that do not express HLAs and cannot present antigens to T cells. Therefore, CTAs are considered expressional neoantigens when expressed in cancer cells.

CTAs are a good choice for cancer vaccine targets because their expression is (i) specific for tumor cells, (ii) more frequent in metastases than in primary tumors and (iii) conserved among metastases of the same patient (Gajewski ed. Targeted Therapeutics in Melanoma. Springer New York. 2012).

The peptides of the disclosure may comprise or consist of one or more fragments of one or more breast cancer associated antigens selected from SPAG9 (SEQ ID NO: 143), AKAP-4 (SEQ ID NO: 144), BORIS (SEQ ID NO: 145), NY-SAR-35 (SEQ ID NO: 146), NY-BR-1 (SEQ ID NO: 147), SURVIVIN (SEQ ID NO: 148), MAGE-A11 (SEQ ID NO: 149), PRAME (SEQ ID NO: 150), MAGE-A9 (SEQ ID NO: 151), HOM-TES-85 (SEQ ID NO: 152), PIWIL-2 (SEQ ID NO: 349), EpCAM (SEQ ID NO: 154), HIWI (SEQ ID NO: 350), PLU-1 (SEQ ID NO: 351), TSGA10 (SEQ ID NO: 351), ODF-4 (SEQ ID NO: 352), SP17 (SEQ ID NO:354), RHOXF-2 (SEQ ID NO: 355), and NY-ESO-1 (SEQ ID NO: 356); one or more ovarian cancer-associated antigens selected from PIWIL-4 (SEQ ID NO: 357), WT1 (SEQ ID NO: 358), EpCAM (SEQ ID NO: 154), BORIS (SEQ ID NO: 145), AKAP-4 (SEQ ID NO: 144), OY-TES-1 (SEQ ID NO: 359), SP17 (SEQ ID NO: 354), PIWIL-2 (SEQ ID NO: 349), PIWIL-3 (SEQ ID NO: 360), SPAG9 (SEQ ID NO: 143), PRAME (SEQ ID NO: 150), HIWI (SEQ ID NO: 350), SURVIVIN (SEQ ID NO: 148), and AKAP-3 (SEQ ID NO: 361); and/or one or more colorectal cancer-associated antigens selected from TSP50 (SEQ ID NO: 153), EpCAM (SEQ ID NO: 154), SPAG9 (SEQ ID NO: 143), CAGE1 (SEQ ID NO: 155), FBXO39 (SEQ ID NO: 156), SURVIVIN (SEQ ID NO: 148), MAGE-A8 (SEQ ID NO 157), MAGE-A6 (SEQ ID NO: 158), LEMD1 (SEQ ID NO:348) and MAGE-A3 (SEQ ID NO: 347). In some cases the peptide comprises or consists of one or more amino acid sequences selected from SEQ ID NOs: 41-80, or from SEQ ID NOs: 41-80, 195-233, 251-271 and 302-331 that are optimised for T cell activation/binding to all HLA types across the population.

In some cases the amino acid sequence is flanked at the N and/or C terminus by additional amino acids that are not part of the sequence of the target polypeptide antigen, in other words that are not the same sequence of consecutive amino acids found adjacent to the selected fragments in the target polypeptide antigen. In some cases the sequence is flanked by up to 41 or 35 or 30 or 25 or 20 or 15 or 10, or 9 or 8 or 7 or 6 or 5 or 4 or 3 or 2 or 1 additional amino acid at the N and/or C terminus or between target polypeptide fragments. In other cases each polypeptide either consists of a fragment of a target polypeptide antigen, or consists of two or more such fragments arranged end to end (arranged sequentially in the peptide end to end) or overlapping in a single peptide (where two or more of the fragments comprise partially overlapping sequences, for example where two PEPIs in the same polypeptide are within 50 amino acids of each other).

When fragments of different polypeptides or from different regions of the same polypeptide are joined together in an engineered peptide there is the potential for neoepitopes to be generated around the join or junction. Such neoepitopes encompass at least one amino acid from each fragment on either side of the join or junction, and may be referred to herein as junctional amino acid sequences. The neoepitopes may induce undesired T cell responses against healthy cells (autoimmunity). The polypeptides may be designed, or the polypeptides may be screened, to avoid, eliminate or minimise neoepitopes that correspond to a fragment of a protein expressed in normal healthy human cells and/or neoepitopes that are capable of binding to at least two, or in some cases at least three, or at least four HLA class I molecules of the subject, or in some cases at least two, or at least three or four or five HLA class II molecules of the subject. In some cases the peptide is designed, or the polypeptide screened, to eliminate polypeptides having a junctional neoepitope that is capable of binding in more than a threshold percentage of human subjects in an intent-to-treat population, to at least two HLA class I molecules expressed by individual subjects of the population. In some cases the threshold is 20%, or 15%, or 10%, or 5%, or 2%, or 1%, or 0.5% of said population. Alignment may be determined using known methods such as BLAST algorithms. Software for performing BLAST analyses is publicly available through the National Center for Biotechnology Information (www.ncbi.nlm.nih.gov/).

The presence in a vaccine or immunotherapy composition of at least two polypeptide fragments (epitopes) that can bind to at least three HLA class I of an individual (≥2 PEPI3+) is predictive for a clinical response. In other words, if ≥2 PEPI3+ can be identified within the active ingredient polypeptide(s) of a vaccine or immunotherapy composition, then an individual is a likely clinical responder. The at least two multiple HLA-binding PEPIs of the composition polypeptides may both target a single antigen (e.g a polypeptide vaccine comprising two multiple HLA-binding PEPIs derived from a single tumor associated antigen targeted by the vaccine) or may target different antigens (e.g. a polypeptide vaccine comprising one multiple HLA-binding PEPI derived from one tumor associated antigen and a second multiple HLA-binding PEPI derived from a different tumor associated antigen).

Without wishing to be bound by theory, the inventors believe that one reason for the increased likelihood of deriving clinical benefit from a vaccine/immunotherapy comprising at least two multiple-HLA binding PEPIs, is that diseased cell populations, such as cancer or tumor cells or cells infected by viruses or pathogens such as HIV, are often heterogenous both within and between effected subjects. A specific cancer patient, for example, may or may not express or overexpress a particular cancer associated target polypeptide antigen of a vaccine, or their cancer may comprise heterogeneous cell populations, some of which (over-)express the antigen and some of which do not. In addition, the likelihood of developing resistance is decreased when more multiple HLA-binding PEPIs are included or targeted by a vaccine/immunotherapy because a patient is less likely to develop resistance to the composition through mutation of the target PEPI(s).

Currently most vaccines and immunotherapy compositions target only a single polypeptide antigen. However according to the present disclosure it is in some cases beneficial to provide a pharmaceutical composition that targets two or more different polypeptide antigens. For example, most cancers or tumors are heterogeneous, meaning that different cancer or tumor cells of a subject (over-) express different antigens. The tumour cells of different cancer patients also express different combinations of tumour-associated antigens. The anti-cancer immunogenic compositions that are most likely to be effective are those that target multiple antigens expressed by the tumor, and therefore more cancer or tumor cells, in an individual human subject or in a population.

The beneficial effect of combining multiple bestEPIs in a single treatment (administration of one or more pharmaceutical compositions that together comprise multiple PEPIs), can be illustrated by the personalised vaccine polypeptides described in Examples 15 and 16 below. Exemplary CTA expression probabilities in ovarian cancer are as follows: BAGE: 30%; MAGE A9: 37%; MAGE A4: 34%; MAGE A10: 52%. If patient XYZ were treated with a vaccine comprising PEPIs in only BAGE and MAGE A9, then the probability of having a mAGP (multiple expressed antigens with PEPI) would be 11%. If patent XYZ were treated with a vaccine comprising only PEPIs for the MAGE A4 and MAGE A10 CTAs, then the probability of having a multi AGP would be 19%. However if a vaccine contained all 4 of these CTAs (BAGE, MAGE A9, MAGE A4 and MAGE A10), then the probability of having a mAGP would be 50%. In other words the effect would be greater than the combined probabilities of mAGP for both two-PEPI treatments (probability mAGP for BAGE/MAGE+ probability mAGP for MAGE A4 and MAGE A10). Patient XYZ's PIT vaccine described in Example 21 contains a further 9 PEPIs, and thus, the probability of having a mAGP is over 99.95%.

Likewise exemplary CTA expression probabilities in breast cancer are as follows: MAGE C2: 21%; MAGE A1: 37%; SPC1: 38%; MAGE A9: 44%. Treatment of patient ABC with a vaccine comprising PEPIs in only MAGE C2: 21% and MAGE A1 has a mAGP probability of 7%. Treatment of patient ABC with a vaccine comprising PEPIs in only SPC1: 38%; MAGE A9 has a mAGP probability of 11%. Treatment of patient ABC with a vaccine comprising PEPIs in MAGE C2: 21%; MAGE A1: 37%; SPC1: 38%; MAGE A9 has a mAGP probability of 44% (44>7+11). Patient ABC's PIT vaccine described in Example 22 contains a further 8 PEPIs, and thus, the probability of having a mAGP is over 99.93%.

Accordingly in some cases, the polypeptide or panel of polypeptides of the disclosure or an active ingredient polypeptide of a pharmaceutical composition or kit of the disclosure may comprise or consist of any combination of at least 1, 2, 3, 4, 5, 6, 7, 8, 9, 10, 11, 12, 13, 14, 15, 16, 17, 18, 19, 20, 21, 22, 23, 24 or 25 fragments of at least 1, 2, 3, 4, 5, 6, 7, 8, 9, 10, 11, 12, 13, 14, 15, 16, 17, 18, 19, 20, 21, 22, 23, 24 or 25 one or more of the cancer associated antigens, or CTAs, such as the CTA discussed above. Each fragment comprises or consists of a different target epitope having an amino acid sequence selected from SEQ ID NOs: 1-40; or selected from SEQ ID NOs: 1 to 20; or selected from SEQ ID NOs: 21 to 40; or selected from SEQ ID NOs: 1-20, 24 and 172-194; or selected from SEQ ID NOs: 21-40 and 234-250; or selected from SEQ ID NOs: 272-301; or selected from SEQ ID NOs: 1-40, 172-194 and 234-250; or selected from SEQ ID NOs: 21-40, 234-250 and 272-301; or selected from SEQ ID NOs: 1-20, 24, 172-194 and 272-301; or selected from SEQ ID NOs: 1-40, 172-194, 234-250 and 272-301; or selected from SEQ ID NOs: 41-60, 64 and 195-233; or selected from SEQ ID NOs: 61-80 and 251-271; or selected from SEQ ID NOs: 302-331; or selected from SEQ ID NOs: 41-80, 195-233 and 251-271; or selected from SEQ ID NOs: 61-80, 251-271 and 302 to 331; or selected from SEQ ID NOs: 41-60, 64, 191-233 and 302 to 331; or selected from SEQ ID NOs: 41-80, 195-233, 251-271 and 332-346; or selected from SEQ ID NOs: 1-20, 24, 41-60, 64, 172-194 and 195-233; or selected from SEQ ID NOs: 21-40, 61-80, 234-250 and 251-271; or selected from SEQ ID NOs: 271-331; or selected from SEQ ID NOs: 1-80, 172-194, 195-233, 234-250 and 251-271; or selected from SEQ ID NOs: 21-40, 61-80, 234-250, 251-271, 272-301 and 302-331; or selected from SEQ ID NOs: 1-80, 172-233, 234-271 and 272-331; or selected from SEQ ID NOs: 81-111 and 435-449; or selected from SEQ ID NOs: 112-142; or selected from SEQ ID NOs: 332-346; or selected from SEQ ID NOs: 81-142; or selected from SEQ ID NOs: 112-142 and 332-346; or selected from SEQ ID NOs: 81-111, 435-449 and 332-346; or selected from SEQ ID NOs: 81-142 and 332-346; or selected from SEQ ID NOs: 41-60, 64, 81-111, 435-449 and 195-233; or selected from SEQ ID NOs: 61-80, 112-142 and 251-271; or selected from SEQ ID NOs: 302-346; or selected from SEQ ID NOs: 41-142, 195-233 and 251-271; or selected from SEQ ID NOs: 61-80, 112-142, 251-271 and 302-346; or selected from SEQ ID NOs: 41-60, 64, 81-111, 435-449, 195-233 and 302-346; or selected from SEQ ID NOs: 41-142, 195-233, 251-271 and 302-346; or selected from SEQ ID NOs: 1-20, 24, 41-60, 64, 81-111, 435-449 and 172-233; or selected from SEQ ID NOs: 21-40, 61-80, 112-142, or 234-271; or selected from SEQ ID NOs: 272-346; or selected from SEQ ID NOs: 1-142 and 172-271; or selected from SEQ ID NOs: 21-40, 61-80, 112-142 and 234-346; or selected from SEQ ID NOs: 1-20, 24, 41-60, 64, 81-111, 435-449, 172-233 and 272 to 346; or selected from SEQ ID NOs: 1-142 and 172-346; or selected from SEQ ID NOs: 1 to 2, or to 3, or 4, or 5, or 6, or 7, or 8, or 9, or 10, or 11, or 12, or 13, or 14, or 15, or 16, or 17, or 18, or 19, or SEQ ID NOs: 20 to 21, or to 22, or 23, or 24, or 25, or 26, or 27, or 28, or 29, or 30, or 31, or 32, or 33, or 34, or 35, or 36, or 37, or 38, or 39; or a different amino acid sequences selected from SEQ ID NOs: 41 to 80, or SEQ ID NOs: 41 to 60, or SEQ ID NOs: 61-80; or SEQ ID NOs: 41 to 42, or to 43, or to 44, or to 45, or to 46, or to 47, or to 48, or to 49, or 50, or 51, or 52, or 53, or 54, or 55, or 56, or 57, or 58, or 59, SEQ ID NOs: 60 to 61, or to 62, or to 63, or to 64, or to 65, or to 66, or to 67, or to 68, or to 69, or to 70, or to 71, or to 72, or to 73, or to 74, or to 75, or to 76, or to 77, or to 78, or to 79; a different amino acid sequences selected from SEQ ID NOs: 81 to 142; or selected from SEQ ID NOs: 81 to 82, 83, 84, 85, 86, 87, 88, 89, 90, 91, 92, 93, 94, 95, 96, 97, 98, 99, 100, 101, 102, 103, 105, 106, 107, 108, 109, 110, or 111; or selected from SEQ ID NOs: 81 to 105; or selected from SEQ ID NOs: 99, 100, 92, 93, 101, 103, 104, 105 and 98; or selected from SEQ ID NOs: 112 to 142; or selected from SEQ ID NOs: 112 to 113, 114, 115, 116, 117, 118, 119, 120, 121, 123, 124, 125, 126, 127, 128, 129, 130, 131, 132, 133, 134, 135, 136, 137, 138, 139, 140, 141 or 142; or selected from SEQ ID NOs: 112 to 134; or selected from SEQ ID NOs: 121, 124, 126, 127, 130, 131, 132, 133 and 134; or selected from SEQ ID NOs: 1 to 2, or to 3, or 4, or 5, or 6, or 7, or 8, or 9, or 10, or 11, or 12, or 13, or 14, or 15, or 16, or 17, or 18, or 19, or SEQ ID NOs: 20 to 21, or to 22, or 23, or 24, or 25, or 26, or 27, or 28, or 29, or 30, or 31, or 32, or 33, or 34, or 35, or 36, or 37, or 38, or 39; or a different amino acid sequences selected from SEQ ID NOs: 41 to 80, or SEQ ID NOs: 41 to 60, or SEQ ID NOs: 61-80; or SEQ ID NOs: 41 to 42, or to 43, or to 44, or to 45, or to 46, or to 47, or to 48, or to 49, or 50, or 51, or 52, or 53, or 54, or 55, or 56, or 57, or 58, or 59, SEQ ID NOs: 60 to 61, or to 62, or to 63, or to 64, or to 65, or to 66, or to 67, or to 68, or to 69, or to 70, or to 71, or to 72, or to 73, or to 74, or to 75, or to 76, or to 77, or to 78, or to 79; a different amino acid sequences selected from SEQ ID NOs: 81 to 142; or selected from SEQ ID NOs: 81 to 82, 83, 84, 85, 86, 87, 88, 89, 90, 91, 92, 93, 94, 95, 96, 97, 98, 99, 100, 101, 102, 103, 105, 106, 107, 108, 109, 110, or 111; or selected from SEQ ID NOs: 81 to 105; or selected from SEQ ID NOs: 99, 100, 92, 93, 101, 103, 104, 105 and 98; or selected from SEQ ID NOs: 112 to 142; or selected from SEQ ID NOs: 112 to 113, 114, 115, 116, 117, 118, 119, 120, 121, 123, 124, 125, 126, 127, 128, 129, 130, 131, 132, 133, 134, 135, 136, 137, 138, 139, 140, 141 or 142; or selected from SEQ ID NOs: 112 to 134; or selected from SEQ ID NOs: 121, 124, 126, 127, 130, 131, 132, 133 and 134; or selected from SEQ ID Nos: 130, 121, 131, 124, 134, 126; or selected from SEQ ID NO: 435-449; or selected from any of these groups of sequences excluding SEQ ID NOs: 12, 32, 19 and/or 39, and/or SEQ ID NOs: 21, 41, 23 and/or 43 and/or SEQ ID NOs: 172, 177, 195 and/or 203, and/or SEQ ID NOs: 1, 41 and/or 197, and/or SEQ ID NOs: 4, 44 and/or 201, and/or SEQ ID NOs: 1, 4, 44, 197 and/or 201, and/or SEQ ID NOs: 1, 41, 197, 184 and/or 212, and/or SEQ ID NOs: 3, 43 and/or 200, and/or SEQ ID NOs: 3, 43, 200, 7 and/or 47, and/or SEQ ID NOs: 10, 50 and/or 220, and/or SEQ ID NOs: 24, 64 and/or 202, and/or SEQ ID NOs: 6, 46 and/or 209, and/or SEQ ID NOs: 182, 210, 185 and/or 213, and/or SEQ ID NOs: 14, 54, 225 and 226, and/or SEQ ID NOs: 190, 218, 11, 51 and/or 219, and/or SEQ ID NOs: 12, 224 and/or 52, and/or SEQ ID NOs: 192, 227 and/or 228, and/or SEQ ID NOs: 17, 229, 230 and/or 57, and/or SEQ ID NOs: 21, 252, 61 and/or 253, and/or SEQ ID NOs: 23, 63 and/or 256, and/or SEQ ID NOs: 21, 252, 61, 253, 23, 63 and/or 256, and/or SEQ ID NOs: 237 and/or 238, and/or SEQ ID NOs: 26 and/or 240, and/or SEQ ID NOs: 242, 244, 263 and/or 265, and/or SEQ ID NOs: 29, 69 and/or 259, and/or SEQ ID NOs: 24, 64 and/or 255, and/or SEQ ID NOs: 236, 257 and/or 258, and/or SEQ ID NOs: 27, 67, 241 and/or 262, and/or SEQ ID NOs: 252, 249 and/or 264, and/or SEQ ID NOs: 35, 250 and/or 75, and/or SEQ ID NOs: 252, 249, 264, 35, 250 and/or 75, and/or SEQ ID NOs: 36, 266 and/or 76, and/or SEQ ID NOs: 36, 266, 76, 39 and/or 79, and/or SEQ ID NOs: 38, 268 and/or 78, and/or SEQ ID NOs: 38, 268, 78, 246 and/or 270, and/or SEQ ID NOs: 245, 269, and/or 248, and/or SEQ ID NOs: 245, 269, 248, 40 and/or 80, and/or SEQ ID NOs: 272, 302, 281 and/or 311, and/or SEQ ID NOs: 276, 306, 300 and/or 330, and/or SEQ ID NOs: 276, 306, 289 and/or 319, and/or SEQ ID NOs: 277, 307, 283 and/or 313, and/or SEQ ID NOs: 277, 307, 290 and/or 320, and/or SEQ ID NOs: 282, 312, 297 and/or 327, or any other combinations of the sequences disclosed herein that are within 50-60 amino acids of each other in any one or more of the antigens of SEQ ID NOs: 143-158 and 347 to 351; and/or SEQ ID NOs: 18, 19 and/or 20 and/or SEQ ID NOs: 34-40; and/or SEQ ID NOs corresponding to peptides shown in Table 17, 20 and/or 23 having a N %*B % value of less than 12% or 13% or 14% or 17.6% or 17.8% or 18% or 20% or 21% or 22% or 22.2% or 24% or 25% or 27% or 28% or 30% or 31% or 31.5% or 32% or 32.5% or 35%. In some cases the panel of peptides comprises or consists of one or more polypeptides comprising or consisting of the amino acid sequences of SEQ ID NOs: 130, 121, 131, 124, 134, 126 and/or SEQ ID NOs: 435-449.

In some cases the disclosure provides a panel of any two or more of the peptides or groups of peptides described above. For example the panel may comprise 2, 3, 4, 5, 6, 7, 8, 9, 10, 11, 12, 13, 14, 15, 16, 17, 18, 19, 20, 21, 22, 23, 24, 25 or more such peptides. In some cases the panel comprises or consists of peptides comprising or consisting of all or any combination of the amino acid sequences of SEQ ID NOs: 99, 100, 92, 93, 101, 103, 104, 105 and 98; or the amino acid sequences of SEQ ID NOs: 121, 124, 126, 127, 130, 131, 132, 133 and 134. In some cases the panel comprises or consists of peptides comprising or consisting of all or any combination of the amino acid sequences of SEQ ID NOs: SEQ ID NOs: 130, 121, 131, 124, 134, 126 and/or SEQ ID NOs: 435-449.

Pharmaceutical Compositions, Methods of Treatment and Modes of Administration

In some aspects the disclosure relates to a pharmaceutical composition, kit, or panels of polypeptides as described above having one or more polypeptides as active ingredient(s). These may be for use in a method of inducing an immune response, treating, vaccinating or providing immunotherapy to a subject, and the pharmaceutical composition may be a vaccine or immunotherapy composition. Such a treatment comprises administering one or more polypeptides or pharmaceutical compositions that together comprise all of the active ingredient polypeptides of the treatment to the subject. Multiple polypeptides or pharmaceutical compositions may be administered together or sequentially, for example all of the pharmaceutical compositions or polypeptides may be administered to the subject within a period of 1 year, or 6 months, or 3 months, or 60 or 50 or 40 or 30 days.

The term "active ingredient" as used herein refers to a polypeptide that is intended to induce an immune response and may include a polypeptide product of a vaccine or immunotherapy composition that is produced in vivo after administration to a subject. For a DNA or RNA immunotherapy composition, the polypeptide may be produced in vivo by the cells of a subject to whom the composition is administered. For a cell-based composition, the polypeptide may be processed and/or presented by cells of the composition, for example autologous dendritic cells or antigen presenting cells pulsed with the polypeptide or comprising an expression construct encoding the polypeptide. The pharmaceutical composition may comprise a polynucleotide or cell encoding one or more active ingredient polypeptides.

The composition/kit may optionally further comprise at least one pharmaceutically acceptable diluent, carrier, or preservative and/or additional polypeptides that do not comprise any PEPIs. The polypeptides may be engineered or non-naturally occurring. The kit may comprise one or more separate containers each containing one or more of the active ingredient peptides. The composition/kit may be a personalised medicine to prevent, diagnose, alleviate, treat, or cure a disease of an individual, such as a cancer.

The immunogenic or pharmaceutical compositions or kits described herein may comprise, in addition to one or more immunogenic peptides, a pharmaceutically acceptable excipient, carrier, diluent, buffer, stabiliser, preservative, adjuvant or other materials well known to those skilled in the art. Such materials are preferably non-toxic and preferably do not interfere with the pharmaceutical activity of the active ingredient(s). The pharmaceutical carrier or diluent may be, for example, water containing solutions. The precise nature of the carrier or other material may depend on the route of administration, e.g. oral, intravenous, cutaneous or subcutaneous, nasal, intramuscular, intradermal, and intraperitoneal routes.

The pharmaceutical compositions of the disclosure may comprise one or more "pharmaceutically acceptable carriers". These are typically large, slowly metabolized macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The pharmaceutical compositions may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier (Gennaro, 2000, Remington: The Science and Practice of Pharmacy, 20th edition, ISBN:0683306472).

The pharmaceutical compositions of the disclosure may be lyophilized or in aqueous form, i.e. solutions or suspensions. Liquid formulations of this type allow the compositions to be administered direct from their packaged form, without the need for reconstitution in an aqueous medium, and are thus ideal for injection. The pharmaceutical compositions may be presented in vials, or they may be presented in ready filled syringes. The syringes may be supplied with or without needles. A syringe will include a single dose, whereas a vial may include a single dose or multiple doses.

Liquid formulations of the disclosure are also suitable for reconstituting other medicaments from a lyophilized form. Where a pharmaceutical composition is to be used for such extemporaneous reconstitution, the disclosure provides a kit, which may comprise two vials, or may comprise one ready-filled syringe and one vial, with the contents of the syringe being used to reconstitute the contents of the vial prior to injection.

The pharmaceutical compositions of the disclosure may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

The pharmaceutical compositions of the disclosure may comprise detergent e.g. Tween (polysorbate), DMSO (dimethyl sulfoxide), DMF (dimethylformamide). Detergents are generally present at low levels, e.g. <0.01%, but may also be used at higher levels, e.g. 0.01-50%.

The pharmaceutical compositions of the disclosure may include sodium salts (e.g. sodium chloride) and free phosphate ions in solution (e.g. by the use of a phosphate buffer).

In certain embodiments, the pharmaceutical composition may be encapsulated in a suitable vehicle either to deliver the peptides into antigen presenting cells or to increase the stability. As will be appreciated by a skilled artisan, a variety of vehicles are suitable for delivering a pharmaceutical composition of the disclosure. Non-limiting examples of suitable structured fluid delivery systems may include nanoparticles, liposomes, microemulsions, micelles, dendrimers and other phospholipid-containing systems. Methods of incorporating pharmaceutical compositions into delivery vehicles are known in the art.

In order to increase the immunogenicity of the composition, the pharmacological compositions may comprise one or more adjuvants and/or cytokines.

Suitable adjuvants include an aluminum salt such as aluminum hydroxide or aluminum phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants.

In some embodiments, the compositions comprise an adjuvant selected from the group consisting of Montanide ISA-51 (a water-in-oil emulsion, Seppic, Inc., Fairfield, N.J., United States of America), QS-21 (Aquila Biopharmaceuticals, Inc., Lexington, Mass., United States of America), GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, oil emulsions, dinitrophenol, diphtheria toxin (DT).

By way of example, the cytokine may be selected from the group consisting of a transforming growth factor (TGF) such as but not limited to TGF-α and TGF-β insulin-like growth factor-I and/or insulin-like growth factor-II; erythropoietin (EPO); an osteoinductive factor; an interferon such as but not limited to interferon-α, -β, and -γ; a colony stimulating factor (CSF) such as but not limited to macrophage-CSF (M-CSF); granulocyte-macrophage-CSF (GM-CSF); and granulocyte-CSF (G-CSF). In some embodiments, the cytokine is selected from the group consisting of nerve growth factors such as NGF-β; platelet-growth factor; a transforming growth factor (TGF) such as but not limited to TGF-α. and TGF-β; insulin-like growth factor-I and insulin-like growth factor-II; erythropoietin (EPO); an osteoinductive factor; an interferon (IFN) such as but not limited to IFN-α, IFN-β, and IFN-γ; a colony stimulating factor (CSF) such as macrophage-CSF (M-CSF); granulocyte-macrophage-CSF (GM-CSF); and granulocyte-CSF (G-CSF); an interleukin (II) such as but not limited to IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18; LIF; kit-ligand or FLT-3; angiostatin; thrombospondin; endostatin; a tumor necrosis factor (TNF); and LT.

It is expected that an adjuvant or cytokine can be added in an amount of about 0.01 mg to about 10 mg per dose, preferably in an amount of about 0.2 mg to about 5 mg per dose. Alternatively, the adjuvant or cytokine may be at a concentration of about 0.01 to 50%, preferably at a concentration of about 2% to 30%.

In certain aspects, the pharmaceutical compositions of the disclosure are prepared by physically mixing the adjuvant and/or cytokine with the peptides of the disclosure under appropriate sterile conditions in accordance with known techniques to produce the final product.

Examples of suitable compositions of the invented polypeptide fragments and methods of administration are provided in Esseku and Adeyeye (2011) and Van den Mooter G. (2006). Vaccine and immunotherapy composition preparation is generally described in Vaccine Design ("The subunit and adjuvant approach" (eds Powell M. F. & Newman M. J. (1995) Plenum Press New York). Encapsulation within liposomes, which is also envisaged, is described by Fullerton, U.S. Pat. No. 4,235,877.

In some embodiments, the compositions disclosed herein are prepared as a nucleic acid vaccine. In some embodiments, the nucleic acid vaccine is a DNA vaccine. In some embodiments, DNA vaccines, or gene vaccines, comprise a plasmid with a promoter and appropriate transcription and translation control elements and a nucleic acid sequence encoding one or more polypeptides of the disclosure. In some embodiments, the plasmids also include sequences to enhance, for example, expression levels, intracellular targeting, or proteasomal processing. In some embodiments, DNA vaccines comprise a viral vector containing a nucleic acid sequence encoding one or more polypeptides of the disclosure. In additional aspects, the compositions disclosed herein comprise one or more nucleic acids encoding peptides determined to have immunoreactivity with a biological sample. For example, in some embodiments, the compositions comprise one or more nucleotide sequences encoding 1, 2, 3, 4, 5, 6, 7, 8, 9, 10, 11, 12, 13, 14, 15, 16, 17, 18, 19, 20, or more peptides comprising a fragment that is a T cell epitope capable of binding to at least three HLA class I molecules and/or at least three HLA class II molecules of a patient. In some embodiments, the peptides are derived from an antigen that is expressed in cancer. In some embodiments the DNA or gene vaccine also encodes immunomodulatory molecules to manipulate the resulting immune responses, such as enhancing the potency of the vaccine, stimulating the immune system or reducing immunosuppression. Strategies for enhancing the immunogenicity of DNA or gene vaccines include encoding of xenogeneic versions of antigens, fusion of antigens to molecules that activate T cells or trigger associative recognition, priming with DNA vectors followed by boosting with viral vector, and utilization of immunomodulatory molecules. In some embodiments, the DNA vaccine is introduced by a needle, a gene gun, an aerosol injector, with patches, via microneedles, by abrasion, among other forms. In some forms the DNA vaccine is incorporated into liposomes or other forms of nanobodies. In some embodiments, the DNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle. In some embodiments, the DNA vaccines is administered by inhalation or ingestion. In some embodiments, the DNA vaccine is introduced into the blood, the thymus, the pancreas, the skin, the muscle, a tumor, or other sites.

In some embodiments, the compositions disclosed herein are prepared as an RNA vaccine. In some embodiments, the RNA is non-replicating mRNA or virally derived, self-amplifying RNA. In some embodiments, the non-replicating mRNA encodes the peptides disclosed herein and contains 5' and 3' untranslated regions (UTRs). In some embodiments, the virally derived, self-amplifying RNA encodes not only the peptides disclosed herein but also the viral replication machinery that enables intracellular RNA amplification and abundant protein expression. In some embodiments, the RNA is directly introduced into the individual. In some embodiments, the RNA is chemically synthesized or transcribed in vitro. In some embodiments, the mRNA is produced from a linear DNA template using a T7, a T3, or an Sp6 phage RNA polymerase, and the resulting product contains an open reading frame that encodes the peptides disclosed herein, flanking UTRs, a 5' cap, and a poly(A) tail. In some embodiments, various versions of 5' caps are added during or after the transcription reaction using a vaccinia virus capping enzyme or by incorporating synthetic cap or anti-reverse cap analogues. In some embodiments, an optimal length of the poly(A) tail is added to mRNA either directly from the encoding DNA template or by using poly(A) polymerase. The RNA encodes one or more peptides comprising a fragment that is a T cell epitope capable of binding to at least three HLA class I and/or at least three HLA class II molecules of a patient. In some embodiments, the fragments are derived from an antigen that is expressed in cancer. In some embodiments, the RNA includes signals to enhance stability and translation. In some embodiments, the RNA also includes unnatural nucleotides to increase the half-life or modified nucleosides to change the immunostimulatory profile. In some embodiments, the RNAs is introduced by a needle, a gene gun, an aerosol injector, with patches, via microneedles, by abrasion, among other forms. In some forms the RNA vaccine is incorporated into liposomes or other forms of nanobodies that facilitate cellular uptake of RNA and protect it from degradation. In some embodiments, the RNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle; and/or naked mRNA; naked mRNA with in vivo electroporation; protamine-complexed mRNA; mRNA associated with a positively charged oil-in-water cationic nanoemulsion; mRNA associated with a chemically modified dendrimer and complexed with polyethylene glycol (PEG)-lipid; protamine-complexed mRNA in a PEG-lipid nanoparticle; mRNA associated with a cationic polymer such as polyethylenimine (PEI); mRNA associated with a cationic polymer such as PEI and a lipid component; mRNA associated with a polysaccharide (for example, chitosan) particle or gel; mRNA in a cationic lipid nanoparticle (for example, 1,2-dioleoyloxy-3-trimethylammoniumpropane (DOTAP) or dioleoylphosphatidylethanolamine (DOPE) lipids); mRNA complexed with cationic lipids and cholesterol; or mRNA complexed with cationic lipids, cholesterol and PEG-lipid. In some embodiments, the RNA vaccine is administered by inhalation or ingestion. In some embodiments, the RNA is introduced into the blood, the thymus, the pancreas, the skin, the muscle, a tumor, or other sites, and/or by an intradermal, intramuscular, subcutaneous, intranasal, intranodal, intravenous, intrasplenic, intratumoral or other delivery route.

Polynucleotide or oligonucleotide components may be naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

Administration is typically in a "prophylactically effective amount" or a "therapeutically effective amount" (as the case may be, although prophylaxis may be considered therapy), this being sufficient to result in a clinical response or to show clinical benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. The amount of antigen in each dose is selected as an amount which induces an immune response. A physician will be able to determine the required route of administration and dosage for any particular individual. The dose may be provided as a single dose or may be provided as multiple doses, for example taken at regular intervals, for example 2, 3 or 4 doses administered hourly. Typically peptides, polynucleotides or oligonucleotides are typically administered in the range of 1 µg to 1 mg, more typically 1 pg to 10 µg for particle mediated delivery and 1 µg to 1 mg, more typically 1-100 µg, more typically 5-50 µg for other routes. Generally, it is expected that each dose will comprise 0.01-3 mg of antigen. An optimal amount for a particular vaccine can be ascertained by studies involving observation of immune responses in subjects.

Examples of the techniques and protocols mentioned above can be found in Remington's Pharmaceutical Sciences, 20th Edition, 2000, pub. Lippincott, Williams & Wilkins.

In some cases in accordance with the disclosure, more than one peptide or composition of peptides is administered. Two or more pharmaceutical compositions may be administered together/simultaneously and/or at different times or sequentially. Thus, the disclosure includes sets of pharmaceutical compositions and uses thereof. The use of combination of different peptides, optionally targeting different antigens, is important to overcome the challenges of genetic heterogeneity of tumors and HLA heterogeneity of individuals. The use of peptides of the disclosure in combination expands the group of individuals who can experience clinical benefit from vaccination. Multiple pharmaceutical compositions of peptides of the disclosure, manufactured for use in one regimen, may define a drug product.

Routes of administration include but are not limited to intranasal, oral, subcutaneous, intradermal, and intramuscular. The subcutaneous administration is particularly preferred. Subcutaneous administration may for example be by injection into the abdomen, lateral and anterior aspects of upper arm or thigh, scapular area of back, or upper ventrodorsal gluteal area.

The compositions of the disclosure may also be administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullarly, intrapulmonarily, and intravaginally. Depending on the desired duration of the treatment, the compositions according to the disclosure may be administered once or several times, also intermittently, for instance on a monthly basis for several months or years and in different dosages.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

One or more compositions of the disclosure may be administered, or the methods and uses for treatment according to the disclosure may be performed, alone or in combination with other pharmacological compositions or treatments, for example chemotherapy and/or immunotherapy and/or vaccine. The other therapeutic compositions or treatments may for example be one or more of those discussed herein, and may be administered either simultaneously or sequentially with (before or after) the composition or treatment of the disclosure.

In some cases the treatment may be administered in combination with checkpoint blockade therapy, co-stimulatory antibodies, chemotherapy and/or radiotherapy, targeted therapy or monoclonal antibody therapy. It has been demonstrated that chemotherapy sensitizes tumors to be killed by tumor specific cytotoxic T cells induced by vaccination (Ramakrishnan et al. *J Clin Invest*. 2010; 120(4): 1111-1124). Examples for checkpoint inhibitors are CTLA-4 inhibitor, Ipilimumab and programmed cell death-1/programmed cell death ligand-1 (PD-1/PD-L1) signaling inhibitors, Nibolumab, Pembrolizumab, Atezolizumab and Durvalumab. Examples of chemotherapy agents include alkylating agents including nitrogen mustards such as mechlorethamine (HN2), cyclophosphamide, ifosfamide, melphalan (L-sarcolysin) and chlorambucil; anthracyclines; epothilones; nitrosoureas such as carmustine (BCNU), lomustine (CCNU), semustine (methyl-CCNU) and streptozocin (streptozotocin); triazenes such as decarbazine (DTIC; dimethyltriazenoimidazole-carboxamide; ethylenimines/methylmelamines such as hexamethylmelamine, thiotepa; alkyl sulfonates such as busulfan; Antimetabolites including folic acid analogues such as methotrexate (amethopterin); alkylating agents, antimetabolites, pyrimidine analogs such as fluorouracil (5-fluorouracil; 5-FU), floxuridine (fluorodeoxyuridine; FUdR) and cytarabine (cytosine arabinoside); purine analogues and related inhibitors such as mercaptopurine (6-mercaptopurine; 6-MP), thioguanine (6-thioguanine; TG) and pentostatin (2'-deoxycoformycin); epipodophylotoxins; enzymes such as L-asparaginase; biological response modifiers such as IFNα, IL-2, G-CSF and GM-CSF; platinum coordination complexes such as cisplatin (cis-DDP), oxaliplatin and carboplatin; anthracenediones such as mitoxantrone and anthracycline; substituted urea such as hydroxyurea; methylhydrazine derivatives including procarbazine (N-methylhydrazine, MIH) and procarbazine; adrenocortical suppressants such as mitotane (o,p'-DDD) and aminoglutethimide; taxol and analogues/derivatives; hormones and agonists/antagonists including adrenocorticosteroid antagonists such as prednisone and equivalents, dexamethasone and aminoglutethimide, progestin such as hydroxyprogesterone caproate, medroxyprogesterone acetate and megestrol acetate, estrogen such as diethylstilbestrol and ethinyl estradiol equivalents, antiestrogen such as tamoxifen, androgens including testosterone propionate and fluoxymesterone/equivalents, antiandrogens such as flutamide, gonadotropin-releasing hormone analogs and leuprolide and non-steroidal antiandrogens such as flutamide; natural products including vinca alkaloids such as vinblastine (VLB) and vincristine, epipodophyllotoxins such as etoposide and teniposide, antibiotics such as dactinomycin (actinomycin D), daunorubicin (daunomycin; rubidomycin), doxorubicin, bleomycin, plicamycin (mithramycin) and mitomycin (mitomycin C), enzymes such as L-asparaginase, and biological response modifiers such as interferon alphenomes.

In some cases the method of treatment is a method of vaccination or a method of providing immunotherapy. As used herein, "immunotherapy" is the prevention or treatment of a disease or condition by inducing or enhancing an immune response in an individual. In certain embodiments, immunotherapy refers to a therapy that comprises the administration of one or more drugs to an individual to elicit T cell responses. In a specific embodiment, immunotherapy refers to a therapy that comprises the administration or expression of polypeptides that contain one or more PEPIs to an individual to elicit a T cell response to recognize and kill cells that display the one or more PEPIs on their cell surface in conjunction with a class I HLAs. In another specific embodiment, immunotherapy comprises the administration of one or more PEPIs to an individual to elicit a cytotoxic T cell response against cells that display tumor associated antigens (TAAs) or cancer testis antigens (CTAs) comprising the one or more PEPIs on their cell surface. In another embodiment, immunotherapy refers to a therapy that comprises the administration or expression of polypeptides that contain one or more PEPIs presented by class II HLAs to an individual to elicit a T helper response to provide co-stimulation to cytotoxic T cells that recognize and kill diseased cells that display the one or more PEPIs on their cell surface in conjunction with a class I HLAs. In still another specific embodiment, immunotherapy refers to a therapy that comprises administration of one or more drugs to an individual that re-activate existing T cells to kill target cells. The theory is that the cytotoxic T cell response will eliminate the cells displaying the one or more PEPIs, thereby improving the clinical condition of the individual. In some instances, immunotherapy may be used to treat tumors. In other instances, immunotherapy may be used to treat intracellular pathogen-based diseases or disorders.

In some cases the disclosure relates to the treatment of cancer or the treatment of solid tumors. In some cases the treatment is of breast cancer, ovarian cancer or colorectal cancer. In other cases the treatment may be of any other cancer or solid tumor that expresses a target tumor associated antigen of the present peptides as described herein, or any cancer in which such target polypeptide antigens are expressed in some or a high percentage of subjects. The treatment may be of cancers or malignant or benign tumors of any cell, tissue, or organ type. The cancer may or may not be metastatic. Exemplary cancers include carcinomas, sarcomas, lymphomas, leukemias, germ cell tumors, or blastomas. The cancer may or may not be a hormone related or dependent cancer (e.g., an estrogen or androgen related cancer).

Selection of Polypeptides and Patients

Specific polypeptide antigens, and particularly short peptides derived from such antigens that are commonly used in vaccination and immunotherapy, induce immune responses in only a fraction of human subjects. The polypeptides of the present disclosure are specifically selected to induce immune responses in a high proportion of the general population, but they may not be effective in all individuals due to HLA genotype heterogeneity. HLA genotype population heterogeneity means that the immune or clinical response rate to the vaccines described herein will differ between different human subpopulations. In some cases the vaccines described herein are for use to treat a specific or target subpopulation, for example an Asian population, or a Vietnamese, Chinese, and/or Japanese population.

The disclosure also provides a method of identifying a human subject who will likely have a cytotoxic T cell response to administration of a pharmaceutical composition comprising a peptide of the disclosure (likely responders), or of predicting the likelihood that a subject will have a cytotoxic T cell response.

As provided herein T cell epitope presentation by multiple HLAs of an individual is generally needed to trigger a T cell response. The best predictor of a cytotoxic T cell response to a given polypeptide, as determined by the inventors, is the presence of at least one T cell epitope that is presented by three or more HLA class I of an individual (≥1 PEPI3+). Accordingly the presence within the active ingredient peptides of a pharmaceutical composition of one or more T cell epitopes that is capable of binding to at least three HLA of a subject is predictive for the subject having a cytotoxic T cell response to administration of the pharmaceutical composition. The subject is a likely immune responder.

In some cases the T cell epitope that is capable of binding to at least three HLA class I of the subject has the amino acid sequence of any one of SEQ ID NOs: 1 to 40, or SEQ ID NOs: 1 to 40, 172-194, 234-250 and 272-301. In other cases the T cell epitope may have a different amino acid sequence within the one or more peptides of the pharmaceutical composition.

The inventors have further discovered that the presence in a vaccine or immunotherapy composition of at least two epitopes that can bind to at least three HLA of an individual is predictive for a clinical response. In other words, if an individual has a total of ≥2 PEPI3+ within the active ingredient polypeptide(s) of a vaccine or immunotherapy composition, and these PEPI3+s are derived from antigen sequences that are in fact expressed in the individual (for example, target tumor cells of the individual express the target tumor-associated antigens), then the individual is a likely clinical responder (i.e. a clinically relevant immune responder).

Accordingly some aspects of the disclosure relate to a method of identifying a subject who will likely have a clinical response to a method of treatment according to the disclosure, or of predicting the likelihood that a subject will have a clinical response. A "clinical response" or "clinical benefit" as used herein may be the prevention or a delay in the onset of a disease or condition, the amelioration of one or more symptoms, the induction or prolonging of remission, or the delay of a relapse or recurrence or deterioration, or any other improvement or stabilisation in the disease status of a subject. Where appropriate, a "clinical response" may correlate to "disease control" or an "objective response" as defined by the Response Evaluation Criteria In Solid Tumors (RECIST) guidelines.

In some embodiments the method comprises determining that one or more cancer-associated antigens selected from SPAG9, AKAP-4, BORIS, NY-SAR-35, NY-BR-1, SURVIVIN, MAGE-A11, PRAME, MAGE-A9, HOM-TES-85, TSP50, EpCAM, CAGE1, FBXO39, MAGE-A8 and MAGE-A6 is expressed by a cancer. For example expression of the cancer associated antigen may be detected in a sample obtained from the subject, for example a tumor biopsy, using methods that are known in the art.

The inventors have discovered that it is not sufficient that a vaccine or immunotherapy composition targets an antigen that is expressed by cancer or tumor cells of a patient, nor that the target sequences of that antigen can bind to HLA class I of the patient (HLA restricted epitopes). The composition is likely effective only in patients that both express the target antigen and have three or more HLA class I that bind to a single T cell epitope of the target antigen. Moreover, as described above, at least two epitopes that binds to at least 3 HLAs of the patient are generally needed to induce a clinically relevant immune response.

Therefore the method further comprises determining that the active ingredient peptide(s) of the pharmaceutical composition comprise two or more different amino acid sequences each of which is a) a fragment of a cancer-associated antigen expressed by cancer cells of the subject, determined as described above; and b) a T cell epitope capable of binding to at least three HLA class I of the subject.

In some cases the T cell epitope that is capable of binding to at least three HLA class I of the subject has the amino acid sequence of any one of SEQ ID NOs: 1 to 40, or SEQ ID NOs: 1 to 40, 172-194, 234-250 and 272-301. In other cases the T cell epitope may have a different amino acid sequence within the one or more peptides of the pharmaceutical composition.

In some cases the likelihood that a subject will have a clinical response to a peptide vaccine or immunotherapy composition, such as those described herein, can be determined without knowing whether the target antigens are expressed in cancer or tumor cells of the subject and/or without determining the HLA class I genotype of the subject. Known antigen expression frequencies in the disease (e.g. MAGE-A3 in a tumor type like breast or colorectal cancer) and/or known frequencies for HLA class I and class II genotype of subjects in the target population (e.g ethnic population, general population, diseased population) may be used instead. Moreover by combining peptides that target the most frequently presented PEPIs across the population (BestEPIs) in multiple frequently expressed target antigens in the disease, as identified and described herein, it is possible to design a cancer vaccine regime that is effective for a high proportion of patients. However, using the companion diagnostic methods described herein to pre-select patients who are most likely to have a clinical response will increase clinical response rates amongst treated patients.

The likelihood that a subject will respond to treatment is increased by (i) the presence of more multiple HLA-binding PEPIs in the active ingredient polypeptides; (ii) the presence of PEPIs in more target polypeptide antigens; and (iii) expression of the target polypeptide antigens in the subject or in diseased cells of the subject. In some cases expression of the target polypeptide antigens in the subject may be known, for example if target polypeptide antigens are in a sample obtained from the subject. In other cases, the probability that a specific subject, or diseased cells of a specific subject, (over-)express a specific or any combination of target polypeptide antigens may be determined using population expression frequency data, e.g. probability of expression of an antigen in breast cancer, colorectal cancer or ovarian cancer. The population expression frequency data may relate to a subject- and/or disease-matched population or the intent-to-treat population. For example, the frequency or probability of expression of a particular cancer-associated antigen in a particular cancer or subject having a particular cancer, for example breast cancer, can be determined by detecting the antigen in tumor, e.g. breast cancer tumor samples. In some cases such expression frequencies may be determined from published figures and scientific publications. In some cases a method of the disclosure comprises a step of determining the expression frequency of a relevant target polypeptide antigen in a relevant population.

Disclosed is a range of pharmacodynamic biomarkers to predict the activity/effect of vaccines in individual human subjects as well as in populations of human subjects. These biomarkers expedite more effective vaccine development and also decrease the development cost and may be used to assess and compare different compositions. Exemplary biomarkers are as follows.

AG95—potency of a vaccine: The number of antigens in a cancer vaccine that a specific tumor type expresses with 95% probability. AG95 is an indicator of the vaccine's potency, and is independent of the immunogenicity of the vaccine antigens. AG95 is calculated from the tumor antigen expression rate data. Such data may be obtained from experiments published in peer reviewed scientific journals. Technically, AG95 is determined from the binomial distribution of antigens in the vaccine, and takes into account all possible variations and expression rates.

PEPI3+ count—immunogenicity of a vaccine in a subject: Vaccine-derived PEPI3+ are personal epitopes that bind to et least 3 HLAs of a subject and induce T cell responses. PEPI3+ can be determined using the PEPI3+ Test in subjects who's complete 4-digit ELLA genotype is known.

AP count—antigenicity of a vaccine in a subject: Number of vaccine antigens with PEPI3+. Vaccines contain sequences from target polypeptide antigens expressed by diseased cells. AP count is the number of antigens in the vaccine that contain PEPI3+, and the AP count represents the number of antigens in the vaccine that can induce T cell responses in a subject. AP count characterizes the vaccine-antigen specific T cell responses of the subject since it depends only on the ELLA genotype of the subject and is independent of the subject's disease, age, and medication. The correct value is between 0 (no PEPI presented by the antigen) and maximum number of antigens (all antigens present PEPIs).

AP50—antigenicity of a vaccine in a population: The mean number of vaccine antigens with a PEPI in a population. The AP50 is suitable for the characterization of vaccine-antigen specific T cell responses in a given population since it depends on the HLA genotype of subjects in a population.

AGP count—effectiveness of a vaccine in a subject: Number of vaccine antigens expressed in the tumor with PEPI. The AGP count indicates the number of tumor antigens that vaccine recognizes and induces a T cell response against (hit the target). The AGP count depends on the vaccine-antigen expression rate in the subject's tumor and the HLA genotype of the subject. The correct value is between 0 (no PEPI presented by expressed antigen) and maximum number of antigens (all antigens are expressed and present a PEPI).

AGP50—effectiveness of a cancer vaccine in a population: The mean number of vaccine antigens expressed in the indicated tumor with PEPI (i.e., AGP) in a population. The AGP50 indicates the mean number of tumor antigens that the T cell responses induced by the vaccine can recognize. AGP50 is dependent on the expression rate of the antigens in the indicated tumor type and the immunogenicity of the antigens in the target population. AGP50 can estimate a vaccine's effectiveness in different populations and can be used to compare different vaccines in the same population. The computation of AGP50 is similar to that used for AG50, except the expression is weighted by the occurrence of the PEPI3+ in the subject on the expressed vaccine antigens. In a theoretical population, where each subject has a PEPI from each vaccine antigen, the AGP50 will be equal to AG50. In another theoretical population, where no subject has a PEPI from any vaccine antigen, the AGP50 will be 0. In general, the following statement is valid: 0≤AGP50≤AG50.

mAGP—a candidate biomarker for the selection of likely responders: Likelihood that a cancer vaccine induces T cell responses against multiple antigens expressed in the indicated tumor. mAGP is calculated from the expression rates of vaccine-antigens in the tumor and the presence of vaccine derived PEPIs in the subject. Technically, based on the AGP distribution, the mAGP is the sum of probabilities of the multiple AGP (≥2 AGPs).

The results of a prediction as set out above may be used to inform a physician's decisions concerning treatment of the subject. Accordingly, in some cases the method of the disclosure predicts that a subject will have or is likely to have a T cell response and/or a clinical response to a treatment as described herein, and the method further comprises selecting the treatment for the human subject. In some cases a subject is selected for treatment if their likelihood of a response targeted at a predefined number of target polypeptide antigens, optionally wherein the target polypeptide antigens are (predicted to be) expressed, is above a predetermined threshold. In some cases the number of target polypeptide antigens or epitopes is two. In some cases the number of target polypeptide antigens or epitopes is three, or four, or five, or six, or seven, or eight, or nine, or ten. The method may further comprise administering the treatment to the human subject. Alternatively, the method may predict that the subject will not have an immune response and/or a clinical response and further comprise selecting a different treatment for the subject.

Further Embodiments of the Disclosure

1. A polypeptide that comprises a fragment of up to 50 consecutive amino acids of
   (a) a colorectal cancer-associated antigen selected from TSP50, EpCAM, SPAG9, CAGE1, FBXO39, SURVIVIN, LEMD1, MAGE-A8, MAGE-A6 and MAGE-A3, wherein the fragment comprises an amino acid sequence selected from any one of SEQ ID NOs: 21 to 40 and 234 to 250;
   (b) an ovarian cancer-associated antigen selected from PIWIL-4, WT1, EpCAM, BORIS, AKAP-4, OY-TES-1, SP17, PIWIL-2, PIWIL-3, SPAG9, PRAME, HIWI, SURVIVIN, and AKAP-3 wherein the fragment comprises the amino acid sequence of any one of SEQ ID NOs: 272 to 301; and/or
   (c) a breast cancer associated antigen selected from PIWIL-2, AKAP-4, EpCAM, BORIS, HIWI, SPAG9, PLU-1, TSGA10, ODF-4, SP17, RHOXF-2, PRAME, NY-SAR-35, MAGE-A9, NY-BR-1, SURVIVIN, MAGE-A11, HOM-TES-85 and NY-ESO-1 wherein the fragment comprises an amino acid sequence selected from any one of SEQ ID NOs: 1 to 20, 24 and 172 to 194;
   optionally wherein the fragment is flanked at the N and/or C terminus by additional amino acids that are not part of the sequence of the breast, ovarian or colorectal cancer-associated antigen.

2. The polypeptide of item 1, wherein the polypeptide
   a. is a fragment of a colorectal cancer-associated antigen selected from TSP50, EpCAM, SPAG9, CAGE1, FBXO39, SURVIVIN, MAGE-A8, MAGE-A6, MAGE-A3 and LEMD1, wherein the fragment comprises an amino acid sequence selected from any one of SEQ ID NOs: 21 to 40 and 234 to 250; or
   b. comprises or consists of two or more fragments of one or more colorectal cancer associated antigens selected from TSP50, EpCAM, SPAG9, CAGE1, FBXO39, SURVIVIN, MAGE-A8, MAGE-A6, MAGE-A3 and LEMD1, wherein each fragment comprises a different amino acid sequence selected from any one of SEQ ID NOs: 21 to 40 and 234 to 250, optionally wherein the fragments overlap or are arranged end to end in the polypeptide; or
   c. is a fragment of a ovarian cancer-associated antigen selected from PIWIL-4, WT1, EpCAM, BORIS, AKAP-4, OY-TES-1, SP17, PIWIL-2, PIWIL-3, SPAG9, PRAME, HIWI, SURVIVIN and AKAP-3, wherein the fragment comprises an amino acid sequence selected from any one of SEQ ID NOs: 272 to 301; or
   d. comprises or consists of two or more fragments of one or more ovarian cancer associated antigens selected from PIWIL-4, WT1, EpCAM, BORIS, AKAP-4, OY-TES-1, SP17, PIWIL-2, PIWIL-3, SPAG9, PRAME, HIWI, SURVIVIN and AKAP-3, wherein each fragment comprises a different amino acid sequence selected from any one of SEQ ID NOs: 272 to 301, optionally wherein the fragments overlap or are arranged end to end in the polypeptide; or
   e. is a fragment of a breast cancer associated antigen selected from SPAG9, AKAP-4, BORIS, NY-SAR-35, NY-BR-1, SURVIVIN, MAGE-A11, PRAME, MAGE-A9, HOM-TES-85, PIWIL-2, EpCAM, HIWI, PLU-1, TSGA10, ODF-4, SP17, RHOXF-2, wherein the fragment comprises the amino acid sequence from any one of SEQ ID NOs: 1 to 20, 24 and 172 to 194; or
   f. comprises or consists of two or more fragments of one or more breast cancer associated antigens selected from SPAG9, AKAP-4, BORIS, NY-SAR-35, NY-BR-1, SURVIVIN, MAGE-A11, PRAME, MAGE-A9, HOM-TES-8, PIWIL-2, EpCAM, HIWI, PLU-1, TSGA10, ODF-4, SP17, RHOXF-2, wherein each fragment comprises a different amino acid sequence selected from any one of SEQ ID NOs: 1 to 20, 24 and 172 to 194; optionally wherein the fragments overlap or are arranged end to end in the polypeptide and.

3. The polypeptide according to item 1 or item 2, wherein the polypeptide comprises or consists of fragments of at least two different cancer-associated antigens, wherein the cancer-associated antigens are selected from
   (a) TSP50, EpCAM, SPAG9, CAGE1, FBXO39, SURVIVIN, MAGE-A8, MAGE-A6, MAGE-A3 and LEMD1;
   (b) PIWIL-4, WT1, EpCAM, BORIS, AKAP-4, OY-TES-1, SP17, PIWIL-2, PIWIL-3, SPAG9, PRAME, HIWI, SURVIVIN and AKAP-3; and/or
   (c) SPAG9, AKAP-4, BORIS, NY-SAR-35, NY-BR-1, SURVIVIN, MAGE-A11, PRAME, MAGE-A9, HOM-TES-8, PIWIL-2, EpCAM, HIWI, PLU-1, TSGA10, ODF-4, SP17, RHOXF-2;
wherein each fragment comprises a different amino acid sequence selected from SEQ ID NOs: 21 to 40 and 234 to 250; SEQ ID NOs: 272 to 301; and/or SEQ ID NOs: 1 to 20, 24 and 172 to 194.

4. The polypeptide according to any one of items 1 to 3, comprising or consisting of one or more amino acid sequences selected from SEQ ID NOs: 41-80, 251 to 271, 302 to 331 and 196 to 233.

5. The polypeptide according to any one of items 1 to 4 comprising or consisting of the amino acid sequence of any one of SEQ ID NOs: 81 to 142, 332 to 346 and 435-449.

6. A panel of two or more polypeptides according to any one of items 1 to 5, wherein
(a) each polypeptide comprises a different amino acid sequence selected from SEQ ID NOs: 21 to 40 and 234 to 250; or
(b) each polypeptide comprises a different amino acid sequence selected from SEQ ID NOs: 272 to 301; or
(c) each peptide comprises a different amino acid sequence selected from SEQ ID NOs: 1 to 20, 24 and 172 to 194; or (c) each peptide comprises a different amino acid sequence selected from SEQ ID NOs: 1 to 40, 234 to 250, 272 to 301 and 172 to 194.

7. The panel of polypeptides according to item 6 comprising six peptides having the amino acid sequences of SEQ ID NOs: 130, 121, 131, 124, 134, 126.

8. A pharmaceutical composition or kit having one or more polypeptides according to any one of items 1 to 5, or a panel of polypeptides according to item 6 or item 7, or a polypeptide comprising at least two amino acid sequences selected SEQ ID NOs: 21 to 40 and 234 to 250; SEQ ID NOs: 272 to 301; and/or SEQ ID NOs: 1 to 20, 24 and 172 to 194 as an active ingredient.

9. A method of vaccination, providing immunotherapy or inducing a cytotoxic T cell response in a subject, the method comprising administering to the subject a pharmaceutical composition according to item 8.

10. The method of item 9 that is a method of treating cancer, optionally colorectal cancer, ovarian cancer or breast cancer.

11. A method of identifying a human subject who will likely have a cytotoxic T cell response to administration of a pharmaceutical composition according to item 8, the method comprising
(i) determining that the active ingredient polypeptide(s) of the pharmaceutical composition comprise a sequence that is a T cell epitope capable of binding to at least three HLA class I molecules of the subject; and
(ii) identifying the subject as likely to have a cytotoxic T cell response to administration of the pharmaceutical composition.

12. The method of item 11 further comprising using population expression data for each antigen that
(a) is selected from TSP50, EpCAM, SPAG9, CAGE1, FBXO39, SURVIVIN, LEMD1, MAGE-A8, MAGE-A6, MAGE-A3, PIWIL-4, WT1, BORIS, AKAP-4, OY-TES-1, SP17, PIWIL-2, PIWIL-3, PRAME, HIWI, PLU-1, TSGA10, ODF-4, RHOXF-2, NY-SAR-35, MAGE-A9, NY-BR-1, MAGE-A11, HOM-TES-85, NY-ESO-1 and AKAP-3; and
(b) comprises an amino acid sequence that is
  i. a fragment of an active ingredient peptide of the pharmaceutical composition; and
  ii. a T cell epitope capable of binding to at least three ELLA class I molecules of the subject;
to determine the likelihood that the subject will have a cytotoxic T cell response that targets one or more polypeptide antigens that are expressed by cancer cells of the subject.

13. A method of identifying a subject who will likely have a clinical response to a method of treatment according to item 10, the method comprising
(i) determining that the active ingredient polypeptide(s) of the pharmaceutical composition comprise two or more different amino acid sequences each of which is
  a. a T cell epitope capable of binding to at least three ELLA class I molecules of the subject; and
  b. a fragment of a cancer-associated antigen expressed by cancer cells of the subject, optionally wherein the cancer-associated antigen is present in a sample obtained from the subject; and
(ii) identifying the subject as likely to have a clinical response to the method of treatment.

14. A method of determining the likelihood that a specific human subject will have a clinical response to a method of treatment according to item 10, wherein one or more of the following factors corresponds to a higher likelihood of a clinical response:
(a) presence in the active ingredient polypeptide(s) of a higher number of amino acid sequences and/or different amino acid sequences that are each a T cell epitope capable of binding to at least three ELLA class I of the subject;
(b) a higher number of target polypeptide antigens, comprising at least one amino acid sequence that is both
  A. comprised in an active ingredient polypeptide; and
  B. a T cell epitope capable of binding to at least three ELLA class I of the subject; optionally wherein the target polypeptide antigens are expressed in the subject, further optionally wherein the target polypeptides antigens are in one or more samples obtained from the subject;
(c) a higher probability that the subject expresses target polypeptide antigens, optionally a threshold number of the target polypeptide antigens and/or optionally target polypeptide antigens that have been determined to comprise at least one amino acid sequence that is both
  A. comprised in in an active ingredient polypeptide; and
  B. a T cell epitope capable of binding to at least three HLA class I of the subject; and/or
(d) a higher number of target polypeptide antigens that the subject is predicted to express, optionally a higher number of target polypeptide antigens that the subject expresses with a threshold probability, and/or optionally the target polypeptide antigens that have been determined to comprise at least one amino acid sequence that is both
  A. comprised in in an active ingredient polypeptide; and
  B. a T cell epitope capable of binding to at least three HLA class I of the subject.

15. The method of item 14, wherein the method comprises
(i) identifying which polypeptide antigens targeted by the active ingredient polypeptide(s) comprise an amino acid sequence that is both
  A. comprised in an active ingredient polypeptide; and
  B. a T cell epitope capable of binding to at least three HLA class I of the subject;
(ii) using population expression data for each antigen identified in step (i) to determine the probability that the subject expresses one or more of the antigens identified in step (i) that together comprise at least two different amino acid sequences of step (i); and
(iii) determining the likelihood that the subject will have a clinical response to administration of the pharmaceutical composition, kit or panel of polypeptides, wherein a higher probability determined in step (ii) corresponds to a more likely clinical response.

16. The method of item 15, wherein the at least two different amino acid sequences are comprised in the amino acid sequence of two different polypeptide antigens targeted by the active ingredient polypeptide(s).

The method of any one of items 13 to 16 further comprising selecting or recommending administration of the pharmaceutical composition as a method of treatment for the subject, and optionally further treating the subject by administering the pharmaceutical composition.

A method of treatment according to item 10, wherein the subject has been identified as likely to have a clinical response or as having above a threshold minimum likelihood of having a clinical response to the treatment by a method according to any one of items 13 to 16.

The method of any one of items 9, 10, 17 and 18 wherein the treatment is administered in combination with chemotherapy, targeted therapy or a checkpoint inhibitor.

A method of identifying a human subject who will likely not have a clinical response to a method of treatment according to item 10, the method comprising (i) determining that the active ingredient peptide(s) of the pharmaceutical composition do not comprise two or more different amino acid sequences each of which is a T cell epitope capable of binding to at least three HLA class I molecules of the subject; and (iii) identifying the subject as likely not to have a clinical response to the method of treatment.

EXAMPLES

Example 1—HLA-Epitope Binding Prediction Process and Validation

Predicted binding between particular HLA and epitopes (9 mer peptides) was based on the Immune Epitope Database tool for epitope prediction (www.iedb.org).

The HLA I-epitope binding prediction process was validated by comparison with HLA I-epitope pairs determined by laboratory experiments. A dataset was compiled of HLA I-epitope pairs reported in peer reviewed publications or public immunological databases.

The rate of agreement with the experimentally determined dataset was determined (Table 2). The binding HLA I-epitope pairs of the dataset were correctly predicted with a 93% probability. Coincidentally the non-binding HLA I-epitope pairs were also correctly predicted with a 93% probability.

TABLE 2

Analytical specificity and sensitivity of the HLA-epitope binding prediction process.

| HLA-epitope pairs | True epitopes (n = 327) (Binder match) | False epitopes (n = 100) (Non-binder match) |
|---|---|---|
| HIV | 91% (32) | 82% (14) |
| Viral | 100% (35) | 100% (11) |
| Tumor | 90% (172) | 94% (32) |
| Other (fungi, bacteria, etc.) | 100% (65) | 95% (36) |
| All | 93% (304) | 93% (93) |

The accuracy of the prediction of multiple HLA binding epitopes was determined. Based on the analytical specificity and sensitivity using the 93% probability for both true positive and true negative prediction and 7% (=100%−93%) probability for false positive and false negative prediction, the probability of the existence of a multiple HLA binding epitope in a person can be calculated. The probability of multiple HLA binding to an epitope shows the relationship between the number of HLAs binding an epitope and the expected minimum number of real binding. Per PEPI definition three is the expected minimum number of HLA to bind an epitope (bold).

TABLE 3

Accuracy of multiple HLA binding epitopes predictions.

| Expected minimum number of real HLA binding | Predicted number of HLAs binding to an epitope | | | | | | |
|---|---|---|---|---|---|---|---|
| | 0 | 1 | 2 | 3 | 4 | 5 | 6 |
| 1 | 35% | 95% | 100% | 100% | 100% | 100% | 100% |
| 2 | 6% | 29% | 90% | 99% | 100% | 100% | 100% |
| 3 | 1% | 4% | 22% | 84% | 98% | 100% | 100% |
| 4 | 0% | 0% | 2% | 16% | 78% | 96% | 99% |
| 5 | 0% | 0% | 0% | 1% | 10% | 71% | 94% |
| 6 | 0% | 0% | 0% | 0% | 0% | 5% | 65% |

The validated HLA-epitope binding prediction process was used to determine all HLA-epitope binding pairs described in the Examples below.

Example 2—Epitope Presentation by Multiple HLA Predicts Cytotoxic T Lymphocyte (CTL) Response The presentation of one or more epitopes of a polypeptide antigen by one or more HLA I of an individual is predictive for a CTL response was determined.

The study was carried out by retrospective analysis of six clinical trials, conducted on 71 cancer and 9 HIV-infected patients (Table 4)[1-7]. Patients from these studies were treated with an HPV vaccine, three different NY-ESO-1 specific cancer vaccines, one HIV-1 vaccine and a CTLA-4 specific monoclonal antibody (Ipilimumab) that was shown to reactivate CTLs against NY-ESO-1 antigen in melanoma patients. All of these clinical trials measured antigen specific CD8+ CTL responses (immunogenicity) in the study subjects after vaccination. In some cases, correlation between CTL responses and clinical responses were reported.

No patient was excluded from the retroactive study for any reason other than data availability. The 157 patient datasets (Table 4) were randomized with a standard random number generator to create two independent cohorts for training and evaluation studies. In some cases the cohorts contained multiple datasets from the same patient, resulting in a training cohort of 76 datasets from 48 patients and a test/validation cohort of 81 datasets from 51 patients.

particular decision threshold (epitope (PEPI) count). The area under the ROC curve (AUC) is a measure of how well the classifier can distinguish between two diagnostic groups (CTL responder or non-responder).

TABLE 4

Summary of patient datasets

| Clinical trial | Immunotherapy | Target Antigen | Disease | # Patients* | # Datasets (#antigen × #patient) | Immunoassay performed in the clinical trials** | HLA genotyping method | Ref |
|---|---|---|---|---|---|---|---|---|
| 1 | VGX-3100 | HPV16-E6 HPV16-E7 HPV18-E6 HPV18-E7 HPV16/18 | Cervical cancer | 17/18 | 5 × 17 | IFN-γ ELISPOT | High Resolution SBT | 1 |
| 2 | HIVIS vaccine | HIV-1 Gag HIV-1 RT | AIDS | 9/12 | 2 × 9 | IFN-γ ELISPOT | Low-Medium Resolution SSO | 2 |
| 3 | rNY-ESO-1 | NY-ESO-1 | Breast-and ovarian cancers, melanoma and sarcoma | 18/18 | 1 × 18 | In vitro and Ex vivo IFN-γ ELISPOT | High Resolution SBT | 3 4 |
| 4 | Ipilimumab | NY-ESO-1 | Metastatic melanoma | 19/20 | 1 × 19 | ICS after T-cell stimulation | Low to medium resolution typing, SSP of genomic DNA, high resolution sequencing | 5 |
| 5 | NY-ESO-1f | NY-ESO-1 (91-110) | Esophageal-, non-small-cell lung- and gastric cancer | 10/10 | 1 × 10 | ICS after T-cell stimulation | SSO probing and SSP of genomic DNA | 6 |
| 6 | NY-ESO-1 overlapping peptides | NY-ESO-1 (79-173) | Esophageal- and lung cancer, malignant melanoma | 7/9 | 1 × 7 | ICS after T-cell stimulation | SSO probing and SSP of genomic DNA | 7 |
| Total | 6 | 7 | | 80 | 157 | N/A | | |

*Number of patients used in the retrospective analysis from the original number of patient of the clinical trials.
**Immunoassays are based on T cell stimulation with antigen-specific peptide pools and quantify the released cytokines by different techniques.
CT: Clinical trial;
SBT: Sequence Based Typing;
SSO: Sequence-Specific Oligonucleotide;
ICS: Intracellular cytokine staining;
SSP: Sequence-specific priming The reported CTL responses of the training dataset were compared with the HLA I restriction profile of epitopes (9 mers) of the vaccine antigens. The antigen sequences and the HLA I genotype of each patient were obtained from publicly available protein sequence databases or peer reviewed publications and the HLA I-epitope binding prediction process was blinded to patients' clinical CTL response data. The number of epitopes from each antigen predicted to bind to at least 1 (PEPI1+), or at least 2 (PEPI2+), or at least 3 (PEPI3+), or at least 4 (PEPI4+), or at least 5 (PEPI5+), or all 6 (PEPI6) HLA class I molecules of each patient was determined and the number of HLA bound were used as classifiers for the reported CTL responses. The true positive rate (sensitivity) and true negative rate (specificity) were determined from the training dataset for each classifier (number of HLA bound) separately.

ROC analysis was performed for each classifier. In a ROC curve, the true positive rate (Sensitivity) was plotted in function of the false positive rate (1-Specificity) for different cut-off points (FIG. 1). Each point on the ROC curve represents a sensitivity/specificity pair corresponding to a The analysis unexpectedly revealed that predicted epitope presentation by multiple class I HLAs of a subject (PEPI2+, PEPI3+, PEPI4+, PEPI5+, or PEPI6), was in every case a better predictor of CTL response than epitope presentation by merely one or more ELLA class I (PEPI1+, AUC=0.48, Table 5).

TABLE 5

Determination of diagnostic value of the PEPI biomarker by ROC analysis

| Classifiers | AUC |
|---|---|
| PEPI1+ | 0.48 |
| PEPI2+ | 0.51 |
| PEPI3+ | 0.65 |
| PEPI4+ | 0.52 |
| PEPI5+ | 0.5 |
| PEPI6+ | 0.5 |

The CTL response of an individual was best predicted by considering the epitopes of an antigen that could be presented by at least 3 ELLA class I of an individual (PEPI3+, AUC=0.65, Table 5). The threshold count of PEPI3+(number of antigen-specific epitopes presented by 3 or more ELLA of an individual) that best predicted a positive CTL response was 1 (Table 6). In other words, at least one antigen-derived epitope is presented by at least 3 HLA class I of a subject (≥1 PEPI3+), then the antigen can trigger at least one CTL clone, and the subject is a likely CTL responder. Using the ≥1 PEPI3+ threshold to predict likely CTL responders ("≥1 PEPI3+ Test") provided 76% diagnostic sensitivity (Table 12).

TABLE 6

Determination of the ≥1 PEPI3+ threshold to predict likely CTL responders in the training dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.76 | 0.60 | 0.31 | 0.26 | 0.14 | 0.02 | 0 | 0 | 0 | 0 | 0 | 0 |
| 1− | | 0.59 | 0.24 | 0.21 | 0.15 | 0.09 | 0.06 | 0.06 | 0.03 | 0.03 | 0.03 | 0.03 |

Example 3—Validation of the ≥1 PEPI3+ Test

The test cohort of 81 datasets from 51 patients was used to validate the ≥1 PEPI3+ threshold to predict an antigen-specific CTL response. For each dataset in the test cohort it was determined whether the ≥1 PEPI3+ threshold was met (at least one antigen-derived epitope presented by at least three class I ELLA of the individual). This was compared with the experimentally determined CTL responses reported from the clinical trials (Table 7).

The clinical validation demonstrated that a PEPI3+ peptide induce CTL response in an individual with 84% probability. 84% is the same value that was determined in the analytical validation of the PEPI3+ prediction, epitopes that binds to at least 3 HLAs of an individual (Table 3). These data provide strong evidences that immune responses are induced by PEPIs in individuals.

TABLE 7

Diagnostic performance characteristics of the ≥ 1 PEPI3 + Test (n = 81).

| Performance characteristic | | Description | Result |
|---|---|---|---|
| Positive predictive value (PPV) | 100%[A/(A + B)] | The likelihood that an individual that meets the ≥ 1 PEPI3 + threshold has antigen-specific CTL responses after treatment with immunotherapy. | 84% |
| Sensitivity | 100%[A/(A + C)] | The proportion of subjects with antigen-specific CTL responses after treatment with immunotherapy who meet the ≥ 1 PEPI3 + threshold. | 75% |
| Specificity | 100%[D/(B + D)] | The proportion of subjects without antigen-specific CTL responses after treatment with immunotherapy who do not meet the ≥ 1 PEPI3 + threshold. | 55% |
| Negative predictive value (NPV) | 100%[D/(C + D)] | The likelihood that an individual who does not meet the ≥ 1 PEPI3 + threshold does not have antigen-specific CTL responses after treatment with immunotherapy. | 42% |
| Overall percent agreement (OPA) | 100%[(A + D)/N] | The percentage of predictions based on the ≥ 1 PEPI3 + threshold that match the experimentally determined result, whether positive or negative. | 70% |
| Fisher's exact (p) | | | 0.01 |

Figure 2:
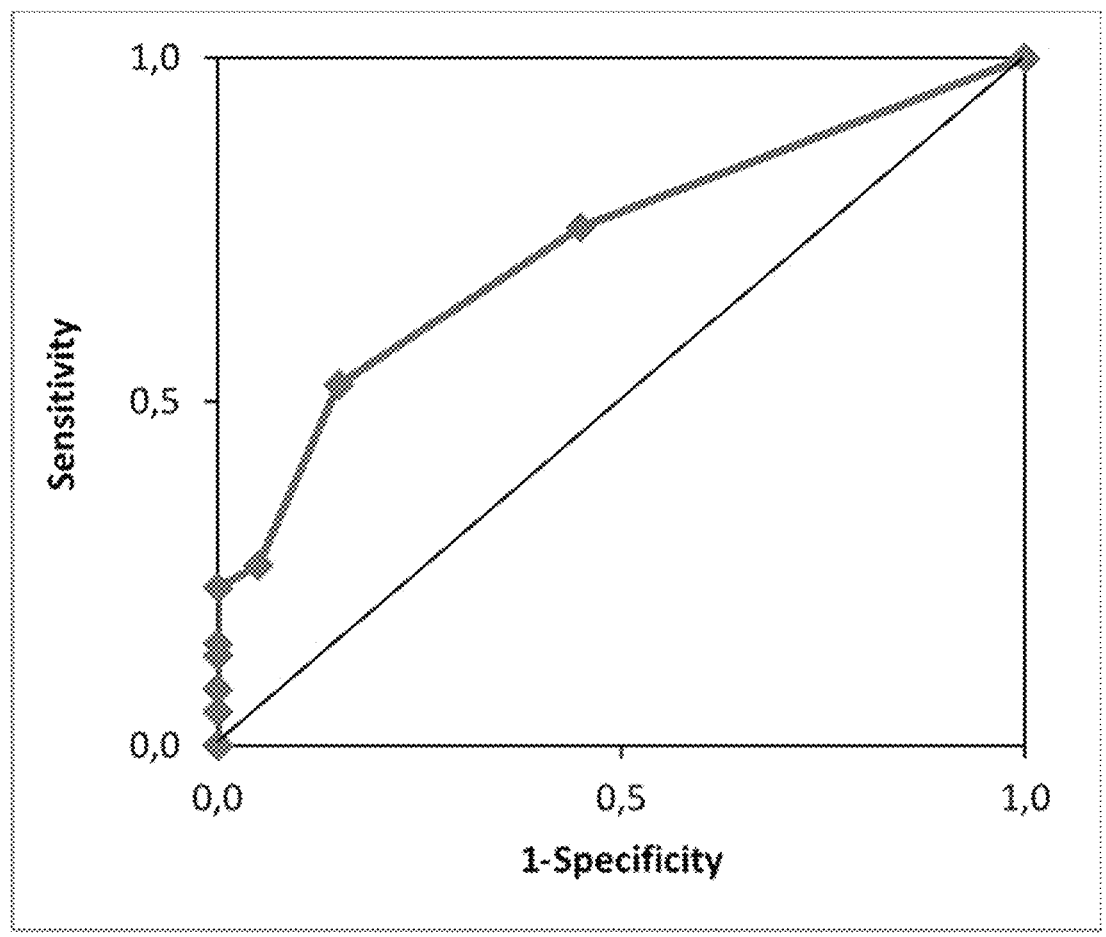
FIG. 2—ROC curve of ≥1 PEPI3+ Test for the determination of the diagnostic accuracy.
Figure 5A:
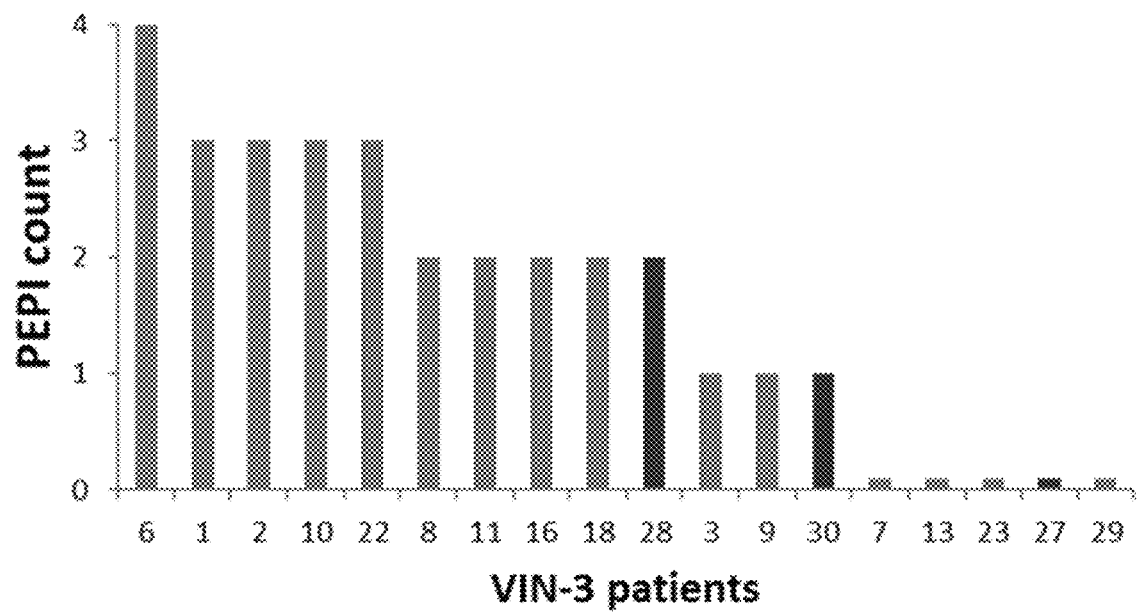
FIGS. 5A-D—Multiple HLA binding peptides that define the HPV-16 LPV vaccine specific T cell response set of 18 VIN-3 and 5 cervical cancer patients. HLA class I restricted PEPI3 counts (FIGS. 5A and 5B) and HLA class II restricted PEPI3 counts (FIGS. 5C and 5C) derived from LPV antigens of each patient. Light grey: immune responders measured after vaccination in the clinical trial; Dark grey: Immune non-responders measured after vaccination in the clinical trial. Results show that ≥3 HLA class I binding peptides predict the CD8+ T cell reactivity and ≥4 HLA class II binding peptides predict the CD4+ T cell reactivity.
Figure 5B:
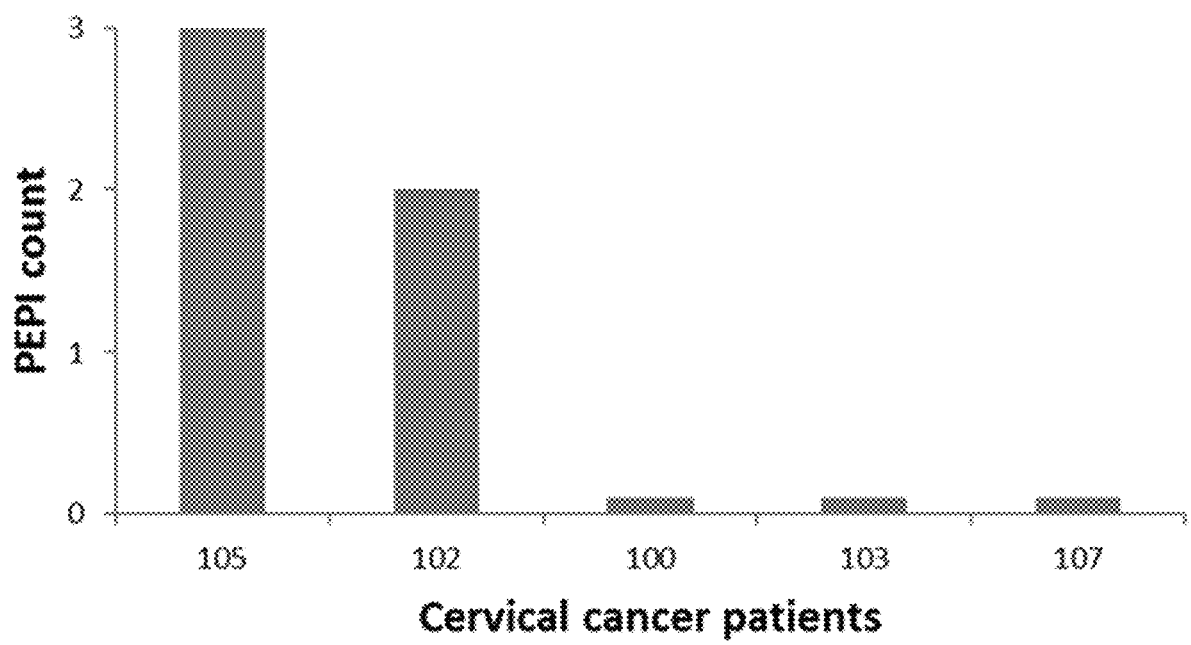
Figure 5C:
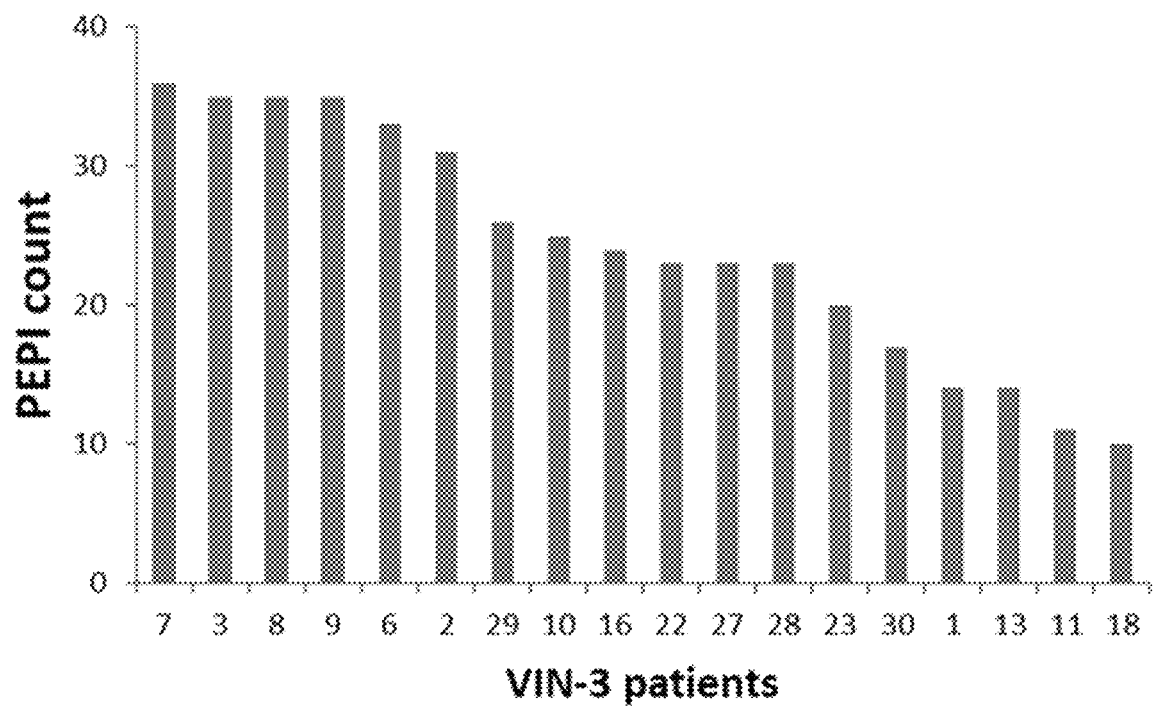
Figure 5D:
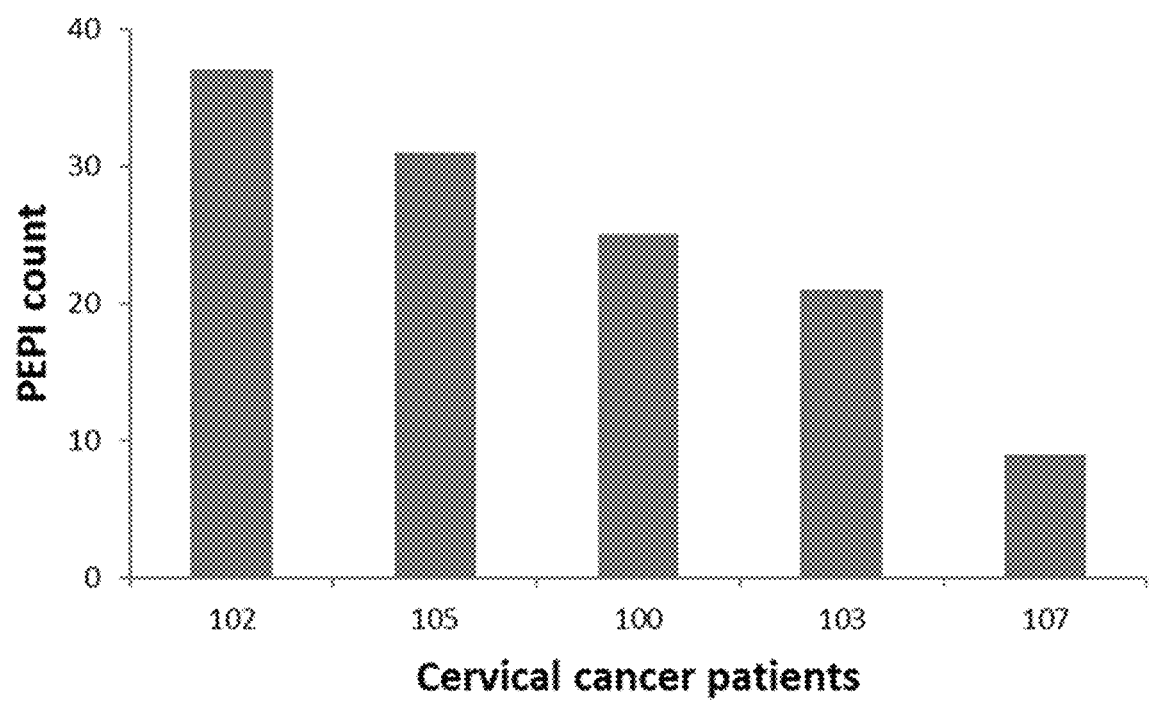
Figure 6:
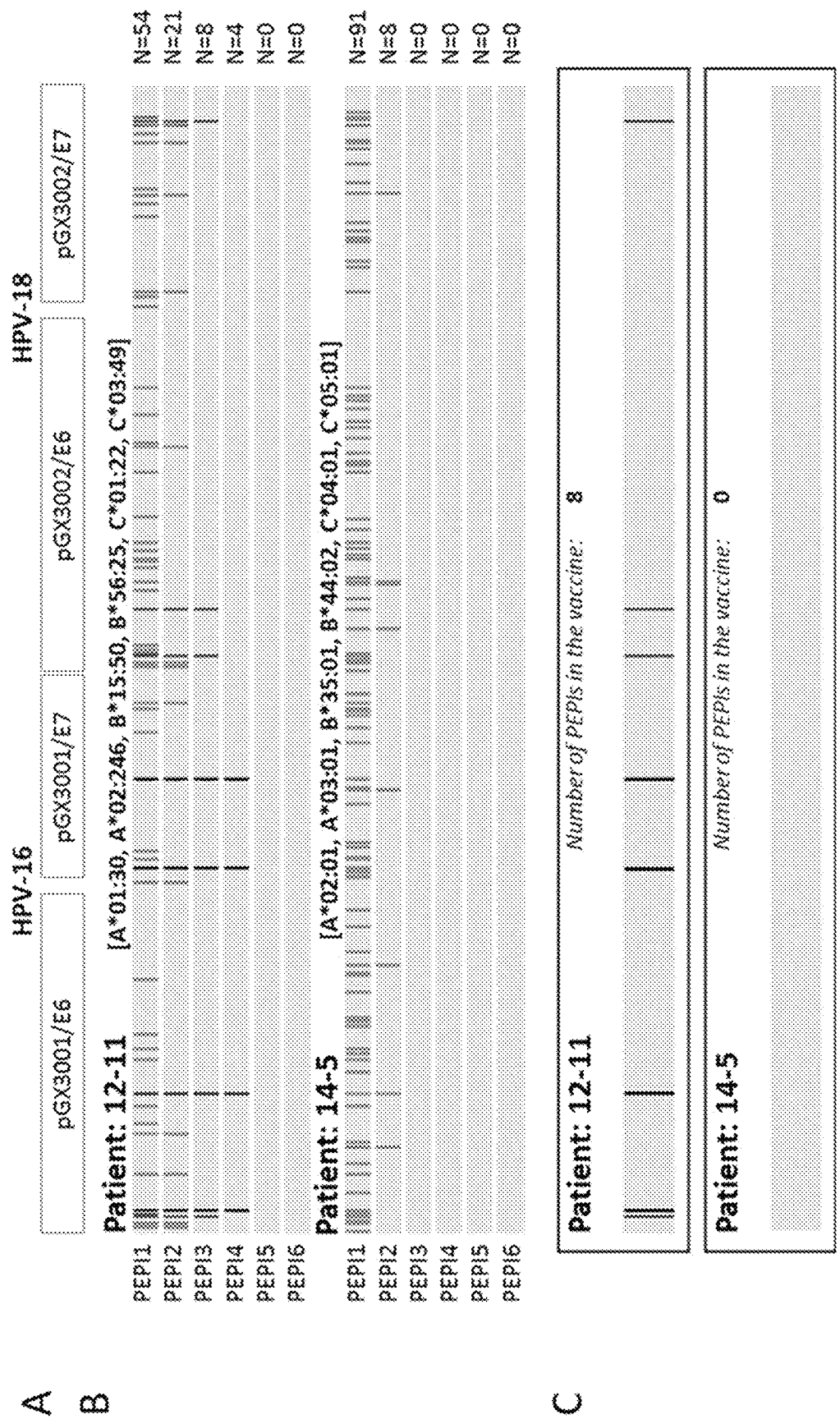
FIG. 6—The multiple HLA class I binding peptides that define the HPV vaccine specific T cell response set of 2 patients. Panel A: Four HPV antigens in the HPV vaccine. Boxes represent the length of the amino acid sequences from the N terminus to the C terminus. Panel B: Process to identify the multiple HLA binding peptides of two patients: HLA sequences of the patients labelled as 4-digit HLA genotype right from the patient's ID. The location of the 1$^{st}$ amino acid of the 54 and 91 epitopes that can bind to the patient 12-11 and patient 14-5 HLAs (PEPI1+) respectively are depicted with lines. PEPI2 represents the peptides selected from PEPI1+s that can bind to multiple HLAs of a patient (PEPI2+). PEPI3 represent peptides that can bind to ≥3 HLAs of a patient (PEPI3+). PEPI4 represent peptides that can bind to ≥4 HLAs of a patient (PEPI4+). PEPI5 represent peptides that can bind to ≥5 HLAs of a patient (PEPI5+). PEPI6 represent peptides that can bind to 6 HLAs of a patient (PEPI6). Panel C: The DNA vaccine specific PEPI3+ set of two patients characterizes their vaccine specific T cell responses.

ROC analysis determined the diagnostic accuracy, using the PEPI3+ count as cut-off values (FIG. 2). The AUC value=0.73. For ROC analysis an AUC of 0.7 to 0.8 is generally considered as fair diagnostic.

A PEPI3+ count of at least 1 (≥1 PEPI3+) best predicted a CTL response in the test dataset (Table 8). This result confirmed the threshold determined during the training (Table 5).

TABLE 8

Confirmation of the ≥1 PEPI3+ threshold to predict likely CTL responders in the test/validation dataset.

| | PEPI3+ Count | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Sensitivity: | 0.75 | 0.52 | 0.26 | 0.23 | 0.15 | 0.13 | 0.08 | 0.05 | 0 | 0 | 0 | 0 |
| 1-Specificity: | 0.45 | 0.15 | 0.05 | 0 | 0 | 0 | 0 | 0 | 0 | 0 | 0 | 0 |

Example 4—the ≥1 PEPI3+ Test Predicts CD8+ CTL Reactivities

The ≥1 PEPI3+ Test was compared with a previously reported method for predicting a specific human subject's CTL response to peptide antigens.

The HLA genotypes of 28 cervical cancer and VIN-3 patients that received the HPV-16 synthetic long peptide vaccine (LPV) in two different clinical trials were determined from DNA samples[8][9][10]. The LPV consists of long peptides covering the HPV-16 viral oncoproteins E6 and E7. The amino acid sequence of the LPV was obtained from these publications. The publications also report the T cell responses of each vaccinated patient to pools of overlapping peptides of the vaccine.

For each patient epitopes (9 mers) of the LPV that are presented by at least three patient class I HLA (PEPI3+s) were identified and their distribution among the peptide pools was determined. Peptides that comprised at least one PEPI3+(≥1 PEPI3+) were predicted to induce a CTL response. Peptides that comprised no PEPI3+ were predicted not to induce a CTL response.

Figure 3A:
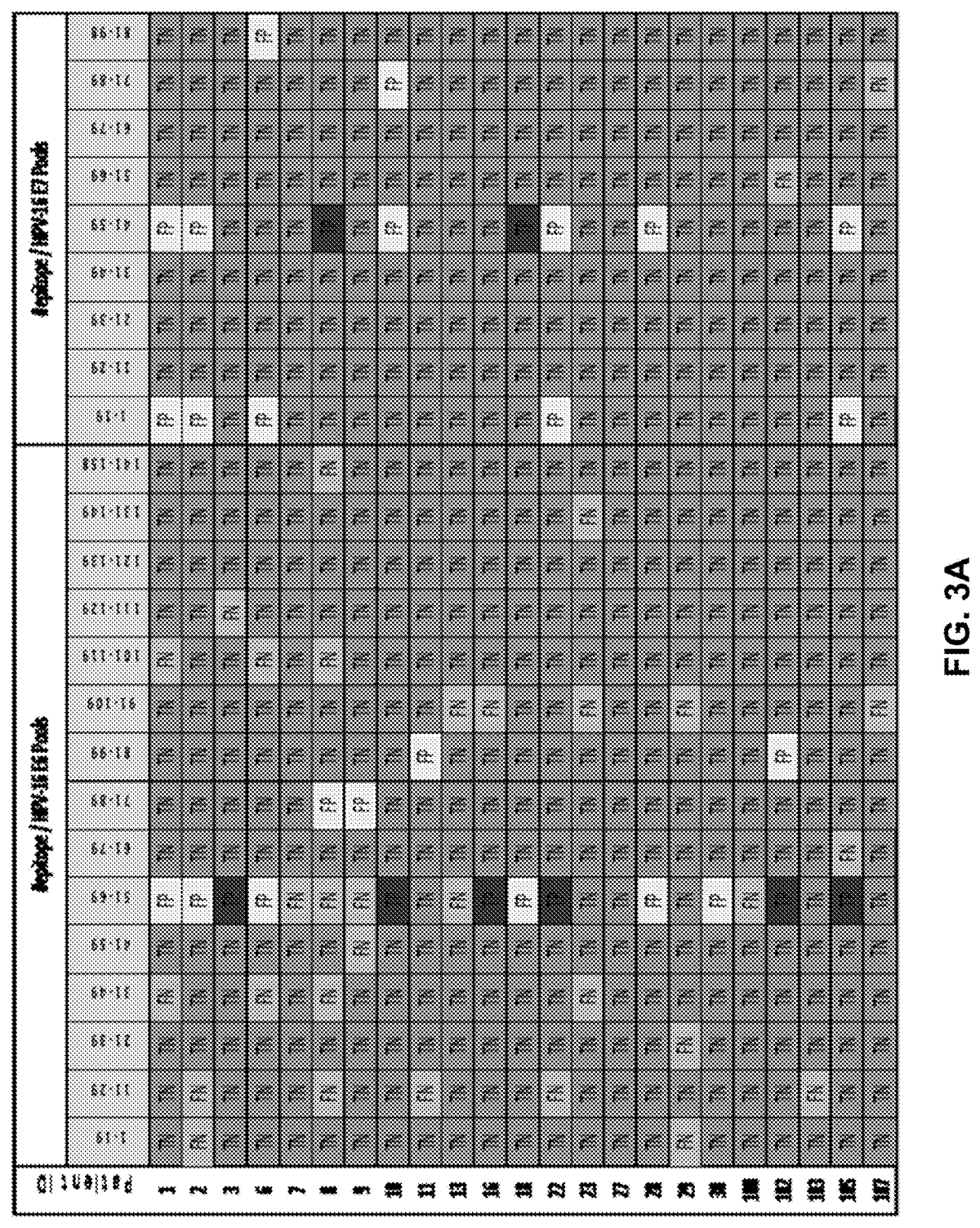

The ≥1 PEPI3+ Test correctly predicted 489 out of 512 negative CTL responses and 8 out of 40 positive CTL responses measured after vaccination (FIG. 3A). Overall, the agreement between the ≥1 PEPI3+ Test and experimentally determined CD8+ T cell reactivity was 90% (p<0.001).

Figure 3B:
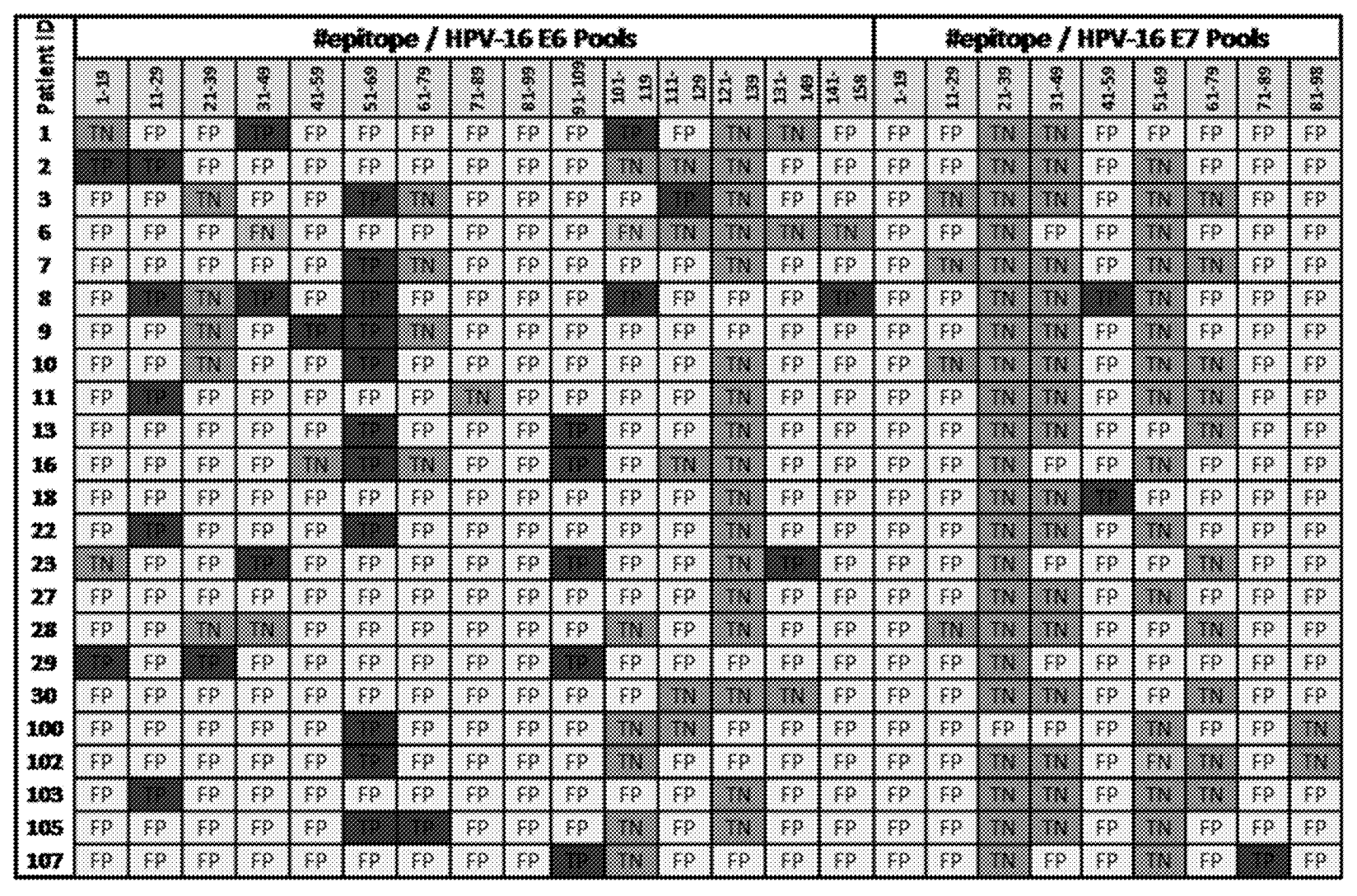

For each patient the distribution among the peptide pools of epitopes that are presented by at least one patient class I HLA (≥1 PEPI1+, ELLA restricted epitope prediction, prior art method) was also determined. ≥1 PEPI1+ correctly predicted 116 out of 512 negative CTL responses and 37 out of 40 positive CTL responses measured after vaccination (FIG. 3B). Overall, the agreement between the HLA restricted epitope prediction (≥1 PEPI1+) and CD8+ T cell reactivity was 28% (not significant).

Example 5—Prediction of HLA Class II Restricted CD4+ Helper T Cell Epitopes

The 28 cervical cancer and VIN-3 patients that received the HPV-16 synthetic long peptide vaccine (LPV) in two different clinical trials (as detailed in Example 4) were investigated for CD4+ T helper responses following LPV vaccination (FIGS. 4A-B). The sensitivity of the prediction of HLA class II restricted epitopes was 78%, since the State of Art tool predicted 84 positive responses (positive CD4+ T cell reactivity to a peptide pool for a person's DP alleles) out of 107 (sensitivity=78%). The specificity was 22% since it could rule out 7 negative responses out of 31. Overall, the agreement between HLA-restricted class II epitope prediction and CD4+ T cell reactivity was 66%, which was statistically not significant.

Example 6—the ≥1 PEPI3+ Test Predicts T Cell Responses to Full Length LPV Polypeptides Using the same reported studies as Examples 4 and 5, the ≥1 PEPI3+ Test was used to predict patient CD8+ and CD4+ T cell responses to the full length E6 and E7 polypeptide antigens of the LPV vaccine. Results were compared to the experimentally determined responses were reported. The Test correctly predicted the CD8+ T cell reactivity (PEPI3+) of 11 out of 15 VIN-3 patients with positive CD8+ T cell reactivity test results (sensitivity 73%, PPV 85%) and of 2 out of 5 cervical cancer patients (sensitivity 40%, PPV 100%). The CD4+ T cell reactivities (PEPI4+) were correctly predicted 100% both of VIN-3 and cervical cancer patients (FIG. 5).

Class I and class II HLA restricted PEPI3+ count was also observed to correlate with the reported clinical benefit to LPV vaccinated patients. Patients with higher PEPI3+ counts had either complete or partial response already after 3 months.

Example 7—Case Study pGX3001 is an HPV16 based DNA vaccine containing full length E6 and E7 antigens with a linker in between. pGX3002 is an HPV18 based DNA vaccine containing full length E6 and E7 antigens with a linker in between. A Phase II clinical trial investigated the T cell responses of 17 HPV-infected patients with cervical cancer who were vaccinated with both pGX3001 and pGX3002 (VGX-3100 vaccination)[1].

FIGS. 5A-D and FIG. 6 shows for two illustrative patients (patient 12-11 and patient 14-5) the position of each epitope (9 mer) presented by at least 1 (PEPI1+), at least 2 (PEPI2+), at least 3 (PEPI3+), at least 4 (PEPI4+), at least 5 (PEPI5+), or all 6 (PEPI6) class I HLA of these patients within the full length sequence of the two HPV-16 and two HPV-18 antigens.

Patient 12-11 had an overall PEPI1+ count of 54 for the combined vaccines (54 epitopes presented by one or more class I HLA). Patient 14-5 had a PEPI1+ count of 91. Therefore patient 14-5 has a higher PEPI1+ count than patient 12-11 with respect to the four HPV antigens. The PEPI1+s represent the distinct vaccine antigen specific HLA restricted epitope sets of patients 12-11 and 14-5. Only 27 PEPI1+s were common between these two patients.

For the PEPI3+ counts (number of epitopes presented by three or more patient class I HLA), the results for patients 12-11 and 14-5 were reversed. Patient 12-11 had a PEPI3+ count of 8, including at least one PEPI3+ in each of the four HPV16/18 antigens. Patient 14-5 had a PEPI3+ count of 0.

The reported immune responses of these two patients matched the PEPI3+ counts, not the PEPI1+ counts. Patient 12-11 developed immune responses to each of the four antigens post-vaccination as measured by ELISpot, whilst patient 14-5 did not develop immune responses to any of the four antigens of the vaccines. A similar pattern was observed when the PEPI1+ and PEPI3+ sets of all 17 patients in the trial were compared. There was no correlation between the PEPI1+ count and the experimentally determined T cell responses reported from the clinical trial. However, correlation between the T cell immunity predicted by the ≥1 PEPI3+ Test and the reported T cell immunity was observed. The ≥1 PEPI3+ Test predicted the immune responders to HPV DNA vaccine.

Moreover, the diversity of the patient's PEPI3+ set resembled the diversity of T cell responses generally found in cancer vaccine trials. Patients 12-3 and 12-6, similar to patient 14-5, did not have PEPI3+s predicting that the HPV vaccine could not trigger T cell immunity. All other patients had at least one PEPI3 predicting the likelihood that the HPV vaccine can trigger T cell immunity. 11 patients had multiple PEPI3+ predicting that the HPV vaccine likely triggers polyclonal T cell responses. Patients 15-2 and 15-3 could mount high magnitude T cell immunity to E6 of both HPV, but poor immunity to E7. Other patients 15-1 and 12-11 had the same magnitude response to E7 of HPV18 and HPV16, respectively.

Example 8—Design of a Model Population for Conducting in Silico Trials and Identifying Candidate Precision Vaccine Targets for Large Population An in silico human trial cohort of 433 subjects with complete 4-digit HLA class I genotype (2×HLA-A*xx:xx; 2×HLA-B*xx:xx; 2×HLA-C*xx:xx) and demographic information was compiled. This Model Population has subjects with mixed ethnicity having a total of 152 different HLA alleles that are representative for >85% of presently known allele G-groups.

A database of a "Big Population" containing 7,189 subjects characterized with 4-digit HLA genotype and demographic information was also established. The Big Population has 328 different HLA class I alleles. The HLA allele distribution of the Model Population significantly correlated with the Big Population (Table 9) (Pearson p<001). Therefore the 433 patient Model Population is representative for a 16 times larger population.

The Model Population is representative for 85% of the human race as given by HLA diversity as well as HLA frequency.

TABLE 9

Statistical analysis of HLA distributions in "Model Population" vs. "Big Population".

| Group name 1 | Group name 2 | Pearson R value | Correlation | P Value |
|---|---|---|---|---|
| 433 Model Population | 7,189 Big Population | 0.89 | Strong | P < 0.001 |

Example 9—In Silico Trials Based on the Identification of Multiple HLA Binding Epitopes Predict the Reported T Cell Response Rates of Clinical Trials The objective of this study was to determine whether a model population, such as the one described in Example 8, may be used to predict CTL reactivity rates of vaccines, i.e. used in an in silico efficacy trials.

Figure 7:
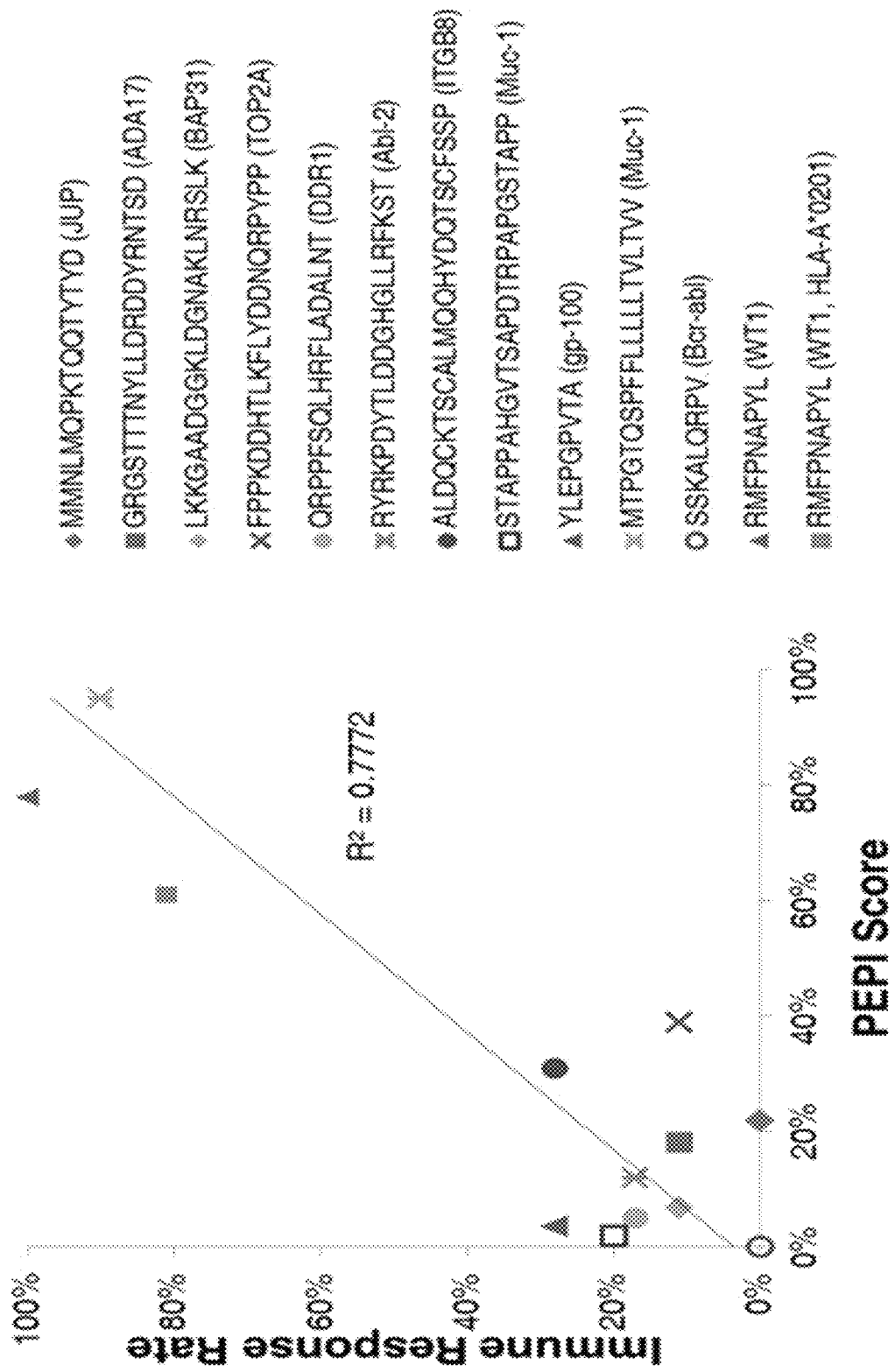
FIG. 7—Correlation between the ≥1 PEPI3+ Score and CTL response rates of peptide targets determined in clinical trials.

Twelve peptide vaccines derived from cancer antigens that induced T cell responses in a subpopulation of subjects were identified from peer reviewed publications. These peptides have been investigated in clinical trials enrolling a total of 172 patients (4 ethnicities). T cell responses induced by the vaccine peptides have been determined from blood specimens and reported. The immune response rate as the percentage of study subjects with positive T cell responses measured in the clinical trials was determined (FIG. 7).

TABLE 10

Clinical trials conducted with peptide vaccines.

| Peptide vaccines | Source antigen | Peptide length | T cell assay | Pop. (n) | Ethnicity | Ref |
|---|---|---|---|---|---|---|
| MMNLMQPKTQQTYTYD | JUP | 16 mer | Multimer staining | 18 | Canadian | 12 |
| GRGSTTTNYLLDRDDYRNTSD | ADA17 | 21 mer | Multimer staining | 18 | Canadian | 12 |
| LKKGAADGGKLDGNAKLNRSLK | BAP31 | 22 mer | Multimer staining | 18 | Canadian | 12 |
| FPPKDDHTLKFLYDDNQRPYPP | TOP2A | 22 mer | Multimer staining | 18 | Canadian | 12 |
| RYRKPDYTLDDGHGLLRFKST | Ab1-2 | 21 mer | Multimer staining | 18 | Canadian | 12 |
| QRPPFSQLHRFLADALNT | DDR1 | 18 mer | Multimer staining | 18 | Canadian | 12 |
| ALDQCKTSCALMQQHYDQTSCFSSP | ITGB8 | 25 mer | Multimer staining | 18 | Canadian | 12 |

TABLE 10-continued

Clinical trials conducted with peptide vaccines.

| Peptide vaccines | Source antigen | Peptide length | T cell assay | Pop. (n) | Ethnicity | Ref |
|---|---|---|---|---|---|---|
| STAPPAHGVTSAPDTRPAPGSTAPP | MUC-1 | 25 mer | Proliferation | 80 | Canadian | 13 |
| YLEPGPVTA | gp 100 | 9 mer | Tetramer | 18 | U.S. | 14 |
| MTPGTQSPFFLLLLLTVLTVV | MUC-1 | 21 mer | Cytotoxicity | 10 | Israeli | 15 |
| SSKALQRPV | Bcr-Abl | 9 mer | ELISPOT | 4 | U.S. | 16 |
| RMFPNAPYL | WT-1 | 9 mer | Multimer staining | 24 | U.S. | 17 |
| RMFPNAPYL (HLA-A*0201) | WT-1 | 9 mer | Cytokine staining | 18 | CEU | 18 |

The 12 peptides were investigated with the ≥1 PEPI3+ Test in each of the 433 subjects of the Model Population described in Example 8. The "≥1 PEPI3+ Score" for each peptide was calculated as the proportion of subjects in the Model Population having at least one vaccine derived epitope that could bind to at least three subject-specific HLA class I (≥1 PEPI3+). If the corresponding clinical trial stratified patients for HLA allele selected population, the Model Population was also filtered for subjects with the respective allele(s) (Example: WT1, HLA-A*0201).

The experimentally determined response rates reported from the trials were compared with the ≥1 PEPI3+ Scores. The Overall Percentage of Agreements (OPA) were calculated on the paired data (Table 11). A linear correlation between ≥1 PEPI3+ Score and response rate ($R^2$=0.77) was observed (FIG. 7). This result shows that the identification of peptides predicted to bind to multiple HLAs of an individual is useful to predict in silico the outcome of clinical trials.

TABLE 11

Comparison of ≥1 PEPI3+ Scores and CTL response rates of 12 peptide vaccines.

| Peptide vaccine | Source antigen | Response rate (Clinical Trials) | ≥1 PEPI3+ Score* (Model Population) | OPA |
|---|---|---|---|---|
| MMNLMQPKTQQTYTYD | JUP | 0% | 22% | NA |
| GRGSTTTNYLLDRDDYRNTSD | ADA17 | 11% | 18% | 61% |
| LKKGAADGGKLDGNAKLNRSLK | BAP31 | 11% | 7% | 64% |
| FPPKDDHTLKFLYDDNQRPYPP | TOP2A | 11% | 39% | 28% |
| RYRKPDYTLDDGHGLLRFKST | Abl-2 | 17% | 12% | 71% |
| QRPPFSQLHRFLADALNT | DDR1 | 17% | 5% | 29% |
| ALDQCKTSCALMQQHYDQTSCFSSP | ITGB8 | 28% | 31% | 90% |
| STAPPAHGVTSAPDTRPAPGSTAPP | MUC-1 | 20% | 2% | 10% |
| YLEPGPVTA | gp100 | 28% | 4% | 14% |
| MTPGTQSPFFLLLLLTVLTVV | MUC-1 | 90% | 95% | 95% |
| SSKALQRPV | Bcr-Abl | 0% | 0% | 100% |
| RMFPNAPYL | WT-1 | 100% | 78% | 78% |
| RMFPNAPYL (HLA-A*0201) | WT-1 | 81% | 61% | 75% |

*% subjects in the Model Population with ≥1 vaccine derived PEPI3+

Example 10. In Silico Trials Based on the Identification of Multiple HLA Binding Epitopes Predict the Reported T Cell Response Rates of Clinical Trials II Nineteen clinical trials with published immune response rates (IRR) conducted with peptide or DNA based vaccines were identified (Table 19). These trials involved 604 patients (9 ethnicities) and covered 38 vaccines derived from tumor and viral antigens. Vaccine antigen specific CTL responses were measured in each study patient and the response rate in the clinical study populations was calculated and reported.

Figure 8:
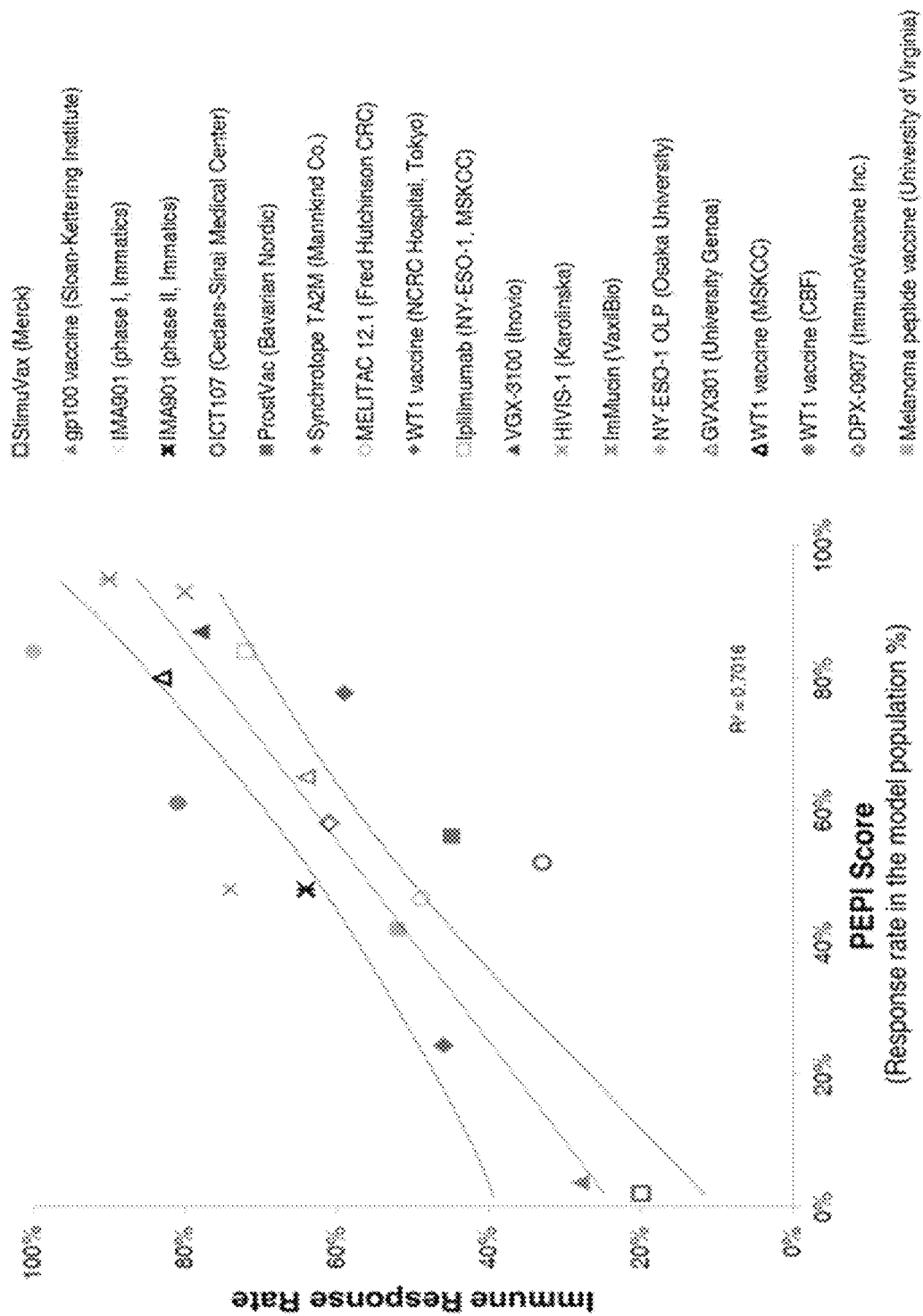
FIG. 8—Correlation between the ≥1 PEPI3+ Score and the clinical Immune Response Rate (IRR) of immunotherapy vaccines. Dashed lines: 95% confidence band.

Each vaccine peptide of the 19 clinical trials was investigated with the ≥1 PEPI3+ Test in each subject of the Model Population. The ≥1 PEPI3+ Score for each peptide was calculated as the proportion of subjects in the Model Population having at least one vaccine derived PEPI3+. The experimentally determined response rates reported from the trials were compared with the PEPI Scores, as in Example 9 (Table 20). A linear correlation between the response rate and ≥1 PEPI3+ Score ($R^2$=0.70) was observed (FIG. 8). This result confirms that the identification of peptides predicted to bind to multiple HLAs of an individual can predict T cell responses of subjects, and in silico trials can predict the outcome of clinical trials.

TABLE 12

Response rates published in clinical trials.

| Immuno-therapy | Type | CTL assay | Pop. (n) | Race/Ethnicity | Ref. |
|---|---|---|---|---|---|
| StimuVax | peptide | Proliferation | 80 | Canadian | 13 |
| gp100 vaccine | DNA | Tetramer | 18 | US | 14 |
| IMA901 phase I | peptide | ELISPOT | 64 | CEU | 19 |
| IMA901 phase II | peptide | Multimer staining | 27 | CEU | |
| ICT107 | peptide | ICC | 15 | US | 20 |
| ProstVac | DNA | ELISPOT | 32 | CEU87%, Afr. Am.12%, Hisp.1% | 21 |
| Synchrotope TA2M | DNA | Tetramer | 26 | US | 22 |
| MELITAC 12.1 | peptide | ELISPOT | 167 | US | 23 |
| WT1 vaccine | peptide | Tetramer | 22 | Japanese | 24 |
| Ipilimumab (NY-ESO-1) | check-point inhibitor** | ICC | 19 | US | 5 |
| VGX-3100 | DNA | ELISPOT | 17 | US | 1 |
| HIVIS-1 | DNA | ELISPOT | 12 | CEU98%, Asian1%, Hisp.1% | 2 |
| ImMucin | peptide | Cytotoxicity | 10 | Israeli | 15 |
| NY-ESO-1 OLP | peptide | IFN-gamma | 7 | Japanese | 7 |
| GVX301 | peptide | Proliferation | 14 | CEU | 25 |
| WT1 vaccine | peptide | ELISPOT | 12 | US | 26 |
| WT1 vaccine | peptide | ICC | 18 | CEU | 18 |
| DPX-0907* | peptide | Multimer staining | 18 | Canadian | 12 |
| Melanoma peptide vaccine | peptide | ELISPOT | 26 | White | 27 |

TABLE 13

Linear correlation between PEPI Score and response rate ($R^2$ = 0.7).

| Immunotherapy | Clinical Trial Response Rate | ≥1PEPI3 + Score* | OPA |
|---|---|---|---|
| StimuVax (failed to show efficacy in Phase III) | 20% | 2% | 10% |
| gp100 vaccine | 28% | 4% | 14% |
| IMA901 phase I | 74% | 48% | 65% |
| IMA901 phase II | 64% | 48% | 75% |
| ICT107 | 33% | 52% | 63% |
| ProstVac | 45% | 56% | 80% |
| Synchrotope TA2M | 46% | 24% | 52% |

TABLE 13-continued

Linear correlation between PEPI Score and response rate ($R^2$ = 0.7).

| Immunotherapy | Clinical Trial Response Rate | ≥1PEPI3 + Score* | OPA |
|---|---|---|---|
| MELITAC 12.1 | 49% | 47% | 96% |
| WT1 vaccine | 59% | 78% | 76% |
| Ipilimumab (NY-ESO-1*) | 72% | 84% | 86% |
| VGX-3100 | 78% | 87% | 90% |
| HIVIS-1 | 80% | 93% | 86% |
| ImMucin | 90% | 95% | 95% |
| NY-ESO-1 OLP | 100% | 84% | 84% |
| GVX301 | 64% | 65% | 98% |
| WT1 vaccine | 83% | 80% | 96% |
| WT1 vaccine | 81% | 61% | 75% |
| DPX-0907 | 61% | 58% | 95% |
| Melanoma peptide vaccine | 52% | 42% | 81% |

*% subjects in the Model Population with ≥ 1 vaccine derived PEPI3+

Example 11—in Silico Trial Based on the Identification of Multiple HLA Binding Epitopes in a Multi-Peptide Vaccine Predict the Repotted Clinical Trial Immune Response Rate IMA901 is a therapeutic vaccine for renal cell cancer (RCC) comprising 9 peptides derived from tumor-associated peptides (TUMAPs) that are naturally presented in human cancer tissue. A total of 96 HLA-A*02+ subjects with advanced RCC were treated with IMA901 in two independent clinical studies (phase I and phase II). Each of the 9 peptides of IMA901 have been identified in the prior art as HLA-A2-restricted epitopes. Based on currently accepted standards, they are all strong candidate peptides to boost T cell responses against renal cancer in the trial subjects, because their presence has been detected in renal cancer patients, and because the trial patients were specifically selected to have at least one HLA molecule capable of presenting each of the peptides.

For each subject in the Model population how many of the nine peptides of the IMA901 vaccine were capable of binding to three or more HLA was determined. Since each peptide in the IMA901 vaccine is a 9 mer this corresponds to the PEPI3+ count. The results were compared with the immune response rates reported for the Phase I and Phase II clinical trials (Table 14).

TABLE 14

Immune Response Rates in the Model Population and in two clinical trials to IMA901

| Immune responses to TUMAPs | Model Population (HLA-A2+) (n = 180) | Phase I (n = 27)* | Phase II (n = 64)* |
|---|---|---|---|
| No peptide | 39% | 25% | 36% |
| 1 peptide | 34% | 44% | 38% |
| ≥2 peptides | 27% (MultiPEPI Score) | 29% | 26% |
| ≥3 peptides | 3% | ND | 3% |

*No of patients evaluated for immune responses

The phase I and phase II study results show the variability of the immune responses to the same vaccine in different trial cohorts. Overall, however, there was a good agreement between response rates predicted by the ≥2 PEPI3+ Test and the reported clinical response rates.

In a retrospective analysis, the clinical investigators of the trials discussed above found that subjects who responded to multiple peptides of the IMA901 vaccine were significantly (p=0.019) more likely to experience disease control (stable disease, partial response) than subjects who responded only to one peptide or had no response. 6 of 8 subjects (75%) who responded to multiple peptides experienced clinical benefit in the trial, in contrast to 14% and 33% of 0 and 1 peptide responders, respectively. The randomized phase II trial confirmed that immune responses to multiple TUMAPs were associated with a longer overall survival.

Since the presence of PEPIs accurately predicted responders to TUMAPs, clinical responders to IMA901 are likely patients who can present ≥2 PEPIs from TUMAPs. This subpopulation is only 27% of HLA-A*02 selected patients, and according to the clinical trial result, 75% of this subpopulation is expected to experience clinical benefit. The same clinical results suggest that 100% of patients would experience clinical benefit if patient selection is based on ≥3 PEPIs from TUMAPs, albeit this population would represent only 3% of the HLA-A*02 selected patient population. These results suggest that the disease control rate (stable disease or partial response) is between 3% and 27% in the patient population which was investigated in the IMA901 clinical trials. In the absence of complete response, only a portion of these patients can experience survival benefit.

These findings explain the absence of improved survival in the Phase III IMA901 clinical trial. These results also demonstrated that HLA-A*02 enrichment of the study population was not sufficient to reach the primary overall survival endpoint in the Phase III IMA901 trial. As the IMA901 trial investigators noted, there is a need for the development of a companion diagnostic (CDx) to select likely responders to peptide vaccines. These findings also suggest that selection of patients with ≥2 TUMAP specific PEPIs may provide sufficient enrichment to demonstrate significant clinical benefit of IMA901.

Example 12—in Silico Trial Based on the Identification of Vaccine-Derived Multiple HLA Binding Epitopes Predict Reported Experimental Clinical Response Rates A correlation between the ≥2 PEPI3+ Score of immunotherapy vaccines determined in the Model Population described in Example 8 and the reported Disease Control Rate (DCR, proportion of patients with complete responses and partial responses and stable disease) determined in clinical trials was determined.

Seventeen clinical trials conducted with peptide- and DNA-based cancer immunotherapy vaccines that have published Disease Control Rates (DCRs) or objective response rate (ORR) were identified from peer reviewed scientific journals (Table 15). These trials involved 594 patients (5 ethnicities) and covered 29 tumor and viral antigens. DCRs were determined according to the Response Evaluation Criteria in Solid Tumors (RECIST), which is the current standard for clinical trials, in which clinical responses are based on changes in maximum cross-sectional dimensions[42, 43, 44]. In case there was no available DCR data, objective response rate (ORR) data was used, which is also defined according to the RECIST guidelines.

Figure 9:
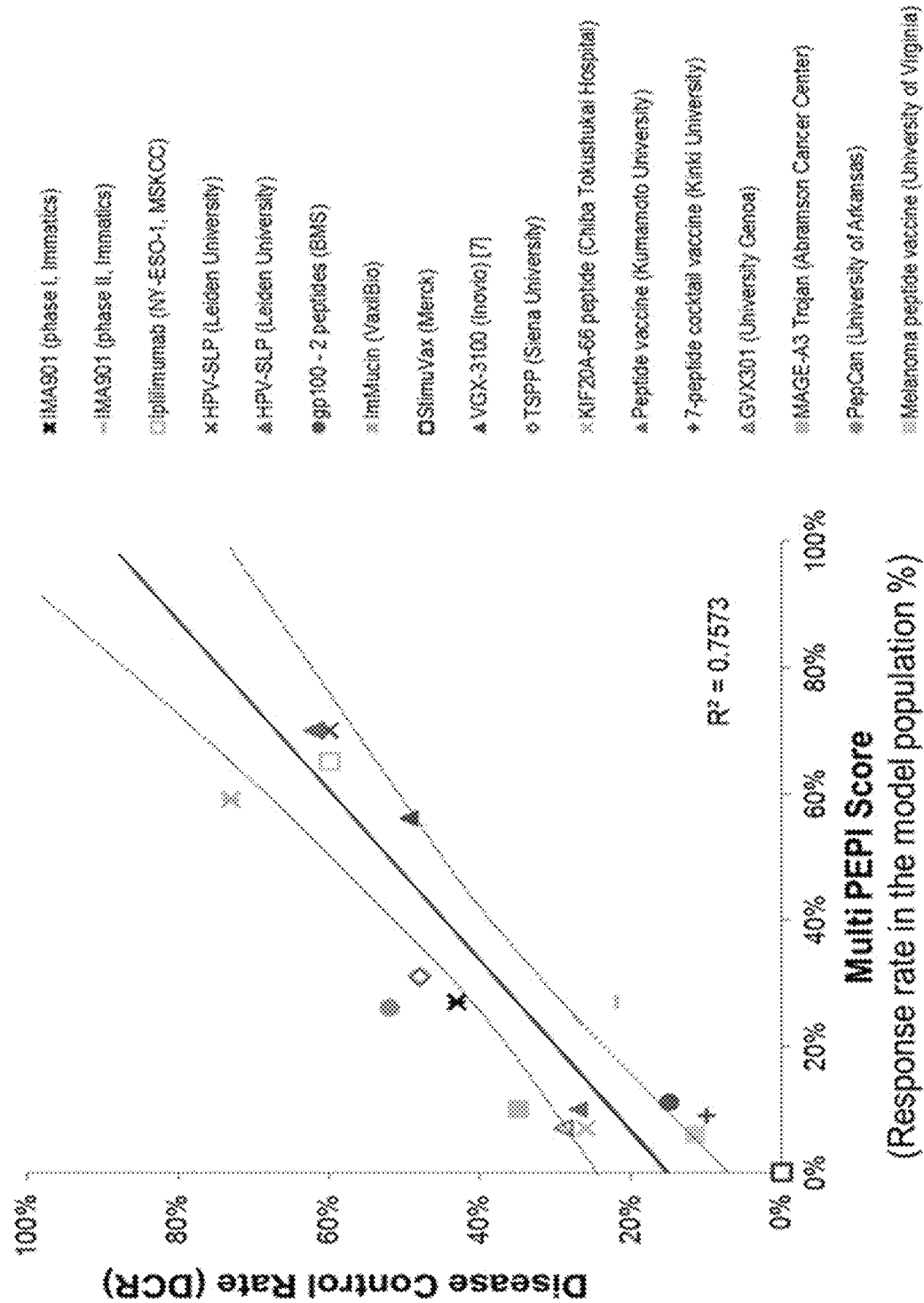
FIG. 9—Correlation between the ≥2 PEPI3+ Score and Disease Control Rate (DCR) of immunotherapy vaccines. Dashed lines: 95% confidence band.

Table 16 compares the ≥2 PEPI3+ Score for each vaccine in the Model Population and the published DCR or ORR. A correlation between the predicted and measured DCR was observed providing further evidence that not only the immunogenicity but also the potency of cancer vaccines depends on the multiple HLA sequences of individuals ($R2=0.76$) (FIG. 9).

TABLE 15

Clinical trials selected for Disease Control Rate (DCR) prediction.

| Immuno-therapy | Antigen | Sponsor | Disease | Pop. (n) | Study pop./ Ethnicity | HLA restriction | Adm. form | Dose (mg) | Dosing schedule | Assessment time (weeks) | Ref. |
|---|---|---|---|---|---|---|---|---|---|---|---|
| IMA901 phase I | 9 TAAs | Immatics | Renal cell cancer | 28 | CEU | A02 | i.d. | 0.4 | 8× in 10 wks | 12 | 19 |
| IMA901 phase II | 9 TAAs | Immatics | Renal cell cancer | 68 | CEU | A02 | i.d | 0.4 | 7× in 5 wks then 10× 3 wks | 24 | 19 |
| Ipilimumab | NY-ESO-1 | MSKCC | Melanoma | 19 | US | no | i.v. | 0.3 3 10 | 4× every 3 wks | 24 | 5 |
| HPV-SLP* | HPV-16 E6, E7 | Leiden University | VIN | 20 | CEU | no | s.c. | 0.3 | 3× every 3 wks | 12 | 9 |
| HPV-SLP* | | Leiden University | HPV-related cervical cancer | 5 | CEU | no | s.c. | 0.3 | 3× every 3 wks | 12 (OR) | 10 |
| gP100-2 peptides* | gp100 | BMS | Melanoma | 136 | US | A*0201 | s.c. | 1 | 4× every 3 wks | 12 | [2]8 |
| Immucin | Muc-1 | VaxilBio | Myeloma | 15 | Israeli | no | s.c. | 0.1 | 6× every 2 wks | 12** | 29 |
| StimuVax | Muc-1 | Merck | NSCLC | 80 | Canadian | no | s.c. | 1 | 8× wkly then every 6 wks | 12 | 13, 30 |
| VGX-3100 | HPV-16&18 | Inovio | HPV-related cervical cancer | 125 | US | no | i.m. | 6 | 0, 4, 12 wks | 36 | [3]1 |
| TSPP peptide vaccine | Thymidylate synthase | Siena University | CRC, NSCLC, Gallbladder carc., Breast-, Gastric cancer | 21 | CEU | no | s.c. | 0.1 0.2 0.3 | 3 × 3 wks | 12 | 32 |
| KIF20A-66 peptide vaccine* | KIF20A | Chiba Tokushukai Hospital | Metastatic pancreatic cancer | 29 | Japanese | A*2402 | s.c. | 1 3 | 2 cycles 1, 8, 15, 22 days then every 2 wks | 12 (OR) | 33 |

TABLE 15-continued

Clinical trials selected for Disease Control Rate (DCR) prediction.

| Immuno-therapy | Antigen | Sponsor | Disease | Pop. (n) | Study pop./ Ethnicity | HLA restriction | Adm. form | Dose (mg) | Dosing schedule | Assessment time (weeks) | Ref. |
|---|---|---|---|---|---|---|---|---|---|---|---|
| Peptide vaccine* | 3 TAAs | Kumamoto University | HNSCC | 37 | Japanese | A*2402 | s.c. | 1 | 8× wkly then every 4 wks | 12 | [3][4] |
| 7-peptide cocktail vaccine* | 7 TAAs | Kinki University | Metastatic colorectal cancer | 30 | Japanese | A*2402 | s.c. | 1 | Cycles: 5× wkly then 1 wk rest | 10 (OR) | [3][5] |
| GVX301* | hTERT | University Genoa | Prostate and renal cancer | 14 | Japanese | A02 | i.d. | 0.5 | 1, 3, 5, 7, 14, 21, 35, 63 days | 12 | 25 |
| MAGE-A3 Trojan* | MAGE-A3 | Abramson Cancer Center | Multiple myeloma | 26 | US | no | s.c. | 0.3 | 14, 42, 90, 120, 150 days | 24 | [3][6] |
| PepCan | HPV-16 E6 | University of Arkansas | CIN2/3 | 23 | US | no | i.m. | 0.05 0.1 0.25 0.5 | 4 × 3 wks | 24 | [3][7] |
| Melanoma peptide vaccine* | Tyrosinase, gp100 | University of Virginia | Melanoma | 26 | US | A1, A2 or A3 | s.c. | 0.1 | 6 cycles: 0, 7, 14, 28, 35, 42 days | 6 | 27 |

*Montanide ISA51 VG as adjuvant
**Disease response was assessed according to the International Myeloma Working Group response criteria[45]

TABLE 16

The Disease Control Rates (DCRs) and MultiPEPI Scores (predicted DCR) in 17 clinical trials.

| Immunotherapy | DCR | MultiPEPI Score (Predicted DCR) | Overall Percentage of Agreement |
|---|---|---|---|
| IMA901 phase I | 43% | 27% | 61% |
| IMA901 phase II | 22% | 27% | 81% |
| Ipilimumab | 60% | 65% | 92% |
| HPV-SLP | 60% | 70% | 86% |
| HPV-SLP | 62% | 70% | 89% |
| gp100 - 2 peptides | 15% | 11% | 73% |
| Immucin | 73% | 59% | 81% |
| StimuVax | 0% | 0% | 100% |
| VGX-3100 | 50% | 56% | 89% |
| TSPP peptide vaccine | 48% | 31% | 65% |
| KIF20A-66 peptide vaccine | 26% | 7% | 27% |
| Peptide vaccine | 27% | 10% | 37% |
| 7-peptide cocktail vaccine | 10% | 9% | 90% |
| GVX301 | 29% | 7% | 24% |
| MAGE-A3 Trojan | 35% | 10% | 29% |
| PepCan | 52% | 26% | 50% |
| Melanoma peptide vaccine | 12% | 6% | 50% |

Example 13—Breast Cancer Vaccine Design for Large Population and Composition

We used the PEPI3+ Test described above to design peptides for use in breast cancer vaccines that are effective in a large percentage of patients, taking into account the heterogeneities of both tumour antigens and patients' HLAs.

Breast cancer CTAs were identified and ranked based on the overall expression frequencies of antigens found in breast cancer tumor samples as reported in peer reviewed publications (Chen et al. Multiple Cancer/Testis Antigens Are Preferentially Expressed in Hormone-Receptor Negative and High-Grade Breast Cancers. Plos One 2011; 6(3): e17876; Kanojia et al. Sperm-Associated Antigen 9, a Novel Biomarker for Early Detection of Breast Cancer. Cancer Epidemiol Biomarkers Prev 2009; 18(2):630-639; Saini et al. A Novel Cancer Testis Antigen, A-Kinase Anchor Protein 4 (AKAP4) Is a Potential Biomarker for Breast Cancer. Plos One 2013; 8(2): e57095).

Figure 11:
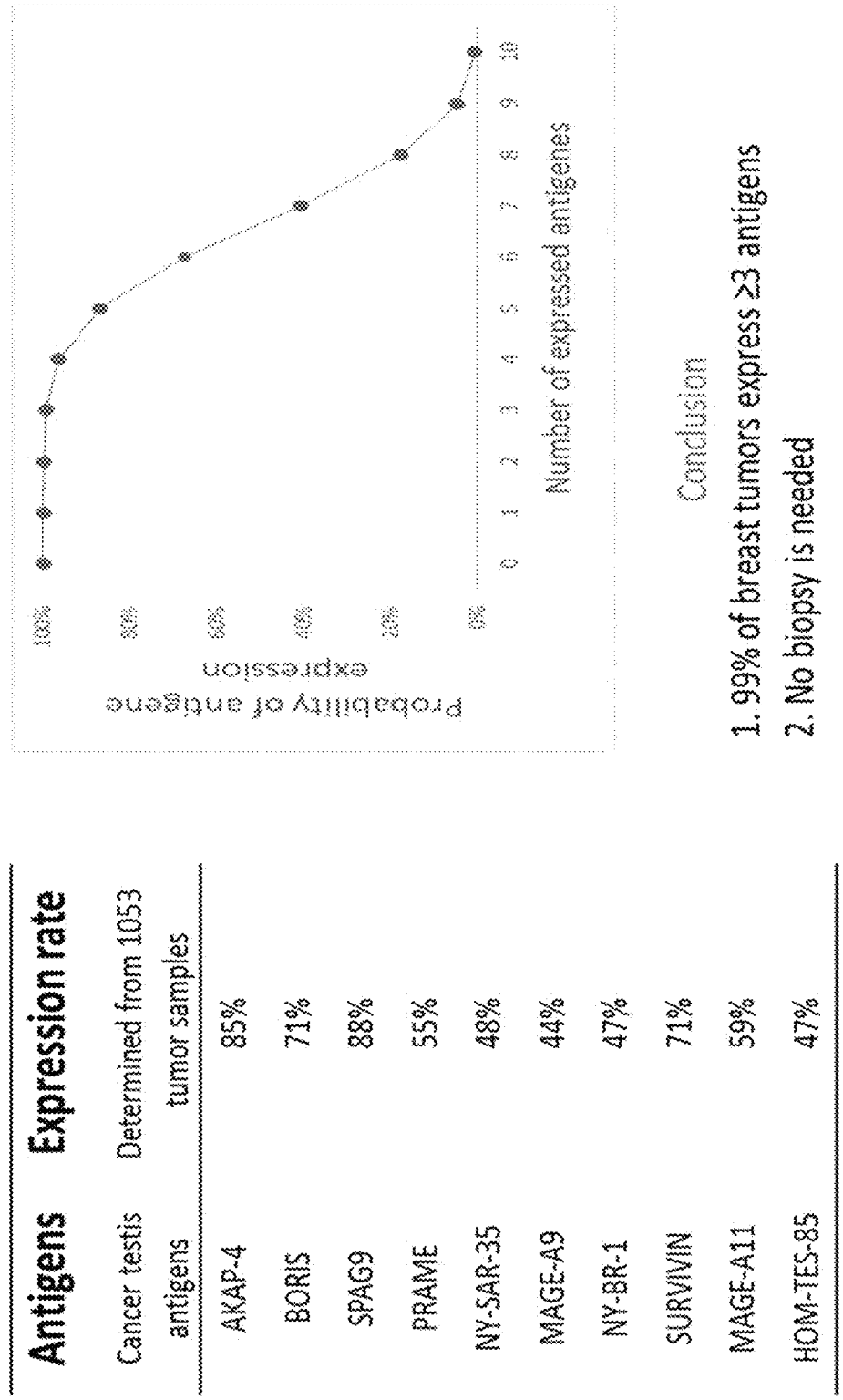
FIG. 11—CTA Expression Curve calculated by analyzing expression frequency data of tumor specific antigens (CTAs) in human breast cancer tissues. (No cell line data were included.)

Based on the ranked expression rate we have selected the most frequently expressed CTA as target antigens for breast cancer vaccine. The expression rates of the selected breast cancer specific CTAs are illustrated in FIG. 11.

Figure 10:
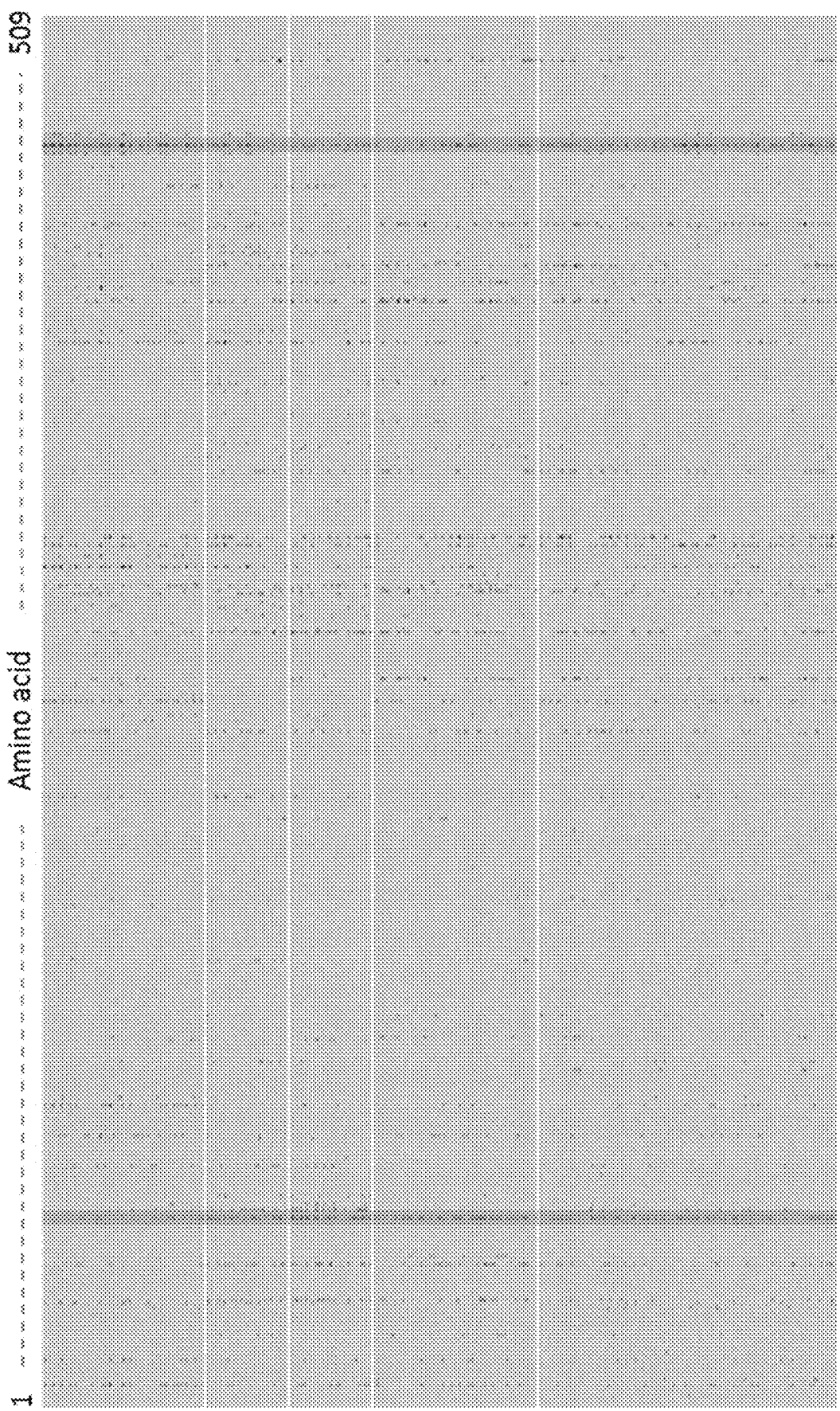
FIG. 10—Peptide hotspot analysis example: PRAME antigen hotspot on 433 patients of the Model Population. On the y axis are the 433 patients of the Model Population, on the x axis is the amino acid sequence of the PRAME antigen (CTA). Each data point represents a PEPI presented by ≥3 HLA class I of one patient starting at the specified amino acid position. The two most frequent PEPIs (called bestEPIs) of the PRAME antigen are highlighted in dark gray (peptide hotspots=PEPI Hotspots).

To select immunogenic peptides from the target CTAs we used the PEPI3+ Test and the Model Population described in Example 8 to identify the 9 mer epitopes (PEPI3+s) that are most frequently presented by at least 3HLAs of the individuals in the Model Population. We refer to these epitopes herein as "bestEPIs". An illustrative example of the "PEPI3+ hotspot" analysis and bestEPI identification is shown in FIG. 10 for the PRAME antigen.

We multiplied the reported expression frequency for each CTA by the frequency of the PEPI3+ hotspots in the Model Population to identify the T cell epitopes (9 mers) that will induce a cytotoxic T cell response against breast cancer antigens in the highest proportion of individuals (Table 17). We then selected 15 mers encompassing each of the selected 9 mers (Table 17). The 15 mers were selected to bind to most ELLA class II alleles of most subjects, using the process described in Example 19 below. These 15 mers can induce both CTL and T helper responses in the highest proportion of subjects.

TABLE 17

BestEPI list (9-mers underlined) for selecting breast cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ T cell specific PEPI4+ within normal donors (n = 400); N% * B%: N% multiplied by B%.

| SEQ ID NO. 9 mer | SEQ ID NO. 15 mer | Antigen | N% | BestEPIs and Optimized 15 mer |  |  |  |
|---|---|---|---|---|---|---|---|
|  |  |  |  | Opt. 15 mer | Opt. Position | B% | HLAII** (CD4) | B% * N% |

| SEQ ID NO. 9 mer | SEQ ID NO. 15 mer | Antigen | N% | Opt. 15 mer | Position | B% | HLAII** (CD4) | B% * N% |
|---|---|---|---|---|---|---|---|---|
| 172 | 195 | PIWIL-2 | 94% | FVASINLTLTKWYSR | 760 | 67% | 93% | 64% |
| 173 | 196 | PIWIL-2 | 94% | RNFYDPTSAMVLQQH | 341 | 60% | 49% | 57% |
| 1 | 41 | AKAP4 | 85% | DQVNIDYLMNRPQNL | 161 | 52% | 46% | 44% |
| 1 | 197 | AKAP4 | 85% | VNIDYLMNRPQNLRL | 163 | 52% | 57% | 44% |
| 174 | 198 | EpCam | 84% | RTYWIIIELKHKARE | 140 | 51% | 100% | 43% |
| 2 | 42 | AKAP4 | 85% | MMAYSDTTMMSDDID | 1 | 49% | 0% | 41% |
| 3 | 43 | BORIS | 71% | MFTSSRMSSFNRHMK | 263 | 57% | 66% | 40% |
| 3 | 199 | BORIS | 71% | VCMFTSSRMSSFNRH | 261 | 57% | 96% | 40% |
| 175 | 200 | HIWI | 100% | HAFDGTILFLPKRLQ | 161 | 39% | 83% | 39% |
| 4 | 201 | AKAP4 | 85% | SDLQKYALGFQHALS | 116 | 46% | 81% | 39% |
| 4 | 44 | AKAP4 | 85% | LQKYALGFQHALSPS | 118 | 46% | 88% | 39% |
| 24 | 64 | SPAG9 | 88% | GTGKLGFSFVRITAL | 1137 | 44% | 94% | 39% |
| 24 | 202 | SPAG9 | 88% | KLGFSFVRITALMVS | 1140 | 44% | 100% | 39% |
| 5 | 45 | SPAG9 | 88% | AQKMSSLLPTMWLGA | 962 | 43% | 69% | 38% |
| 176 | 203 | PIWIL-2 | 94% | YSRVVFQMPHQEIVD | 772 | 40% | 77% | 38% |
| 177 | 204 | HIWI | 100% | GFTTSILQYENSIML | 251 | 37% | 86% | 37% |
| 178 | 205 | PLU-1 | 82% | LRYRYTLDDLYPMMN | 732 | 45% | 84% | 37% |
| 179 | 206 | TSGA10 | 70% | YSSNAYHMSSTMKPN | 653 | 48% | 33% | 34% |
| 180 | 207 | TSGA10 | 70% | LQKVQFEKVSALADL | 494 | 46% | 97% | 32% |
| 181 | 208 | PLU-1 | 82% | NRTSYLHSPFSTGRS | 1321 | 38% | 37% | 31% |
| 6 | 46 | SPAG9 | 88% | GNILDSFTVCNSHVL | 779 | 36% | 4% | 31% |
| 6 | 209 | SPAG9 | 88% | LDSFTVCNSHVLCIA | 782 | 36% | 6% | 31% |
| 7 | 47 | BORIS | 71% | NMAFVTSGELVRHRR | 319 | 44% | 75% | 31% |
| 182 | 210 | ODF-4 | 63% | NSPLPFQWRITHSFR | 63 | 49% | 35% | 30% |
| 183 | 211 | SP17 | 47% | AFAAAYFESLLEKRE | 37 | 65% | 100% | 30% |
| 184 | 212 | AKAP4 | 85% | DLSFYVNRLSSLVIQ | 216 | 36% | 100% | 30% |
| 185 | 213 | ODF-4 | 63% | QDGRLLSSTLSLSSN | 41 | 47% | 75% | 29% |
| 186 | 214 | RHOXF-2 | 60% | WEEAYTFEGARYYIN | 62 | 48% | 79% | 29% |
| 187 | 215 | PLU-1 | 82% | EKAMARLQELLTVSE | 955 | 34% | 69% | 28% |
| 188 | 216 | HIWI | 100% | RSIAGFVASINEGMT | 642 | 28% | 57% | 28% |
| 8 | 48 | PRAME | 53% | LERLAYLHARLRELL | 457 | 52% | 100% | 28% |
| 189 | 217 | RHOXF-2 | 60% | SDYAVHPMSPVGRTS | 132 | 43% | 5% | 26% |

TABLE 17-continued

BestEPI list (9-mers underlined) for selecting breast cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ T cell specific PEPI4+ within normal donors (n = 400); N% * B%: N% multiplied by B%.

| SEQ ID NO. 9 mer | SEQ ID NO. 15 mer | Antigen | N% | Opt. 15 mer | Opt. Position | B% | HLAII** (CD4) | B% * N% |
|---|---|---|---|---|---|---|---|---|
| 190 | 218 | NY-SAR-35 | 55% | MMQMFGLGAISLILV | 184 | 46% | 69% | 25% |
| 11 | 51 | NY-SAR-35 | 55% | FSSSGTTSFKCFAPF | 163 | 45% | 0% | 25% |
| 11 | 219 | NY-SAR-35 | 55% | LRHKCCFSSSGTTSF | 157 | 45% | 1% | 25% |
| 9 | 49 | SPAG9 | 88% | SGAVMSERVSGLAGS | 16 | 28% | 9% | 25% |
| 10 | 220 | BORIS | 71% | RFTQSGTMKIHILQK | 406 | 35% | 69% | 25% |
| 10 | 50 | BORIS | 71% | HTRFTQSGTMKIHIL | 404 | 35% | 80% | 25% |
| 191 | 221 | EpCam | 84% | QTLIYYVDEKAPEFS | 246 | 28% | 34% | 24% |
| 13 | 222 | NY-SAR-35 | 55% | FVLANGHILPNSENA | 97 | 42% | 6% | 23% |
| 13 | 53 | NY-SAR-35 | 55% | CSGSSYFVLANGHIL | 91 | 42% | 78% | 23% |
| 13 | 223 | NY-SAR-35 | 55% | SSYFVLANGHILPNS | 94 | 42% | 85% | 23% |
| 12 | 224 | MAGE-A9 | 44% | FMFQEALKLVAELV | 102 | 49% | 100% | 22% |
| 12 | 52 | MAGE-A9 | 44% | QLEFMFQEALKLKVA | 99 | 49% | 100% | 22% |
| 14 | 54 | PRAME | 53% | RHSQTLKAMVQAWPF | 64 | 37% | 38% | 20% |
| 14 | 225 | PRAME | 53% | HSQTLKAMVQAWPFT | 65 | 37% | 37% | 20% |
| 14 | 226 | PRAME | 53% | QTLKAMVQAWPFTCL | 67 | 37% | 85% | 20% |
| 15 | 55 | NY-BR-1 | 47% | YSCDSRSLFESSAKI | 424 | 39% | 0% | 18% |
| 16 | 56 | Survivin | 66% | TAKKVRRAIEQLAAM | 127 | 26% | 26% | 17% |
| 192 | 227 | MAGE-A11 | 59% | SHSYVLVTSLNLSYD | 286 | 26% | 100% | 15% |
| 192 | 228 | MAGE-A11 | 59% | TSHSYVLVTSLNLSY | 285 | 26% | 100% | 15% |
| 17 | 229 | MAGE-A11 | 59% | AMDAIFGSLSDEGSG | 184 | 23% | 0% | 14% |
| 17 | 230 | MAGE-A11 | 59% | ESFSPTAMDAIFGSL | 178 | 23% | 0% | 14% |
| 17 | 57 | MAGE-A11 | 59% | SPTAMDAIFGSLSDE | 181 | 23% | 0% | 14% |
| 18 | 58 | HOM-TES-85 | 47% | MASFRKLTLSEKVPP | 1 | 29% | 51% | 13% |
| 19 | 59 | MAGE-A9 | 44% | SSISVYYTLWSQFDE | 67 | 30% | 97% | 13% |
| 20 | 231 | NY-BR-1 | 47% | KPSAFEPATEMQKSV | 582 | 27% | 0% | 12% |
| 20 | 60 | NY-BR-1 | 47% | PGKPSAFEPATEMQK | 580 | 27% | 0% | 12% |
| 193 | 232 | NY-ESO-1 | 9% | SRLLEFYLAMPFATP | 85 | 52% | 98% | 5% |
| 194 | 233 | NY-ESO-1 | 9% | FYLAMPFATPMEAEL | 90 | 51% | 96% | 5% |

Then we designed thirty-one 30 mer peptides (Table 18a). The 30 mers may each consist of two optimized 15 mer fragments, generally from different frequent CTAs, arranged end to end, each fragment comprising one of the 9 mers (BestEPIs) from Table 17. Nine of these 30 mer peptides were selected for a panel of peptides, referred to as Poly-PEPI915 (Table 18b). Expression frequencies for the 10 CTAs targeted by PolyPEPI915, singly and in combination, are shown in FIG. 11.

TABLE 18a 30 mer breast cancer vaccine peptides

| SEQID | TREOSID | Source Antigen | Peptide (30 mer) | HLAI* (CD8) | HLAII** (CD4) |
|---|---|---|---|---|---|
| 81 | BCV900-2-1 | AKAP4 | LQKYALGFQHALSPSMMAYSDTTMMSDDID | 69% | 88% |
| 82 | BCV900-2-2 | BORIS/AKAP4 | VCMFTSSRMSSFNRHVNIDYLMNRPQNLRL | 76% | 97% |
| 83 | BCV900-2-3 | BORIS | NMAFVTSGELVRHRRHTRFTQSGTMKIHIL | 57% | 92% |
| 84 | BCV900-2-4 | SPAG9 | LDSFTVCNSHVLCIAKLGFSFVRITALMVS | 58% | 100% |
| 85 | BCV900-2-5 | SPAG9/NY-SAR-35 | AQKMSSLLPTMWLGAMMQMFGLGAISLILV | 66% | 83% |
| 86 | BCV900-2-6 | PRAME | LERLAYLHARLRELLQTLKAMVQAWPFTCL | 71% | 100% |
| 87 | BCV900-2-7 | NY-SAR-35 | SSYFVLANGHILPNSLRHKCCFSSSGTTSF | 64% | 85% |
| 88 | BCV900-2-8 | Survivin/MAGE-A9 | TAKKVRRAIEQLAAMQLEFMFQEALKLKVA | 58% | 100% |
| 89 | BCV900-2-9 | MAGE-A11/NY-BR-1 | TSHSYVLVTSLNLSYYSCDSRSLFESSAKI | 65% | 100% |
| 90 | BCV900-3-1 | SPAG9/BORIS | LDSFTVCNSHVLCIAVCMFTSSRMSSFNRH | 65% | 96% |
| 91 | BCV900-3-2 | NY-SAR-35/PRAME | LRHKCCFSSSGTTSFQTLKAMVQAWPFTCL | 59% | 85% |
| 92 | BCV900-3-3 | NY-BR-1/SURVIVIN | YSCDSRSLFESSAKITAKKVRRAIEQLAAM | 55% | 26% |
| 93 | BCV900-3-4 | AKAP-4/BORIS | MMAYSDTTMMSDDIDHTRFTQSGTMKIHIL | 72% | 80% |
| 94 | BCV900-3-5 | SPAG9/AKAP-4 | AQKMSSLLPTMWLGALQKYALGFQHALSPS | 64% | 92% |
| 95 | BCV900-3-6 | MAGE-A11/BORIS | TSHSYVLVTSLNLSYNMAFVTSGELVRHRR | 61% | 100% |
| 96 | BCV900-3-7 | NY-SAR-35/AKAP-4 | MMQMFGLGAISLILVVNIDYLMNRPQNLRL | 71% | 84% |
| 97 | BCV900-3-8 | NY-SAR-35/SPAG-9 | SSYFVLANGHILPNSKLGFSFVRITALMVS | 65% | 100% |
| 98 | BCV900-3-9 | PRAME/MAGE-A9 | LERLAYLHARLRELLQLEFMFQEALKLKVA | 73% | 100% |
| 99 | BCV900-4-1 | SPAG9/AKAP4 | GNILDSFTVCNSHVLLQKYALGFQHALSPS | 53% | 88% |
| 100 | BCV900-4-2 | BORIS/NY-SAR-35 | NMAFVTSGELVRHRRFSSSGTTSFKCFAPF | 65% | 75% |
| 101 | BCV900-4-5 | SPAG9/BORIS | AQKMSSLLPTMWLGAMFTSSRMSSFNRHMK | 72% | 87% |
| 102 | BCV900-4-6 | MAGE-A11/PRAME | TSHSYVLVTSLNLSYHSQTLKAMVQAWPFT | 60% | 100% |
| 103 | BCV900-5-6 | HomTes85/MageA11 | MASFRKLTLSEKVPPSPTAMDAIFGSLSDE | 45% | 51% |
| 104 | BCV900-5-7 | AKAP4/PRAME | DQVNIDYLMNRPQNLRHSQTLKAMVQAWPF | 64% | 67% |
| 105 | BCV900-5-8 | NYSAR/SPAG9 | CSGSSYFVLANGHILSGAVMSERVSGLAGS | 46% | 78% |
| 106 | BCV900-S-2 | AKAP-4/MAGE-A9 | DLSFYVNRLSSLVIQSSISVYYTLWSQFDE | 60% | 100% |
| 107 | BCV900-S-4 | SPAG9/NY-ESO-1 | SGAVMSERVSGLAGSSRLLEFYLAMPFATP | 59% | 98% |
| 108 | BCV900-S-6 | HOM-TES-85/MAGE-A11 | MASFRKLTLSEKVPPESFSPTAMDAIFGSL | 46% | 51% |
| 109 | BCV900-S-7 | NY-ESO-1/NY-BR-1 | FYLAMPFATPMEAELKPSAFEPATEMQKSV | 60% | 96% |
| 110 | BCV900-T-27 | MAGE-A11/PRAME | AMDAIFGSLSDEGSGHSQTLKAMVQAWPFT | 54% | 37% |
| 111 | BCV900-T-28 | NY-SAR-35/SPAG9 | FVLANGHILPNSENAGTGKLGFSFVRITAL | 61% | 94% |

TABLE 18a-continued

30 mer breast cancer vaccine peptides

| SEQID | TREOSID | Source Antigen | Peptide (30 mer) | HLAI* (CD8) | HLAII** (CD4) |
|---|---|---|---|---|---|
| 435 | BCV900-6-1 | TSGA10/PIWIL-2 | YSSNAYHMSSTMKPNFVASINLTLTKWYSR | 80% | 95% |
| 436 | BCV900-6-2 | PIWIL-2/AKAP4 | RNFYDPTSAMVLQQHMMAYSDTTMMSDDID | 88% | 49% |
| 437 | BCV900-6-3 | PLU-1/RHOXF-2 | LRYRYTLDDLYPMMNSDYAVHPMSPVGRTS | 67% | 85% |
| 438 | BCV900-6-4 | SPAG9/EpCam | SGAVMSERVSGLAGSRTYWIIIELKHKARE | 60% | 100% |
| 439 | BCV900-6-5 | AKAP4/PLU-1 | DLSFYVNRLSSLVIQNRTSYLHSPFSTGRS | 66% | 100% |
| 440 | BCV900-6-6 | AKAP4/HIWI | VNIDYLMNRPQNLRLHAFDGTILFLPKRLQ | 70% | 94% |
| 441 | BCV900-6-7 | AKAP4/PLU-1 | SDLQKYALGFQHALSEKAMARLQELLTVSE | 56% | 92% |
| 442 | BCV900-6-8 | HIWI/ODF-4 | GFTTSILQYENSIMLQDGRLLSSTLSLSSN | 61% | 94% |
| 443 | BCV900-6-9 | PIWIL-2/BORIS | YSRVVFQMPHQEIVDNMAFVTSGELVRHRR | 61% | 85% |
| 444 | BCV900-6-10 | SP17/BORIS | AFAAAYFESLLEKREMFTSSRMSSFNRHMK | 82% | 100% |
| 445 | BCV900-6-11 | ODF-4/HIWI | NSPLPFQWRITHSFRRSIAGFVASINEGMT | 60% | 69% |
| 446 | BCV900-6-12 | NY-SAR-35/RHOXF-2 | SSYFVLANGHILPNSWEEAYTFEGARYYIN | 74% | 93% |
| 447 | BCV900-6-13 | TSGA10/PRAME | LQKVQFEKVSALADLLERLAYLHARLRELL | 68% | 100% |
| 448 | BCV900-6-14 | MAGE-A11/MAGE-A9 | SHSYVLVTSLNLSYDFMFQEALKLKVAELV | 65% | 100% |
| 449 | BCV900-6-15 | BORIS/EpCam | RFTQSGTMKIHILQKQTLIYYVDEKAPEFS | 53% | 80% |

TABLE 18b

Selected Breast Cancer Vaccine peptides for PolyPEPI915 panel/composition

| SEQID | TREOSID | Source Antigen | Peptide (30 mer) | HLAI* (CD8) | HLAII** (CD4) |
|---|---|---|---|---|---|
| 99 | BCV900-4-1 | SPAG9/AKAP4 | GNILDSFTVCNSHVLLQKYALGFQHALSPS | 53% | 75% |
| 100 | BCV900-4-2 | BORIS/NY-SAR-35 | NMAFVTSGELVRHRRFSSSGTTSFKCFAPF | 65% | 46% |
| 92 | BCV900-3-3 | NY-BR-1/SURVIVIN | YSCDSRSLFESSAKITAKKVRRAIEQLAAM | 55% | 11% |
| 93 | BCV900-3-4 | AKAP-4/BORIS | MMAYSDTTMMSDDIDHTRFTQSGTMKIHIL | 72% | 45% |
| 101 | BCV900-4-5 | SPAG9/BORIS | AQKMSSLLPTMWLGAMFTSSRMSSFNRHMK | 72% | 50% |
| 103 | BCV900-5-6 | HonnTes85/MageA11 | MASFRKLTLSEKVPPSPTAMDAIFGSLSDE | 45% | 16% |
| 104 | BCV900-5-7 | AKAP4/PRAME | DQVNIDYLMNRPQNLRHSQTLKAMVQAWPF | 64% | 33% |
| 105 | BCV900-5-8 | NYSAR/SPAG9 | CSGSSYFVLANGHILSGAVMSERVSGLAGS | 46% | 48% |
| 98 | BCV900-3-9 | PRAME/MAGE-A9 | LERLAYLHARLRELLQLEFMFQEALKLKVA PolyPEPI915 (9 peptide together) | 73% 96% | 100% 100% |

*Percentage of individuals having CD8+ T cell specific PEPI3+ within the HLA class I Model Population (n = 433).
**Percentage of individuals having CD4+ T cell specific PEPI4+ within the normal donors (n = 400).

Characterization of PolyPEPI915

Figure 12A:
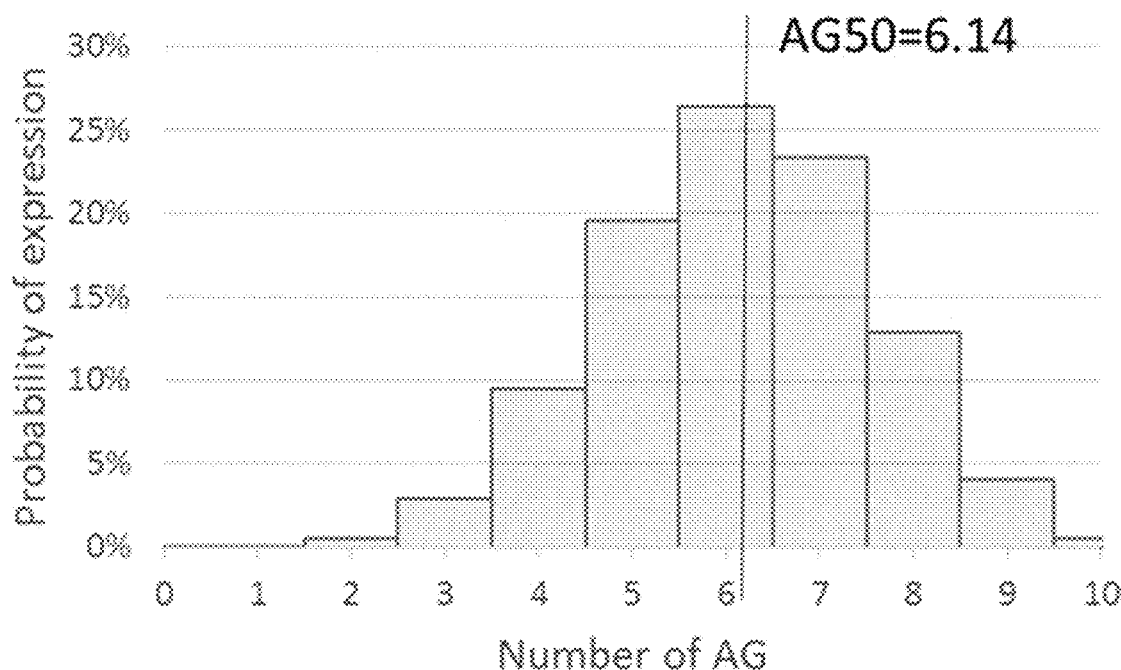
FIGS. 12A-B—Antigen expression distribution for breast cancer based on the calculation of multi-antigen responses from expression frequencies of the selected 10 different CTAs.
Figure 12B:
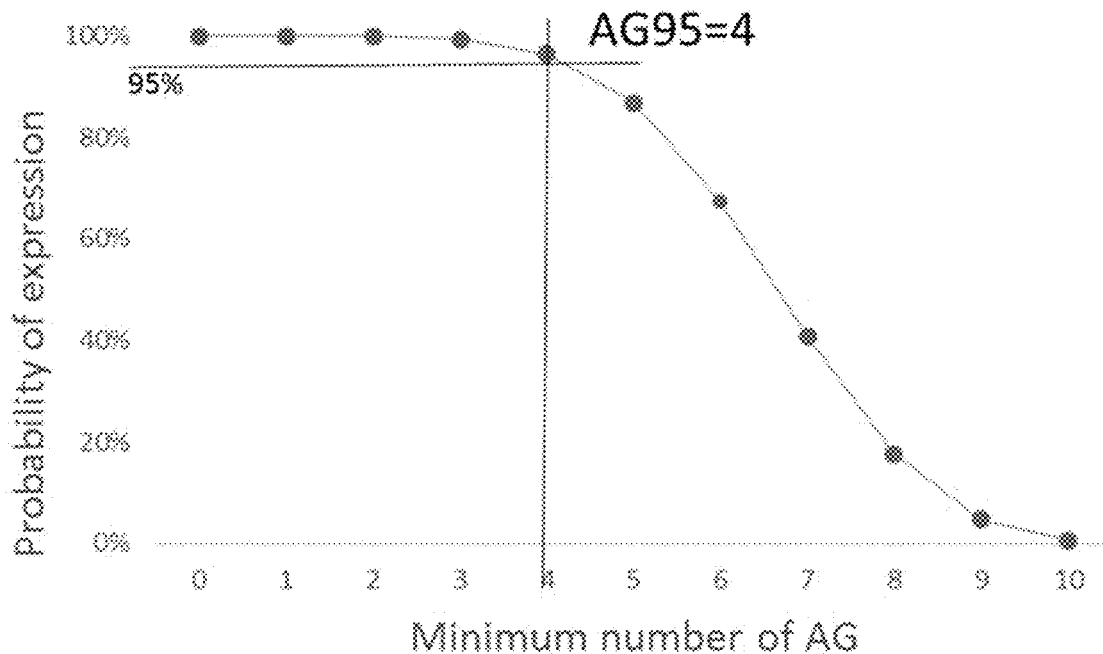

Tumor heterogeneity can be addressed by including peptide sequences that target multiple CTAs in a vaccine or immunotherapy regime. The PolyPEPI915 composition targets 10 different CTAs. Based on the antigen expression rates for these 10 CTAs, we modelled the predicted average number of expressed antigens (AG50) and the minimum number of expressed antigens with 95% likelihood (AG95) in the cancer cells. 95% of individuals expressed minimum 4 of the 10 target antigens (AG95=4) as shown by the antigen expression curve in FIGS. 12A-B.

The AG values described above characterize a vaccine independently from the target patient population. They can be used to predict the likelihood that a specific cancer (e.g. breast cancer) expresses antigens targeted by a specific vaccine or immunotherapy composition. AG values are based on known tumor heterogeneity, but do not take HLA heterogeneity into account.

Figure 13A:
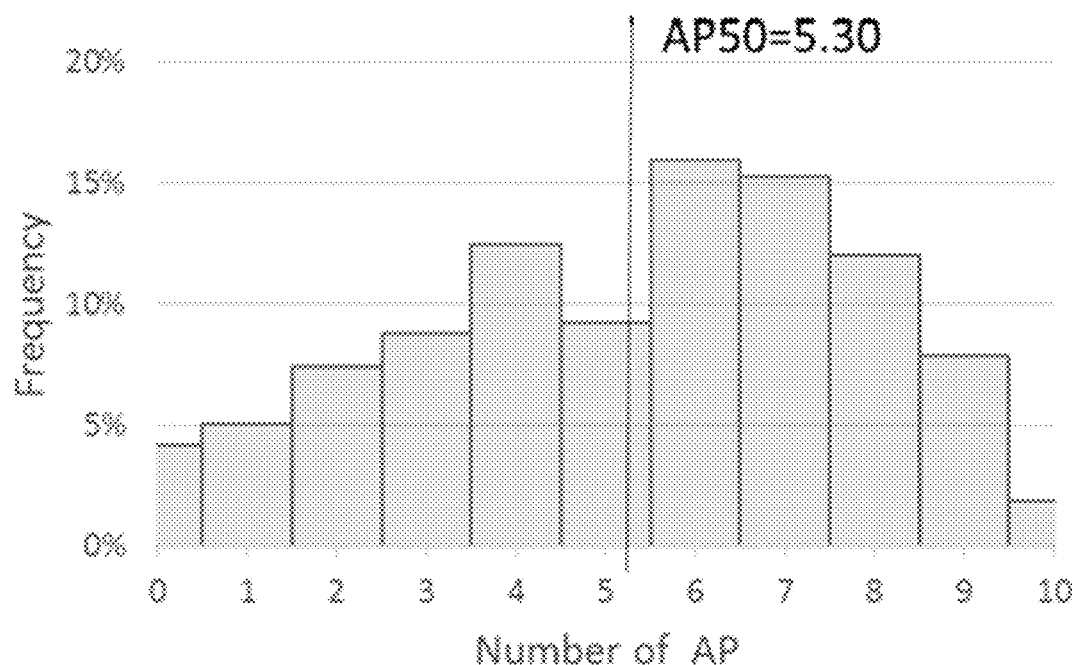
FIGS. 13A-B—PEPI representing antigens: breast cancer vaccine-specific CTA antigens with ≥1 PEPI, called as "AP") distribution within the Model Population (n=433) for breast cancer vaccine.
Figure 13B:
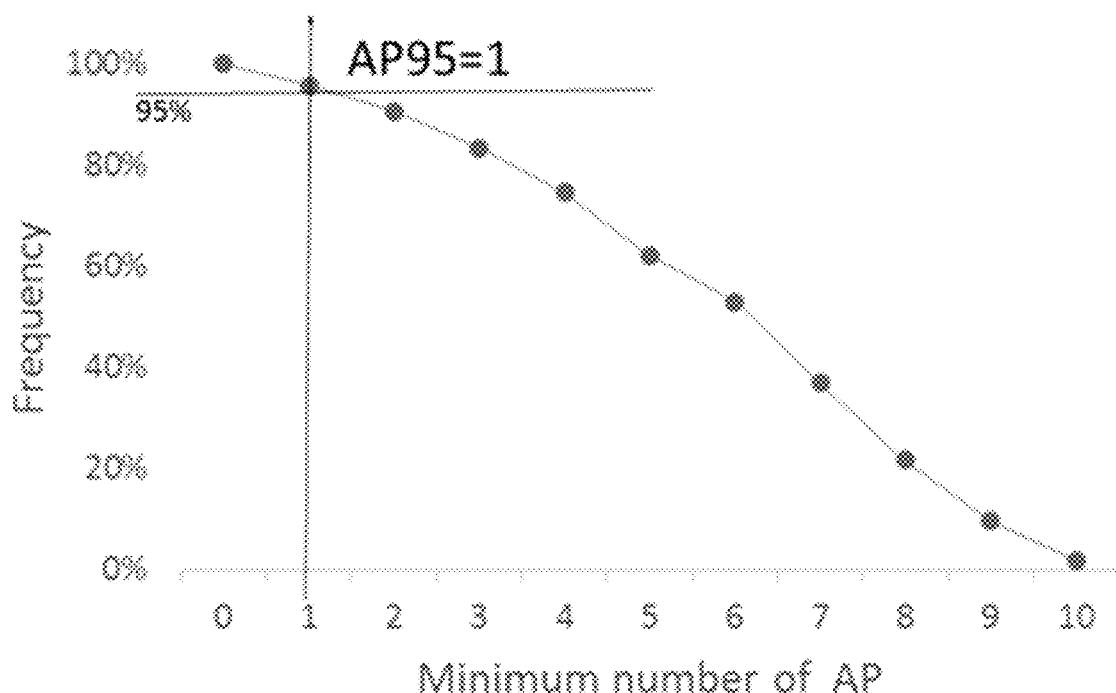

HLA heterogeneity of a certain population can be characterised from the viewpoint of an immunotherapy or vaccine composition by the number of antigens representing PEPI3+. These are the vaccine-specific CTA antigens for which ≥1 PEPI3+ is predicted, referred to herein as the "AP". The average number of antigens with PEPI3+(AP50) shows how the vaccine can induce immune response against the antigens targeted by the composition (breast cancer vaccine specific immune response). The PolyPEPI915 composition can induce immune response against an average of 5.3 vaccine antigens (AP50=5.30) and 95% of the Model Population can induce immune response against at least one vaccine antigen (AP95=1)(FIGS. 13A-B).

Vaccines can be further characterized by AGP values that refers to antigens with PEPIs". This parameter is the combination of the previous two parameters: (1) AG is depending on the antigen expression frequencies in the specific tumor type but not on the HLA genotype of individuals in the population, and (2) AP is depending on the HLA genotype of individuals in a population without taking account the expression frequencies of the antigen. The AGP is depending on both, the expression frequencies of vaccine antigens in the disease and the HLA genotype of individuals in a population.

Figure 14A:
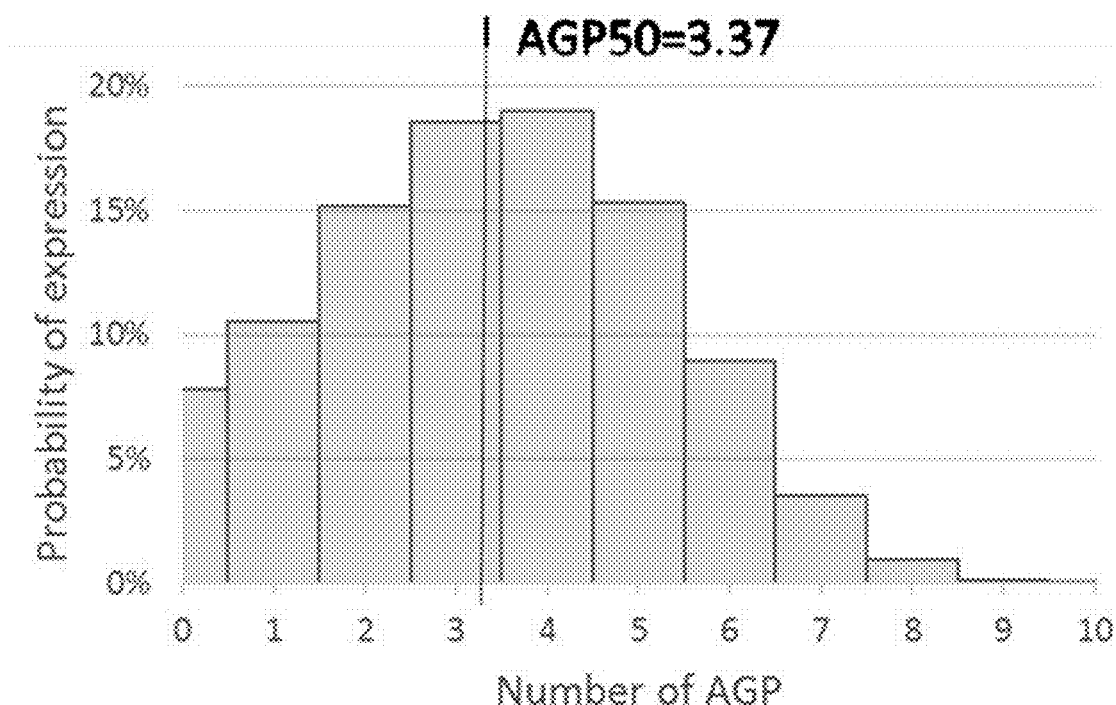
FIGS. 14A-B—PEPI represented expressed antigen (breast cancer vaccine-specific CTA antigens expressed by the tumor, for which ≥1 PEPI is predicted, called as "AGP") distribution within the model population (n=433) calculated with CTA expression rates for breast cancer.
Figure 14B:
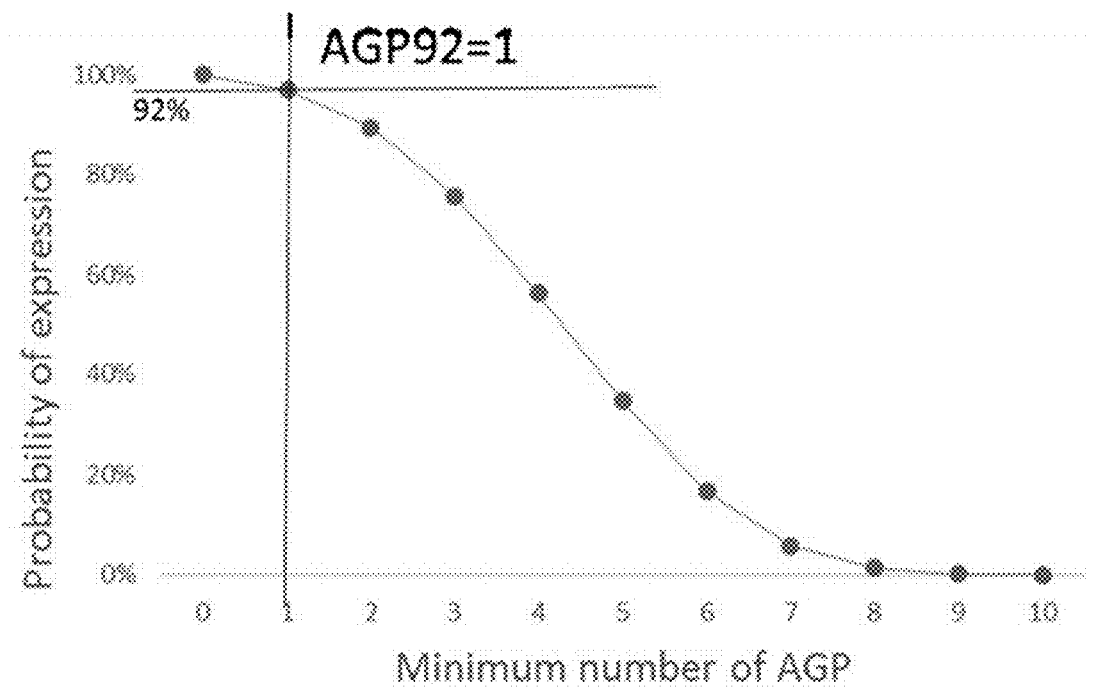

Combining the data of AG of breast cancer and AP in the Model Population we determined the AGP value of Poly-PEPI915 that represents the probability distribution of vaccine antigens that are induce immune responses against antigens expressed in breast tumors. For PolyPEPI915, the AGP50 value in the Model Population is 3.37. The AGP92=1, means that 92% of the subjects in the Model Population induce immune responses against at least one expressed vaccine antigen (FIGS. 14A-B).

Example 14—Patient Selection Using Companion Diagnostic for Breast Cancer Vaccine The likelihood that a specific patient will have an immune response or a clinical response to treatment with one or more cancer vaccine peptides, for example as described above, can be determined based on (i) the identification of PEPI3+ within the vaccine peptide(s) (9 mer epitopes capable of binding at least three HLA of the patient); and/or (ii) a determination of target antigen expression in cancer cells of the patient, for example as measured in a tumour biopsy. Ideally both parameters are determined and the optimal combination of vaccine peptides is selected for use in treatment of the patient. However, PEPI3+ analysis alone may be used if a determination of the expressed tumour antigens, for example by biopsy, is not possible, not advised, or unreliable due to biopsy error (i.e. biopsy tissue samples taken from a small portion of the tumor or metastasised tumors do not represent the complete repertoire of CTAs expressed in the patient).

Example 15—Comparison of PolyPEPI915 with Competing Breast Cancer Vaccines

We used the in silico clinical trial model described in above to predict the immune response rates of competing breast cancer vaccines that investigated in clinical trials (Table 19). The immune response rate of these products were between 3% and 91%.

The single peptide vaccines were immunogenic in 3%-23% of individuals. In comparison, peptides having an amino acid sequence selected from SEQ ID NOs: 81-111 were immunogenic in from 44% to 73% of individuals in the same cohorts. This result represents substantial improvement in immunogenicity of each peptide in PolyPEPI915.

Competing combination peptide products immune response rates were between 10-62%. The invented Poly-PEPI915 combination product were 96% in the Model Population and 93% in a breast cancer patient population representing improvement in immunogenicity.

TABLE 19

Predicted immune response rates of competing breast cancer vaccines

| Breast Cancer Vaccines | Sponsors | Target antigens | Predicted immune response rates* | |
|---|---|---|---|---|
| | | | 433 normal donors (Model Population) | 90 patients with breast cancer |
| DPX0907 Multipeptide | Immuno Vaccine Tech. | 7 | 58% | 62% |
| Multipeptide vaccine | University of Virginia | 5 | 22% | 31% |
| Ad-sig-hMUC-1/ecdCD40L | Singapore CRI | 1 | 91% | 80% |
| NY-ESO-1 IDC-G305 | Immune Design Corp. | 1 | 84% | 84% |
| 6 HER2 peptide pulsed DC | University Pennsylvania | 1 | 29% | 36% |
| HER-2 B Cell peptide | Ohio State University | 1 | 18% | 23% |
| HER-2/neu ID protein | University Washington | 1 | 10% | 11% |
| NeuVax peptide | Galena Biopharma | 1 | 6% | 3% |
| StimuVax ® L-BLP25) peptide | EMD Serono | 1 | 6% | 8% |
| PolyPEPI915 | Treos Bio | 10 | 96% | 93% |

*Proportion of subjects with ≥ 1 PEPI3+

Another improvement of using the PolyPEPI915 vaccine is the lower chance of tumor escape. Each 30 mer peptide in PolyPEPI915 targets 2 tumor antigens. CTLs against more tumor antigens are more effective against heterologous tumor cells that CTLs against a single tumor antigen.

Another improvement is that PolyPEPI915 vaccine that individuals who likely respond to vaccination can be identified based on their HLA genotype (sequence) and optionally antigen expression in their tumor using the methods described here. Pharmaceutical compositions with PolyPEPI vaccines will not be administered to individuals whose HLA cannot present any PEPI3 from the vaccines. During clinical trials correlation will be made between the mAGP or number of AGP in the PolyPEPI915 regimen and the duration of individual's responses. A vaccine combination with >1 AGP is most likely required to destroy heterologous tumor cells. Pharmaceutical compositions with PolyPEPI vaccines will not be administered to individuals whose HLA cannot present any PEPI3 from the vaccines.

Example 16 Colorectal Cancer Vaccine Design and Composition

We show another example for colorectal vaccine composition using the same design method demonstrated above. We used the PEPI3+ Test described above to design peptides for use in colorectal cancer vaccines that are effective in a large percentage of patients, taking into account the heterogeneities of both tumour antigens and patient HLAs.

Colorectal cancer CTAs were identified and ranked based on the overall expression frequencies of antigens found in breast cancer tumor samples as reported in peer reviewed publications (FIG. 15) (Choi J, Chang H. The expression of MAGE and SSX, and correlation of COX2, VEGF, and survivin in colorectal cancer. Anticancer Res 2012. 32(2): 559-564; Goossens-Beumer I J, Zeestraten E C, Benard A, Christen T, Reimers M S, Keijzer R, Sier C F, Liefers G J, Morreau H, Putter H, Vahrmeijer A L, van de Velde C J, Kuppen P J. Clinical prognostic value of combined analysis of Aldh1, Survivin, and EpCAM expression in colorectal cancer. Br J Cancer 2014. 110(12):2935-2944; Li M, Yuan Y H, Han Y, Liu Y X, Yan L, Wang Y, Gu J. Expression profile of cancer-testis genes in 121 human colorectal cancer tissue and adjacent normal tissue. Clinical Cancer Res 2005. 11(5): 1809-1814).

Figure 15:
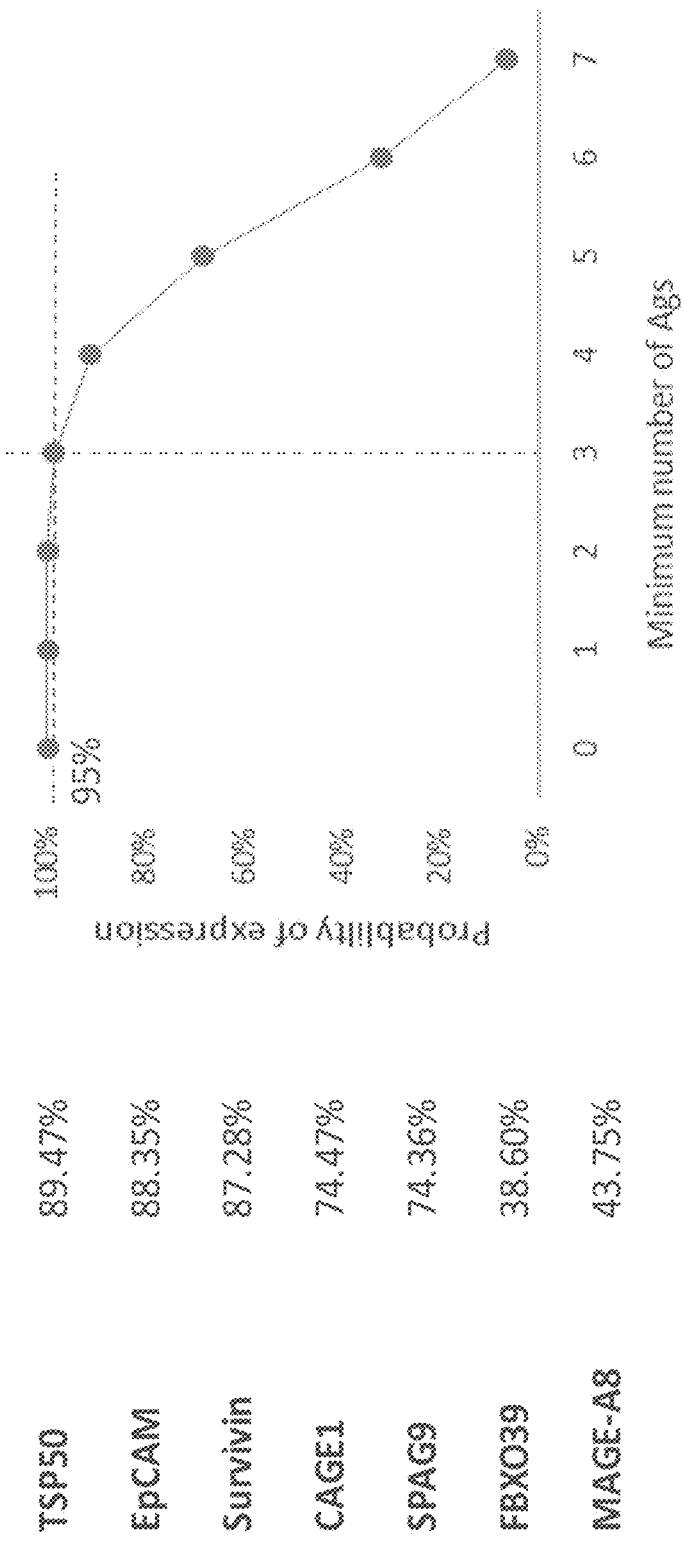
FIG. 15—CTA Expression Curve calculated by analyzing expression frequency data of tumor specific antigens (CTAs) in human colorectal cancer tissues. (No cell line data were included.)

Based on the ranked expression rate we have selected the most frequently expressed CTA as target antigens for the colorectal cancer vaccine. The expression rates of the selected breast cancer specific CTAs are illustrated in FIG. 15.

To select immunogenic peptides from the most frequently expressed colorectal cancer CTAs we used the PEPI3+ Test and the Model Population described in Example 8 to identify the "bestEPIs".

We multiplied the reported expression frequency for each CTA (N %) by the frequency of the PEPI3+ hotspots in the Model Population (B %) to identify the T cell epitopes (9 mers) that will induce an immune response against colorectal cancer antigens in the highest proportion of individuals (Table 20). We then selected 15 mers encompassing each of the selected 9 mers (Table 20). The 15 mers were selected to bind to most HLA class II alleles of most subjects, using the process described in Example 19 below. These 15 mers can induce both CTL and T helper responses in the highest proportion of subjects.

TABLE 20

BestEPI list (9-mers underlined) for selecting colorectal cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ cell specific PEPI4+ within normal donors (n = 400); N% * B%: N% multiplied by B%.

| SEQ ID NO. 9 mer | SEQ ID NO. 15 mer | Antigen | N% | Opt. 15 mer | Opt. Position | B% | HLAII** (CD4) | B% * N% |
|---|---|---|---|---|---|---|---|---|
| 234 | 251 | TSP50 | 89% | VCSMEGTWYLVGLVS | 315 | 58% | 72% | 52% |
| 21 | 252 | TSP50 | 89% | GFSYEQDPTLRDPEA | 105 | 51% | 0% | 45% |
| 21 | 61 | TSP50 | 89% | RSCGFSYEQDPTLRD | 102 | 51% | 0% | 45% |
| 21 | 253 | TSP50 | 89% | YRSCGFSYEQDPTLR | 101 | 51% | 0% | 45% |
| 22 | 62 | EpCAM | 88% | VRTYWIIIELKHKAR | 139 | 51% | 100% | 45% |
| 235 | 254 | EpCAM | 88% | LLAAATATFAAAQEE | 12 | 39% | 28% | 34% |
| 24 | 255 | SPAG9 | 74% | KLGFSFVRITALMVS | 1140 | 44% | 100% | 33% |
| 23 | 63 | TSP50 | 89% | PSTTMETQFPVSEGK | 83 | 36% | 0% | 32% |
| 24 | 64 | SPAG9 | 74% | GTGKLGFSFVRITAL | 1137 | 44% | 94% | 32% |
| 23 | 256 | TSP50 | 89% | LPSTTMETQFPVSEG | 82 | 36% | 0% | 32% |
| 25 | 65 | SPAG9 | 74% | AQKMSSLLPTMWLGA | 962 | 43% | 69% | 32% |

TABLE 20-continued

BestEPI list (9-mers underlined) for selecting colorectal cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ cell specific PEPI4+ within normal donors (n = 400); N% * B%: N% multiplied by B%.

| SEQ ID NO. 9 mer | SEQ ID NO. 15 mer | Antigen | N% | BestEPIs and Optimized 15 mer Opt. 15 mer | Opt. Position | B% | HLAII** (CD4) | B% * N% |
|---|---|---|---|---|---|---|---|---|
| 26 | 66 | CAGE1 | 74% | LASKMHSLLALMVGL | 613 | 42% | 99% | 31% |
| 27 | 67 | FBXO39 | 39% | KFMNPYNAVLTKKFQ | 95 | 78% | 43% | 30% |
| 28 | 68 | CAGE1 | 74% | PKSMTMMPALFKENR | 759 | 37% | 87% | 27% |
| 238 | 257 | SPAG9 | 74% | LDSFTVCNSHVLCIA | 782 | 36% | 6% | 27% |
| 236 | 258 | SPAG9 | 74% | GNILDSFTVCNSHVL | 779 | 36% | 4% | 26% |
| 29 | 69 | EpCAM | 88% | YVDEKAPEFSMQGLK | 251 | 28% | 0% | 25% |
| 29 | 259 | EpCAM | 88% | QTLIYYVDEKAPEFS | 246 | 28% | 34% | 25% |
| 30 | 70 | FBXO39 | 39% | FKKTMSTFHNLVSLN | 216 | 58% | 92% | 23% |
| 31 | 71 | Survivin | 86% | TAKKVRRAIEQLAAM | 127 | 26% | 26% | 22% |
| 237 | 260 | TSP50 | 89% | SRTLLLALPLPLSLL | 368 | 24% | 100% | 21% |
| 32 | 72 | SPAG9 | 74% | SGAVMSERVSGLAGS | 16 | 28% | 9% | 21% |
| 238 | 260 | TSP50 | 89% | SRTLLLALPLPLSLL | 368 | 23% | 100% | 20% |
| 34 | 74 | FBXO39 | 39% | KVNFFFERIMKYERL | 284 | 46% | 100% | 18% |
| 33 | 73 | TSP50 | 89% | SRYRAQRFWSWVGQA | 190 | 20% | 88% | 18% |
| 239 | 261 | LEMD1 | 56% | FIIVVFVYLTVENKS | 164 | 30% | 97% | 17% |
| 240 | 66 | CAGE1 | 74% | LASKMHSLLALMVGL | 613 | 22% | 99% | 16% |
| 241 | 262 | FBXO39 | 39% | RNSIRSSFISSLSFF | 142 | 40% | 100% | 16% |
| 242 | 263 | CAGE1 | 74% | NIENYSTNALIQPVD | 97 | 21% | 14% | 16% |
| 243 | 264 | Survivin | 86% | MGAPTLPPAWQPFLK | 1 | 17% | 0% | 15% |
| 244 | 265 | CAGE1 | 74% | RQFETVCKFHWVEAF | 119 | 18% | 45% | 13% |
| 35 | 75 | Survivin | 86% | KDHRISTFKNWPFLE | 15 | 15% | 83% | 13% |
| 36 | 266 | MAGE-A8 | 44% | PEEAIWEALSVMGLY | 220 | 20% | 78% | 9% |
| 36 | 76 | MAGE-A8 | 44% | SRAPEEAIWEALSVM | 217 | 20% | 6% | 9% |
| 37 | 77 | MAGE-A8 | 44% | DEKVAELVRFLLRKY | 113 | 18% | 95% | 8% |
| 37 | 267 | MAGE-A8 | 44% | EKVAELVRFLLRKYQ | 114 | 18% | 99% | 8% |
| 38 | 268 | MAGE-A6 | 28% | KLLTQYFVQENYLEY | 244 | 27% | 98% | 8% |
| 38 | 78 | MAGE-A6 | 28% | QYFVQENYLEYRQVP | 248 | 27% | 93% | 8% |
| 40 | 80 | MAGE-A6 | 28% | IGHVYIFATCLGLSY | 172 | 25% | 82% | 7% |
| 39 | 79 | MAGE-A8 | 44% | EFLWGPRALAETSYV | 273 | 16% | 44% | 7% |
| 245 | 269 | MAGE-A3 | 23% | IGHLYIFATCLGLSY | 172 | 28% | 85% | 6% |
| 246 | 270 | MAGE-A3 | 23% | KLLTQHFVQENYLEY | 244 | 27% | 77% | 6% |
| 247 | 271 | MAGE-A8 | 44% | ASSSSTLIMGTLEEV | 39 | 14% | 19% | 6% |

TABLE 20-continued

BestEPI list (9-mers underlined) for selecting colorectal cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ cell specific PEPI4+ within normal donors (n = 400); N% * B%: N% multiplied by B%.

| SEQ ID NO. 9 mer | SEQ ID NO. 15 mer | Antigen | N% | BestEPIs and Optimized 15 mer Opt. 15 mer | Opt. Position | B% | HLAII** (CD4) | B% * N% |
|---|---|---|---|---|---|---|---|---|
| 248 | 269 | MAGE-A3 | 23% | IGHLYIFATCLGLSY | 172 | 25% | 85% | 6% |
| 249 | 264 | Survivin | 86% | MGAPTLPPAWQPFLK | 1 | 5% | 0% | 4% |
| 250 | 75 | Survivin | 86% | KDHRISTFKNWPFLE | 15 | 4% | 83% | 3% |

Then we designed thirty-one 30 mer peptides (Table 21a). The 30 mers each consist of two optimized 15 mer fragments, generally from different frequent CTAs, each 30 mer generally containing at least one high frequency HLA class-II binding PEPI. The 15 mer fragments are arranged end to end, and each comprises one of the 9 mers (BestEPIs) from Table 20 as described above. Nine of these 30 mer peptides were selected for a panel of peptide vaccines, referred to as PolyPEPI1015 (Table 21b). Expression frequencies for the 8 CTAs targeted by PolyPEPI1015, singly and in combination, are shown in FIG. 15.

TABLE 21a 30 mer colorectal cancer vaccine peptides

| SEQ ID | TREOSID | Source Antigen | Peptide (30 mer) | HLAI* (CD8) | HLAII** (CD4) |
|---|---|---|---|---|---|
| 112 | CCV1000-1-1 | TSP50 | VCSMEGTWYLVGLVSYRSCGFSYEQDPTLR | 71% | 72% |
| 113 | CCV1000-1-2 | EpCAM/TSP50 | VRTYWIIIELKHKARLPSTTMETQFPVSEG | 62% | 100% |
| 114 | CCV1000-1-4 | Survivin | TAKKVRRAIEQLAAMMGAPTLPPAWQPFLK | 39% | 26% |
| 115 | CCV1000-1-5 | CAGE1 | LASKMHSLLALMVGLPKSMTMMPALFKENR | 68% | 99% |
| 116 | CCV1000-1-6 | Spag9 | KLGFSFVRITALMVSLDSFTVCNSHVLCIA | 58% | 100% |
| 117 | CCV1000-1-7 | FBXO39 | KFMNPYNAVLTKKFQFKKTMSTFHNLVSLN | 91% | 92% |
| 118 | CCV1000-1-8 | Spag9/FBXO39 | AQKMSSLLPTMWLGAKVNFFFERIMKYERL | 75% | 100% |
| 119 | CCV1000-1-9 | Survivin/Mage-A8 | KDHRISTFKNWPFLEPEEAIWEALSVMGLY | 39% | 93% |
| 120 | CCV1000-2-1 | TSP50 | YRSCGFSYEQDPTLRVCSMEGTWYLVGLVS | 71% | 72% |
| 121 | CCV1000-2-2 | EpCAM/Survivin | VRTYWIIIELKHKARTAKKVRRAIEQLAAM | 57% | 100% |
| 122 | CCV1000-2-4 | TSP50/Spag9 | LPSTTMETQFPVSEGKLGFSFVRITALMVS | 61% | 100% |
| 123 | CCV1000-2-5 | Survivin/Mage-A8 | MGAPTLPPAWQPFLKPEEAIWEALSVMGLY | 40% | 78% |
| 124 | CCV1000-2-6 | CAGE1/Survivin | LASKMHSLLALMVGLKDHRISTFKNWPFLE | 58% | 99% |
| 125 | CCV1000-2-7 | CAGE1/Spag9 | PKSMTMMPALFKENRLDSFTVCNSHVLCIA | 61% | 87% |
| 126 | CCV1000-2-8 | FBXO39 | KFMNPYNAVLTKKFQKVNFFFERIMKYERL | 90% | 100% |
| 127 | CCV1000-2-9 | Spag9/FBXO39 | AQKMSSLLPTMWLGAFKKTMSTFHNLVSLN | 67% | 92% |
| 128 | CCV1000-3-1 | TSP50 | GFSYEQDPTLRDPEAVCSMEGTWYLVGLVS | 71% | 72% |
| 129 | CCV1000-3-7 | CAGE1/Spag9 | PKSMTMMPALFKENRGNILDSFTVCNSHVL | 61% | 87% |
| 130 | CCV1000-5-1 | TSP50 | PSTTMETQFPVSEGKSRYRAQRFWSWVGQA | 53% | 88% |
| 131 | CCV1000-5-3 | EpCAM/Mage-A8 | YVDEKAPEFSMQGLKDEKVAELVRFLLRKY | 43% | 95% |

TABLE 21a-continued 30 mer colorectal cancer vaccine peptides

| SEQ ID | TREOSID | Source Antigen | Peptide (30 mer) | HLAI* (CD8) | HLAII** (CD4) |
|---|---|---|---|---|---|
| 132 | CCV1000-5-4 | TSP50/Spag9 | RSCGFSYEQDPTLRDGTGKLGFSFVRITAL | 67% | 94% |
| 133 | CCV1000-5-5 | Mage-A8/Mage-A6 | SRAPEEAIWEALSVMQYFVQENYLEYRQVP | 45% | 94% |
| 134 | CCV1000-5-7 | CAGE1/Spag9 | PKSMTMMPALFKENRSGAVMSERVSGLAGS | 57% | 87% |
| 135 | CCV1000-S-1 | SPAG9/FBXO39 | SGAVMSERVSGLAGSRNSIRSSFISSLSFF | 64% | 100% |
| 136 | CCV1000-S-2 | CAGE1/MAGE-A8 | NIENYSTNALIQPVDEKVAELVRFLLRKYQ | 28% | 99% |
| 137 | CCV1000-S-3 | CAGE1/MAGE-A6 | RQFETVCKFHWVEAFKLLTQYFVQENYLEY | 46% | 98% |
| 138 | CCV1000-S-5 | MAGE-A8/MAGE-A3 | EFLWGPRALAETSYVKLLTQHFVQENYLEY | 39% | 91% |
| 139 | CCV1000-S-6 | MAGE-A8/EpCAM | ASSSSTLIMGTLEEVQTLIYYVDEKAPEFS | 41% | 41% |
| 140 | CCV1000-S-7 | TSP50/MAGE-A3 | SRTLLLALPLPLSLLIGHLYIFATCLGLSY | 60% | 100% |
| 141 | CCV1000-S-9 | LEMD1/MAGE-A6 | FIIVVFVYLTVENKSIGHVYIFATCLGLSY | 51% | 99% |
| 142 | CCV1000-S-17 | EPCAM | LLAAATATFAAAQEEQTLIYYVDEKAPEFS | 52% | 54% |

*Percentage of individuals having CD8+ T cell specific PEPI3+ within the Model Population (n = 433).
**Percentage of individuals having CD4+ T cell specific PEPI4+ within normal donors (n = 400).

TABLE 21b

Selected Colorectal Cancer Vaccine peptides for PolyPEPI1015 composition

| SEQID | TREOSID | Source Antigen | Peptide (30 mer) | HLAI* (CD8) | HLAII** (CD4) |
|---|---|---|---|---|---|
| 130 | CCV1000-5-1 | TSP50 | PSTTMETQFPVSEGKSRYRAQRFWSWVGQA | 53% | 53% |
| 121 | CCV1000-2-2 | EpCAM/Survivin | VRTYWIIIELKHKARTAKKVRRAIEQLAAM | 57% | 98% |
| 131 | CCV1000-5-3 | EpCAM/Mage-A8 | YVDEKAPEFSMQGLKDEKVAELVRFLLRKY | 43% | 72% |
| 132 | CCV1000-5-4 | TSP50/Spag9 | RSCGFSYEQDPTLRDGTGKLGFSFVRITAL | 67% | 82% |
| 133 | CCV1000-5-5 | Mage-A8/Mage-A6 | SRAPEEAIWEALSVMQYFVQENYLEYRQVP | 45% | 76% |
| 124 | CCV1000-2-6 | CAGE1/Survivin | LASKMHSLLALMVGLKDHRISTFKNWPFLE | 58% | 95% |
| 134 | CCV1000-5-7 | CAGE1/Spag9 | PKSMTMMPALFKENRSGAVMSERVSGLAGS | 57% | 57% |
| 126 | CCV1000-2-8 | FBXO39 | KFMNPYNAVLTKKFQKVNFFFERIMKYERL | 90% | 98% |
| 127 | CCV1000-2-9 | Spag9/FBXO39 | AQKMSSLLPTMWLGAFKKTMSTFHNLVSLN | 67% | 66% |
|  |  |  | PolyPEPI1015 (9 peptide together) | 100% | 99% |

*Percentage of individuals having CD8+ T cell specific PEPI3+ within the Model Population (n = 433).
**Percentage of individuals having CD4+ T cell specific PEPI4+ within normal donors (n = 400).

Characterization of PolyPEPI1015 Colorectal Cancer Vaccine

Figure 16A:
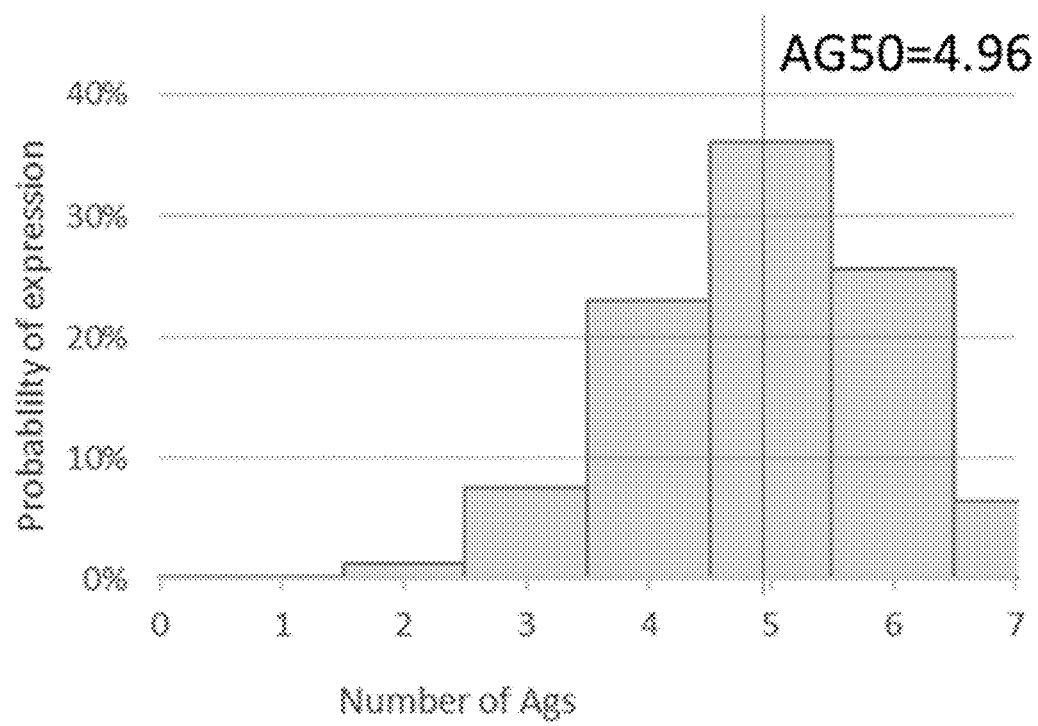
FIGS. 16A-B—Antigen expression distribution for colorectal cancer based on the calculation of multi-antigen responses from expression frequencies of the selected 7 different CTAs.
Figure 16B:
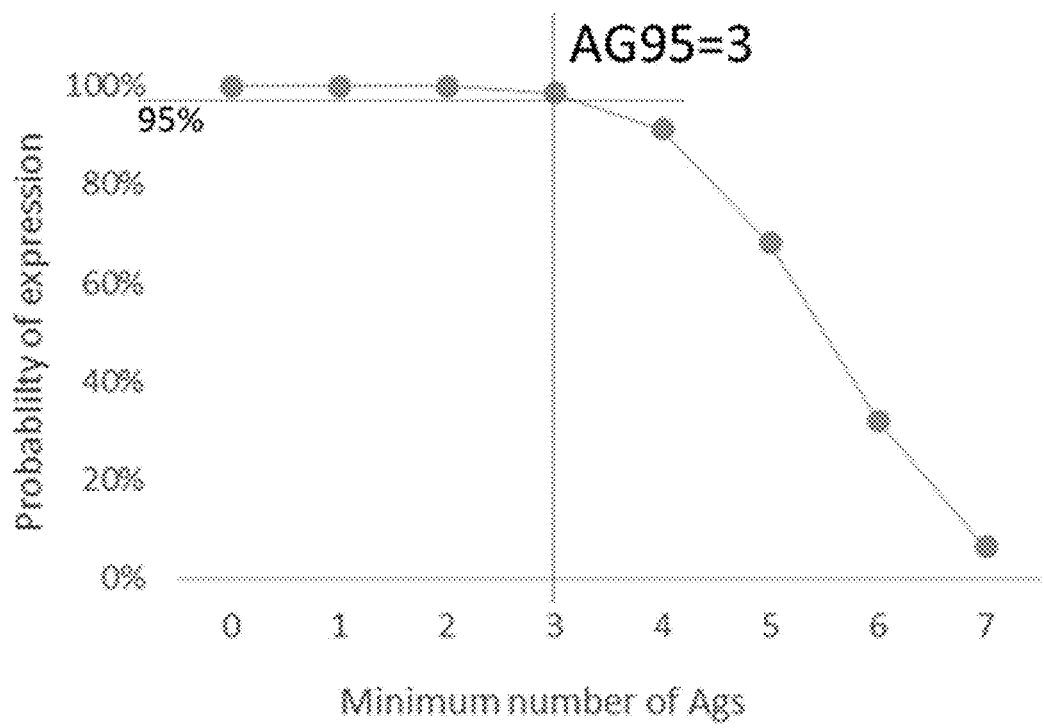

Tumor heterogeneity: The PolyPEPI1015 composition targets 8 different CTAs (FIG. 15). Based on the antigen expression rates for these 8 CTAs, AG50=5.22 and AG95=3 FIGS. 16A-B.

Figure 17A:
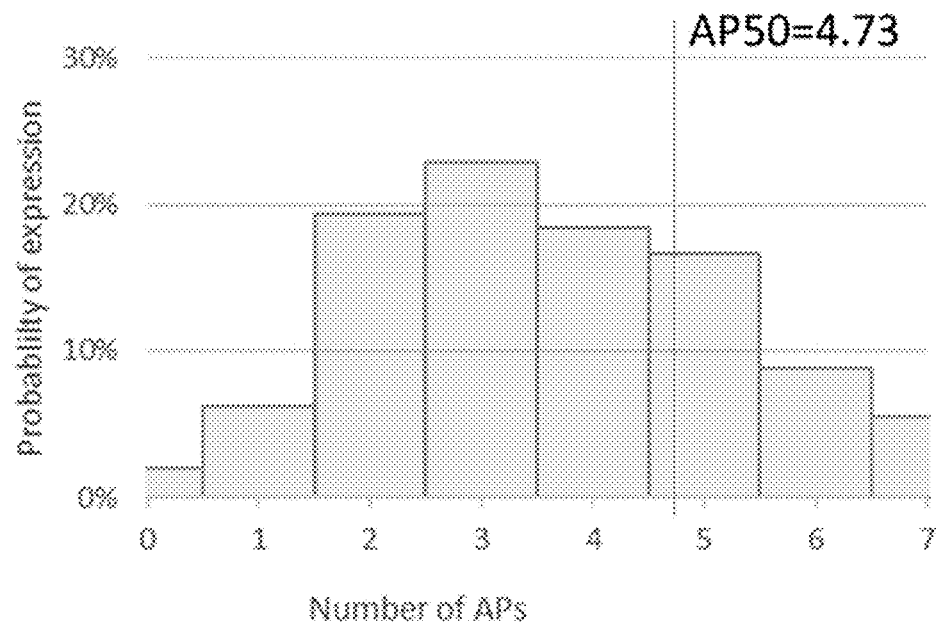
FIGS. 17A-B—PEPI represented antigen (colorectal cancer vaccine-specific CTA antigens for which ≥1 PEPI is predicted. Called as "AP") distribution within the model population (n=433) for colorectal cancer.
Figure 17B:
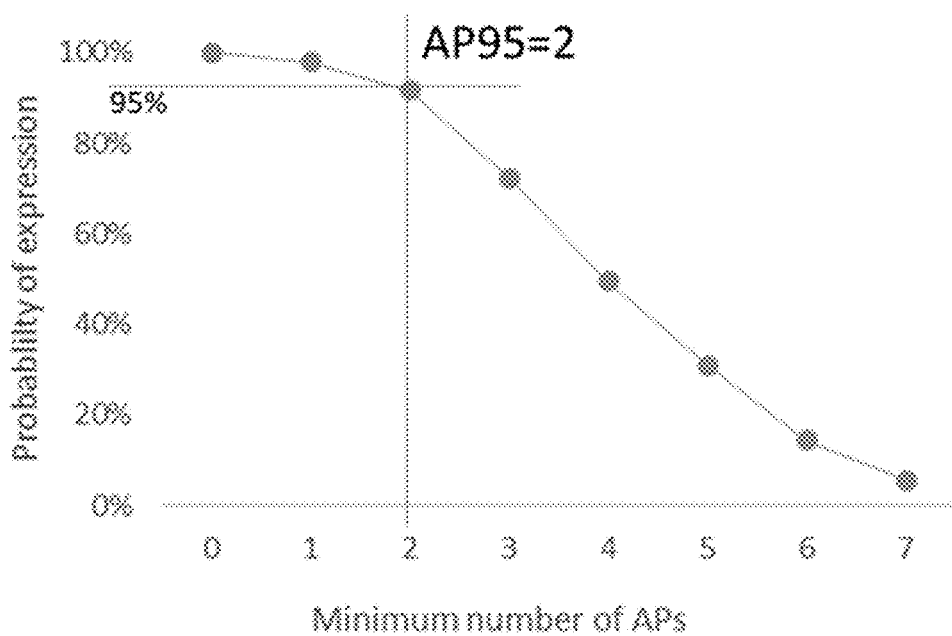
Figure 18A:
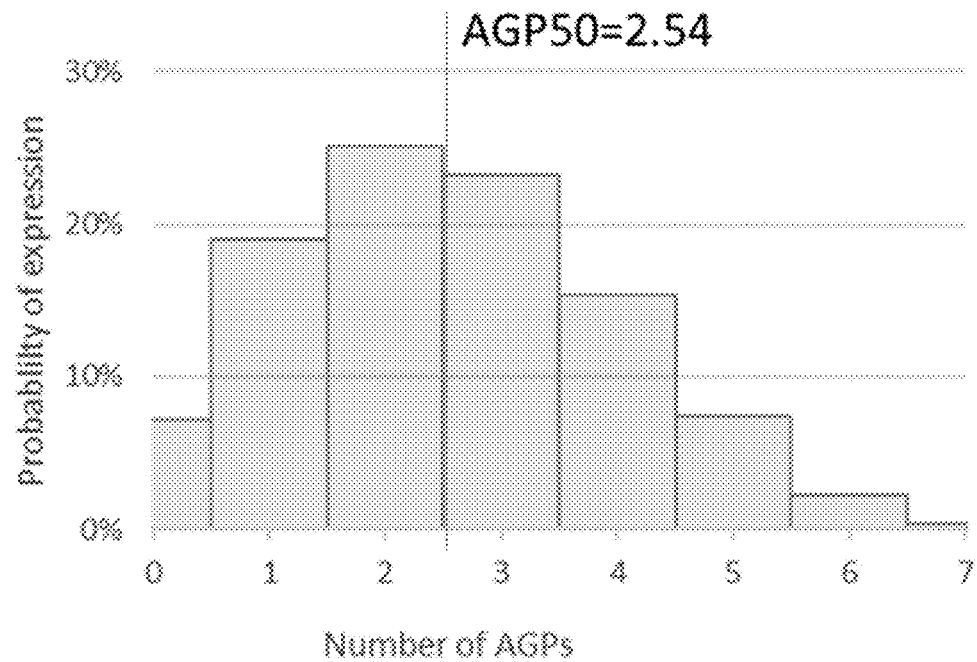
FIGS. 18A-B—PEPI represented expressed antigen (colorectal cancer vaccine-specific CTA antigens expressed by the tumor, for which ≥1 PEPI is predicted. Called as "AGP") distribution within the model population (n=433) calculated with CTA expression rates for colorectal cancer.
Figure 18B:
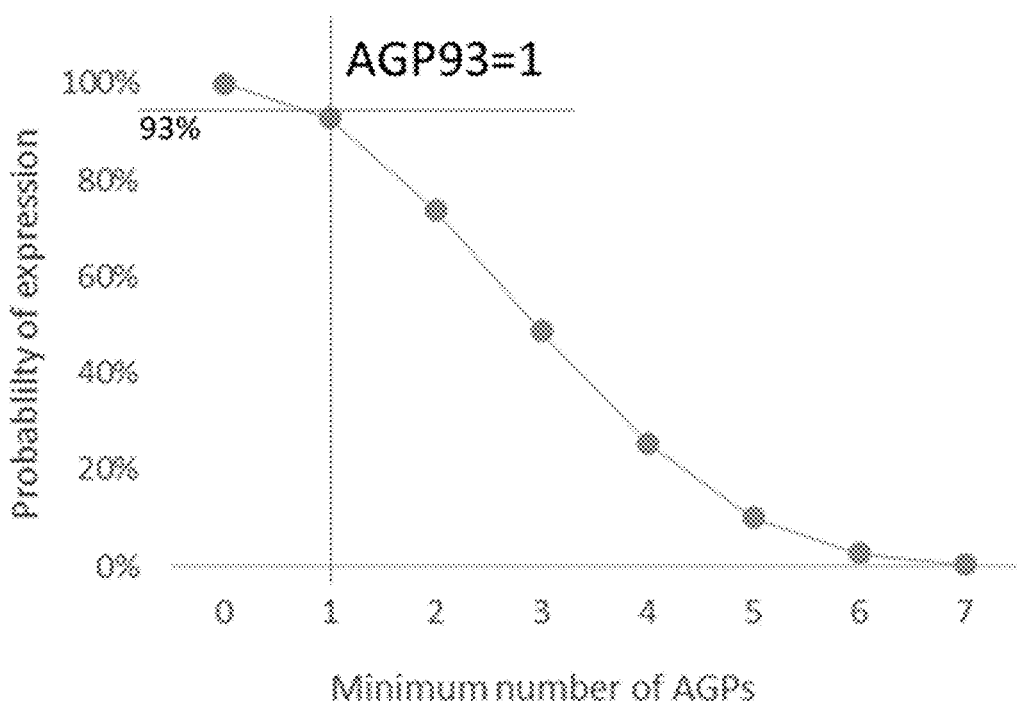

Patient heterogeneity: the AP50=4.73 and AP95=2 (AP95=2) (FIGS. 17A-B). Both tumor and patient heterogeneity: AGP50=3.16 and AGP95=1 (Model Population) (FIGS. 18A-B).

Example 17—Comparison of Colorectal Cancer Vaccine Peptides with Competing Colorectal Cancer Vaccines We used the in silico clinical trial model described above to determine T cell responder rate of state of art and currently developed CRC peptide vaccines and compared to and compared to that of polyPEPI1015 (Table 22). Our PEPI3+ test demonstrate that competing vaccines can induce immune responses against one tumor antigen in a fraction of subjects (2%-77%). However, the multi-antigen (multi-PEPI) response determination for the 2 competitor multi-antigen vaccines resulted in no or 2% responders. *% of responders are the ratio of subjects from the Model population with 1≥PEPI3+ for HLAI (CD8+ T cell responses) in case of 1, or for 2, 3, 4 or 5 antigens of the vaccine compositions. Since multi-PEPI responses correlate with clinical responses induced by tumor vaccines, it is unlikely that any of the competing vaccines will demonstrate clinical benefit in 98% of patients. In contrast, we predicted multi-PEPI responses in 95% of subjects suggesting the likelihood for clinical benefit in the majority of patients.

TABLE 22

Predicted immune response rates of polyPEPI1015 and competing colorectal cancer vaccines

| Colorectal Cancer Vaccines | Sponsor | Vaccine antigens (Ags) | % of CD8+ T cell responders in 433 subjects* | | | | |
|---|---|---|---|---|---|---|---|
| | | | 1 Ag | % responders against multiple Ags | | | |
| | | | | 2 Ags | 3Ags | 4Ags | 5 Ags |
| Stimuvax ®(L-BLP25) Peptide Vaccine | Johannes Gutenberg University Mainz | 1 | 6% | — | — | — | — |
| WT1 Multipeptide Vaccine | Shinshu University, Japan | 1 | 79% | — | — | — | — |
| Multiepitope Peptide Cocktail Vaccine | Kinki University | 7 | 5% | 2% | 0% | 0% | 0% |
| p53 Synthetic Long Peptide Vaccine | Leiden University Medical Center | 1 | 77% | — | — | — | — |
| HER-2 B Cell Peptide Vaccine | Ohio State University Comprehensive Cancer Center | 1 | 18% | — | — | — | — |
| NY-ESO-1 peptide pulsed dendritic cell vaccine | Jonsson Comprehensive Cancer Center | 1 | 0% | — | — | — | — |
| OCV-C02 | Otsuka Pharmaceutical Co., Ltd. | 2 | 2% | 0% | — | — | — |
| PolyPEPI1015 | Treos Bio | 8 | 100% | 95% | 87% | 70% | 54% |

Example 18 Ovarian Cancer Vaccine Design and Composition

We used the PEPI3+ Test to design peptides for use in ovarian cancer vaccines using essentially the same design method described in Examples 13 and 16 above.

We multiplied the reported expression frequency for CTAs associated with ovarian cancer (N %) by the frequency of the PEPI3+ hotspots in the Model Population (B %) to identify the T cell epitopes (9 mers) that will induce an immune response against ovarian cancer antigens in the highest proportion of individuals (Table 23). We then selected 15 mers encompassing each of the selected 9 mers (Table 23). The 15 mers were selected to bind to most ELLA class II alleles of most subjects, using the process described in Example 20 below.

TABLE 23

BestEPI list (9-mers underlined) for selecting ovarian cancer peptides for vaccine composition. N%: Antigen expression frequency in colorectal cancers; B%: bestEPI frequency, ie. the percentage of individuals with epitopes binding to at least 3 HLA class I of subjects in the model population (433 subjects); HLAII**: Percentage of individuals having CD4+ T cell specific PEPI4+ within normal donors (n = 400); N% * B%: N% multiplied by B%.

| SEQ ID NO. 9 mer | SEQ ID NO. 15 mer | Antigen | N% | BestEPIs and Optimized 15 mer Opt. 15 mer | Opt. Position | B% | HLAII** (CD4) | B% * N% |
|---|---|---|---|---|---|---|---|---|
| 272 | 302 | PIWIL-4 | 90% | QGMMMSIATKIAMQM | 585 | 79% | 72% | 71% |
| 273 | 303 | PIWIL-4 | 90% | KAKAFDGAILFLSQK | 153 | 62% | 80% | 56% |
| 274 | 304 | WT1 | 63% | SSGQARMFPNAPYLP | 121 | 78% | 0% | 49% |
| 275 | 305 | EpCam | 92% | RTYWIIIELKHKARE | 140 | 51% | 100% | 47% |
| 276 | 306 | BORIS | 82% | MFTSSRMSSFNRHMK | 263 | 57% | 66% | 46% |
| 277 | 307 | AKAP4 | 88% | QVNIDYLMNRPQNLR | 162 | 52% | 46% | 46% |
| 278 | 308 | OY-TES-1 | 65% | STPMIMENIQELIRS | 277 | 67% | 82% | 43% |
| 279 | 309 | AKAP4 | 88% | MMAYSDTTMMSDDID | 1 | 49% | 0% | 43% |
| 280 | 310 | SP17 | 65% | AFAAAYFESLLEKRE | 37 | 65% | 100% | 42% |
| 281 | 311 | PIWIL-4 | 90% | RAIQQYVDPDVQLVM | 534 | 46% | 5% | 42% |
| 282 | 312 | PIWIL-2 | 61% | GFVASINLTLTKWYS | 759 | 67% | 93% | 41% |
| 283 | 313 | AKAP4 | 88% | DLQKYALGFQHALSP | 117 | 46% | 82% | 40% |

TABLE 23-continued

BestEPI list (9-mers underlined) for selecting ovarian cancer
peptides for vaccine composition. N%: Antigen expression
frequency in colorectal cancers; B%: bestEPI frequency,
ie. the percentage of individuals with epitopes binding to
at least 3 HLA class I of subjects in the model population
(433 subjects); HLAII**: Percentage of individuals having CD4+
T cell specific PEPI4+ within normal donors (n = 400);
N% * B%: N% multiplied by B%.

| SEQ ID NO. 9 mer | SEQ ID NO. 15 mer | Antigen | N% | BestEPIs and Optimized 15 mer Opt. 15 mer | Opt. Position | B% | HLAII** (CD4) | B% * N% |
|---|---|---|---|---|---|---|---|---|
| 284 | 314 | PIWIL-3 | 88% | GYVTSVLQYENSITL | 266 | 44% | 54% | 39% |
| 285 | 315 | SPAG9 | 90% | VREEAQKMSSLLPTM | 958 | 43% | 1% | 39% |
| 286 | 316 | PIWIL-3 | 88% | MSLKGHLQSVTAPMG | 523 | 42% | 17% | 37% |
| 287 | 317 | PIWIL-3 | 88% | QKSIAGFVASTNAEL | 663 | 42% | 37% | 37% |
| 288 | 318 | PIWIL-2 | 61% | RNFYDPTSAMVLQQH | 341 | 60% | 49% | 37% |
| 289 | 319 | BORIS | 82% | NMAFVTSGELVRHRR | 319 | 44% | 75% | 36% |
| 290 | 320 | AKAP4 | 88% | LSFYVNRLSSLVIQM | 217 | 36% | 100% | 31% |
| 291 | 321 | PRAME | 59% | LERLAYLHARLRELL | 457 | 52% | 100% | 30% |
| 292 | 322 | BORIS | 82% | RFTQSGTMKIHILQK | 406 | 35% | 69% | 29% |
| 293 | 323 | HIWI | 68% | HAFDGTILFLPKRLQ | 161 | 39% | 83% | 27% |
| 294 | 324 | EpCam | 92% | YVDEKAPEFSMQGLK | 251 | 28% | 0% | 26% |
| 295 | 325 | SPAG9 | 90% | SGAVMSERVSGLAGS | 16 | 28% | 9% | 25% |
| 296 | 326 | HIWI | 68% | GFTTSILQYENSIML | 251 | 37% | 86% | 25% |
| 297 | 327 | PIWIL-2 | 61% | YSRVVFQMPHQEIVD | 772 | 40% | 77% | 24% |
| 298 | 328 | PRAME | 59% | RHSQTLKAMVQAWPF | 64 | 37% | 38% | 22% |
| 299 | 329 | Survivin | 84% | AKKVRRAIEQLAAMD | 128 | 26% | 25% | 22% |
| 300 | 330 | BORIS | 82% | ERSDEIVLTVSNSNV | 210 | 25% | 2% | 21% |
| 301 | 331 | WT1 | 63% | RTPYSSDNLYQMTSQ | 218 | 32% | 0% | 20% |

Then we designed 15 30 mer peptides (Table 24).

TABLE 24

30 mer ovarian cancer vaccine peptides

| SEQID | TREOSID | Source Antigen | Peptide (30 mer) | HLAI* (CD8) | HLAII** (CD4) |
|---|---|---|---|---|---|
| 332 | OC1212-01 | OY-TES-1/PIWIL-4 | STPMIMENIQELIRSQGMMMSIATKIAMQM | 94% | 98% |
| 333 | OC1212-02 | PIWIL-2/PIWIL-4 | RNFYDPTSAMVLQQHKAKAFDGAILFLSQK | 89% | 90% |
| 334 | OC1212-03 | BORIS/AKAP4 | NMAFVTSGELVRHRRMMAYSDTTMMSDDID | 68% | 75% |
| 335 | OC1212-04 | WT1/WT1 | SSGQARMFPNAPYLPRTPYSSDNLYQMTSQ | 84% | 0% |
| 336 | OC1212-05 | BORIS/HIWI | MFTSSRMSSFNRHMKHAFDGTILFLPKRLQ | 67% | 94% |
| 337 | OC1212-06 | PIWIL-2/EpCam | YSRVVFQMPHQEIVDRTYWIIIELKHKARE | 67% | 100% |
| 338 | OC1212-07 | AKAP4/PIWIL-4 | LSFYVNRLSSLVIQMRAIQQYVDPDVQLVM | 71% | 100% |
| 339 | OC1212-08 | AKAP4/SP17 | QVNIDYLMNRPQNLRAFAAAYFESLLEKRE | 78% | 100% |
| 340 | OC1212-09 | PIWIL-3/PIWIL-3 | GYVTSVLQYENSITLQKSIAGFVASTNAEL | 64% | 65% |

TABLE 24-continued 30 mer ovarian cancer vaccine peptides

| SEQID | TREOSID | Source Antigen | Peptide (30 mer) | HLAI* (CD8) | HLAII** (CD4) |
|---|---|---|---|---|---|
| 341 | OC1212-10 | SPAG9/BORIS | VREEAQKMSSLLPTMRFTQSGTMKIHILQK | 62% | 69% |
| 342 | OC1212-11 | PIWIL-2/EpCam | GFVASINLTLTKWYSYVDEKAPEFSMQGLK | 74% | 93% |
| 343 | OC1212-12 | PIWIL-3/SPAG9 | MSLKGHLQSVTAPMGSGAVMSERVSGLAGS | 52% | 19% |
| 344 | OC1212-13 | AKAP4/PRAME | DLQKYALGFQHALSPLERLAYLHARLRELL | 67% | 100% |
| 345 | OC1212-14 | HIWI/BORIS | GFTTSILQYENSIMLERSDEIVLTVSNSNV | 49% | 86% |
| 346 | OC1212-15 | PRAME/Survivin | RHSQTLKAMVQAWPFAKKVRRAIEQLAAMD | 48% | 42% |

*Percentage of individuals having CD8+ T cell specific PEPI3+ within the Model Population (n = 433).
**Percentage of individuals having CD4+ T cell specific PEPI4+ within normal donors (n = 400).

Example 19, Efficacy by Design Procedure Exemplified for PolyPEPI1018 Colorectal Cancer Vaccine The PolyPEPI1018 Colorectal Cancer (CRC) Vaccine (PolyPEPI1018) composition is a peptide vaccine intended to be used as an add-on immunotherapy to standard-of-care CRC treatment options in patients identified as likely responders using a companion in vitro diagnostic test (CDx). Clinical trials are ongoing in the US and Italy to evaluate PolyPEPI1018 in metastatic colorectal cancer patients. The product contains 6 peptides (6 of the 30 mer peptides PolyPEPI1015 described in examples 16 and 17) mixed with the adjuvant Montanide. The 6 peptides were selected to induce T cell responses against 12 epitopes from 7 cancer testis antigens (CTAs) that are most frequently expressed in CRC. The 6 peptides were optimized to induce long lasting CRC specific T cell responses. Likely responder patients with T cell responses against multiple CTAs expressed in the tumor can be selected with a companion diagnostic (CDx). This example sets out the precision process used to design PolyPEPI1018. This process can be applied to design vaccines against other cancers and diseases.

A. Selection of Multiple Antigen Targets

The selection of tumor antigens is essential for the safety and efficacy of cancer vaccines. The feature of a good antigen is to have restricted expression in normal tissues so that autoimmunity is prevented. Several categories of antigen meet this requirement, including uniquely mutated antigens (e.g. p53), viral antigens (e.g. human papillomavirus antigens in cervical cancer), and differentiation antigens (e.g. CD20 in B-cell lymphoma).

The inventors selected multiple cancer testis antigens (CTAs) as target antigens since they are expressed in various types of tumor cells and testis cells, but not expressed in any other normal somatic tissues or cells. CTAs are desirable targets for vaccines for at least the following reasons:

tumors of higher histological grade and later clinical stage often show higher frequency of CTA expression only a subpopulation of tumor cells express a certain CTA different cancer types are significantly different in their frequency of CTA expression tumors that are positive for a CTA often show simultaneous expression of more than one CTA None of the CTAs appear to be cell surface antigens, therefore these are unique targets for cancer vaccines (they are not suitable targets for antibody based immunotherapies)

To identify the target CTAs for PolyPEPI1018, the inventors built a CTA expression knowledgebase. This knowledgebase contains CTAs that are expressed in CRC ranked in order by expression rate. Correlation studies conducted by the inventors (see Example 11) suggest that vaccines which induce CTL responses against multiple antigens that are expressed in tumor cells can benefit patients. Therefore, seven CTAs with high expression rates in CRC were selected for inclusion in PolyPEPI1018 development. Details are set out in Table 25.

TABLE 25

Target CTAs in PolyPEPI1018 CRC vaccine

| CTA Name | Expression Rate | Characterization |
|---|---|---|
| TSP50 | 89.47% | Testis-Specific Protease-Like Protein 50 is an oncogene which induces cell proliferation, cell invasion, and tumor growth. It is frequently expressed in gastric-, breast-, cervical- and colorectal cancer samples; and rarely expressed in normal human tissues, except in spermatocytes of testes. |
| EpCAM | 88.35% | Epithelial Cell Adhesion Molecule is a tumor associated antigen, which is expressed in colon cancers and over-expressed in various human carcinomas. The high expression of EpCAM in cancer-initiating stem cells makes it a valuable target for cancer vaccines. EpCAM is also expressed in at low or negligible levels in normal epithelial cells, with the exception of squamous epithelium, hepatocytes and keratinocytes. |

TABLE 25-continued

Target CTAs in PolyPEPI1018 CRC vaccine

| CTA Name | Expression Rate | Characterization |
|---|---|---|
| Survivin | 87.28% | Survivin (Baculoviral IAP repeat-containing protein 5) is a multi-tasking protein that promotes cell proliferation and inhibits apoptosis. Though it is strongly expressed in fetal tissues and necessary for normal development, it is not expressed in most adult tissues. Survivin is expressed in various cancers including carcinomas. Normal tissues that express low level survivin include thymus, CD34+ bone-marrow-derived stem cells, and basal colonic epithelium. Dramatic over-expression of survivin compared with normal tissues is observed in tumors in the lung, breast, colon, stomach, esophagus, pancreas, bladder, uterus, ovaries, large-cell non-Hodgkin's lymphoma, leukemias, neuroblastoma, melanoma and non-melanoma skin cancers. |
| CAGE1 | 74.47% | Cancer-associated gene 1 protein is a typical CTA, which might play a role in cell proliferation and tumorigenesis. CAGE1 is highly expressed in colorectal cancer tissues and weakly expressed in adjacent normal colorectal mucosa. In addition, CAGE1 is expressed in melanoma, hepatoma, and breast tumors. No CAGE1 protein expression is detected in healthy human tissues, other than testes. |
| SPAG9 | 74.36% | Sperm-associated antigen 9 is involved in c-Jun N-terminal kinase-signaling and functions as a scaffold protein, thus playing an important role in cell survival, proliferation, apoptosis and tumor development. SPAG9 expression was detected in epithelial ovarian cancer (90%), breast cancer (88%), cervical cancer (82%), renal cell cancer (88%) and colorectal cancer (74%) patients. None of the adjacent noncancerous tissues showed antigen expression. SPAG9 expression is restricted to testis. |
| FBXO39 | 38.60% | FBXO39 (BCP-20) is a testis specific protein and is an important part of the E3 ubiquitin ligase complex. It participates in ubiquitination and has a role in regulating the cell cycle, immune responses, signaling, and proteasomal degradation of proteins. FBXO39 is expressed in colon and breast cancers. FBXO39 expression has also been detected in ovary, placenta, and lung. FBXO39 expression is 100-fold higher in testis and 1,000-fold higher in colorectal cancers compared with normal tissue. |
| MAGEA8 | 43.75% | Melanoma-associated antigen 8 function is not known, though it may play a role in embryonal development and tumor transformation or aspects of tumor progression. MAGE-A8 gene is expressed in CRC and hepatocellular carcinoma. MAGE-A8 expression in normal tissues is restricted to the testis and the placenta. |

B. Precise Targeting is Achieved by PEPI3+ Biomarker Based Vaccine Design

As described above the PEPI3+ biomarker predicts a subject's vaccine induced T cell responses. The inventors developed and validated a test to accurately identify the PEPIs from antigen sequences and HLA genotypes (Examples 1, 2, 3). The PEPI Test algorithm was used to identify the dominant PEPIs (besEPIs) from the 7 target CTAs to be included in PolyPEPI1018 CRC vaccine.

The dominant PEPIs identified with the process described here can induce CTL responses in the highest proportion of subjects:

i. Identification of all HLA class I binding PEPIs from the 7 CTA targets in each of the 433 subjects in the Model Population ii. Identification of the dominant PEPIs (BestEPIs) that are PEPIs present in the largest subpopulation.

The 12 dominant PEPIs that are derived from the 7 CTAs in PolyPEPI1018 are presented in the Table 26. The PEPI % in Model Population indicates the proportion of 433 subjects with the indicated PEPI, i.e. the proportion of subjects where the indicated PEPI can induce CTL responses. There is very high variability (18%-78%) in the dominant PEPIs to induce CTL responses despite the optimization steps used in the identification process.

TABLE 26

CRC specific HLA class I binding dominant PEPIs in PolyPEPI1018
Dominant PEPI3+ for each of the 7 CTAs in PolyPEPI1018 in CRC patients

| Peptides in PolyPEPI1018 | CRC Antigens | Dominant PEPI3+ | PEPI3+% in Model Population |
|---|---|---|---|
| CRC-P1 | TSP50 | TTMETQFPV | 36% |
|  |  | YRAQRFWSW | 20% |
| CRC-P2 | EpCAM | RTYWIIIEL | 51% |
|  | Survivin | RAIEQLAAM | 26% |
| CRC-P3 | EpCAM | YVDEKAPEF | 28% |
|  | MAGE-A8 | KVAELVRFL | 18% |
| CRC-P6 | CAGE1 | KMHSLLALM | 42% |
|  | Survivin | STFKNWPFL | 15% |
| CRC-P7 | CAGE1 | KSMTMMPAL | 37% |
|  | SPAG9 | VMSERVSGL | 28% |
| CRC-P8 | FBXO39 | FMNPYNAVL | 78% |
|  |  | FFFERIMKY | 46% |

The inventors optimized each dominant PEPI to bind to most HLA class II alleles of most subjects. This should enhance efficacy, because it will induce CD4+ T helper cells that can augment CD8+ CTL responses and contribute to long lasting T cell responses. The example presented in FIG. 4 demonstrates that PEPIs that bind to ≥3 HLA class II alleles most likely activate T helper cells.

The 15-mer peptides selected with the process described here contain both HLA class I and class II binding dominant PEPIs. Therefore, these peptides can induce both CTL and T helper responses in the highest proportion of subjects.

Process:
1. Identification the HLA class II genotype of 400 normal donors*
2. Extension of each 9-mer dominant PEPI (Table 20) on both sides with amino acids that match the source antigen
3. Prediction of HLA class II PEPIs of 400 normal donors using an IEDB algorithm
4. Selection the 15-mer peptide with the highest proportion of subject have HLA Class II binding PEPIs
5. Ensure the presence of one dominant HLA class II PEPI in each vaccine peptide when joining two 15-mer peptides The 12 optimized 15-mer peptides derived from the 7 CTAs in PolyPEPI1018 are presented in the Table 27. These peptides have different HLA class II binding characteristics. There is a high variability (0%-100%) in PEPI generation capacity (≥3 HLA binding) among these peptides despite such an optimized personalized vaccine design.

The 30-mer vaccine peptides have the following advantages compared to shorter peptides:
(i) Multiple precisely selected tumor specific immunogens: each 30 mer contains two precisely selected cancer specific immunogenic peptides that are capable to induce CTL and T helper responses in the majority of the relevant population (similar to the model population).
(ii) Ensure natural antigen presentation. 30-mer long polypeptides can be viewed as pro-drugs: They are not biologically active by themselves, but are processed to smaller peptides (9 to 15 amino acid long) to be loaded into the HLA molecules of professional antigen presenting cells. The antigen presentation resulting from long peptide vaccination reflects physiological pathways for presentation in both HLA class I and class II molecules. In addition, long peptide processing in the cells is much more efficient than that of large intact proteins.
(iii) Exclude induction of tolerizing T cell responses. 9-mer peptides do not require processing by professional antigen-presenting cells and therefore bind exogenously to the HLA class I molecules. Thus, injected short peptides will bind in large numbers to HLA class I molecules of all nucleated cells that have surface HLA class I. In contrast, >20-mers long peptides are processed by antigen presenting cells before binding to HLA class I. Therefore, vaccination with long peptides is less likely to lead to tolerance and will promote the desired antitumor activity.
(iv) Induce long lasting T cell responses because it can stimulate T helper responses by binding to multiple HLA class II molecules
(v) Utility. GMP manufacturing, formulation, quality control and administration of a smaller number of peptides (each with all of the above characteristics) is more feasible than a larger number of peptides supplying different characteristics.

Each 30-mer peptide in PolyPEPI1018 consists of 2 HLA class I binding dominant PEPIs and at least one strong HLA

TABLE 27

Antigen specific HLA class II binding PEPIs in PolyPEPI1018.

| Nr. | CRC antigens | Average HLA class II binding alleles | % subjects with ≥1 HLA class II binding | % subjects with ≥2 HLA class II binding | % subjects with ≥3 HLA class II binding | % subjects with ≥4 HLA class II binding |
|---|---|---|---|---|---|---|
| CRC-P1 | TSP50 (83-97) | 0 | 0% | 0% | 0% | 0% |
|  | TSP50 (190-204) | 4 | 100% | 99% | 88% | 53% |
| CRC-P2 | EPCAM(139-153) | 5 | 100% | 100% | 100% | 98% |
|  | SURVIVIN(127-141) | 2 | 84% | 58% | 26% | 11% |
| CRC-P3 | EPCAM(251-265) | 0 | 0% | 0% | 0% | 0% |
|  | MAGE-A8(113-127) | 4 | 100% | 100% | 95% | 72% |
| CRC-P6 | CAGE1(613-627) | 5 | 100% | 100% | 99% | 95% |
|  | SURVIVIN(15-29) | 3 | 100% | 97% | 83% | 45% |
| CRC-P7 | CAGE1(759-773) | 3 | 100% | 98% | 87% | 56% |
|  | SPAG9(16-30) | 1 | 66% | 35% | 9% | 2% |
| CRC-P8 | FBXO39(95-109) | 3 | 100% | 94% | 43% | 13% |
|  | FBXO39(284-298) | 5 | 100% | 100% | 100% | 98% | class II binding PEPI. Strong binding PEPIs bind to 4 HLA class II alleles in >50% of individuals. Therefore, the vaccine peptides are tailored to both HLA class I and class II alleles of individual subjects in a general population (which is a relevant population for CRC vaccine design).

As demonstrated above the high HLA genotype variability in subjects results in high variability of T cell responses induced by PolyPEPI1018. This justifies the co-development of a CDx that determines likely responders. The PEPI3+ and >2PEPI3+ biomarkers could predict the immune response and clinical responses, respectively, of subjects vaccinated with PolyPEPI1018 as detailed in Examples 11 and 12. These biomarkers will be used to co-develop a CDx which predicts likely responders to Poly-PEPI1018 CRC vaccine.

Example 20—Analysis of the Composition and Immunogenicity of PolyPEPI1018 CRC Vaccine Selected peptides for the PolyPEPI1018 composition are as shown in Table 28.

TABLE 28

Selected Colorectal Cancer Vaccine peptides for PolyPEPI1018 composition

| SEQID | TREOSID | Source Antigen | Peptide (30 mer) | HLAI* (CD8) | HLAII** (CD4) |
|---|---|---|---|---|---|
| 130 | CCV1000-5-1 | TSP50 | PSTTMETQFPVSEGKSRYRAQRFWSWVGQA | 53% | 88% |
| 121 | CCV1000-2-2 | EpCAM/Survivin | VRTYWIIIELKHKARTAKKVRRAIEQLAAM | 57% | 100% |
| 131 | CCV1000-5-3 | EpCAM/Mage-A8 | YVDEKAPEFSMQGLKDEKVAELVRFLLRKY | 43% | 95% |
| 124 | CCV1000-2-6 | Cage/Survivin | LASKMHSLLALMVGLKDHRISTFKNWPFLE | 58% | 99% |
| 134 | CCV1000-5-7 | Cage/Spag9 | PKSMTMMPALFKENRSGAVMSERVSGLAGS | 57% | 87% |
| 126 | CCV1000-2-8 | FBXO39 | KFMNPYNAVLTKKFQKVNFFFERIMKYERL | 90% | 100% |
|  |  |  | PolyPEPI1018 (6 peptide together) | 98% | 100% |

*Percentage of individuals having HLA class I binding PEPI3+ within the Model Population (n = 433).
**Percentage of individuals having HLA class II binding PEPI3+ within the Model Population (n = 433).

The peptides of PolyPEPI1018 are formulated in two mixtures, MIX1 containing the peptides of SEQ ID: 130, 131 and MIX2 containing the peptides of SEQ ID: 121, 124, 134, 126. MIX 1 and MIX 2 may be administered sequentially.

Characterization of Immunogenicity

The inventors used the PEPI3+ Test to characterized the immunogenicity of PolyPEPI1018 in a cohort of 37 CRC patients with complete HLA genotype data. T cell responses were predicted in each patient against the same 9 mer peptides that will be used in clinical trials. These peptides represent the 12 dominant PEPI3+ within the PolyPEPI1018 peptides. The 9 mers are shown in Table 26.

The specificity and sensitivity of PEPI3+ prediction depends on the actual number of HLAs predicted to bind a particular epitope. Specifically, the inventors have determined that the probability that one HLA-restricted epitope induces a T cell response in a subject is typically 4%, which explains the poor sensitivity of the state-of-art prediction methods based on HLA restricted epitope prediction. Applying the PEPI3+ methodology, the inventors determined the probability that T cell response to each of the dominant PEPI3+-specific would be induced by PolyPEPI1018 in the 37 CRC patients. The results from this analysis are summarized in the Table 29.

TABLE 29

Probability of Dominant PEPI in the 6 Peptides of PolyPEPI1018 in 37 CRC Patients

|  | CRC-P1 | | CRC-P2 | | CRC-P3 | | CRC-P6 |
|---|---|---|---|---|---|---|---|
| CRC Patient | TSP50 (83-97) | TSP50 (190-204) | EpCAM (139-153) | Survivin (127-141) | EpCAM (251-265) | MAGEA8 (113-127) | CAGE1 (613-627) |
| CRC-01 | 22% | 4% | 22% | 4% | 22% | 22% | 100% |
| CRC-02 | 22% | 1% | 22% | 22% | 22% | 22% | 100% |
| CRC-03 | 84% | 22% | 84% | 22% | 22% | 22% | 84% |
| CRC-04 | 22% | 84% | 22% | 4% | 22% | 4% | 98% |
| CRC-05 | 22% | 22% | 4% | 4% | 22% | 4% | 98% |
| CRC-06 | 84% | 22% | 4% | 84% | 98% | 4% | 22% |
| CRC-07 | 22% | 22% | 22% | 22% | 22% | 4% | 98% |
| CRC-08 | 22% | 22% | 22% | 98% | 84% | 22% | 84% |
| CRC-09 | 22% | 84% | 84% | 84% | 84% | 22% | 100% |
| CRC-10 | 4% | 98% | 22% | 22% | 4% | 4% | 4% |
| CRC-11 | 22% | 22% | 4% | 4% | 22% | 4% | 84% |
| CRC-12 | 84% | 22% | 4% | 22% | 4% | 4% | 84% |
| CRC-13 | 84% | 22% | 4% | 22% | 84% | 4% | 84% |
| CRC-14 | 22% | 84% | 4% | 4% | 22% | 4% | 84% |
| CRC-15 | 84% | 22% | 22% | 22% | 22% | 4% | 84% |
| CRC-16 | 4% | 84% | 4% | 4% | 22% | 4% | 84% |
| CRC-17 | 84% | 84% | 4% | 84% | 84% | 4% | 4% |
| CRC-18 | 84% | 22% | 22% | 84% | 84% | 4% | 22% |
| CRC-19 | 22% | 22% | 22% | 22% | 22% | 4% | 98% |
| CRC-20 | 84% | 22% | 4% | 22% | 84% | 4% | 84% |
| CRC-21 | 22% | 22% | 22% | 22% | 84% | 22% | 98% |
| CRC-22 | 22% | 98% | 84% | 4% | 22% | 22% | 84% |
| CRC-23 | 84% | 84% | 84% | 84% | 84% | 22% | 84% |

TABLE 29-continued

Probability of Dominant PEPI in the 6 Peptides of PolyPEPI1018 in 37 CRC Patients

| CRC-24 | 22% | 22% | 4%  | 4%  | 22% | 4% | 84% |
|--------|-----|-----|-----|-----|-----|-----|-----|
| CRC-25 | 22% | 84% | 22% | 4%  | 22% | 4% | 84% |
| CRC-26 | 84% | 22% | 4%  | 22% | 84% | 4% | 84% |
| CRC-27 | 22% | 22% | 4%  | 4%  | 22% | 4% | 98% |
| CRC-28 | 84% | 22% | 4%  | 22% | 84% | 4% | 84% |
| CRC-29 | 84% | 84% | 4%  | 22% | 22% | 4% | 84% |
| CRC-30 | 84% | 22% | 4%  | 22% | 84% | 4% | 84% |
| CRC-31 | 22% | 84% | 22% | 4%  | 4%  | 4% | 22% |
| CRC-32 | 84% | 84% | 4%  | 84% | 22% | 4% | 4%  |
| CRC-33 | 84% | 22% | 4%  | 22% | 84% | 4% | 84% |
| CRC-34 | 22% | 22% | 22% | 22% | 22% | 4% | 84% |
| CRC-35 | 22% | 4%  | 4%  | 1%  | 22% | 4% | 4%  |
| CRC-36 | 22% | 4%  | 4%  | 1%  | 22% | 4% | 4%  |
| CRC-37 | 22% | 4%  | 4%  | 1%  | 22% | 4% | 4%  |

| CRC Patient | CRC-P6 Survivin (15-29) | CRC-P7 CAGE1 (759-773) | CRC-P7 SPAG9 (16-30) | CRC-P8 FBXO39 (95-109) | CRC-P8 FBXO39 (284-298) | Expected Number of PEPIs |
|---|---|---|---|---|---|---|
| CRC-01 | 1%  | 98% | 84% | 100% | 22% | 5.01 |
| CRC-02 | 1%  | 98% | 22% | 100% | 98% | 5.29 |
| CRC-03 | 22% | 22% | 22% | 100% | 22% | 5.29 |
| CRC-04 | 4%  | 4%  | 22% | 100% | 84% | 4.70 |
| CRC-05 | 1%  | 4%  | 4%  | 100% | 84% | 3.68 |
| CRC-06 | 4%  | 4%  | 4%  | 100% | 98% | 5.27 |
| CRC-07 | 1%  | 22% | 22% | 100% | 84% | 4.41 |
| CRC-08 | 22% | 22% | 22% | 100% | 84% | 6.04 |
| CRC-09 | 4%  | 22% | 22% | 98%  | 84% | 7.10 |
| CRC-10 | 22% | 22% | 22% | 98%  | 84% | 4.06 |
| CRC-11 | 1%  | 4%  | 4%  | 98%  | 84% | 3.53 |
| CRC-12 | 4%  | 84% | 4%  | 100% | 22% | 4.38 |
| CRC-13 | 1%  | 1%  | 4%  | 100% | 98% | 5.07 |
| CRC-14 | 1%  | 4%  | 4%  | 100% | 84% | 4.16 |
| CRC-15 | 4%  | 22% | 4%  | 100% | 84% | 4.74 |
| CRC-16 | 1%  | 4%  | 22% | 100% | 84% | 4.16 |
| CRC-17 | 4%  | 4%  | 4%  | 100% | 22% | 4.82 |
| CRC-18 | 22% | 4%  | 4%  | 100% | 84% | 5.36 |
| CRC-19 | 4%  | 22% | 22% | 100% | 84% | 4.45 |
| CRC-20 | 1%  | 4%  | 4%  | 100% | 98% | 5.10 |
| CRC-21 | 4%  | 4%  | 22% | 100% | 84% | 5.06 |
| CRC-22 | 22% | 84% | 22% | 98%  | 22% | 5.84 |
| CRC-23 | 84% | 84% | 4%  | 100% | 84% | 8.82 |
| CRC-24 | 1%  | 4%  | 4%  | 100% | 84% | 3.55 |
| CRC-25 | 4%  | 22% | 4%  | 100% | 84% | 4.56 |
| CRC-26 | 1%  | 4%  | 4%  | 100% | 84% | 4.97 |
| CRC-27 | 1%  | 4%  | 4%  | 100% | 84% | 3.68 |
| CRC-28 | 1%  | 4%  | 4%  | 100% | 98% | 5.10 |
| CRC-29 | 1%  | 22% | 22% | 100% | 84% | 5.33 |
| CRC-30 | 1%  | 4%  | 4%  | 100% | 98% | 5.10 |
| CRC-31 | 1%  | 4%  | 4%  | 98%  | 84% | 3.53 |
| CRC-32 | 4%  | 4%  | 4%  | 98%  | 84% | 4.80 |
| CRC-33 | 1%  | 4%  | 4%  | 100% | 98% | 5.10 |
| CRC-34 | 1%  | 22% | 4%  | 100% | 84% | 4.09 |
| CRC-35 | 1%  | 4%  | 4%  | 84%  | 84% | 2.37 |
| CRC-36 | 1%  | 4%  | 4%  | 84%  | 84% | 2.37 |
| CRC-37 | 1%  | 4%  | 4%  | 84%  | 84% | 2.37 |

Abbreviations:
CRC = colorectal cancer;
PEPI = personal epitope
Note:
Percentages represent the likelihood of CD8+ T cell Responses Induced by PolyPEPI1018.

Overall, these results show that the most immunogenic peptide in PolyPEPI1018 is CRC-P8, which it is predicted to bind to >3 HLAs in most patients. The least immunogenic peptide, CRC-P3, binds to >1 HLA in many patients and has a 22% chance of inducing T cell responses. Since bioassays used to detect T cell responses are less accurate than PEPI3+, this calculation may be the most accurate characterization of the T cell responses in CRC patients. Though MAGE-A8 and SPAG9 were immunogenic in the Model Population used for vaccine design, MAGE-A8-specific PEPI3+ were absent in the 37 CRC patients, and only one patient (3%) had SPAG9 specific PEPI3+.

Further characterization of the predicted PolyPEPI1018 response rate in the model population described in Example 8 and in 295 CRC patients with known HLA class I genotypes are shown in Tables 30 and 31.

TABLE 30

PolyPEPI1018 Response Rates in the Model Population (433 Normal donors)

| PolyPEPI1018 Response Rates | >=1 | >=2 | >=3 | >=4 | >=5 | >=6 | >=7 | >=8 | >=9 |
|---|---|---|---|---|---|---|---|---|---|
| Multi PEPI | 98% | 94% | 83% | 70% | 52% | 38% | 27% | 18% | 11% |
| Multi Peptide | 98% | 91% | 73% | 52% | 30% | 12% | N/D | N/D | N/D |
| Multi Antigen | 98% | 92% | 72% | 49% | 31% | 14% | 6% | N/D | N/D |

TABLE 31

PolyPEPI1018 Response Rates for 295 CRC patients

| PolyPEPI1018 Response Rates | >=1 | >=2 | >=3 | >=4 | >=5 | >=6 | >=7 | >=8 | >=9 |
|---|---|---|---|---|---|---|---|---|---|
| Multi PEPI | 99% | 96% | 92% | 85% | 69% | 53% | 40% | 32% | 25% |
| Multi Peptide | 99% | 93% | 86% | 71% | 49% | 29% | N/D | N/D | N/D |
| Multi Antigen | 99% | 93% | 86% | 72% | 49% | 32% | 13% | N/D | N/D |

Characterization of Toxicity—immunoBLAST

A method was developed that can be performed on any antigen to determine its potential to induce toxic immune reaction, like autoimmunity. The method is referred to herein as immunoBLAST. PolyPEPI1018 contains six 30-mer polypeptides. Each polypeptide consists of two 15-mer peptide fragments derived from antigens expressed in CRC. Neoepitopes might be generated in the joint region of the two 15-mer peptides and could induce undesired T cell responses against healthy cells (autoimmunity). This was assesses using the immunoBLAST methodology.

A 16-mer peptide for each of the 30-mer components of PolyPEPI1018 was designed. Each 16-mer contains 8 amino acids from the end of the first 15 residues of the 30-mer and 8 amino acids from the beginning of the second 15 residues of the 30-mer—thus precisely spanning the joint region of the two 15-mers. These 16-mers are then analysed to identify cross-reactive regions of local similarity with human sequences using BLAST (blast.ncbi.nlm.nih.gov/Blast.cgi), which compares protein sequences to sequence databases and calculates the statistical significance of matches. 8-mers within the 16-mers were selected as the examination length since that length represents the minimum length needed for a peptide to form an epitope, and is the distance between the anchor points during HLA binding.

Figure 19:
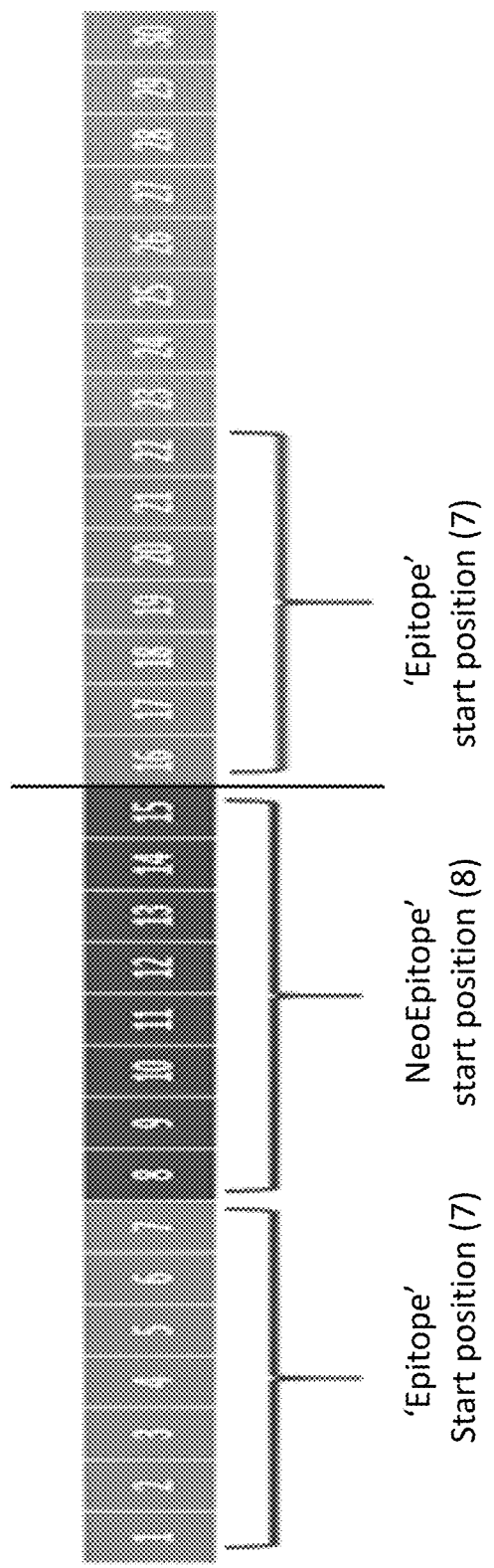
FIG. 19—Schematic showing exemplary positions of amino acids in overlapping HLA class I- and HLA class-II binding epitopes in a 30-mer peptide.

As shown in FIG. 19, the positions of amino acids in a polypeptide are numbered. The start positions of potential 9-mer peptides that can bind to HLAs and form neoepitopes are the 8 amino acids in positions 8-15. The start positions of tumor antigen derived peptides harbored by the 15-mers that can form the pharmaceutically active epitopes are 7+7=14 amino acids at position 1-7 and 16-22. The ratio of possible neoepitope generating peptides is 36.4% (8/22).

The PEPI3+ Test was to identify neoepitopes and neoPEPI among the 9-mer epitopes in the joint region. The risk of PolyPEPI1018 inducing unwanted T cell responses was assessed in the 433 subjects in the Model Population by determining the proportion of subjects with PEPI3+ among the 9-mers in the joint region. The result of neoepitope/neoPEPI analysis is summarized in Table 32. In the 433 subjects of the Model Population, the average predicted epitope number that could be generated by intracellular processing was 40.12. Neoepitopes were frequently generated; 11.61 out of 40.12 (28.9%) epitopes are neoepitopes. Most of the peptides were able to be identified as a neoepitope, but the number of subjects that present neoepitopes varied.

Epitopes harbored by PolyPEPI1018 create an average of 5.21 PEPI3+. These PEPIs can activate T cells in a subject. The amount of potential neoPEPIs was much lower than neoepitopes (3.7%). There is a marginal possibility that these neoPEPIs compete on T cell activation with PEPIs in some subjects. Importantly, the activated neoPEPI specific T cells had no targets on healthy tissue.

TABLE 32

Identification of Potential Neoepitopes of PolyPEPI1018

| | | Epitope & PEPI3+ binding in 433 Subjects of the Model Population | | | | | | |
|---|---|---|---|---|---|---|---|---|
| | | Epitope Binding (1 x HLA) | | | | PEPI3+ binding (3 x HLA) | | |
| PolyPEPI1018 Peptide ID: | Potential Neoepitope | Sub# | Sub % | NeoEPI | NeoEPI count | Sub# | Sub % | NeoPEPI | NeoPEPI count |
| CRC-P1 | QFPVSEGKS | 0 | 0.0% | | 7 | 0 | 0.0% | | 3 |
| | FPVSEGKSR | 160 | 37.0% | X | | 1 | 0.2% | X | |
| | PVSEGKSRY | 150 | 34.6% | X | | 0 | 0.0% | | |
| | VSEGKSRYR | 194 | 44.8% | X | | 1 | 0.2% | X | |
| | SEGKSRYRA | 113 | 26.1% | X | | 0 | 0.0% | | |

TABLE 32-continued

Identification of Potential Neoepitopes of PolyPEPI1018

| PolyPEPI1018 Peptide ID: | Potential Neoepitope | Epitope & PEPI3+ binding in 433 Subjects of the Model Population | | | | | | |
|---|---|---|---|---|---|---|---|---|
| | | Epitope Binding (1 × HLA) | | | | PEPI3+ binding (3 × HLA) | | |
| | | Sub# | Sub % | NeoEPI | NeoEPI count | Sub# | Sub % NeoPEPI | NeoPEPI count |
| | EGKSRYRAQ | 77 | 17.8% | X | | 0 | 0.0% | |
| | GKSRYRAQR | 37 | 8.5% | X | | 0 | 0.0% | |
| | KSRYRAQRF | 337 | 77.8% | X | | 33 | 7.6% X | |
| CRC-P2 | IELKHKART | 32 | 7.4% | X | 7 | 0 | 0.0% | 1 |
| | ELKHKARTA | 63 | 14.5% | X | | 0 | 0.0% | |
| | LKHKARTAK | 59 | 13.6% | X | | 0 | 0.0% | |
| | KHKARTAKK | 166 | 38.3% | X | | 1 | 0.2% X | |
| | HKARTAKKV | 0 | 0.0% | | | 0 | 0.0% | |
| | KARTAKKVR | 70 | 16.2% | X | | 0 | 0.0% | |
| | ARTAKKVRR | 134 | 30.9% | X | | 0 | 0.0% | |
| | RTAKKVRRA | 41 | 9.5% | X | | 0 | 0.0% | |
| CRC-P3 | EFSMQGLKD | 0 | 0.0% | | 5 | 0 | 0.0% | 1 |
| | FSMQGLKDE | 188 | 43.4% | X | | 0 | 0.0% | |
| | SMQGLKDEK | 138 | 31.9% | X | | 0 | 0.0% | |
| | MQGLKDEKV | 16 | 3.7% | X | | 0 | 0.0% | |
| | QGLKDEKVA | 0 | 0.0% | | | 0 | 0.0% | |
| | GLKDEKVAE | 0 | 0.0% | | | 0 | 0.0% | |
| | LKDEKVAEL | 186 | 43.0% | X | | 3 | 0.7% X | |
| | KDEKVAELV | 51 | 11.8% | X | | 0 | 0.0% | |
| CRC-P6 | LLALMVGLK | 252 | 58.2% | X | 7 | 0 | 0.0% | 1 |
| | LALMVGLKD | 86 | 19.9% | X | | 0 | 0.0% | |
| | ALMVGLKDH | 65 | 15.0% | X | | 0 | 0.0% | |
| | LMVGLKDHR | 97 | 22.4% | X | | 0 | 0.0% | |
| | MVGLKDHRI | 67 | 15.5% | X | | 0 | 0.0% | |
| | VGLKDHRIS | 0 | 0.0% | | | 0 | 0.0% | |
| | GLKDHRIST | 4 | 0.9% | X | | 0 | 0.0% | |
| | LKDHRISTF | 195 | 45.0% | X | | 5 | 1.2% X | |
| CRC-P7 | PALFKENRS | 0 | 0.0% | | 5 | 0 | 0.0% | 1 |
| | ALFKENRSG | 0 | 0.0% | | | 0 | 0.0% | |
| | LFKENRSGA | 41 | 9.5% | X | | 0 | 0.0% | |
| | FKENRSGAV | 114 | 26.3% | X | | 0 | 0.0% | |
| | KENRSGAVM | 261 | 60.3% | X | | 0 | 0.0% | |
| | ENRSGAVMS | 0 | 0.0% | | | 0 | 0.0% | |
| | NRSGAVMSE | 227 | 52.4% | X | | 0 | 0.0% | |
| | RSGAVMSER | 197 | 45.5% | X | | 2 | 0.5% X | |
| CRC-P8 | AVLTKKFQK | 181 | 41.8% | X | 7 | 0 | 0.0% | 3 |
| | VLTKKFQKV | 208 | 48.0% | X | | 2 | 0.5% X | |
| | LTKKFQKVN | 0 | 0.0% | | | 0 | 0.0% | |
| | TKKFQKVNF | 25 | 5.8% | X | | 0 | 0.0% | |
| | KKFQKVNFF | 250 | 57.7% | X | | 12 | 2.8% X | |
| | KFQKVNFFF | 273 | 63.0% | X | | 23 | 5.3% X | |
| | FQKVNFFFE | 163 | 37.6% | X | | 0 | 0.0% | |
| | QKVNFFFER | 110 | 25.4% | X | | 0 | 0.0% | |

Abbreviations:
CRC = colorectal cancer;
HLA = human leukocytic antigen;
PEPI = personal epitope Each of the 30-mer peptides in PolyPEPI1018 were released for clinical development since none of the 8-mers in the joint regions matched any human protein, except the target CTAs.

Characterisation of Activity/Efficacy

The inventors have developed pharmacodynamic biomarkers to predict the activity/effect of vaccines in individual human subjects as well as in populations of human subjects. These biomarkers expedite more effective vaccine development and also decrease the development cost. The inventors have the following tools:

Antigen expression knowledgebase: The inventors have collected data from experiments published in peer reviewed scientific journals regarding the tumor antigens expressed by tumor cells and organized by tumor type to create a database of CTA expression levels—CTA database (CTADB). As of April 2017, the CTADB contained data from 145 CTAs from 41,132 tumor specimens, and was organized by the CTA expression frequencies in different types of cancer.

In silico trial populations: The inventors have also collected data on the HLA genotypes of several different model populations. Each individual in the populations has complete 4-digit HLA genotype and ethnicity data. The populations are summarized in Table 33.

TABLE 33

In silico trial populations

| Population | Number of Subjects | Inclusion criteria |
|---|---|---|
| Model Population | 433 | Complete HLA class I genotype Diverse ethnicity |
| CRC patients | 37 | Complete HLA class I genotype CRC diagnosis, unknown ethnicity |
| "Big" Population | 7,189 | Complete HLA class I genotype Diverse ethnicity |
| Chinese Population | 234 | Complete HLA class I genotype Chinese ethnicity |
| Irish Population | 999 | Complete HLA class I genotype Irish ethnicity |

Abbreviations: CRC = colorectal cancer; HLA = human leukocyte antigen

Using these tools (or potentially equivalent databases or model populations), the following markers can be assessed:

AG95—potency of a vaccine: The number of antigens in a cancer vaccine that a specific tumor type expresses with 95% probability. AG95 is an indicator of the vaccine's potency, and is independent of the immunogenicity of the vaccine antigens. AG95 is calculated from the tumor antigen expression rate data, which is collected in the CTADB. Technically, AG95 is determined from the binomial distribution of CTAs, and takes into account all possible variations and expression rates. In this study, AG95 was calculated by cumulating the probabilities of a certain number of expressed antigens, by the widest range of antigens where the sum of probabilities was less than or equal to 95%. The correct value is between 0 (no expression expected with 95% probability) and maximum number of antigens (all antigens expressed with 95% probability).

PEPI3+ count—immunogenicity of a vaccine in a subject: Vaccine-derived PEPI3+ are personal epitopes that induce T cell responses in a subject. PEPI3+ can be determined using the PEPI3+ Test in subjects who's complete 4-digit HLA genotype is known.

AP count—antigenicity of a vaccine in a subject: Number of vaccine antigens with PEPI3+. Vaccines like PolyPEPI1018 contain sequences from antigens expressed in tumor cells. AP count is the number of antigens in the vaccine that contain PEPI3+, and the AP count represents the number of antigens in the vaccine that can induce T cell responses in a subject. AP count characterizes the vaccine-antigen specific T cell responses of the subject since it depends only on the HLA genotype of the subject and is independent of the subject's disease, age, and medication. The correct value is between 0 (no PEPI presented by the antigen) and maximum number of antigens (all antigens present PEPIs).

AP50—antigenicity of a vaccine in a population: The mean number of vaccine antigens with a PEPI in a population. The AP50 is suitable for the characterization of vaccine-antigen specific T cell responses in a given population since it depends on the HLA genotype of subjects in a population. Technically, the AP count was calculated in the Model Population and the binomial distribution of the result was used to calculate the AP50.

AGP count—effectiveness of a vaccine in a subject: Number of vaccine antigens expressed in the tumor with PEPI. The AGP count indicates the number of tumor antigens that vaccine recognizes and induces a T cell response against (hit the target). The AGP count depends on the vaccine-antigen expression rate in the subject's tumor and the HLA genotype of the subject. The correct value is between 0 (no PEPI presented by expressed antigen) and maximum number of antigens (all antigens are expressed and present a PEPI).

AGP50—effectiveness of a cancer vaccine in a population: The mean number of vaccine antigens expressed in the indicated tumor with PEPI (i.e., AGP) in a population. The AGP50 indicates the mean number of tumor antigens that the T cell responses induced by the vaccine can recognize. AGP50 is dependent on the expression rate of the antigens in the indicated tumor type and the immunogenicity of the antigens in the target population. AGP50 can estimate a vaccine's effectiveness in different populations and can be used to compare different vaccines in the same population. The computation of AGP50 is similar to that used for AG50, except the expression is weighted by the occurrence of the PEPI3+ in the subject on the expressed vaccine antigens. In a theoretical population, where each subject has a PEPI from each vaccine antigen, the AGP50 will be equal to AG50. In another theoretical population, where no subject has a PEPI from any vaccine antigen, the AGP50 will be 0. In general, the following statement is valid: $0 \leq AGP50 \leq AG50$.

mAGP—a candidate biomarker for the selection of likely responders: Likelihood that a cancer vaccine induces T cell responses against multiple antigens expressed in the indicated tumor. mAGP is calculated from the expression rates of vaccine-antigens in CRC and the presence of vaccine derived PEPIs in the subject. Technically, based on the AGP distribution, the mAGP is the sum of probabilities of the multiple AGP ($\geq 2$ AGPs).

Application of these Markers to Assess Antigenicity and Effectiveness PolyPEPI1018 in Individual Patients with CRC Table 34 shows the antigenicity and effectiveness of PolyPEPI1018 in 37 CRC patients using AP and AGP50, respectively. As expected from the high variability of PolyPEPI1018 specific T cell responses (see Table 29), the AP and AGP50 have high variability. The most immunogenic antigen in PolyPEPI1018 was FOX039; each patient had a PEPI3+. However, FOX039 is expressed only 39% of CRC tumors, suggesting that 61% of patients will have FOX039 specific T cell responses that do not recognize the tumor. The least immunogenic antigen was MAGE-A8; none of the 37 CRC patients had a PEPI3+ despite the antigen being expressed in 44% of CRC tumors. These results illustrate that both expression and immunogenicity of antigens can be taken into account when determining a cancer vaccine's effectiveness.

AGP50 indicates the mean number of expressed antigens in CRC tumor with PEPIs. Patients with higher AGP50 values are more likely to respond to PolyPEPI1018 since higher AGP50 values indicate that the vaccine can induce T cell responses against more antigens expressed in CRC cells.

The last column in the table 32 shows the probability of mAGP (multiple AGP; i.e., at least 2 AGPs) in each of the 37 CRC patients. The average mAGP in patients with CRC is 66%, suggesting that there is a 66% likelihood that a CRC patient will induce T cell responses against multiple antigens expressed in the tumor.

TABLE 34

Antigenicity (AP count), Effectiveness (AGP50 count), and mAGP of PolyPEPI1018 in 37 CRC Patients

| CRC Patients | Antigens (CTAs) in PolyPEPI1018 | | | | | | | Number of AP (AP count) | Number of AGP50 (AGP50 count) | mAGP |
|---|---|---|---|---|---|---|---|---|---|---|
| | TSP50 | EpCAM | Survivin | CAGE1 | SPAG9 | FBXO39 | MAGE-A8 | | | |
| | 89% | 88% | 87% | 74% | 74% | 39% | 44% | | | |
| CRC-01 | 0 | 0 | 0 | 1 | 1 | 1 | 0 | 3 | 1.87 | 90% |
| CRC-02 | 0 | 0 | 0 | 1 | 0 | 1 | 0 | 2 | 1.13 | 85% |
| CRC-03 | 1 | 1 | 0 | 1 | 0 | 1 | 0 | 4 | 2.91 | 97% |
| CRC-04 | 1 | 0 | 0 | 1 | 0 | 1 | 0 | 3 | 2.03 | 91% |
| CRC-05 | 0 | 0 | 0 | 1 | 0 | 1 | 0 | 2 | 1.13 | 78% |
| CRC-06 | 1 | 1 | 1 | 1 | 0 | 1 | 0 | 5 | 3.78 | 99% |
| CRC-07 | 0 | 0 | 0 | 1 | 0 | 1 | 0 | 2 | 1.13 | 84% |
| CRC-08 | 0 | 1 | 1 | 1 | 0 | 1 | 0 | 4 | 2.89 | 98% |
| CRC-09 | 1 | 1 | 1 | 1 | 0 | 1 | 0 | 5 | 3.78 | 99% |
| CRC-10 | 1 | 0 | 0 | 0 | 0 | 1 | 0 | 2 | 1.28 | 86% |
| CRC-11 | 0 | 0 | 0 | 1 | 0 | 1 | 0 | 2 | 1.13 | 79% |
| CRC-12 | 1 | 0 | 0 | 1 | 0 | 1 | 0 | 3 | 2.03 | 88% |
| CRC-13 | 1 | 1 | 1 | 1 | 0 | 1 | 0 | 5 | 3.78 | 98% |
| CRC-14 | 1 | 0 | 0 | 1 | 0 | 1 | 0 | 3 | 2.03 | 87% |
| CRC-15 | 1 | 0 | 0 | 1 | 0 | 1 | 0 | 3 | 2.03 | 90% |
| CRC-16 | 1 | 0 | 0 | 1 | 0 | 1 | 0 | 3 | 2.03 | 85% |
| CRC-17 | 1 | 1 | 1 | 0 | 0 | 1 | 0 | 4 | 3.04 | 96% |
| CRC-18 | 1 | 1 | 1 | 1 | 0 | 1 | 0 | 5 | 3.78 | 98% |
| CRC-19 | 0 | 0 | 0 | 1 | 0 | 1 | 0 | 2 | 1.13 | 85% |
| CRC-20 | 1 | 1 | 1 | 1 | 0 | 1 | 0 | 5 | 3.78 | 98% |
| CRC-21 | 0 | 1 | 0 | 1 | 0 | 1 | 0 | 3 | 2.01 | 93% |
| CRC-22 | 1 | 1 | 0 | 1 | 0 | 1 | 0 | 4 | 2.91 | 97% |
| CRC-23 | 1 | 1 | 1 | 1 | 0 | 1 | 0 | 5 | 3.78 | 99% |
| CRC-24 | 0 | 0 | 0 | 1 | 0 | 1 | 0 | 2 | 1.13 | 82% |
| CRC-25 | 1 | 0 | 0 | 1 | 0 | 1 | 0 | 3 | 2.03 | 89% |
| CRC-26 | 1 | 1 | 0 | 1 | 0 | 1 | 0 | 4 | 2.91 | 95% |
| CRC-27 | 0 | 0 | 0 | 1 | 0 | 1 | 0 | 2 | 1.13 | 78% |
| CRC-28 | 1 | 1 | 1 | 1 | 0 | 1 | 0 | 5 | 3.78 | 98% |
| CRC-29 | 1 | 0 | 0 | 1 | 0 | 1 | 0 | 3 | 2.03 | 92% |
| CRC-30 | 1 | 1 | 1 | 1 | 0 | 1 | 0 | 5 | 3.78 | 98% |
| CRC-31 | 1 | 0 | 0 | 0 | 0 | 1 | 0 | 2 | 1.28 | 80% |
| CRC-32 | 1 | 0 | 1 | 0 | 0 | 1 | 0 | 3 | 2.15 | 91% |
| CRC-33 | 1 | 1 | 1 | 1 | 0 | 1 | 0 | 5 | 3.78 | 98% |
| CRC-34 | 0 | 0 | 0 | 1 | 0 | 1 | 0 | 2 | 1.13 | 82% |
| CRC-35 | 0 | 0 | 0 | 0 | 0 | 1 | 0 | 1 | 0.39 | 55% |
| CRC-36 | 0 | 0 | 0 | 0 | 0 | 1 | 0 | 1 | 0.39 | 55% |
| CRC-37 | 0 | 0 | 0 | 0 | 0 | 1 | 0 | 1 | 0.39 | 55% |

Abbreviations:
CRC = colorectal cancer;
PEPI = personal epitope;
CTA = cancer testis antigen;
AP = expressed antigens with ≥1 PEPI These biomarkers have immediate utility in vaccine development and in the routine clinical practice because they do not require invasive biopsies. Antigen expression data can be obtained from achieved tumor specimen and organized in databases. 4-digit HLA genotyping can be done from a saliva specimen. It is a validated test performed by certified laboratories worldwide for transplantation and paternity testing. These assessments will allow drug developers and physicians to gain deeper insights into the immunogenicity and activity of tumor response and the possible emergence of resistance.

Application of these Markers to Asses Antigenicity and Effectiveness PolyPEPI1018 in Populations Antigenicity of PolyPEPI1018 CRC Vaccine in a General Population The antigenicity of PolyPEPI1018 in a subject is determined by the AP count, which indicates the number of vaccine antigens that induce T cell responses in a subject. The AP count of PolyPEPI1018 was determined in each of the 433 subjects in the Model Population using the PEPI Test, and the AP50 count was then calculated for the Model Population.

Figure 20A:
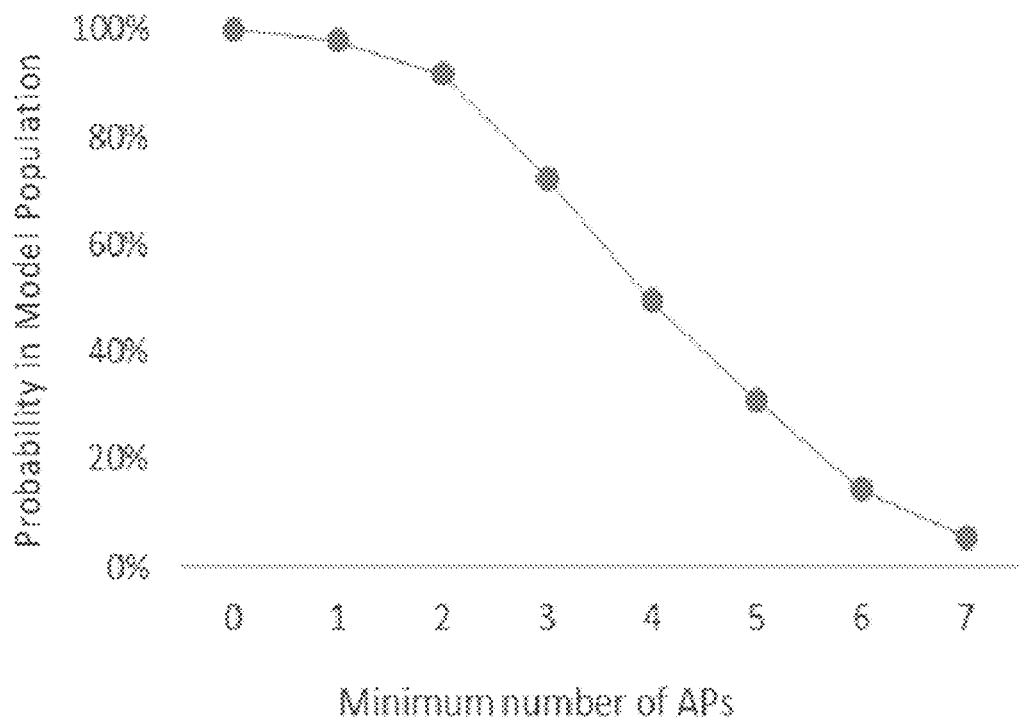
FIGS. 20A-B—Antigenicity of PolyPEPI1018 CRC Vaccine in a general population. The antigenicity of Poly-PEPI1018 in a subject is determined by the AP count, which indicates the number of vaccine antigens that induce T cell responses in a subject. The AP count of PolyPEPI1018 was determined in each of the 433 subjects in the Model Population using the PEPI Test, and the AP50 count was then calculated for the Model Population. The AP50 of Poly-PEPI1018 in the Model Population is 4.73. The mean number of immunogenic antigens (i.e., antigens with ≥1 PEPI) in PolyPEPI1018 in a general population is 4.73. Abbreviations: AP=antigens with ≥1 PEPI. Left Panel: Cumulative distribution curve. Right Panel: Distinct distribution curve.
Figure 20B:
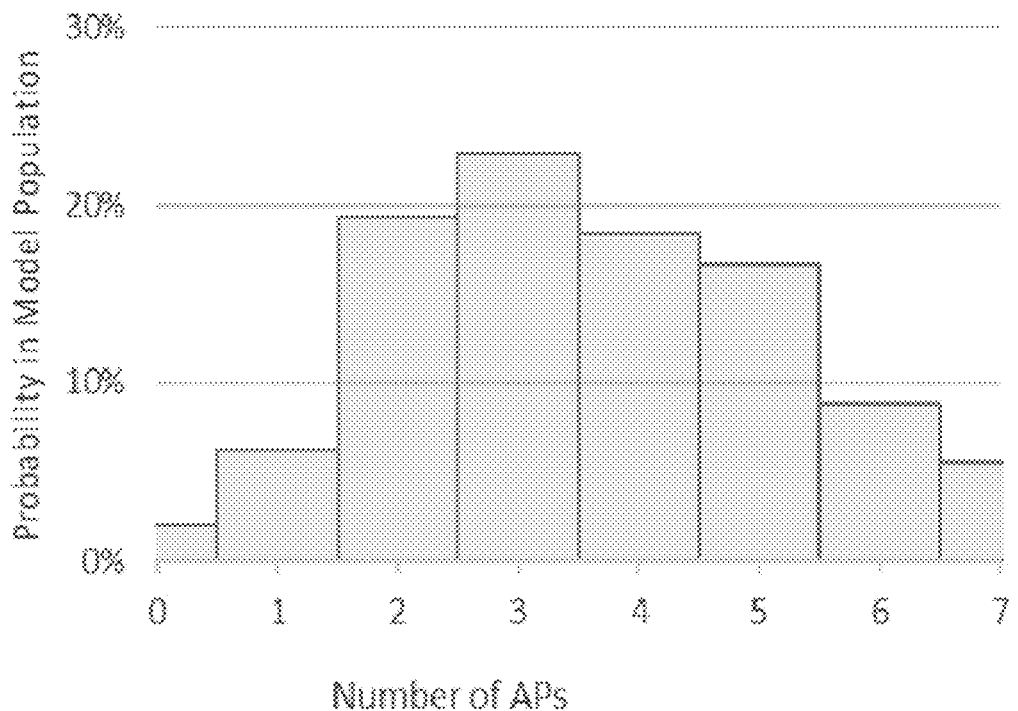

As shown in FIG. 20 the AP50 of PolyPEPI1018 in the Model Population is 3.62. Therefore, the mean number of immunogenic antigens (i.e., antigens with ≥1 PEPI) in PolyPEPI1018 in a general population is 3.62.

Effectiveness of PolyPEPI1018 CRC Vaccine in a General Population

Figure 21A:
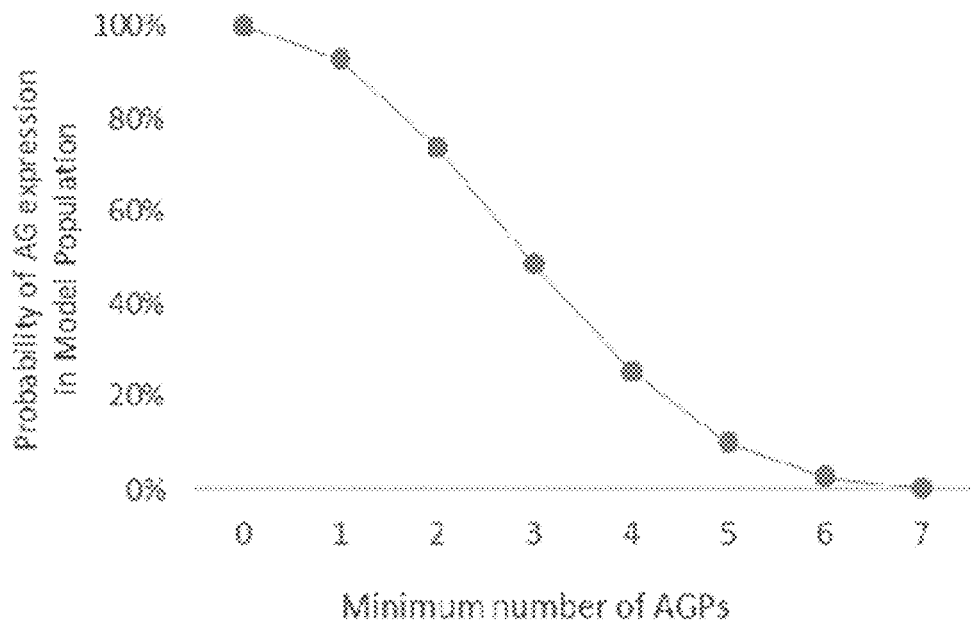
FIGS. 21A-B—Effectiveness of PolyPEPI1018 CRC Vaccine in a general population. Vaccine induced T cells can recognize and kill tumor cells if a PEPI in the vaccine is presented by the tumor cell. The number of AGPs (expressed antigens with PEPI) is an indicator of vaccine effectiveness in an individual, and is dependent on both the potency and antigenicity of PolyPEPI1018. The mean number of immunogenic CTAs (i.e., AP [expressed antigens with ≥1 PEPI]) in PolyPEPI1018 is 2.54 in the Model Population. The likelihood that PolyPEPI1018 induces T cell responses against multiple antigens in a subject (i.e., mAGP) in the Model Population is 77%.
Figure 21B:
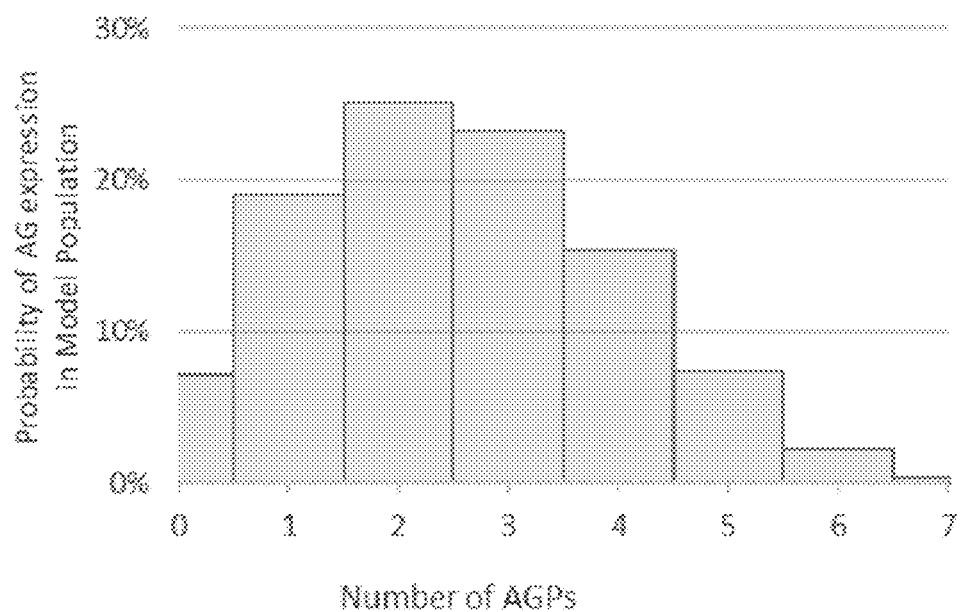

Vaccine induced T cells can recognize and kill tumor cells if a PEPI in the vaccine is presented by the tumor cell. The number of AGPs (expressed antigens with PEPI) is an indicator of vaccine effectiveness in an individual, and is dependent on both the potency and antigenicity of PolyPEPI1018. As shown in FIG. 21, the mean number of immunogenic CTAs (i.e., AP [expressed antigens with ≥1 PEPI]) in PolyPEPI1018 is 2.54 in the Model Population. The likelihood that PolyPEPI1018 induces T cell responses against multiple antigens in a subject (i.e., mAGP) in the Model Population is 77%.

Comparison of the PolyPEPI1018 CRC Vaccine Activities in Different Populations

Tables 35 to 37 show comparison of the immunogenicity, antigenicity, and effectiveness of PolyPEPI1018 in different populations.

TABLE 35

Comparison of Immunogenicity, Antigenicity, and Effectiveness of PolyPEPI1018 in Different Sub-populations

| Populations | Number of subject | Number of PEPI3+ Average | SD | Number of AP Average | SD | Number of AGP50 Average | SD |
|---|---|---|---|---|---|---|---|
| CRC | 37 | 5.16 | 1.98 | 3.19 | 1.31 | 2.21 | 1.13 |
| Model | 433 | 5.02 | 2.62 | 3.62 | 1.67 | 2.54 | 1.25 |
| Big | 7,189 | 5.20 | 2.82 | 3.75 | 1.74 | 2.66 | 1.30 |
| Chinese | 324 | 5.97 | 3.16 | 4.28 | 1.78 | 3.11 | 1.30 |
| Irish | 999 | 3.72 | 1.92 | 2.86 | 1.46 | 1.94 | 1.10 |

Abbreviations:
CRC = colorectal cancer;
PEPI = personal epitope;
SD = standard deviation;
AP = expressed antigens with ≥1 PEPI The average number of PEPI3+ and AP results demonstrate that PolyPEPI1018 is highly immunogenic and antigenic in all populations; PolyPEPI1018 can induce an average of 3.7-6.0 CRC specific T cell clones against 2.9-3.7 CRC antigens. PolyPEPI1018 immunogenicity was similar in patients with CRC and the average population (p>0.05), this similarity may have been due to the small sample size of the CRC population. Additional analyses suggest that PolyPEPI1018 is significantly more immunogenic in a Chinese population compared to an Irish or a general population (p<0.0001). The differences in immunogenicity are also reflected in the effectiveness of the vaccine as characterized by AGP50; PolyPEPI1018 is most effective in a Chinese population and less effective in an Irish population. Since a CDx will be used to select likely responders to Poly-PEPI1018, ethnic differences will only be reflected in the higher percentage of Chinese individuals that might be eligible for treatment compared with Irish individuals.

TABLE 36

PolyPEPI1018 CRC Vaccine, Predicted Immune Response Rates Against Multiple CRC Antigens

| | Population | No. subjects | PolyPEPI1018 MultiAG CTL Responses ≥3 | ≥4 | ≥5 | ≥6 | 7 |
|---|---|---|---|---|---|---|---|
| CRC Patients | Vietnamese | 211 | 91% | 81% | 56% | 38% | 17% |
| | US | 44 | 57% | 34% | 20% | 5% | 0% |
| | Caucasian | 83 | 75% | 51% | 30% | 17% | 4% |
| Normal Donors | US | 400 | 61% | 39% | 25% | 12% | 3% |
| | Europe | 1,386 | 55% | 30% | 18% | 7% | 1% |
| | Chinese | 324 | 84% | 68% | 45% | 26% | 15% |
| | Okinawan (JP) | 104 | 81% | 57% | 36% | 16% | 13% |
| | Japanese | 45 | 77% | 55% | 34% | 16% | 13% |

TABLE 37

PolyPEPI1018 CRC Vaccine, Predicted Immune Response Rates Against Multiple CRC Antigens

| | Population | No. subjects | Number of PEPI Average | SD | Number of AP Average | SD | Number of AGP50 Average | SD |
|---|---|---|---|---|---|---|---|---|
| CRC Patients | Vietnamese | 211 | 6.96 | 3.01 | 4.81 | 1.58 | 3.47 | 1.16 |
| | US | 44 | 4.05 | 2.05 | 3.00 | 1.46 | 2.05 | 1.12 |
| | Caucasian | 83 | 4.75 | 2.39 | 3.57 | 1.76 | 2.50 | 1.27 |
| Normal Donors | US | 400 | 4.30 | 2.50 | 3.19 | 1.74 | 2.17 | 1.30 |
| | Europe | 1,386 | 3.84 | 2.01 | 2.94 | 1.51 | 2.00 | 1.14 |
| | Chinese | 324 | 5.97 | 3.16 | 4.28 | 1.78 | 3.11 | 1.30 |
| | Okinawan (JP) | 104 | 5.29 | 2.58 | 4.01 | 1.63 | 2.91 | 1.19 |
| | Japanese | 45 | 5.31 | 3.27 | 3.67 | 1.77 | 2.66 | 1.29 |

Example 21—Personalised Immunotherapy Composition for Treatment of Ovarian Cancer This example describes the treatment of an ovarian cancer patient with a personalised immunotherapy composition, wherein the composition was specifically designed for the patient based on her HLA genotype based on the disclosure described herein. This Example and Example 22 below provide clinical data to support the principals regarding binding of epitopes by multiple HLA of a subject to induce a cytotoxic T cell response on which the present disclosure is based. The HLA class I and class II genotype of metastatic ovarian adenocarcinoma cancer patient XYZ was determined from a saliva sample.

To make a personalized pharmaceutical composition for patient XYZ thirteen peptides were selected, each of which met the following two criteria: (i) derived from an antigen that is expressed in ovarian cancers, as reported in peer reviewed scientific publications; and (ii) comprises a fragment that is a T cell epitope capable of binding to at least three HLA class I of patient XYZ (Table 38). In addition, each peptide is optimized to bind the maximum number of HLA class II of the patient.

of tumor antigens that vaccine recognizes and induces a T cell response against the patient's tumor (hit the target). The AGP count depends on the vaccine-antigen expression rate in the subject's tumor and the HLA genotype of the subject. The correct value is between 0 (no PEPI presented by expressed antigen) and maximum number of antigens (all antigens are expressed and present a PEPI).

Figure 22A:
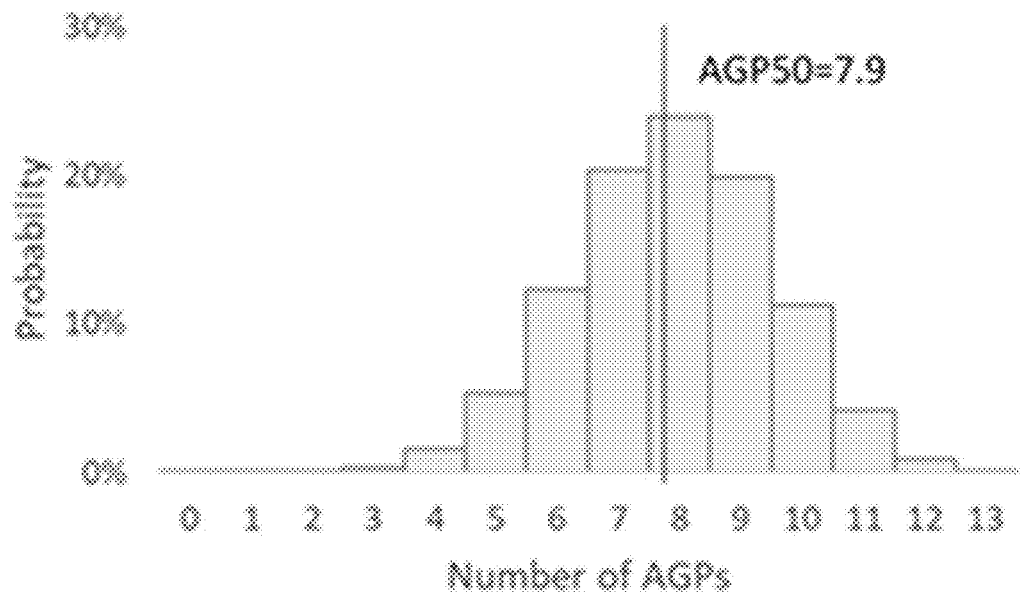
FIGS. 22A-B—Probability of vaccine antigen expression in the XYZ patient's tumor cells. There is over 95% probability that 5 out of the 12 target antigens in the vaccine regimen is expressed in the patient's tumor. Consequently, the 12 peptide vaccines together can induce immune responses against at least 5 ovarian cancer antigens with 95% probability (AGP95). It has 84% probability that each peptide will induce immune responses in the XYZ patient. AGP50 is the mean (expected value)=7.9 (it is a measure of the effectiveness of the vaccine in attacking the tumor of XYZ patient).
Figure 22B:
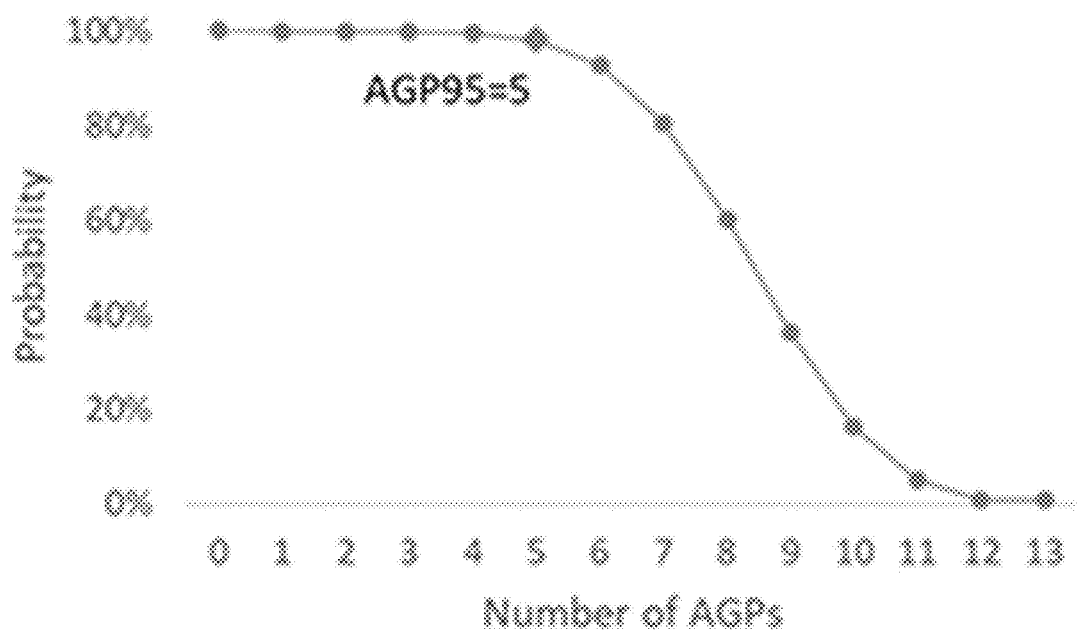

The probability that patient XYZ will express one or more of the 12 antigens is shown in FIGS. 22A-B. AGP95=5, AGP50=7.9, mAGP=100%, AP=13.

A pharmaceutical composition for patient XYZ may be comprised of at least 2 from the 13 peptides (Table 38), because the presence in a vaccine or immunotherapy composition of at least two polypeptide fragments (epitopes) that can bind to at least three HLA of an individual (≥2 PEPI3+) was determined to be predictive for a clinical response. The peptides are synthetized, solved in a pharmaceutically acceptable solvent and mixed with an adjuvant prior to injection. It is desirable for the patient to receive personalized immunotherapy with at least two peptide vaccines, but preferable more to increase the probability of killing cancer cells and decrease the chance of relapse.

TABLE 38

XYZ ovarian cancer patient's personalized vaccine

| XYZ's vaccine | Target Antigen | Antigen Expression | 20mer peptides | MAX HLA classI | MAX HLA classII |
|---|---|---|---|---|---|
| POC01_P1 | AKAP4 | 89% | NSLQKQLQAVLQWIAASQFN | 3 | 5 |
| POC01_P2 | BORIS | 82% | SGDERSDEIVLTVSNSNVEE | 4 | 2 |
| POC01_P3 | SPAG9 | 76% | VQKEDGRVQAFGWSLPQKYK | 3 | 3 |
| POC01_P4 | OY-TES-1 | 75% | EVESTPMIMENIQELIRSAQ | 3 | 4 |
| POC01_P5 | SP17 | 69% | AYFESLLEKREKTNFDPAEW | 3 | 1 |
| POC01_P6 | WT1 | 63% | PSQASSGQARMFPNAPYLPS | 4 | 1 |
| POC01_P7 | HIWI | 63% | RRSIAGFVASINEGMTRWFS | 3 | 4 |
| POC01_P8 | PRAME | 60% | MQDIKMILKMVQLDSIEDLE | 3 | 4 |
| POC01_P9 | AKAP-3 | 58% | ANSVVSDMMVSIMKTLKIQV | 3 | 4 |
| POC01_P10 | MAGE-A4 | 37% | REALSNKVDELAHFLLRKYR | 3 | 2 |
| POC01_P11 | MAGE-A9 | 37% | ETSYEKVINYLVMLNAREPI | 3 | 4 |
| POC01_P12a | MAGE-A10 | 52% | DVKEVDPTGHSFVLVTSLGL | 3 | 4 |
| POC01_P12b | BAGE | 30% | SAQLLQARLMKEESPVVSWR | 3 | 2 |

Eleven PEPI3 peptides in this immunotherapy composition can induce T cell responses in XYZ with 84% probability and the two PEPI4 peptides (POC01-P2 and POC01-P5) with 98% probability, according to the validation of the PEPI Test shown in Table 3. T cell responses target 13 antigens expressed in ovarian cancers. Expression of these cancer antigens in patient XYZ was not tested. Instead the probability of successful killing of cancer cells was determined based on the probability of antigen expression in the patient's cancer cells and the positive predictive value of the ≥1 PEPI3+ Test (AGP count). AGP count predicts the effectiveness of a vaccine in a subject: Number of vaccine antigens expressed in the patient's tumor (ovarian adenocarcinoma) with PEPI. The AGP count indicates the number For treatment of patient XYZ the 12 peptides were formulated as 4×3/4 peptide (POC01/1, POC01/2, POC01/3, POC01/4). One treatment cycle is defined as administration of all 13 peptides within 30 days.

Patient History:
Diagnosis: Metastatic ovarian adenocarcinoma
Age: 51
Family anamnesis: colon and ovary cancer (mother) breast cancer (grandmother)
Tumor Pathology:
BRCA1-185delAG, BRAF-D594Y, MAP2K1-P293S, NOTCH1-S2450N
2011: first diagnosis of ovarian adenocarcinoma; Wertheim operation and chemotherapy; lymph node removal 2015: metastasis in pericardial adipose tissue, excised
2016: hepatic metastases
2017: retroperitoneal and mesenteric lymph nodes have progressed; incipient peritoneal carcinosis with small accompanying ascites Prior Therapy:
2012: Paclitaxel-carboplatin (6×)
2014: Caelyx-carboplatin (1×)
2016-2017 (9 months): Lymparza (Olaparib) 2×400 mg/day, oral
2017: Hycamtin inf. 5×2.5 mg (3× one seria/month)
PIT vaccine treatment began on 21 Apr. 2017.

TABLE 39

Patient XYZ peptide treatment schedule

| Lot # | | $1^{st}$ cycle | $2^{nd}$ cycle | $3^{rd}$ cycle | $4^{th}$ cycle |
|---|---|---|---|---|---|
| POC01/1 | N1727 | 21.04.2017 | 16.06.2017 | 30.08.2017 | 19.10.2017 |
| POC01/2 | N1728 | 28.04.2017 | 31.05.2017 | | |
| POC01/3 | N1732 | | 16.06.2017 | 02.08.2017 | 20.09.2017 |
| POC01/4 | N1736 | 15.05.2017 | 06.07.2017 | | |

Figure 23:
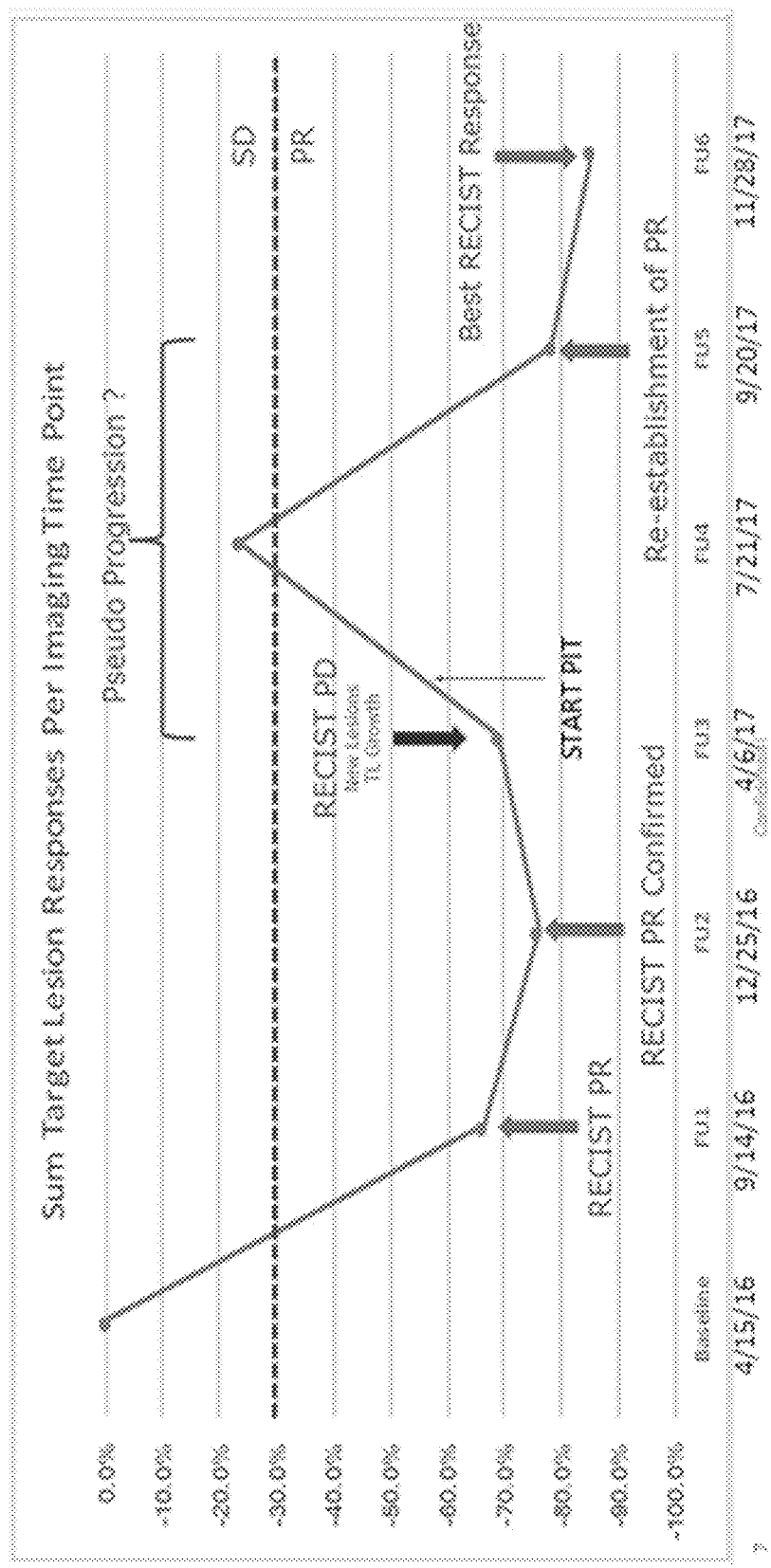
FIG. 23—MRI findings of patient XYZ treated with personalised (PIT) vaccine. This late stage, heavily pre-treated ovarian cancer patient had an unexpected objective response after the PIT vaccine treatment. These MRI findings suggest that PIT vaccine in combination with chemotherapy significantly reduced her tumor burden. The patient now continues the PIT vaccine treatment.

Patient' Tumor MRI Findings (Baseline Apr. 15, 2016)
Disease was confined primarily to liver and lymph nodes. The use of MRI limits detection of lung (pulmonary) metastasis
May 2016-January 2017: Olaparib treatment
Dec. 25, 2016 (before PIT vaccine treatment) There was dramatic reduction in tumor burden with confirmation of response obtained at FU2
January-March 2017—TOPO protocol (topoisomerase)
Apr. 6, 2017 FU3 demonstrated regrowth of existing lesions and appearance of new lesions leading to disease progression
Apr. 21, 2017 START PIT
Jul. 21, 2017 (after the $2^{nd}$ Cycle of PIT) FU4 demonstrated continued growth in lesions and general enlargement of pancreas and abnormal para pancreatic signal along with increased ascites
Jul. 26, 2017—CBP+Gem+Avastin
Sep. 20, 2017 (after 3 Cycles of PIT) FU5 demonstrated reversal of lesion growth and improved pancreatic/parapancreatic signal. The findings suggest pseudo progression
Nov. 28, 2017 (after 4 Cycles of PIT) FU6 demonstrated best response with resolution of non-target lesions
MRI data for patient XYZ is shown in Table 40 and FIG. 23.

TABLE 40

Summary Table of Lesions Responses

| Lesion/Time Point | Baseline (%Δ from BL) | FU1 %Δ from BL) | FU2 %Δ from BL) | FU3 %Δ from BL) | FU4 %Δ from BL) | FU5 %Δ from BL) | FU6 %Δ from BL) | Best Response Cycle | PD Time Point |
|---|---|---|---|---|---|---|---|---|---|
| TL1 | NA | −56.1 | −44.4 | −44.8 | +109.3 | −47.8 | −67.3 | FU6 | FU4 |
| TL2 | NA | −100.0 | −100.0 | −47.1 | −13.1 | −100.0 | −100.0 | FU1 | FU3 |
| TL3 | NA | −59.4 | −62.3 | −62.0 | −30.9 | −66.7 | −75.9 | FU6 | FU4 |
| TL4 | NA | −65.8 | −100.0 | −100.0 | −100.0 | −100.0 | −100.0 | FU2 | NA |
| SUM | NA | −66.3 | −76.0 | −68.9 | −23.5 | −78.2 | −85.2 | FU6 | FU4 |

Figure 24A:
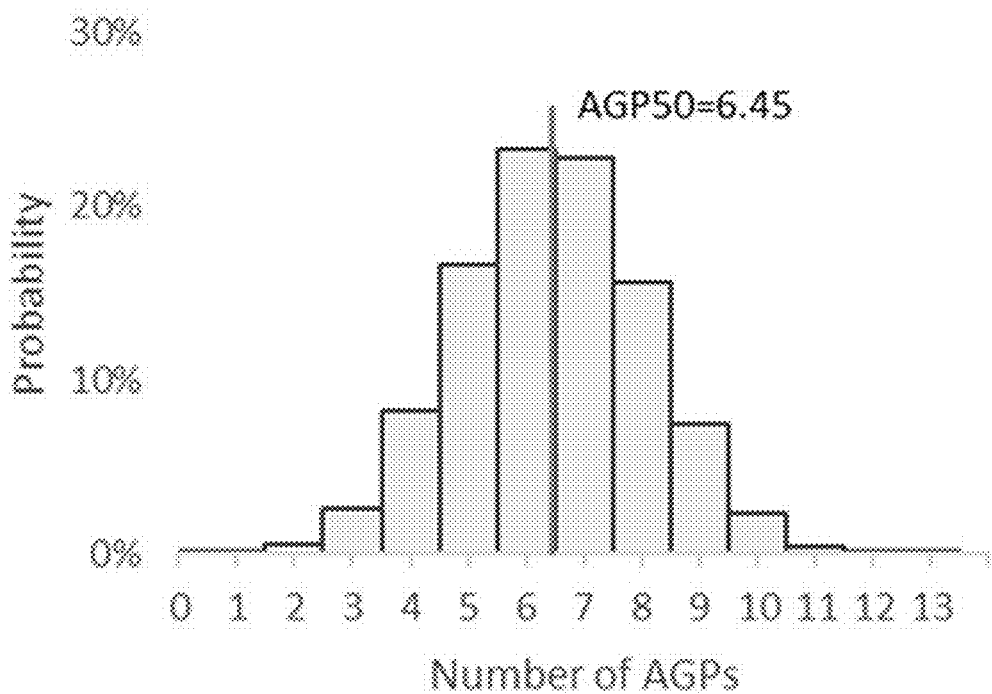
FIGS. 24A-B—Probability of vaccine antigen expression in the ABC patient's tumor cells. There is over 95% probability that 4 out of the 13 target antigens in the vaccine is expressed in the patient's tumor. Consequently, the 12 peptide vaccines together can induce immune responses against at least 4 breast cancer antigens with 95% probability (AGP95). It has 84% probability that each peptide will induce immune responses in the ABC patient. AGP50 is the mean (expected value) of the discrete probability distribution=6.45 (it is a measure of the effectiveness of the vaccine in attacking the tumor of ABC patient).
Figure 24B:
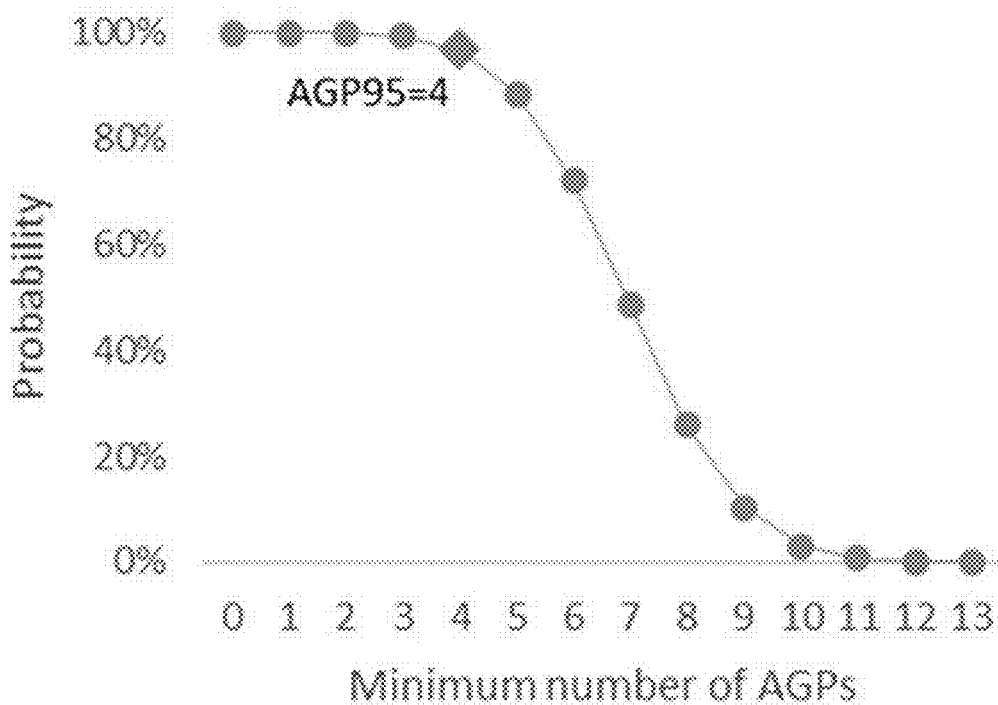

Example 22 Design of Personalised Immunotherapy Composition for Treatment of Breast Cancer The HLA class I and class II genotype of metastatic breast cancer patient ABC was determined from a saliva sample. To make a personalized pharmaceutical composition for patient ABC twelve peptides were selected, each of which met the following two criteria: (i) derived from an antigen that is expressed in breast cancers, as reported in peer reviewed scientific publications; and (ii) comprises a fragment that is a T cell epitope capable of binding to at least three HLA class I of patient ABC (Table 41). In addition, each peptide is optimized to bind the maximum number of HLA class II of the patient. The twelve peptides target twelve breast cancer antigens. The probability that patient ABC will express one or more of the 12 antigens is shown in FIG. 24.

TABLE 41

12 peptides for ABC breast cancer patient

| BRC09 vaccine peptides | Target Antigen | Antigen Expression | 20mer peptide | MAXHLA Class I | MAXHLA Class II |
|---|---|---|---|---|---|
| PBRC01_cP1 | FSIP1 | 49% | ISDTKDYFMSKTLGIGRLKR | 3 | 6 |
| PBRC01_cP2 | SPAG9 | 88% | FDRNTESLFEELSSAGSGLI | 3 | 2 |

TABLE 41-continued 12 peptides for ABC breast cancer patient

| BRC09 vaccine peptides | Target Antigen | Antigen Expression | 20mer peptide | MAXHLA Class I | MAXHLA Class II |
|---|---|---|---|---|---|
| PBRC01_cP3 | AKAP4 | 85% | SQKMDMSNIVLMLIQKLLNE | 3 | 6 |
| PBRC01_cP4 | BORIS | 71% | SAVFHERYALIQHQKTHKNE | 3 | 6 |
| PBRC01_cP5 | MAGE-A11 | 59% | DVKEVDPTSHSYVLVTSLNL | 3 | 4 |
| PBRC01_cP6 | NY-SAR-35 | 49% | ENAHGQSLEEDSALEALLNF | 3 | 2 |
| PBRC01_cP7 | HOM-TES-85 | 47% | MASFRKLTLSEKVPPNHPSR | 3 | 5 |
| PBRC01_cP8 | NY-BR-1 | 47% | KRASQYSGQLKVLIAENTML | 3 | 6 |
| PBRC01_cP9 | MAGE-A9 | 44% | VDPAQLEFMFQEALKLKVAE | 3 | 8 |
| PBRC01_cP10 | SCP-1 | 38% | EYEREETRQVYMDLNNNIEK | 3 | 3 |
| PBRC01_cP11 | MAGE-A1 | 37% | PEIFGKASESLQLVFGIDVK | 3 | 3 |
| PBRC01_cP12 | MAGE-C2 | 21% | DSESSFTYTLDEKVAELVEF | 4 | 2 |

Predicted efficacy: AGP95=4; 95% likelihood that the PIT Vaccine induces CTL responses against 4 CTAs expressed in the breast cancer cells of BRC09. Additional efficacy parameters: AGP50=6.3, mAGP=100%, AP=12.

Detected efficacy after the $1^{st}$ vaccination with all 12 peptides: 83% reduction of tumor metabolic activity (PET CT data).

For treatment of patient ABC the 12 peptides were formulated as 4×3 peptide (PBR01/1, PBR01/2, PBR01/3, PBR01/4). One treatment cycle is defined as administration of all 12 different peptide vaccines within 30 days.

Patient History
Diagnosis: bilateral metastatic breast carcinoma: Right breast is ER positive, PR negative, Her2 negative, Left Breast is ER, PR and Her2 negative.
First diagnosis: 2013 (4 years before PIT vaccine treatment)
2016: extensive metastatic disease with nodal involvement both above and below the diaphragm. Multiple liver and pulmonar metastases.
2016-2017 treatment: Etrozole, Ibrance (Palbociclib) and Zoladex
Results
Mar. 7, 2017: Prior PIT Vaccine treatment
Hepatic multi-metastatic disease with truly extrinsic compression of the origin of the choledochal duct and massive dilatation of the entire intrahepatic biliary tract. Celiac, hepatic hilar and retroperitoneal adenopathy
May 26, 2017: After 1 cycle of PIT
Detected efficacy: 83% reduction of tumor metabolic activity (PET CT) liver, lung lymph nodes and other metastases.
Detected safety: Skin reactions
Local inflammation at the site of the injections within 48 hours following vaccine administrations
Follow Up:
BRC-09 was treated with 5 cycles of PIT vaccine. She was feeling very well and she refused a PET CT examination in September 2017. In November she had symptoms, PET CT scan showed progressive disease, but she refused all treatments. In addition, her oncologist found out that she did not take Palbocyclib since spring/summer. Patient ABC passed away in January 2018.

The combination of pablocyclib and the personalised vaccine was likely to have been responsible for the remarkable early response observed following administration of the vaccine. Palbociclib has been shown to improve the activity of immunotherapies by increases CTA presentation by HLAs and decreasing the proliferation of Tregs: (Goel et al. Nature. 2017:471-475). The PIT vaccine may be used as add-on to the state-of-art therapy to obtain maximal efficacy.

Example 23—Personalised Immunotherapy Composition for Treatment of Patient with Late Stage Metastatic Breast Cancer Patient BRC05 was diagnosed with inflammatory breast cancer on the right with extensive lymphangiosis carcinomatose. Inflammatory breast cancer (IBC) is a rare, but aggressive form of locally advanced breast cancer. It's called inflammatory breast cancer because its main symptoms are swelling and redness (the breast often looks inflamed). Most inflammatory breast cancers are invasive ductal carcinomas (begin in the milk ducts). This type of breast cancer is associated with the expression of oncoproteins of high risk Human Papilloma Virus. Indeed, HPV16 DNA was diagnosed in the tumor of this patient.

Patient's stage in 2011 (6 years prior to PIT vaccine treatment):

T4: Tumor of any size with direct extension to the chest wall and/or to the skin (ulceration or skin nodules)

pN3a: Metastases in ≥10 axillary lymph nodes (at least 1 tumor deposit ≥2.0 mm); or metastases to the infraclavicular (level III axillary lymph) nodes.

14 vaccine peptides were designed and prepared for patient BRC05 (Table 42). Peptides PBRC05-P01-P10 were made for this patient based on population expression data. The last 3 peptides in the Table 42 (SSX-2, MORC, MAGE-B1) were designed from antigens that expression was measured directly in the tumor of the patient.

TABLE 42

Vaccine peptides for patient BRC05

| BRC05 vaccine peptides | Target Antigen | Antigen Expression | 20mer peptide | MAXHLA Class I | MAXHLA Class II |
|---|---|---|---|---|---|
| PBRC05_P1 | SPAG9 | 88% | XXXXXXXXXXXXXXXXXXXX | 3 | 4 |
| PBRC05_P2 | AKAP4 | 85% | XXXXXXXXXXXXXXXXXXXX | 3 | 4 |
| PBRC05_P3 | MAGE-A11 | 59% | XXXXXXXXXXXXXXXXXXXX | 3 | 3 |
| PBRC05_P4 | NY-SAR-35 | 49% | XXXXXXXXXXXXXXXXXXXX | 3 | 3 |
| PBRC05_P5 | FSIP1 | 49% | XXXXXXXXXXXXXXXXXXXX | 3 | 3 |
| PBRC05_P6 | NY-BR-1 | 47% | XXXXXXXXXXXXXXXXXXXX | 3 | 4 |
| PBRC05_P7 | MAGE-A9 | 44% | XXXXXXXXXXXXXXXXXXXX | 3 | 3 |
| PBRC05_P8 | SCP-1 | 38% | XXXXXXXXXXXXXXXXXXXX | 3 | 6 |
| PBRC05_P9 | MAGE-A1 | 37% | XXXXXXXXXXXXXXXXXXXX | 3 | 3 |
| PBRC05_P10 | MAGE-C2 | 21% | XXXXXXXXXXXXXXXXXXXX | 3 | 3 |
| PBRC05_P11 | MAGE-A12 | 13% | XXXXXXXXXXXXXXXXXXXX | 3 | 4 |
| PBRC05_P12 | SSX-2 | 6% | XXXXXXXXXXXXXXXXXXXX | 3 | 1 |
| PBRC05_P13 | MORC | ND | XXXXXXXXXXXXXXXXXXXX | 3 | 4 |
| PBRC05_P14 | MAGE-B1 | ND | XXXXXXXXXXXXXXXXXXXX | 3 | 3 |

T cell responses were measured cells in peripheral mononuclear cells 2 weeks after the 1$^{st}$ vaccination with the mix of peptides PBRC05_P1, PBRC05_P2, PBRC05_P3, PBRC05_P4, PBRC05_P5, PBRC05_P6, PBRC05_P7.

TABLE 43

Antigen specific T cell responses: Number of spots/300,000 PBMC

| Antigen | Stimulant | Exp1 | Exp2 | Average |
|---|---|---|---|---|
| SPAG9 | PBRC05_P1 | 2 | 1 | 1.5 |
| AKAP4 | PBRC05_P2 | 11 | 4 | 7.5 |
| MAGE-A11 | PBRC05_P3 | 26 | 32 | 29 |
| NY-SAR-35 | PBRC05_P4 | 472 | 497 | 484.5 |
| FSIP1 | PBRC05_P5 | 317 | 321 | 319 |
| NY-BR-1 | PBRC05_P6 | 8 | 12 | 10 |
| MAGE-A9 | PBRC05_P7 | 23 | 27 | 25 |
| None | Negative Control (DMSO) | 0 | 3 | 1.5 |

The results show that a single immunization with 7 peptides induced potent T cell responses against 3 out of the 7 peptides demonstrating potent MAGE-A11, NY-SAR-35, FSIP1 and MAGE-A9 specific T cell responses. There were weak responses against AKAP4 and NY-BR-1 and no response against SPAG9.

REFERENCES

[1] Bagarazzi et al. Immunotherapy against HPV16/18 generates potent TH1 and cytotoxic cellular immune responses. Science Translational Medicine. 2012; 4(155): 155ra138.

[2] Gudmundsdotter et al. Amplified antigen-specific immune responses in HIV-1 infected individuals in a double blind DNA immunization and therapy interruption trial. Vaccine. 2011; 29(33):5558-66.

[3] Bioley et al. HLA class I—associated immunodominance affects CTL responsiveness to an ESO recombinant protein tumor antigen vaccine. Clin Cancer Res. 2009; 15(1): 299-306.

[4] Valmori et al. Vaccination with NY-ESO-1 protein and CpG in Montanide induces integrated antibody/Th1 responses and CD8 T cells through cross-priming. Proceedings of the National Academy of Sciences of the United States of America. 2007; 104(21):8947-52.

[5] Yuan et al. Integrated NY-ESO-1 antibody and CD8+ T-cell responses correlate with clinical benefit in advanced melanoma patients treated with ipilimumab. Proc Natl Acad Sci USA. 2011; 108(40): 16723-16728.

[6] Kakimi et al. A phase I study of vaccination with NY-ESO-1f peptide mixed with Picibanil OK-432 and Montanide ISA-51 in patients with cancers expressing the NY-ESO-1 antigen. Int J Cancer. 2011; 129(12):2836-46.

[7] Wada et al. Vaccination with NY-ESO-1 overlapping peptides mixed with Picibanil OK-432 and montanide ISA-51 in patients with cancers expressing the NY-ESO-1 antigen. J Immunother. 2014; 37(2):84-92.

[8] Welters et al. Induction of tumor-specific CD4+ and CD8+ T-cell immunity in cervical cancer patients by a human papillomavirus type 16 E6 and E7 long peptides vaccine. Clin. Cancer Res. 2008; 14(1): 178-87.

[9] Renter et al. Vaccination against HPV-16 oncoproteins for vulvar intraepithelial neoplasia. N Engl J Med. 2009; 361(19): 1838-47.

[10] Welters et al. Success or failure of vaccination for HPV16-positive vulvar lesions correlates with kinetics and phenotype of induced T-cell responses. PNAS. 2010; 107 (26): 11895-9.

[11] www.ncbi.nlm.nih.gov/projects/gv/mhc/main.fcgi?cmd=initThe MHC database, NCBI (Accessed Mar. 7, 2016).

[12] Karkada et al. Therapeutic vaccines and cancer: focus on DPX-0907. Biologics. 2014; 8:27-38.

[13] Butts et al. Randomized phase IIB trial of BLP25 liposome vaccine in stage IIIB and IV non-small-cell lung cancer. J Clin Oncol. 2005; 23(27):6674-81.

[14] Yuan et al. Safety and immunogenicity of a human and mouse gp100 DNA vaccine in a phase I trial of patients with melanoma. Cancer Immun. 2009; 9:5.

[15] Kovjazin et al. ImMucin: a novel therapeutic vaccine with promiscuous MHC binding for the treatment of MUC1-expressing tumors. Vaccine. 2011; 29(29-30):4676-86.

[16] Cathcart et al. A multivalent bcr-abl fusion peptide vaccination trial in patients with chronic myeloid leukemia. Blood. 2004; 103:1037-1042.

[17] Chapuis et al. Transferred WT1-reactive CD8+ T cells can mediate antileukemic activity and persist in post-transplant patients. Sci Transl Med. 2013; 5(174):174ra27.

[18] Keilholz et al. A clinical and immunologic phase 2 trial of Wilms tumor gene product 1 (WT1) peptide vaccination in patients with AML and MDS. Blood; 2009; 113(26): 6541-8.

[19] Walter et al. Multipeptide immune response to cancer vaccine IMA901 after single-dose cyclophosphamide associates with longer patient survival. Nat Med. 2012; 18(8): 1254-61.

20. Phuphanich et al. Phase I trial of a multi-epitope-pulsed dendritic cell vaccine for patients with newly diagnosed glioblastoma. Cancer Immunol Immunother. 2013; 62(1): 125-35.
21. Kantoff et al. Overall survival analysis of a phase II randomized controlled trial of a Poxviral-based PSA-targeted immunotherapy in metastatic castration-resistant prostate cancer. J Clin Oncol. 2010; 28(7): 1099-105.
22. Tagawa et al. Phase I study of intranodal delivery of a plasmid DNA vaccine for patients with Stage IV melanoma. Cancer. 2003; 98(1): 144-54.
23. Slingluff et al. Randomized multicenter trial of the effects of melanoma-associated helper peptides and cyclophosphamide on the immunogenicity of a multipeptide melanoma vaccine. J Clin Oncol. 2011; 29(21):2924-32.
24. Kaida et al. Phase 1 trial of Wilms tumor 1 (WT1) peptide vaccine and gemcitabine combination therapy in patients with advanced pancreatic or biliary tract cancer. J Immunother. 2011; 34(1):92-9.
25. Fenoglio et al. A multi-peptide, dual-adjuvant telomerase vaccine (GX301) is highly immunogenic in patients with prostate and renal cancer. Cancer Immunol Immunother; 2013; 62:1041-1052.
26. Krug et al. WT1 peptide vaccinations induce CD4 and CD8 T cell immune responses in patients with mesothelioma and non-small cell lung cancer. Cancer Immunol Immunother; 2010; 59(10): 1467-79.
27. Slingluff et al. Clinical and immunologic results of a randomized phase II trial of vaccination using four melanoma peptides either administered in granulocyte-macrophage colony-stimulating factor in adjuvant or pulsed on dendritic cells. J Clin Oncol; 2003; 21(21):4016-26.
28. Hodi et al. Improved survival with ipilimumab in patients with metastatic melanoma. N Engl J Med; 2010; 363(8): 711-23.
29. Carmon et al. Phase I/II study exploring ImMucin, a pan-major histocompatibility complex, anti-MUC1 signal peptide vaccine, in multiple myeloma patients. Br J Hematol. 2014; 169(1):44-56.
30. www.merckgroup.com/en/media/extNewsDetail.html?newsId=EB4A46A2AC4A52E7C1257AD9001F3186&newsType=1 (Accessed Mar. 28, 2016)
31. Trimble et al. Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial. Lancet. 2015; 386(10008):2078-88.
32. Cusi et al. Phase I trial of thymidylate synthase poly epitope peptide (TSPP) vaccine in advanced cancer patients. Cancer Immunol Immunother; 2015; 64:1159-1173.
33. Asahara et al. Phase I/II clinical trial using HLA-A24-restricted peptide vaccine derived from KIF20A for patients with advanced pancreatic cancer. J Transl Med; 2013; 11:291.
34. Yoshitake et al. Phase II clinical trial of multiple peptide vaccination for advanced head and neck cancer patients revealed induction of immune responses and improved OS. Clin Cancer Res; 2014; 21(2):312-21.
35. Okuno et al. Clinical Trial of a 7-Peptide Cocktail Vaccine with Oral Chemotherapy for Patients with Metastatic Colorectal Cancer. Anticancer Res; 2014; 34: 3045-305.
36. Rapoport et al. Combination Immunotherapy after ASCT for Multiple Myeloma Using MAGE-A3/Poly-ICLC Immunizations Followed by Adoptive Transfer of Vaccine-Primed and Costimulated Autologous T Cells. Clin Cancer Res; 2014; 20(5): 1355-1365.
37. Greenfield et al. A phase I dose-escalation clinical trial of a peptide based human papillomavirus therapeutic vaccine with *Candida* skin test reagent as a novel vaccine adjuvant for treating women with biopsy-proven cervical intraepithelial neoplasia 2/3. Oncoimmunol; 2015; 4:10, e1031439.
38. Snyder et al. Genetic basis for clinical response to CTLA-4 blockade in melanoma. N Engl J Med. 2014; 371 (23):2189-99.
39. Van Allen et al. Genomic correlates of response to CTLA-4 blockade in metastatic melanoma. Science; 2015; 350:6257.
40. Li et al. Thrombocytopenia caused by the development of antibodies to thrombopoietin. Blood; 2001; 98:3241-3248
41. Takedatsu et al. Determination of Thrombopoietin-Derived Peptides Recognized by Both Cellular and Humoral Immunities in Healthy Donors and Patients with Thrombocytopenia. 2005; 23(7): 975-982
42. Eisenhauer et al. New response evaluation criteria in solid tumors: revised RECIST guideline (version 1.1). Eur J Cancer; 2009; 45(2):228-47.
43. Therasse et al. New guidelines to evaluate the response to treatment in solid tumors: European Organization for Research and Treatment of Cancer, National Cancer Institute of the United States, National Cancer Institute of Canada. J Natl Cancer Inst; 2000; 92:205-216.
44. Tsuchida & Therasse. Response evaluation criteria in solid tumors (RECIST): New guidelines. Med Pediatr Oncol. 2001; 37:1-3.
45. Durie et al. International uniform response criteria for multiple myeloma. Leukemia; 2006; 20:1467-1473.

What is claimed is:

1. A method of treating ovarian cancer using immunotherapy in an individual in need thereof, the method comprising: administering to the individual a pharmaceutical composition comprising a peptide having the amino acid sequence of any of SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, or SEQ ID NO: 346.

2. The method of claim 1, wherein the composition comprises two or more peptides, each peptide comprising a different amino acid sequence, and each sequence having the amino acid sequence of any of SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, or SEQ ID NO: 346.

3. The method of claim 1, wherein the composition further comprises at least one additional peptide comprising a fragment of an antigen selected from OY-TES-1, PIWIL-2, PIWIL-3, PIWIL-4, BORIS, AKAP4, WT1, HIWI, EpCam, SP17, SPAG9, PRAME and SURVIVIN.

4. The method of claim 1, wherein the composition further comprises a pharmaceutically acceptable adjuvant, diluent, carrier, preservative, excipient, buffer, stabilizer, or combination thereof.

5. The method of claim 4, wherein the composition further comprises a pharmaceutically acceptable adjuvant.

6. The method of claim 5, wherein the pharmaceutically acceptable adjuvant is selected from the group consisting of water-in-oil emulsions, QS-21, GM-CSF, cyclophosamide, bacillus Calmette-Guerin (BCG), *Corynbacterium parvum*, levamisole, azimezone, isoprinisone, dinitrochlorobenezene (DNCB), keyhole limpet hemocyanins (KLH), complete Freunds adjuvant, incomplete Freunds adjuvant, mineral gels, aluminum hydroxide (Alum), lysolecithin, pluronic polyols, polyanions, oil emulsions, dinitrophenol, diphtheria toxin (DT), and combinations thereof.

7. The method of claim 1, further comprising administering a chemotherapeutic agent, a checkpoint inhibitor, a targeted therapy, radiation therapy, another immunotherapy, or combination thereof to the identified individual.

* * * * *

SEQUENCE LISTING

<160> NUMBER OF SEQ ID NOS: 449

<210> SEQ ID NO 1
<211> LENGTH: 9
<212> TYPE: PRT
<213> ORGANISM: Artificial Sequence
<220> FEATURE:
<223> OTHER INFORMATION: 9mer T cell epitope 1

<400> SEQUENCE: 1

Tyr Leu Met Asn Arg Pro Gln Asn Leu
1               5

```
<210> SEQ ID NO 2
<211> LENGTH: 9
<212> TYPE: PRT
<213> ORGANISM: Artificial Sequence
<220> FEATURE:
<223> OTHER INFORMATION: 9mer T cell epitope 2

<400> SEQUENCE: 2

Met Met Ala Tyr Ser Asp Thr Thr Met
1               5

<210> SEQ ID NO 3
<211> LENGTH: 9
<212> TYPE: PRT
<213> ORGANISM: Artificial Sequence
<220> FEATURE:
<223> OTHER INFORMATION: 9mer T cell epitope 3

<400> SEQUENCE: 3

Phe Thr Ser Ser Arg Met Ser Ser Phe
1               5

<210> SEQ ID NO 4
<211> LENGTH: 9
<212> TYPE: PRT
<213> ORGANISM: Artificial Sequence
<220> FEATURE:
<223> OTHER INFORMATION: 9mer T cell epitope 4

<400> SEQUENCE: 4

Tyr Ala Leu Gly Phe Gln His Ala Leu
1               5

<210> SEQ ID NO 5
<211> LENGTH: 9
<212> TYPE: PRT
<213> ORGANISM: Artificial Sequence
<220> FEATURE:
<223> OTHER INFORMATION: 9mer T cell epitope 5

<400> SEQUENCE: 5

Lys Met Ser Ser Leu Leu Pro Thr Met
1               5

<210> SEQ ID NO 6
<211> LENGTH: 9
<212> TYPE: PRT
<213> ORGANISM: Artificial Sequence
<220> FEATURE:
<223> OTHER INFORMATION: 9mer T cell epitope 6

<400> SEQUENCE: 6

Phe Thr Val Cys Asn Ser His Val Leu
1               5

<210> SEQ ID NO 7
<211> LENGTH: 9
<212> TYPE: PRT
<213> ORGANISM: Artificial Sequence
<220> FEATURE:
<223> OTHER INFORMATION: 9mer T cell epitope 8

<400> SEQUENCE: 7

Met Ala Phe Val Thr Ser Gly Glu Leu
1               5

<210> SEQ ID NO 8
<211> LENGTH: 9
<212> TYPE: PRT
<213> ORGANISM: Artificial Sequence
```

```
<220> FEATURE:
<223> OTHER INFORMATION: 9mer T cell epitope 8

<400> SEQUENCE: 8

Tyr Leu His Ala Arg Leu Arg Glu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: 9mer T cell epitope 9

<400> SEQUENCE: 9

Val Met Ser Glu Arg Val Ser Gly Leu
1               5

<210> SEQ ID NO 10
<211> LENGTH: 9
<212> TYPE: PRT
<213> ORGANISM: Artificial Sequence
<220> FEATURE:
<223> OTHER INFORMATION: 9mer T cell epitope 10

<400> SEQUENCE: 10

Phe Thr Gln Ser Gly Thr Met Lys Ile
1               5

<210> SEQ ID NO 11
<211> LENGTH: 9
<212> TYPE: PRT
<213> ORGANISM: Artificial Sequence
<220> FEATURE:
<223> OTHER INFORMATION: 9mer T cell epitope 11

<400> SEQUENCE: 11

Phe Ser Ser Ser Gly Thr Thr Ser Phe
1               5

<210> SEQ ID NO 12
<211> LENGTH: 9
<212> TYPE: PRT
<213> ORGANISM: Artificial Sequence
<220> FEATURE:
<223> OTHER INFORMATION: 9mer T cell epitope 12

<400> SEQUENCE: 12

Phe Met Phe Gln Glu Ala Leu Lys Leu
1               5

<210> SEQ ID NO 13
<211> LENGTH: 9
<212> TYPE: PRT
<213> ORGANISM: Artificial Sequence
<220> FEATURE:
<223> OTHER INFORMATION: 9mer T cell epitope 13

<400> SEQUENCE: 13

Phe Val Leu Ala Asn Gly His Ile Leu
1               5

<210> SEQ ID NO 14
<211> LENGTH: 9
<212> TYPE: PRT
<213> ORGANISM: Artificial Sequence
<220> FEATURE:
```

```
<223> OTHER INFORMATION: 9mer T cell epitope 15

<400> SEQUENCE: 14

Lys Ala Met Val Gln Ala Trp Pro Phe
1               5

<210> SEQ ID NO 15
<211> LENGTH: 9
<212> TYPE: PRT
<213> ORGANISM: Artificial Sequence
<220> FEATURE:
<223> OTHER INFORMATION: 9mer T cell epitope 15

<400> SEQUENCE: 15

Tyr Ser Cys Asp Ser Arg Ser Leu Phe
1               5

<210> SEQ ID NO 16
<211> LENGTH: 9
<212> TYPE: PRT
<213> ORGANISM: Artificial Sequence
<220> FEATURE:
<223> OTHER INFORMATION: 9mer T cell epitope 16

<400> SEQUENCE: 16

Arg Ala Ile Glu Gln Leu Ala Ala Met
1               5

<210> SEQ ID NO 17
<211> LENGTH: 9
<212> TYPE: PRT
<213> ORGANISM: Artificial Sequence
<220> FEATURE:
<223> OTHER INFORMATION: 9mer T cell epitope 17

<400> SEQUENCE: 17

Ala Met Asp Ala Ile Phe Gly Ser Leu
1               5

<210> SEQ ID NO 18
<211> LENGTH: 9
<212> TYPE: PRT
<213> ORGANISM: Artificial Sequence
<220> FEATURE:
<223> OTHER INFORMATION: 9mer T cell epitope 18

<400> SEQUENCE: 18

Met Ala Ser Phe Arg Lys Leu Thr Leu
1               5

<210> SEQ ID NO 19
<211> LENGTH: 9
<212> TYPE: PRT
<213> ORGANISM: Artificial Sequence
<220> FEATURE:
<223> OTHER INFORMATION: 9mer T cell epitope 19

<400> SEQUENCE: 19

Ser Ser Ile Ser Val Tyr Tyr Thr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: 9mer T cell epitope 20
```

```
<400> SEQUENCE: 20

Ser Ala Phe Glu Pro Ala Thr Glu Met
1               5

<210> SEQ ID NO 21
<211> LENGTH: 9
<212> TYPE: PRT
<213> ORGANISM: Artificial Sequence
<220> FEATURE:
<223> OTHER INFORMATION: 9mer T cell epitope 21

<400> SEQUENCE: 21

Phe Ser Tyr Glu Gln Asp Pro Thr Leu
1               5

<210> SEQ ID NO 22
<211> LENGTH: 9
<212> TYPE: PRT
<213> ORGANISM: Artificial Sequence
<220> FEATURE:
<223> OTHER INFORMATION: 9mer T cell epitope 22

<400> SEQUENCE: 22

Arg Thr Tyr Trp Ile Ile Ile Glu Leu
1               5

<210> SEQ ID NO 23
<211> LENGTH: 9
<212> TYPE: PRT
<213> ORGANISM: Artificial Sequence
<220> FEATURE:
<223> OTHER INFORMATION: 9mer T cell epitope 23

<400> SEQUENCE: 23

Thr Thr Met Glu Thr Gln Phe Pro Val
1               5

<210> SEQ ID NO 24
<211> LENGTH: 9
<212> TYPE: PRT
<213> ORGANISM: Artificial Sequence
<220> FEATURE:
<223> OTHER INFORMATION: 9mer T cell epitope 24

<400> SEQUENCE: 24

Phe Ser Phe Val Arg Ile Thr Ala Leu
1               5

<210> SEQ ID NO 25
<211> LENGTH: 9
<212> TYPE: PRT
<213> ORGANISM: Artificial Sequence
<220> FEATURE:
<223> OTHER INFORMATION: 9mer T cell epitope 25

<400> SEQUENCE: 25

Lys Met Ser Ser Leu Leu Pro Thr Met
1               5

<210> SEQ ID NO 26
<211> LENGTH: 9
<212> TYPE: PRT
<213> ORGANISM: Artificial Sequence
<220> FEATURE:
<223> OTHER INFORMATION: 9mer T cell epitope 26
```

```
<400> SEQUENCE: 26

Lys Met His Ser Leu Leu Ala Leu Met
1               5

<210> SEQ ID NO 27
<211> LENGTH: 9
<212> TYPE: PRT
<213> ORGANISM: Artificial Sequence
<220> FEATURE:
<223> OTHER INFORMATION: 9mer T cell epitope 27

<400> SEQUENCE: 27

Phe Met Asn Pro Tyr Asn Ala Val Leu
1               5

<210> SEQ ID NO 28
<211> LENGTH: 9
<212> TYPE: PRT
<213> ORGANISM: Artificial Sequence
<220> FEATURE:
<223> OTHER INFORMATION: 9mer T cell epitope 28

<400> SEQUENCE: 28

Lys Ser Met Thr Met Met Pro Ala Leu
1               5

<210> SEQ ID NO 29
<211> LENGTH: 9
<212> TYPE: PRT
<213> ORGANISM: Artificial Sequence
<220> FEATURE:
<223> OTHER INFORMATION: 9mer T cell epitope 29

<400> SEQUENCE: 29

Tyr Val Asp Glu Lys Ala Pro Glu Phe
1               5

<210> SEQ ID NO 30
<211> LENGTH: 9
<212> TYPE: PRT
<213> ORGANISM: Artificial Sequence
<220> FEATURE:
<223> OTHER INFORMATION: 9mer T cell epitope 30

<400> SEQUENCE: 30

Lys Thr Met Ser Thr Phe His Asn Leu
1               5

<210> SEQ ID NO 31
<211> LENGTH: 9
<212> TYPE: PRT
<213> ORGANISM: Artificial Sequence
<220> FEATURE:
<223> OTHER INFORMATION: 9mer T cell epitope 31

<400> SEQUENCE: 31

Arg Ala Ile Glu Gln Leu Ala Ala Met
1               5

<210> SEQ ID NO 32
<211> LENGTH: 9
<212> TYPE: PRT
<213> ORGANISM: Artificial Sequence
<220> FEATURE:
<223> OTHER INFORMATION: 9mer T cell epitope 32

<400> SEQUENCE: 32
```

Val Met Ser Glu Arg Val Ser Gly Leu
1               5

<210> SEQ ID NO 33
<211> LENGTH: 9
<212> TYPE: PRT
<213> ORGANISM: Artificial Sequence
<220> FEATURE:
<223> OTHER INFORMATION: 9mer T cell epitope 33

<400> SEQUENCE: 33

Tyr Arg Ala Gln Arg Phe Trp Ser Trp
1               5

<210> SEQ ID NO 34
<211> LENGTH: 9
<212> TYPE: PRT
<213> ORGANISM: Artificial Sequence
<220> FEATURE:
<223> OTHER INFORMATION: 9mer T cell epitope 34

<400> SEQUENCE: 34

Phe Phe Phe Glu Arg Ile Met Lys Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: 9mer T cell epitope 35

<400> SEQUENCE: 35

Ser Thr Phe Lys Asn Trp Pro Phe Leu
1               5

<210> SEQ ID NO 36
<211> LENGTH: 9
<212> TYPE: PRT
<213> ORGANISM: Artificial Sequence
<220> FEATURE:
<223> OTHER INFORMATION: 9mer T cell epitope 36

<400> SEQUENCE: 36

Ala Ile Trp Glu Ala Leu Ser Val Met
1               5

<210> SEQ ID NO 37
<211> LENGTH: 9
<212> TYPE: PRT
<213> ORGANISM: Artificial Sequence
<220> FEATURE:
<223> OTHER INFORMATION: 9mer T cell epitope 37

<400> SEQUENCE: 37

Lys Val Ala Glu Leu Val Arg Phe Leu
1               5

<210> SEQ ID NO 38
<211> LENGTH: 9
<212> TYPE: PRT
<213> ORGANISM: Artificial Sequence
<220> FEATURE:
<223> OTHER INFORMATION: 9mer T cell epitope 38

<400> SEQUENCE: 38

```
Phe Val Gln Glu Asn Tyr Leu Glu Tyr
1               5
```

<210> SEQ ID NO 39
<211> LENGTH: 9
<212> TYPE: PRT
<213> ORGANISM: Artificial Sequence
<220> FEATURE:
<223> OTHER INFORMATION: 9mer T cell epitope 39

<400> SEQUENCE: 39

```
Arg Ala Leu Ala Glu Thr Ser Tyr Val
1               5
```

<210> SEQ ID NO 40
<211> LENGTH: 9
<212> TYPE: PRT
<213> ORGANISM: Artificial Sequence
<220> FEATURE:
<223> OTHER INFORMATION: 9mer T cell epitope 40

<400> SEQUENCE: 40

```
Tyr Ile Phe Ala Thr Cys Leu Gly Leu
1               5
```

<210> SEQ ID NO 41
<211> LENGTH: 15
<212> TYPE: PRT
<213> ORGANISM: Artificial Sequence
<220> FEATURE:
<223> OTHER INFORMATION: 15mer T cell epitope 1

<400> SEQUENCE: 41

```
Asp Gln Val Asn Ile Asp Tyr Leu Met Asn Arg Pro Gln Asn Leu
1               5                   10                  15
```

<210> SEQ ID NO 42
<211> LENGTH: 15
<212> TYPE: PRT
<213> ORGANISM: Artificial Sequence
<220> FEATURE:
<223> OTHER INFORMATION: 15mer T cell epitope 2

<400> SEQUENCE: 42

```
Met Met Ala Tyr Ser Asp Thr Thr Met Met Ser Asp Asp Ile Asp
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: 15mer T cell epitope 3

<400> SEQUENCE: 43

```
Met Phe Thr Ser Ser Arg Met Ser Ser Phe Asn Arg His Met Lys
1               5                   10                  15
```

<210> SEQ ID NO 44
<211> LENGTH: 15
<212> TYPE: PRT
<213> ORGANISM: Artificial Sequence
<220> FEATURE:

```
<223> OTHER INFORMATION: 15mer T cell epitope 4

<400> SEQUENCE: 44

Leu Gln Lys Tyr Ala Leu Gly Phe Gln His Ala Leu Ser Pro Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: 15mer T cell epitope 5

<400> SEQUENCE: 45

Ala Gln Lys Met Ser Ser Leu Leu Pro Thr Met Trp Leu Gly Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: 15mer T cell epitope 6

<400> SEQUENCE: 46

Gly Asn Ile Leu Asp Ser Phe Thr Val Cys Asn Ser His Val Leu
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: 15mer T cell epitope 7

<400> SEQUENCE: 47

Asn Met Ala Phe Val Thr Ser Gly Glu Leu Val Arg His Arg Arg
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: 15mer T cell epitope 8

<400> SEQUENCE: 48

Leu Glu Arg Leu Ala Tyr Leu His Ala Arg Leu Arg Glu Leu Leu
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: 15mer T cell epitope 9

<400> SEQUENCE: 49

Ser Gly Ala Val Met Ser Glu Arg Val Ser Gly Leu Ala Gly Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: 15mer T cell epitope 10
```

```
<400> SEQUENCE: 50

His Thr Arg Phe Thr Gln Ser Gly Thr Met Lys Ile His Ile Leu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: 15mer T cell epitope 11

<400> SEQUENCE: 51

Phe Ser Ser Ser Gly Thr Thr Ser Phe Lys Cys Phe Ala Pro Phe
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: 15mer T cell epitope 12

<400> SEQUENCE: 52

Gln Leu Glu Phe Met Phe Gln Glu Ala Leu Lys Leu Lys Val Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: 15mer T cell epitope 13

<400> SEQUENCE: 53

Cys Ser Gly Ser Ser Tyr Phe Val Leu Ala Asn Gly His Ile Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: 15mer T cell epitope 14

<400> SEQUENCE: 54

Arg His Ser Gln Thr Leu Lys Ala Met Val Gln Ala Trp Pro Phe
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: 15mer T cell epitope 15

<400> SEQUENCE: 55

Tyr Ser Cys Asp Ser Arg Ser Leu Phe Glu Ser Ser Ala Lys Ile
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: 15mer T cell epitope 16
```

```
<400> SEQUENCE: 56

Thr Ala Lys Lys Val Arg Arg Ala Ile Glu Gln Leu Ala Ala Met
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: 15mer T cell epitope 17

<400> SEQUENCE: 57

Ser Pro Thr Ala Met Asp Ala Ile Phe Gly Ser Leu Ser Asp Glu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: 15mer T cell epitope 18

<400> SEQUENCE: 58

Met Ala Ser Phe Arg Lys Leu Thr Leu Ser Glu Lys Val Pro Pro
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: 15mer T cell epitope 19

<400> SEQUENCE: 59

Ser Ser Ile Ser Val Tyr Tyr Thr Leu Trp Ser Gln Phe Asp Glu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: 15mer T cell epitope 20

<400> SEQUENCE: 60

Pro Gly Lys Pro Ser Ala Phe Glu Pro Ala Thr Glu Met Gln Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: 15mer T cell epitope 21

<400> SEQUENCE: 61

Arg Ser Cys Gly Phe Ser Tyr Glu Gln Asp Pro Thr Leu Arg Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: 15mer T cell epitope 22

<400> SEQUENCE: 62
```

Val Arg Thr Tyr Trp Ile Ile Ile Glu Leu Lys His Lys Ala Arg
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: 15mer T cell epitope 23

<400> SEQUENCE: 63

Pro Ser Thr Thr Met Glu Thr Gln Phe Pro Val Ser Glu Gly Lys
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: 15mer T cell epitope 24

<400> SEQUENCE: 64

Gly Thr Gly Lys Leu Gly Phe Ser Phe Val Arg Ile Thr Ala Leu
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: 15mer T cell epitope 25

<400> SEQUENCE: 65

Ala Gln Lys Met Ser Ser Leu Leu Pro Thr Met Trp Leu Gly Ala
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: 15mer T cell epitope 26

<400> SEQUENCE: 66

Leu Ala Ser Lys Met His Ser Leu Leu Ala Leu Met Val Gly Leu
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: 15mer T cell epitope 27

<400> SEQUENCE: 67

Lys Phe Met Asn Pro Tyr Asn Ala Val Leu Thr Lys Lys Phe Gln
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: 15mer T cell epitope 68

<400> SEQUENCE: 68

```
Pro Lys Ser Met Thr Met Met Pro Ala Leu Phe Lys Glu Asn Arg
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: 15mer T cell epitope 29

<400> SEQUENCE: 69

```
Tyr Val Asp Glu Lys Ala Pro Glu Phe Ser Met Gln Gly Leu Lys
1               5                   10                  15
```

<210> SEQ ID NO 70
<211> LENGTH: 15
<212> TYPE: PRT
<213> ORGANISM: Artificial Sequence
<220> FEATURE:
<223> OTHER INFORMATION: 15mer T cell epitope 30

<400> SEQUENCE: 70

```
Phe Lys Lys Thr Met Ser Thr Phe His Asn Leu Val Ser Leu Asn
1               5                   10                  15
```

<210> SEQ ID NO 71
<211> LENGTH: 15
<212> TYPE: PRT
<213> ORGANISM: Artificial Sequence
<220> FEATURE:
<223> OTHER INFORMATION: 15mer T cell epitope 31

<400> SEQUENCE: 71

```
Thr Ala Lys Lys Val Arg Arg Ala Ile Glu Gln Leu Ala Ala Met
1               5                   10                  15
```

<210> SEQ ID NO 72
<211> LENGTH: 15
<212> TYPE: PRT
<213> ORGANISM: Artificial Sequence
<220> FEATURE:
<223> OTHER INFORMATION: 15mer T cell epitope 32

<400> SEQUENCE: 72

```
Ser Gly Ala Val Met Ser Glu Arg Val Ser Gly Leu Ala Gly Ser
1               5                   10                  15
```

<210> SEQ ID NO 73
<211> LENGTH: 15
<212> TYPE: PRT
<213> ORGANISM: Artificial Sequence
<220> FEATURE:
<223> OTHER INFORMATION: 15mer T cell epitope 33

<400> SEQUENCE: 73

```
Ser Arg Tyr Arg Ala Gln Arg Phe Trp Ser Trp Val Gly Gln Ala
1               5                   10                  15
```

<210> SEQ ID NO 74
<211> LENGTH: 15
<212> TYPE: PRT
<213> ORGANISM: Artificial Sequence
<220> FEATURE:
<223> OTHER INFORMATION: 15mer T cell epitope 34

<400> SEQUENCE: 74

```
Lys Val Asn Phe Phe Phe Glu Arg Ile Met Lys Tyr Glu Arg Leu
```

-continued

```
<210> SEQ ID NO 75
<211> LENGTH: 15
<212> TYPE: PRT
<213> ORGANISM: Artificial Sequence
<220> FEATURE:
<223> OTHER INFORMATION: 15mer T cell epitope 35

<400> SEQUENCE: 75

Lys Asp His Arg Ile Ser Thr Phe Lys Asn Trp Pro Phe Leu Glu
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: 15mer T cell epitope 36

<400> SEQUENCE: 76

Ser Arg Ala Pro Glu Glu Ala Ile Trp Glu Ala Leu Ser Val Met
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: 15mer T cell epitope 37

<400> SEQUENCE: 77

Asp Glu Lys Val Ala Glu Leu Val Arg Phe Leu Leu Arg Lys Tyr
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: 15mer T cell epitope 38

<400> SEQUENCE: 78

Gln Tyr Phe Val Gln Glu Asn Tyr Leu Glu Tyr Arg Gln Val Pro
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: 15mer T cell epitope 39

<400> SEQUENCE: 79

Glu Phe Leu Trp Gly Pro Arg Ala Leu Ala Glu Thr Ser Tyr Val
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: 15mer T cell epitope 80

<400> SEQUENCE: 80

Ile Gly His Val Tyr Ile Phe Ala Thr Cys Leu Gly Leu Ser Tyr
1               5                   10                  15
```

<210> SEQ ID NO 81
<211> LENGTH: 30
<212> TYPE: PRT
<213> ORGANISM: Artificial Sequence
<220> FEATURE:
<223> OTHER INFORMATION: breast vaccine pep 1

<400> SEQUENCE: 81

Leu Gln Lys Tyr Ala Leu Gly Phe Gln His Ala Leu Ser Pro Ser Met
1               5                   10                  15

Met Ala Tyr Ser Asp Thr Thr Met Met Ser Asp Asp Ile Asp
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: breast vaccine pep 2

<400> SEQUENCE: 82

Val Cys Met Phe Thr Ser Ser Arg Met Ser Ser Phe Asn Arg His Val
1               5                   10                  15

Asn Ile Asp Tyr Leu Met Asn Arg Pro Gln Asn Leu Arg Leu
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: breast vaccine pep 3

<400> SEQUENCE: 83

Asn Met Ala Phe Val Thr Ser Gly Glu Leu Val Arg His Arg His
1               5                   10                  15

Thr Arg Phe Thr Gln Ser Gly Thr Met Lys Ile His Ile Leu
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: breast vaccine pep 4

<400> SEQUENCE: 84

Leu Asp Ser Phe Thr Val Cys Asn Ser His Val Leu Cys Ile Ala Lys
1               5                   10                  15

Leu Gly Phe Ser Phe Val Arg Ile Thr Ala Leu Met Val Ser
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: breast vaccine pep 5

<400> SEQUENCE: 85

Ala Gln Lys Met Ser Ser Leu Leu Pro Thr Met Trp Leu Gly Ala Met
1               5                   10                  15

Met Gln Met Phe Gly Leu Gly Ala Ile Ser Leu Ile Leu Val

<210> SEQ ID NO 86
<211> LENGTH: 30
<212> TYPE: PRT
<213> ORGANISM: Artificial Sequence
<220> FEATURE:
<223> OTHER INFORMATION: breast vaccine pep 6

<400> SEQUENCE: 86

Leu Glu Arg Leu Ala Tyr Leu His Ala Arg Leu Arg Glu Leu Leu Gln
1               5                   10                  15

Thr Leu Lys Ala Met Val Gln Ala Trp Pro Phe Thr Cys Leu
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: breast vaccine pep 7

<400> SEQUENCE: 87

Ser Ser Tyr Phe Val Leu Ala Asn Gly His Ile Leu Pro Asn Ser Leu
1               5                   10                  15

Arg His Lys Cys Cys Phe Ser Ser Ser Gly Thr Thr Ser Phe
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: breast vaccine pep 8

<400> SEQUENCE: 88

Thr Ala Lys Lys Val Arg Arg Ala Ile Glu Gln Leu Ala Ala Met Gln
1               5                   10                  15

Leu Glu Phe Met Phe Gln Glu Ala Leu Lys Leu Lys Val Ala
            20                  25                  30

<210> SEQ ID NO 89
<211> LENGTH: 30
<212> TYPE: PRT
<213> ORGANISM: Artificial Sequence
<220> FEATURE:
<223> OTHER INFORMATION: breast vaccine pep 9

<400> SEQUENCE: 89

Thr Ser His Ser Tyr Val Leu Val Thr Ser Leu Asn Leu Ser Tyr Tyr
1               5                   10                  15

Ser Cys Asp Ser Arg Ser Leu Phe Glu Ser Ser Ala Lys Ile
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: breast vaccine pep 10

<400> SEQUENCE: 90

Leu Asp Ser Phe Thr Val Cys Asn Ser His Val Leu Cys Ile Ala Val
1               5                   10                  15

Cys Met Phe Thr Ser Ser Arg Met Ser Ser Phe Asn Arg His
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: breast vaccine pep 11

<400> SEQUENCE: 91

Leu Arg His Lys Cys Cys Phe Ser Ser Gly Thr Thr Ser Phe Gln
1               5                   10                  15

Thr Leu Lys Ala Met Val Gln Ala Trp Pro Phe Thr Cys Leu
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: breast vaccine pep 12

<400> SEQUENCE: 92

Tyr Ser Cys Asp Ser Arg Ser Leu Phe Glu Ser Ser Ala Lys Ile Thr
1               5                   10                  15

Ala Lys Lys Val Arg Arg Ala Ile Glu Gln Leu Ala Ala Met
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: breast vaccine pep 13

<400> SEQUENCE: 93

Met Met Ala Tyr Ser Asp Thr Thr Met Met Ser Asp Asp Ile Asp His
1               5                   10                  15

Thr Arg Phe Thr Gln Ser Gly Thr Met Lys Ile His Ile Leu
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: breast vaccine pep 14

<400> SEQUENCE: 94

Ala Gln Lys Met Ser Ser Leu Leu Pro Thr Met Trp Leu Gly Ala Leu
1               5                   10                  15

Gln Lys Tyr Ala Leu Gly Phe Gln His Ala Leu Ser Pro Ser
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: breast vaccine pep 15

<400> SEQUENCE: 95

Thr Ser His Ser Tyr Val Leu Val Thr Ser Leu Asn Leu Ser Tyr Asn
1               5                   10                  15

```
Met Ala Phe Val Thr Ser Gly Glu Leu Val Arg His Arg Arg
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: breast vaccine pep 16

<400> SEQUENCE: 96

Met Met Gln Met Phe Gly Leu Gly Ala Ile Ser Leu Ile Leu Val Val
1               5                   10                  15

Asn Ile Asp Tyr Leu Met Asn Arg Pro Gln Asn Leu Arg Leu
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: breast cancer pep 17

<400> SEQUENCE: 97

Ser Ser Tyr Phe Val Leu Ala Asn Gly His Ile Leu Pro Asn Ser Lys
1               5                   10                  15

Leu Gly Phe Ser Phe Val Arg Ile Thr Ala Leu Met Val Ser
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: breast vaccine pep 18

<400> SEQUENCE: 98

Leu Glu Arg Leu Ala Tyr Leu His Ala Arg Leu Arg Glu Leu Leu Gln
1               5                   10                  15

Leu Glu Phe Met Phe Gln Glu Ala Leu Lys Leu Lys Val Ala
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: breast vaccine pep 19

<400> SEQUENCE: 99

Gly Asn Ile Leu Asp Ser Phe Thr Val Cys Asn Ser His Val Leu Leu
1               5                   10                  15

Gln Lys Tyr Ala Leu Gly Phe Gln His Ala Leu Ser Pro Ser
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: breast vaccine pep 20

<400> SEQUENCE: 100

Asn Met Ala Phe Val Thr Ser Gly Glu Leu Val Arg His Arg Arg Phe
```

```
                1               5                  10                  15
Ser Ser Ser Gly Thr Thr Ser Phe Lys Cys Phe Ala Pro Phe
                20                  25                  30
```

<210> SEQ ID NO 101
<211> LENGTH: 30
<212> TYPE: PRT
<213> ORGANISM: Artificial Sequence
<220> FEATURE:
<223> OTHER INFORMATION: breast vaccine pep 21

<400> SEQUENCE: 101

```
Ala Gln Lys Met Ser Ser Leu Leu Pro Thr Met Trp Leu Gly Ala Met
1               5                   10                  15

Phe Thr Ser Ser Arg Met Ser Ser Phe Asn Arg His Met Lys
                20                  25                  30
```

<210> SEQ ID NO 102
<211> LENGTH: 30
<212> TYPE: PRT
<213> ORGANISM: Artificial Sequence
<220> FEATURE:
<223> OTHER INFORMATION: breast vaccine pep 22

<400> SEQUENCE: 102

```
Thr Ser His Ser Tyr Val Leu Val Thr Ser Leu Asn Leu Ser Tyr His
1               5                   10                  15

Ser Gln Thr Leu Lys Ala Met Val Gln Ala Trp Pro Phe Thr
                20                  25                  30
```

<210> SEQ ID NO 103
<211> LENGTH: 30
<212> TYPE: PRT
<213> ORGANISM: Artificial Sequence
<220> FEATURE:
<223> OTHER INFORMATION: breast vaccine pep 23

<400> SEQUENCE: 103

```
Met Ala Ser Phe Arg Lys Leu Thr Leu Ser Glu Lys Val Pro Pro Ser
1               5                   10                  15

Pro Thr Ala Met Asp Ala Ile Phe Gly Ser Leu Ser Asp Glu
                20                  25                  30
```

<210> SEQ ID NO 104
<211> LENGTH: 30
<212> TYPE: PRT
<213> ORGANISM: Artificial Sequence
<220> FEATURE:
<223> OTHER INFORMATION: breast vaccine pep 24

<400> SEQUENCE: 104

```
Asp Gln Val Asn Ile Asp Tyr Leu Met Asn Arg Pro Gln Asn Leu Arg
1               5                   10                  15

His Ser Gln Thr Leu Lys Ala Met Val Gln Ala Trp Pro Phe
                20                  25                  30
```

<210> SEQ ID NO 105
<211> LENGTH: 30
<212> TYPE: PRT
<213> ORGANISM: Artificial Sequence
<220> FEATURE:
<223> OTHER INFORMATION: breast vaccine pep 25

<400> SEQUENCE: 105

```
Cys Ser Gly Ser Ser Tyr Phe Val Leu Ala Asn Gly His Ile Leu Ser
1               5                   10                  15

Gly Ala Val Met Ser Glu Arg Val Ser Gly Leu Ala Gly Ser
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: breast vaccine 26

<400> SEQUENCE: 106

Asp Leu Ser Phe Tyr Val Asn Arg Leu Ser Ser Leu Val Ile Gln Ser
1               5                   10                  15

Ser Ile Ser Val Tyr Tyr Thr Leu Trp Ser Gln Phe Asp Glu
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: breast vaccine pep 27

<400> SEQUENCE: 107

Ser Gly Ala Val Met Ser Glu Arg Val Ser Gly Leu Ala Gly Ser Ser
1               5                   10                  15

Arg Leu Leu Glu Phe Tyr Leu Ala Met Pro Phe Ala Thr Pro
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: breast vaccine pep 28

<400> SEQUENCE: 108

Met Ala Ser Phe Arg Lys Leu Thr Leu Ser Glu Lys Val Pro Pro Glu
1               5                   10                  15

Ser Phe Ser Pro Thr Ala Met Asp Ala Ile Phe Gly Ser Leu
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: breast vaccine pep 29

<400> SEQUENCE: 109

Phe Tyr Leu Ala Met Pro Phe Ala Thr Pro Met Glu Ala Glu Leu Lys
1               5                   10                  15

Pro Ser Ala Phe Glu Pro Ala Thr Glu Met Gln Lys Ser Val
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: breast vaccine pep 30

<400> SEQUENCE: 110
```

Ala Met Asp Ala Ile Phe Gly Ser Leu Ser Asp Glu Gly Ser Gly His
1               5                   10                  15

Ser Gln Thr Leu Lys Ala Met Val Gln Ala Trp Pro Phe Thr
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: breast vaccine pep 31

<400> SEQUENCE: 111

Phe Val Leu Ala Asn Gly His Ile Leu Pro Asn Ser Glu Asn Ala Gly
1               5                   10                  15

Thr Gly Lys Leu Gly Phe Ser Phe Val Arg Ile Thr Ala Leu
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: colorectal vaccine pep 1

<400> SEQUENCE: 112

Val Cys Ser Met Glu Gly Thr Trp Tyr Leu Val Gly Leu Val Ser Tyr
1               5                   10                  15

Arg Ser Cys Gly Phe Ser Tyr Glu Gln Asp Pro Thr Leu Arg
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: colocrectal vaccine pep 2

<400> SEQUENCE: 113

Val Arg Thr Tyr Trp Ile Ile Ile Glu Leu Lys His Lys Ala Arg Leu
1               5                   10                  15

Pro Ser Thr Thr Met Glu Thr Gln Phe Pro Val Ser Glu Gly
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: colorectal vaccine pep 3

<400> SEQUENCE: 114

Thr Ala Lys Lys Val Arg Arg Ala Ile Glu Gln Leu Ala Ala Met Met
1               5                   10                  15

Gly Ala Pro Thr Leu Pro Pro Ala Trp Gln Pro Phe Leu Lys
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: colorectal vaccine pep 4

```
<400> SEQUENCE: 115

Leu Ala Ser Lys Met His Ser Leu Leu Ala Leu Met Val Gly Leu Pro
1               5                   10                  15

Lys Ser Met Thr Met Met Pro Ala Leu Phe Lys Glu Asn Arg
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: colorectal vaccine pep 5

<400> SEQUENCE: 116

Lys Leu Gly Phe Ser Phe Val Arg Ile Thr Ala Leu Met Val Ser Leu
1               5                   10                  15

Asp Ser Phe Thr Val Cys Asn Ser His Val Leu Cys Ile Ala
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: colorectal vaccine pep 6

<400> SEQUENCE: 117

Lys Phe Met Asn Pro Tyr Asn Ala Val Leu Thr Lys Lys Phe Gln Phe
1               5                   10                  15

Lys Lys Thr Met Ser Thr Phe His Asn Leu Val Ser Leu Asn
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: colorectal vaccine pep 7

<400> SEQUENCE: 118

Ala Gln Lys Met Ser Ser Leu Leu Pro Thr Met Trp Leu Gly Ala Lys
1               5                   10                  15

Val Asn Phe Phe Phe Glu Arg Ile Met Lys Tyr Glu Arg Leu
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: colorectal vaccine pep 8

<400> SEQUENCE: 119

Lys Asp His Arg Ile Ser Thr Phe Lys Asn Trp Pro Phe Leu Glu Pro
1               5                   10                  15

Glu Glu Ala Ile Trp Glu Ala Leu Ser Val Met Gly Leu Tyr
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: colorectal vaccine pep 9
```

```
<400> SEQUENCE: 120

Tyr Arg Ser Cys Gly Phe Ser Tyr Glu Gln Asp Pro Thr Leu Arg Val
1               5                   10                  15

Cys Ser Met Glu Gly Thr Trp Tyr Leu Val Gly Leu Val Ser
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: colorectal vaccine pep 10

<400> SEQUENCE: 121

Val Arg Thr Tyr Trp Ile Ile Ile Glu Leu Lys His Lys Ala Arg Thr
1               5                   10                  15

Ala Lys Lys Val Arg Arg Ala Ile Glu Gln Leu Ala Ala Met
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: colorectal vaccine pep 11

<400> SEQUENCE: 122

Leu Pro Ser Thr Thr Met Glu Thr Gln Phe Pro Val Ser Gly Gly Lys
1               5                   10                  15

Leu Gly Phe Ser Phe Val Arg Ile Thr Ala Leu Met Val Ser
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: colorectal vaccine pep 12

<400> SEQUENCE: 123

Met Gly Ala Pro Thr Leu Pro Pro Ala Trp Gln Pro Phe Leu Lys Pro
1               5                   10                  15

Glu Glu Ala Ile Trp Glu Ala Leu Ser Val Met Gly Leu Tyr
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: colorectal vaccine pep 13

<400> SEQUENCE: 124

Leu Ala Ser Lys Met His Ser Leu Leu Ala Leu Met Val Gly Leu Lys
1               5                   10                  15

Asp His Arg Ile Ser Thr Phe Lys Asn Trp Pro Phe Leu Glu
            20                  25                  30

<210> SEQ ID NO 125
<211> LENGTH: 30
<212> TYPE: PRT
<213> ORGANISM: Artificial Sequence
<220> FEATURE:
```

<223> OTHER INFORMATION: colorectal vaccine pep 14

<400> SEQUENCE: 125

Pro Lys Ser Met Thr Met Met Pro Ala Leu Phe Lys Glu Asn Arg Leu
1               5                   10                  15

Asp Ser Phe Thr Val Cys Asn Ser His Val Leu Cys Ile Ala
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: colorectal vaccine pep 15

<400> SEQUENCE: 126

Lys Phe Met Asn Pro Tyr Asn Ala Val Leu Thr Lys Lys Phe Gln Lys
1               5                   10                  15

Val Asn Phe Phe Phe Glu Arg Ile Met Lys Tyr Glu Arg Leu
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: colorectal vaccine pep 16

<400> SEQUENCE: 127

Ala Gln Lys Met Ser Ser Leu Leu Pro Thr Met Trp Leu Gly Ala Phe
1               5                   10                  15

Lys Lys Thr Met Ser Thr Phe His Asn Leu Val Ser Leu Asn
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: colorectal vaccine pep 17

<400> SEQUENCE: 128

Gly Phe Ser Tyr Glu Gln Asp Pro Thr Leu Arg Asp Pro Glu Ala Val
1               5                   10                  15

Cys Ser Met Glu Gly Thr Trp Tyr Leu Val Gly Leu Val Ser
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: colorectal vaccine pep 18

<400> SEQUENCE: 129

Pro Lys Ser Met Thr Met Met Pro Ala Leu Phe Lys Glu Asn Arg Gly
1               5                   10                  15

Asn Ile Leu Asp Ser Phe Thr Val Cys Asn Ser His Val Leu
            20                  25                  30

<210> SEQ ID NO 130
<211> LENGTH: 30
<212> TYPE: PRT
<213> ORGANISM: Artificial Sequence

```
<220> FEATURE:
<223> OTHER INFORMATION: colorectal vaccine pep 19

<400> SEQUENCE: 130

Pro Ser Thr Thr Met Glu Thr Gln Phe Pro Val Ser Glu Gly Lys Ser
1               5                   10                  15
Arg Tyr Arg Ala Gln Arg Phe Trp Ser Trp Val Gly Gln Ala
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: colorectal vaccine pep 20

<400> SEQUENCE: 131

Tyr Val Asp Glu Lys Ala Pro Glu Phe Ser Met Gln Gly Leu Lys Asp
1               5                   10                  15
Glu Lys Val Ala Glu Leu Val Arg Phe Leu Leu Arg Lys Tyr
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: colorectal vaccine pep 21

<400> SEQUENCE: 132

Arg Ser Cys Gly Phe Ser Tyr Glu Gln Asp Pro Thr Leu Arg Asp Gly
1               5                   10                  15
Thr Gly Lys Leu Gly Phe Ser Phe Val Arg Ile Thr Ala Leu
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: colorectal vaccine pep 22

<400> SEQUENCE: 133

Ser Arg Ala Pro Glu Glu Ala Ile Trp Glu Ala Leu Ser Val Met Gln
1               5                   10                  15
Tyr Phe Val Gln Glu Asn Tyr Leu Glu Tyr Arg Gln Val Pro
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: colorectal vaccine pep 23

<400> SEQUENCE: 134

Pro Lys Ser Met Thr Met Met Pro Ala Leu Phe Lys Glu Asn Arg Ser
1               5                   10                  15
Gly Ala Val Met Ser Glu Arg Val Ser Gly Leu Ala Gly Ser
            20                  25                  30

<210> SEQ ID NO 135
<211> LENGTH: 30
<212> TYPE: PRT
```

```
<213> ORGANISM: Artificial Sequence
<220> FEATURE:
<223> OTHER INFORMATION: colorectal vaccine pep 24

<400> SEQUENCE: 135

Ser Gly Ala Val Met Ser Glu Arg Val Ser Gly Leu Ala Gly Ser Arg
1               5                   10                  15

Asn Ser Ile Arg Ser Ser Phe Ile Ser Ser Leu Ser Phe Phe
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: colorectal vaccine pep 25

<400> SEQUENCE: 136

Asn Ile Glu Asn Tyr Ser Thr Asn Ala Leu Ile Gln Pro Val Asp Glu
1               5                   10                  15

Lys Val Ala Glu Leu Val Arg Phe Leu Leu Arg Lys Tyr Gln
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: colorectal vaccine pep 26

<400> SEQUENCE: 137

Arg Gln Phe Glu Thr Val Cys Lys Phe His Trp Val Glu Ala Phe Lys
1               5                   10                  15

Leu Leu Thr Gln Tyr Phe Val Gln Glu Asn Tyr Leu Glu Tyr
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: colorectal vaccine pep 27

<400> SEQUENCE: 138

Glu Phe Leu Trp Gly Pro Arg Ala Leu Ala Glu Thr Ser Tyr Val Lys
1               5                   10                  15

Leu Leu Thr Gln His Phe Val Gln Glu Asn Tyr Leu Glu Tyr
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: colorectal vaccine pep 28

<400> SEQUENCE: 139

Ala Ser Ser Ser Ser Thr Leu Ile Met Gly Thr Leu Glu Glu Val Gln
1               5                   10                  15

Thr Leu Ile Tyr Tyr Val Asp Glu Lys Ala Pro Glu Phe Ser
            20                  25                  30

<210> SEQ ID NO 140
<211> LENGTH: 30
```

```
<212> TYPE: PRT
<213> ORGANISM: Artificial Sequence
<220> FEATURE:
<223> OTHER INFORMATION: colorectal vaccine pep 29

<400> SEQUENCE: 140

Ser Arg Thr Leu Leu Ala Leu Pro Leu Pro Leu Ser Leu Leu Ile
1               5                   10                  15

Gly His Leu Tyr Ile Phe Ala Thr Cys Leu Gly Leu Ser Tyr
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: colorectal vaccine pep 30

<400> SEQUENCE: 141

Phe Ile Ile Val Val Phe Val Tyr Leu Thr Val Glu Asn Lys Ser Ile
1               5                   10                  15

Gly His Val Tyr Ile Phe Ala Thr Cys Leu Gly Leu Ser Tyr
            20                  25                  30

<210> SEQ ID NO 142
<211> LENGTH: 30
<212> TYPE: PRT
<213> ORGANISM: Artificial Sequence
<220> FEATURE:
<223> OTHER INFORMATION: colorectal vaccine pep 31

<400> SEQUENCE: 142

Leu Leu Ala Ala Ala Thr Ala Thr Phe Ala Ala Ala Gln Glu Gln
1               5                   10                  15

Thr Leu Ile Tyr Tyr Val Asp Glu Lys Ala Pro Glu Phe Ser
            20                  25                  30

<210> SEQ ID NO 143
<211> LENGTH: 1321
<212> TYPE: PRT
<213> ORGANISM: Artificial Sequence
<220> FEATURE:
<223> OTHER INFORMATION: SPAG9 antigen

<400> SEQUENCE: 143

Met Glu Leu Glu Asp Gly Val Val Tyr Gln Glu Glu Pro Gly Gly Ser
1               5                   10                  15

Gly Ala Val Met Ser Glu Arg Val Ser Gly Leu Ala Gly Ser Ile Tyr
            20                  25                  30

Arg Glu Phe Glu Arg Leu Ile Gly Arg Tyr Asp Glu Glu Val Val Lys
        35                  40                  45

Glu Leu Met Pro Leu Val Val Ala Val Leu Glu Asn Leu Asp Ser Val
    50                  55                  60

Phe Ala Gln Asp Gln Glu His Gln Val Glu Leu Leu Leu Arg Asp
65                  70                  75                  80

Asp Asn Glu Gln Leu Ile Thr Gln Tyr Glu Arg Glu Lys Ala Leu Arg
                85                  90                  95

Lys His Ala Glu Glu Lys Phe Ile Glu Phe Glu Asp Ser Gln Glu Gln
            100                 105                 110

Glu Lys Lys Asp Leu Gln Thr Arg Val Glu Ser Leu Glu Ser Gln Thr
        115                 120                 125
```

```
Arg Gln Leu Glu Leu Lys Ala Lys Asn Tyr Ala Asp Gln Ile Ser Arg
    130                 135                 140
Leu Glu Glu Arg Glu Ala Glu Leu Lys Lys Glu Tyr Asn Ala Leu His
145                 150                 155                 160
Gln Arg His Thr Glu Met Ile His Asn Tyr Met Glu His Leu Glu Arg
                165                 170                 175
Thr Lys Leu His Gln Leu Ser Gly Ser Asp Gln Leu Glu Ser Thr Ala
            180                 185                 190
His Ser Arg Ile Arg Lys Glu Arg Pro Ile Ser Leu Gly Ile Phe Pro
        195                 200                 205
Leu Pro Ala Gly Asp Gly Leu Leu Thr Pro Asp Ala Gln Lys Gly Gly
210                 215                 220
Glu Thr Pro Gly Ser Glu Gln Trp Lys Phe Gln Glu Leu Ser Gln Pro
225                 230                 235                 240
Arg Ser His Thr Ser Leu Lys Val Ser Asn Ser Pro Glu Pro Gln Lys
                245                 250                 255
Ala Val Glu Gln Glu Asp Glu Leu Ser Asp Val Ser Gln Gly Gly Ser
            260                 265                 270
Lys Ala Thr Thr Pro Ala Ser Thr Ala Asn Ser Asp Val Ala Thr Ile
        275                 280                 285
Pro Thr Asp Thr Pro Leu Lys Glu Glu Asn Glu Gly Phe Val Lys Val
290                 295                 300
Thr Asp Ala Pro Asn Lys Ser Glu Ile Ser Lys His Ile Glu Val Gln
305                 310                 315                 320
Val Ala Gln Glu Thr Arg Asn Val Ser Thr Gly Ser Ala Glu Asn Glu
                325                 330                 335
Glu Lys Ser Glu Val Gln Ala Ile Ile Glu Ser Thr Pro Glu Leu Asp
            340                 345                 350
Met Asp Lys Asp Leu Ser Gly Tyr Lys Gly Ser Ser Thr Pro Thr Lys
        355                 360                 365
Gly Ile Glu Asn Lys Ala Phe Asp Arg Asn Thr Glu Ser Leu Phe Glu
370                 375                 380
Glu Leu Ser Ser Ala Gly Ser Gly Leu Ile Gly Asp Val Asp Glu Gly
385                 390                 395                 400
Ala Asp Leu Leu Gly Met Gly Arg Glu Val Glu Asn Leu Ile Leu Glu
                405                 410                 415
Asn Thr Gln Leu Leu Glu Thr Lys Asn Ala Leu Asn Ile Val Lys Asn
            420                 425                 430
Asp Leu Ile Ala Lys Val Asp Glu Leu Thr Cys Glu Lys Asp Val Leu
        435                 440                 445
Gln Gly Glu Leu Glu Ala Val Lys Gln Ala Lys Leu Lys Leu Glu Glu
450                 455                 460
Lys Asn Arg Glu Leu Glu Glu Glu Leu Arg Lys Ala Arg Ala Glu Ala
465                 470                 475                 480
Glu Asp Ala Arg Gln Lys Ala Lys Asp Asp Asp Ser Asp Ile Pro
                485                 490                 495
Thr Ala Gln Arg Lys Arg Phe Thr Arg Val Glu Met Ala Arg Val Leu
            500                 505                 510
Met Glu Arg Asn Gln Tyr Lys Glu Arg Leu Met Glu Leu Gln Glu Ala
        515                 520                 525
Val Arg Trp Thr Glu Met Ile Arg Ala Ser Arg Glu Asn Pro Ala Met
530                 535                 540
Gln Glu Lys Lys Arg Ser Ser Ile Trp Gln Phe Phe Ser Arg Leu Phe
```

```
            545                 550                 555                 560
        Ser Ser Ser Ser Asn Thr Thr Lys Lys Pro Glu Pro Pro Val Asn Leu
                        565                 570                 575

Lys Tyr Asn Ala Pro Thr Ser His Val Thr Pro Ser Val Lys Lys Arg
                        580                 585                 590

Ser Ser Thr Leu Ser Gln Leu Pro Gly Asp Lys Ser Lys Ala Phe Asp
                        595                 600                 605

Phe Leu Ser Glu Glu Thr Glu Ala Ser Leu Ala Ser Arg Arg Glu Gln
            610                 615                 620

Lys Arg Glu Gln Tyr Arg Gln Val Lys Ala His Val Gln Lys Glu Asp
        625                 630                 635                 640

Gly Arg Val Gln Ala Phe Gly Trp Ser Leu Pro Gln Lys Tyr Lys Gln
                        645                 650                 655

Val Thr Asn Gly Gln Gly Glu Asn Lys Met Lys Asn Leu Pro Val Pro
                        660                 665                 670

Val Tyr Leu Arg Pro Leu Asp Glu Lys Asp Thr Ser Met Lys Leu Trp
                        675                 680                 685

Cys Ala Val Gly Val Asn Leu Ser Gly Gly Lys Thr Arg Asp Gly Gly
                        690                 695                 700

Ser Val Val Gly Ala Ser Val Phe Tyr Lys Asp Val Ala Gly Leu Asp
        705                 710                 715                 720

Thr Glu Gly Ser Lys Gln Arg Ser Ala Ser Gln Ser Ser Leu Asp Lys
                        725                 730                 735

Leu Asp Gln Glu Leu Lys Glu Gln Gln Lys Glu Leu Lys Asn Gln Glu
                        740                 745                 750

Glu Leu Ser Ser Leu Val Trp Ile Cys Thr Ser Thr His Ser Ala Thr
                        755                 760                 765

Lys Val Leu Ile Ile Asp Ala Val Gln Pro Gly Asn Ile Leu Asp Ser
                        770                 775                 780

Phe Thr Val Cys Asn Ser His Val Leu Cys Ile Ala Ser Val Pro Gly
        785                 790                 795                 800

Ala Arg Glu Thr Asp Tyr Pro Ala Gly Glu Asp Leu Ser Glu Ser Gly
                        805                 810                 815

Gln Val Asp Lys Ala Ser Leu Cys Gly Ser Met Thr Ser Asn Ser Ser
                        820                 825                 830

Ala Glu Thr Asp Ser Leu Leu Gly Gly Ile Thr Val Val Gly Cys Ser
                        835                 840                 845

Ala Glu Gly Val Thr Gly Ala Ala Thr Ser Pro Ser Thr Asn Gly Ala
                        850                 855                 860

Ser Pro Val Met Asp Lys Pro Pro Glu Met Glu Ala Glu Asn Ser Glu
        865                 870                 875                 880

Val Asp Glu Asn Val Pro Thr Ala Glu Ala Thr Glu Ala Thr Glu
                        885                 890                 895

Gly Asn Ala Gly Ser Ala Glu Asp Thr Val Asp Ile Ser Gln Thr Gly
                        900                 905                 910

Val Tyr Thr Glu His Val Phe Thr Asp Pro Leu Gly Val Gln Ile Pro
                        915                 920                 925

Glu Asp Leu Ser Pro Val Tyr Gln Ser Ser Asn Asp Ser Asp Ala Tyr
                        930                 935                 940

Lys Asp Gln Ile Ser Val Leu Pro Asn Glu Gln Asp Leu Val Arg Glu
        945                 950                 955                 960

Glu Ala Gln Lys Met Ser Ser Leu Leu Pro Thr Met Trp Leu Gly Ala
                        965                 970                 975
```

```
Gln Asn Gly Cys Leu Tyr Val His Ser Ser Val Ala Gln Trp Arg Lys
            980                 985                 990

Cys Leu His Ser Ile Lys Leu Lys  Asp Ser Ile Leu Ser  Ile Val His
        995                 1000                 1005

Val Lys Gly Ile Val Leu Val Ala Leu Ala Asp Gly  Thr Leu Ala
   1010                 1015                 1020

Ile Phe His Arg Gly Val Asp Gly Gln Trp Asp Leu  Ser Asn Tyr
   1025                 1030                 1035

His Leu Leu Asp Leu Gly Arg Pro His His Ser Ile  Arg Cys Met
   1040                 1045                 1050

Thr Val Val His Asp Lys Val Trp Cys Gly Tyr Arg  Asn Lys Ile
   1055                 1060                 1065

Tyr Val Val Gln Pro Lys Ala Met Lys Ile Glu Lys  Ser Phe Asp
   1070                 1075                 1080

Ala His Pro Arg Lys Glu Ser Gln Val Arg Gln Leu  Ala Trp Val
   1085                 1090                 1095

Gly Asp Gly Val Trp Val Ser Ile Arg Leu Asp Ser  Thr Leu Arg
   1100                 1105                 1110

Leu Tyr His Ala His Thr Tyr Gln His Leu Gln Asp  Val Asp Ile
   1115                 1120                 1125

Glu Pro Tyr Val Ser Lys Met Leu Gly Thr Gly Lys  Leu Gly Phe
   1130                 1135                 1140

Ser Phe Val Arg Ile Thr Ala Leu Met Val Ser Cys  Asn Arg Leu
   1145                 1150                 1155

Trp Val Gly Thr Gly Asn Gly Val Ile Ser Ile Pro  Leu Thr
   1160                 1165                 1170

Glu Thr Asn Lys Thr Ser Gly Val Pro Gly Asn Arg  Pro Gly Ser
   1175                 1180                 1185

Val Ile Arg Val Tyr Gly Asp Glu Asn Ser Asp Lys  Val Thr Pro
   1190                 1195                 1200

Gly Thr Phe Ile Pro Tyr Cys Ser Met Ala His Ala  Gln Leu Cys
   1205                 1210                 1215

Phe His Gly His Arg Asp Ala Val Lys Phe Phe Val  Ala Val Pro
   1220                 1225                 1230

Gly Gln Val Ile Ser Pro Gln Ser Ser Ser Gly  Thr Asp Leu
   1235                 1240                 1245

Thr Gly Asp Lys Ala Gly Pro Ser Ala Gln Glu Pro  Gly Ser Gln
   1250                 1255                 1260

Thr Pro Leu Lys Ser Met Leu Val Ile Ser Gly Gly  Glu Gly Tyr
   1265                 1270                 1275

Ile Asp Phe Arg Met Gly Asp Glu Gly Gly Glu Ser  Glu Leu Leu
   1280                 1285                 1290

Gly Glu Asp Leu Pro Leu Glu Pro Ser Val Thr Lys  Ala Glu Arg
   1295                 1300                 1305

Ser His Leu Ile Val Trp Gln Val Met Tyr Gly Asn  Glu
   1310                 1315                 1320

<210> SEQ ID NO 144
<211> LENGTH: 854
<212> TYPE: PRT
<213> ORGANISM: Artificial Sequence
<220> FEATURE:
<223> OTHER INFORMATION: AKAP-4 antigen

<400> SEQUENCE: 144
```

```
Met Met Ala Tyr Ser Asp Thr Thr Met Met Ser Asp Ile Asp Trp
1               5                   10                  15

Leu Arg Ser His Arg Gly Val Cys Lys Val Asp Leu Tyr Asn Pro Glu
                20                  25                  30

Gly Gln Gln Asp Gln Asp Arg Lys Val Ile Cys Phe Val Asp Val Ser
        35                  40                  45

Thr Leu Asn Val Glu Asp Lys Asp Tyr Lys Asp Ala Ala Ser Ser Ser
    50                  55                  60

Ser Glu Gly Asn Leu Asn Leu Gly Ser Leu Glu Glu Lys Glu Ile Ile
65                  70                  75                  80

Val Ile Lys Asp Thr Glu Lys Lys Asp Gln Ser Lys Thr Glu Gly Ser
                85                  90                  95

Val Cys Leu Phe Lys Gln Ala Pro Ser Asp Pro Val Ser Val Leu Asn
                100                 105                 110

Trp Leu Leu Ser Asp Leu Gln Lys Tyr Ala Leu Gly Phe Gln His Ala
            115                 120                 125

Leu Ser Pro Ser Thr Ser Thr Cys Lys His Lys Val Gly Asp Thr Glu
        130                 135                 140

Gly Glu Tyr His Arg Ala Ser Ser Glu Asn Cys Tyr Ser Val Tyr Ala
145                 150                 155                 160

Asp Gln Val Asn Ile Asp Tyr Leu Met Asn Arg Pro Gln Asn Leu Arg
                165                 170                 175

Leu Glu Met Thr Ala Ala Lys Asn Thr Asn Asn Gln Ser Pro Ser
            180                 185                 190

Ala Pro Pro Ala Lys Pro Pro Ser Thr Gln Arg Ala Val Ile Ser Pro
        195                 200                 205

Asp Gly Glu Cys Ser Ile Asp Asp Leu Ser Phe Tyr Val Asn Arg Leu
210                 215                 220

Ser Ser Leu Val Ile Gln Met Ala His Lys Glu Ile Lys Glu Lys Leu
225                 230                 235                 240

Glu Gly Lys Ser Lys Cys Leu His His Ser Ile Cys Pro Ser Pro Gly
                245                 250                 255

Asn Lys Glu Arg Ile Ser Pro Arg Thr Pro Ala Ser Lys Ile Ala Ser
                260                 265                 270

Glu Met Ala Tyr Glu Ala Val Glu Leu Thr Ala Ala Glu Met Arg Gly
            275                 280                 285

Thr Gly Glu Glu Ser Arg Glu Gly Gln Lys Ser Phe Leu Tyr Ser
        290                 295                 300

Glu Leu Ser Asn Lys Ser Lys Ser Gly Asp Lys Gln Met Ser Gln Arg
305                 310                 315                 320

Glu Ser Lys Glu Phe Ala Asp Ser Ile Ser Lys Gly Leu Met Val Tyr
                325                 330                 335

Ala Asn Gln Val Ala Ser Asp Met Met Val Ser Leu Met Lys Thr Leu
            340                 345                 350

Lys Val His Ser Ser Gly Lys Pro Ile Pro Ala Ser Val Leu Lys
                355                 360                 365

Arg Val Leu Leu Arg His Thr Lys Glu Ile Val Ser Asp Leu Ile Asp
    370                 375                 380

Ser Cys Met Lys Asn Leu His Asn Ile Thr Gly Val Leu Met Thr Asp
385                 390                 395                 400

Ser Asp Phe Val Ser Ala Val Lys Arg Asn Leu Phe Asn Gln Trp Lys
                405                 410                 415
```

```
Gln Asn Ala Thr Asp Ile Met Glu Ala Met Leu Lys Arg Leu Val Ser
            420                 425                 430

Ala Leu Ile Gly Glu Glu Lys Glu Thr Lys Ser Gln Ser Leu Ser Tyr
        435                 440                 445

Ala Ser Leu Lys Ala Gly Ser His Asp Pro Lys Cys Arg Asn Gln Ser
    450                 455                 460

Leu Glu Phe Ser Thr Met Lys Ala Glu Met Lys Glu Arg Asp Lys Gly
465                 470                 475                 480

Lys Met Lys Ser Asp Pro Cys Lys Ser Leu Thr Ser Ala Glu Lys Val
                485                 490                 495

Gly Glu His Ile Leu Lys Glu Gly Leu Thr Ile Trp Asn Gln Lys Gln
            500                 505                 510

Gly Asn Ser Cys Lys Val Ala Thr Lys Ala Cys Ser Asn Lys Asp Glu
        515                 520                 525

Lys Gly Glu Lys Ile Asn Ala Ser Thr Asp Ser Leu Ala Lys Asp Leu
    530                 535                 540

Ile Val Ser Ala Leu Lys Leu Ile Gln Tyr His Leu Thr Gln Gln Thr
545                 550                 555                 560

Lys Gly Lys Asp Thr Cys Glu Glu Asp Cys Pro Gly Ser Thr Met Gly
                565                 570                 575

Tyr Met Ala Gln Ser Thr Gln Tyr Glu Lys Cys Gly Gly Gln Ser
            580                 585                 590

Ala Lys Ala Leu Ser Val Lys Gln Leu Glu Ser His Arg Ala Pro Gly
        595                 600                 605

Pro Ser Thr Cys Gln Lys Glu Asn Gln His Leu Asp Ser Gln Lys Met
    610                 615                 620

Asp Met Ser Asn Ile Val Leu Met Leu Ile Gln Lys Leu Leu Asn Glu
625                 630                 635                 640

Asn Pro Phe Lys Cys Glu Asp Pro Cys Glu Gly Asn Lys Cys Ser
                645                 650                 655

Glu Pro Arg Ala Ser Lys Ala Ala Ser Met Ser Asn Arg Ser Asp Lys
            660                 665                 670

Ala Glu Glu Gln Cys Gln Glu His Gln Glu Leu Asp Cys Thr Ser Gly
        675                 680                 685

Met Lys Gln Ala Asn Gly Gln Phe Ile Asp Lys Leu Val Glu Ser Val
    690                 695                 700

Met Lys Leu Cys Leu Ile Met Ala Lys Tyr Ser Asn Asp Gly Ala Ala
705                 710                 715                 720

Leu Ala Glu Leu Glu Glu Gln Ala Ala Ser Ala Asn Lys Pro Asn Phe
                725                 730                 735

Arg Gly Thr Arg Cys Ile His Ser Gly Ala Met Pro Gln Asn Tyr Gln
            740                 745                 750

Asp Ser Leu Gly His Glu Val Ile Val Asn Asn Gln Cys Ser Thr Asn
        755                 760                 765

Ser Leu Gln Lys Gln Leu Gln Ala Val Leu Gln Trp Ile Ala Ala Ser
    770                 775                 780

Gln Phe Asn Val Pro Met Leu Tyr Phe Met Gly Asp Lys Asp Gly Gln
785                 790                 795                 800

Leu Glu Lys Leu Pro Gln Val Ser Ala Lys Ala Glu Lys Gly Tyr
                805                 810                 815

Ser Val Gly Gly Leu Leu Gln Glu Val Met Lys Phe Ala Lys Glu Arg
            820                 825                 830

Gln Pro Asp Glu Ala Val Gly Lys Val Ala Arg Lys Gln Leu Leu Asp
```

```
                    835                 840                 845

Trp Leu Leu Ala Asn Leu
    850

<210> SEQ ID NO 145
<211> LENGTH: 663
<212> TYPE: PRT
<213> ORGANISM: Artificial Sequence
<220> FEATURE:
<223> OTHER INFORMATION: BORIS antigen

<400> SEQUENCE: 145

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
```

-continued

```
                340                 345                 350
Glu Ala Ser Lys Leu Lys Arg His Val Arg Ser His Thr Gly Glu Arg
            355                 360                 365
Pro Phe Gln Cys Cys Gln Cys Ser Tyr Ala Ser Arg Asp Thr Tyr Lys
        370                 375                 380
Leu Lys Arg His Met Arg Thr His Ser Gly Glu Lys Pro Tyr Glu Cys
385                 390                 395                 400
His Ile Cys His Thr Arg Phe Thr Gln Ser Gly Thr Met Lys Ile His
                405                 410                 415
Ile Leu Gln Lys His Gly Glu Asn Val Pro Lys Tyr Gln Cys Pro His
            420                 425                 430
Cys Ala Thr Ile Ile Ala Arg Lys Ser Asp Leu Arg Val His Met Arg
        435                 440                 445
Asn Leu His Ala Tyr Ser Ala Ala Glu Leu Lys Cys Arg Tyr Cys Ser
        450                 455                 460
Ala Val Phe His Glu Arg Tyr Ala Leu Ile Gln His Gln Lys Thr His
465                 470                 475                 480
Lys Asn Glu Lys Arg Phe Lys Cys Lys His Cys Ser Tyr Ala Cys Lys
                485                 490                 495
Gln Glu Arg His Met Thr Ala His Ile Arg Thr His Thr Gly Glu Lys
            500                 505                 510
Pro Phe Thr Cys Leu Ser Cys Asn Lys Cys Phe Arg Gln Lys Gln Leu
        515                 520                 525
Leu Asn Ala His Phe Arg Lys Tyr His Asp Ala Asn Phe Ile Pro Thr
        530                 535                 540
Val Tyr Lys Cys Ser Lys Cys Gly Lys Gly Phe Ser Arg Trp Ile Asn
545                 550                 555                 560
Leu His Arg His Ser Glu Lys Cys Gly Ser Gly Glu Ala Lys Ser Ala
                565                 570                 575
Ala Ser Gly Lys Gly Arg Arg Thr Arg Lys Arg Lys Gln Thr Ile Leu
            580                 585                 590
Lys Glu Ala Thr Lys Gly Gln Lys Glu Ala Lys Gly Trp Lys Glu
        595                 600                 605
Ala Ala Asn Gly Asp Glu Ala Ala Glu Glu Ala Ser Thr Thr Lys
        610                 615                 620
Gly Glu Gln Phe Pro Gly Glu Met Phe Pro Val Ala Cys Arg Glu Thr
625                 630                 635                 640
Thr Ala Arg Val Lys Glu Glu Val Asp Glu Gly Val Thr Cys Glu Met
                645                 650                 655
Leu Leu Asn Thr Met Asp Lys
            660

<210> SEQ ID NO 146
<211> LENGTH: 255
<212> TYPE: PRT
<213> ORGANISM: Artificial Sequence
<220> FEATURE:
<223> OTHER INFORMATION: NY-SAR-35

<400> SEQUENCE: 146

Met Ser Ser His Arg Arg Lys Ala Lys Gly Arg Asn Arg Arg Ser His
1               5                   10                  15
Arg Ala Met Arg Val Ala His Leu Glu Leu Ala Thr Tyr Glu Leu Ala
            20                  25                  30
Ala Thr Glu Ser Asn Pro Glu Ser Ser His Pro Gly Tyr Glu Ala Ala
```

```
                35                  40                  45
Met Ala Asp Arg Pro Gln Pro Gly Trp Arg Glu Ser Leu Lys Met Arg
 50                  55                  60

Val Ser Lys Pro Phe Gly Met Leu Met Leu Ser Ile Trp Ile Leu Leu
 65                  70                  75                  80

Phe Val Cys Tyr Tyr Leu Ser Tyr Tyr Leu Cys Ser Gly Ser Ser Tyr
                 85                  90                  95

Phe Val Leu Ala Asn Gly His Ile Leu Pro Asn Ser Glu Asn Ala His
                100                 105                 110

Gly Gln Ser Leu Glu Glu Asp Ser Ala Leu Glu Ala Leu Leu Asn Phe
                115                 120                 125

Phe Phe Pro Thr Thr Cys Asn Leu Arg Glu Asn Gln Val Ala Lys Pro
                130                 135                 140

Cys Asn Glu Leu Gln Asp Leu Ser Glu Ser Cys Leu Arg His Lys
145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
                180                 185                 190

Ile Ser Leu Ile Leu Val Cys Leu Pro Ile Tyr Cys Arg Ser Leu Phe
                195                 200                 205

Trp Arg Ser Glu Pro Ala Asp Asp Leu Gln Arg Gln Asp Asn Arg Val
210                 215                 220

Val Thr Gly Leu Lys Lys Gln Arg Arg Lys Arg Lys Ser Glu
225                 230                 235                 240

Met Leu Gln Lys Ala Ala Arg Gly Arg Glu Glu His Gly Asp Glu
                245                 250                 255

<210> SEQ ID NO 147
<211> LENGTH: 1341
<212> TYPE: PRT
<213> ORGANISM: Artificial Sequence
<220> FEATURE:
<223> OTHER INFORMATION: NY-BR-1

<400> SEQUENCE: 147

Met Thr Lys Arg Lys Thr Ile Asn Leu Asn Ile Gln Asp Ala Gln
 1               5                  10                  15

Lys Arg Thr Ala Leu His Trp Ala Cys Val Asn Gly His Glu Val
                 20                  25                  30

Val Thr Phe Leu Val Asp Arg Lys Cys Gln Leu Asp Val Leu Asp Gly
                 35                  40                  45

Glu His Arg Thr Pro Leu Met Lys Ala Leu Gln Cys His Gln Glu Ala
 50                  55                  60

Cys Ala Asn Ile Leu Ile Asp Ser Gly Ala Asp Ile Asn Leu Val Asp
 65                  70                  75                  80

Val Tyr Gly Asn Thr Ala Leu His Tyr Ala Val Tyr Ser Glu Ile Leu
                 85                  90                  95

Ser Val Val Ala Lys Leu Leu Ser His Gly Ala Val Ile Glu Val His
                100                 105                 110

Asn Lys Ala Ser Leu Thr Pro Leu Leu Leu Ser Ile Thr Lys Arg Ser
                115                 120                 125

Glu Gln Ile Val Glu Phe Leu Leu Ile Lys Asn Ala Asn Ala Asn Ala
                130                 135                 140

Val Asn Lys Tyr Lys Cys Thr Ala Leu Met Leu Ala Val Cys His Gly
```

-continued

```
            145                 150                 155                 160
        Ser Ser Glu Ile Val Gly Met Leu Leu Gln Gln Asn Val Asp Val Phe
                        165                 170                 175

Ala Ala Asp Ile Cys Gly Val Thr Ala Glu His Tyr Ala Val Thr Cys
                        180                 185                 190

Gly Phe His His Ile His Glu Gln Ile Met Glu Tyr Ile Arg Lys Leu
                        195                 200                 205

Ser Lys Asn His Gln Asn Thr Asn Pro Glu Gly Thr Ser Ala Gly Thr
            210                 215                 220

Pro Asp Glu Ala Ala Pro Leu Ala Glu Arg Thr Pro Asp Thr Ala Glu
        225                 230                 235                 240

Ser Leu Val Glu Lys Thr Pro Asp Glu Ala Ala Pro Leu Val Glu Arg
                        245                 250                 255

Thr Pro Asp Thr Ala Glu Ser Leu Val Glu Lys Thr Pro Asp Glu Ala
                        260                 265                 270

Ala Ser Leu Val Glu Gly Thr Ser Asp Lys Ile Gln Cys Leu Glu Lys
                        275                 280                 285

Ala Thr Ser Gly Lys Phe Glu Gln Ser Ala Glu Glu Thr Pro Arg Glu
                        290                 295                 300

Ile Thr Ser Pro Ala Lys Glu Thr Ser Glu Lys Phe Thr Trp Pro Ala
        305                 310                 315                 320

Lys Gly Arg Pro Arg Lys Ile Ala Trp Glu Lys Lys Glu Asp Thr Pro
                        325                 330                 335

Arg Glu Ile Met Ser Pro Ala Lys Glu Thr Ser Glu Lys Phe Thr Trp
                        340                 345                 350

Ala Ala Lys Gly Arg Pro Arg Lys Ile Ala Trp Glu Lys Lys Glu Thr
                        355                 360                 365

Pro Val Lys Thr Gly Cys Val Ala Arg Val Thr Ser Asn Lys Thr Lys
                        370                 375                 380

Val Leu Glu Lys Gly Arg Ser Lys Met Ile Ala Cys Pro Thr Lys Glu
        385                 390                 395                 400

Ser Ser Thr Lys Ala Ser Ala Asn Asp Gln Arg Phe Pro Ser Glu Ser
                        405                 410                 415

Lys Gln Glu Glu Asp Glu Glu Tyr Ser Cys Asp Ser Arg Ser Leu Phe
                        420                 425                 430

Glu Ser Ser Ala Lys Ile Gln Val Cys Ile Pro Glu Ser Ile Tyr Gln
                        435                 440                 445

Lys Val Met Glu Ile Asn Arg Glu Val Glu Glu Pro Pro Lys Lys Pro
            450                 455                 460

Ser Ala Phe Lys Pro Ala Ile Glu Met Gln Asn Ser Val Pro Asn Lys
        465                 470                 475                 480

Ala Phe Glu Leu Lys Asn Glu Gln Thr Leu Arg Ala Asp Pro Met Phe
                        485                 490                 495

Pro Pro Glu Ser Lys Gln Lys Asp Tyr Glu Glu Asn Ser Trp Asp Ser
                        500                 505                 510

Glu Ser Leu Cys Glu Thr Val Ser Gln Lys Asp Val Cys Leu Pro Lys
                        515                 520                 525

Ala Thr His Gln Lys Glu Ile Asp Lys Ile Asn Gly Lys Leu Glu Glu
                        530                 535                 540

Ser Pro Asn Lys Asp Gly Leu Leu Lys Ala Thr Cys Gly Met Lys Val
        545                 550                 555                 560

Ser Ile Pro Thr Lys Ala Leu Glu Leu Lys Asp Met Gln Thr Phe Lys
                        565                 570                 575
```

```
Ala Glu Pro Pro Gly Lys Pro Ser Ala Phe Glu Pro Ala Thr Glu Met
            580                 585                 590
Gln Lys Ser Val Pro Asn Lys Ala Leu Glu Leu Lys Asn Glu Gln Thr
        595                 600                 605
Leu Arg Ala Asp Glu Ile Leu Pro Ser Glu Ser Lys Gln Lys Asp Tyr
    610                 615                 620
Glu Glu Asn Ser Trp Asp Thr Glu Ser Leu Cys Glu Thr Val Ser Gln
625                 630                 635                 640
Lys Asp Val Cys Leu Pro Lys Ala Ala His Gln Lys Glu Ile Asp Lys
                645                 650                 655
Ile Asn Gly Lys Leu Glu Gly Ser Pro Val Lys Asp Gly Leu Leu Lys
            660                 665                 670
Ala Asn Cys Gly Met Lys Val Ser Ile Pro Thr Lys Ala Leu Glu Leu
        675                 680                 685
Met Asp Met Gln Thr Phe Lys Ala Glu Pro Pro Glu Lys Pro Ser Ala
    690                 695                 700
Phe Glu Pro Ala Ile Glu Met Gln Lys Ser Val Pro Asn Lys Ala Leu
705                 710                 715                 720
Glu Leu Lys Asn Glu Gln Thr Leu Arg Ala Asp Glu Ile Leu Pro Ser
                725                 730                 735
Glu Ser Lys Gln Lys Asp Tyr Glu Glu Ser Ser Trp Asp Ser Glu Ser
            740                 745                 750
Leu Cys Glu Thr Val Ser Gln Lys Asp Val Cys Leu Pro Lys Ala Thr
        755                 760                 765
His Gln Lys Glu Ile Asp Lys Ile Asn Gly Lys Leu Glu Glu Ser Pro
    770                 775                 780
Asp Asn Asp Gly Phe Leu Lys Ala Pro Cys Arg Met Lys Val Ser Ile
785                 790                 795                 800
Pro Thr Lys Ala Leu Glu Leu Met Asp Met Gln Thr Phe Lys Ala Glu
                805                 810                 815
Pro Pro Glu Lys Pro Ser Ala Phe Glu Pro Ala Ile Glu Met Gln Lys
            820                 825                 830
Ser Val Pro Asn Lys Ala Leu Glu Leu Lys Asn Glu Gln Thr Leu Arg
        835                 840                 845
Ala Asp Gln Met Phe Pro Ser Glu Ser Lys Gln Lys Lys Val Glu Glu
    850                 855                 860
Asn Ser Trp Asp Ser Glu Ser Leu Arg Glu Thr Val Ser Gln Lys Asp
865                 870                 875                 880
Val Cys Val Pro Lys Ala Thr His Gln Lys Glu Met Asp Lys Ile Ser
                885                 890                 895
Gly Lys Leu Glu Asp Ser Thr Ser Leu Ser Lys Ile Leu Asp Thr Val
            900                 905                 910
His Ser Cys Glu Arg Ala Arg Glu Leu Gln Lys Asp His Cys Glu Gln
        915                 920                 925
Arg Thr Gly Lys Met Glu Gln Met Lys Lys Phe Cys Val Leu Lys
    930                 935                 940
Lys Lys Leu Ser Glu Ala Lys Glu Ile Lys Ser Gln Leu Glu Asn Gln
945                 950                 955                 960
Lys Val Lys Trp Glu Gln Glu Leu Cys Ser Val Arg Leu Thr Leu Asn
                965                 970                 975
Gln Glu Glu Glu Lys Arg Arg Asn Ala Asp Ile Leu Asn Glu Lys Ile
            980                 985                 990
```

```
Arg Glu Glu Leu Gly Arg Ile Glu  Glu Gln His Arg Lys  Glu Leu Glu
            995                 1000                 1005

Val Lys Gln Gln Leu Glu Gln  Ala Leu Arg Ile Gln  Asp Ile Glu
    1010                1015                1020

Leu Lys Ser Val Glu Ser Asn  Leu Asn Gln Val Ser  His Thr His
    1025                1030                1035

Glu Asn Glu Asn Tyr Leu Leu  His Glu Asn Cys Met  Leu Lys Lys
    1040                1045                1050

Glu Ile Ala Met Leu Lys Leu  Glu Ile Ala Thr Leu  Lys His Gln
    1055                1060                1065

Tyr Gln Glu Lys Glu Asn Lys  Tyr Phe Glu Asp Ile  Lys Ile Leu
    1070                1075                1080

Lys Glu Lys Asn Ala Glu Leu  Gln Met Thr Leu Lys  Leu Lys Glu
    1085                1090                1095

Glu Ser Leu Thr Lys Arg Ala  Ser Gln Tyr Ser Gly  Gln Leu Lys
    1100                1105                1110

Val Leu Ile Ala Glu Asn Thr  Met Leu Thr Ser Lys  Leu Lys Glu
    1115                1120                1125

Lys Gln Asp Lys Glu Ile Leu  Glu Ala Glu Ile Glu  Ser His His
    1130                1135                1140

Pro Arg Leu Ala Ser Ala Val  Gln Asp His Asp Gln  Ile Val Thr
    1145                1150                1155

Ser Arg Lys Ser Gln Glu Pro  Ala Phe His Ile Ala  Gly Asp Ala
    1160                1165                1170

Cys Leu Gln Arg Lys Met Asn  Val Asp Val Ser Ser  Thr Ile Tyr
    1175                1180                1185

Asn Asn Glu Val Leu His Gln  Pro Leu Ser Glu Ala  Gln Arg Lys
    1190                1195                1200

Ser Lys Ser Leu Lys Ile Asn  Leu Asn Tyr Ala Gly  Asp Ala Leu
    1205                1210                1215

Arg Glu Asn Thr Leu Val Ser  Glu His Ala Gln Arg  Asp Gln Arg
    1220                1225                1230

Glu Thr Gln Cys Gln Met Lys  Glu Ala Glu His Met  Tyr Gln Asn
    1235                1240                1245

Glu Gln Asp Asn Val Asn Lys  His Thr Glu Gln Gln  Glu Ser Leu
    1250                1255                1260

Asp Gln Lys Leu Phe Gln Leu  Gln Ser Lys Asn Met  Trp Leu Gln
    1265                1270                1275

Gln Gln Leu Val His Ala His  Lys Lys Ala Asp Asn  Lys Ser Lys
    1280                1285                1290

Ile Thr Ile Asp Ile His Phe  Leu Glu Arg Lys Met  Gln His His
    1295                1300                1305

Leu Leu Lys Glu Lys Asn Glu  Glu Ile Phe Asn Tyr  Asn Asn His
    1310                1315                1320

Leu Lys Asn Arg Ile Tyr Gln  Tyr Glu Lys Glu Lys  Ala Glu Thr
    1325                1330                1335

Glu Asn Ser
    1340

<210> SEQ ID NO 148
<211> LENGTH: 142
<212> TYPE: PRT
<213> ORGANISM: Artificial Sequence
<220> FEATURE:
<223> OTHER INFORMATION: SURVIVIN antigen
```

<400> SEQUENCE: 148

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65              70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Lys Lys Val Arg Arg Ala Ile Glu Gln Leu Ala Ala Met Asp
    130                 135                 140

<210> SEQ ID NO 149
<211> LENGTH: 429
<212> TYPE: PRT
<213> ORGANISM: Artificial Sequence
<220> FEATURE:
<223> OTHER INFORMATION: MAGE-A11

<400> SEQUENCE: 149

Met Glu Thr Gln Phe Arg Arg Gly Gly Leu Gly Cys Ser Pro Ala Ser
1               5                   10                  15

Ile Lys Arg Lys Lys Arg Glu Asp Ser Gly Asp Phe Gly Leu Gln
            20                  25                  30

Val Ser Thr Met Phe Ser Glu Asp Asp Phe Gln Ser Thr Glu Arg Ala
        35                  40                  45

Pro Tyr Gly Pro Gln Leu Gln Trp Ser Gln Asp Leu Pro Arg Val Gln
    50                  55                  60

Val Phe Arg Glu Gln Ala Asn Leu Glu Asp Arg Ser Pro Arg Arg Thr
65              70                  75                  80

Gln Arg Ile Thr Gly Gly Glu Gln Val Leu Trp Gly Pro Ile Thr Gln
                85                  90                  95

Ile Phe Pro Thr Val Arg Pro Ala Asp Leu Thr Arg Val Ile Met Pro
            100                 105                 110

Leu Glu Gln Arg Ser Gln His Cys Lys Pro Glu Glu Gly Leu Gln Ala
        115                 120                 125

Gln Glu Glu Asp Leu Gly Leu Val Gly Ala Gln Ala Leu Gln Ala Glu
    130                 135                 140

Glu Gln Glu Ala Ala Phe Phe Ser Ser Thr Leu Asn Val Gly Thr Leu
145                 150                 155                 160

Glu Glu Leu Pro Ala Ala Glu Ser Pro Ser Pro Pro Gln Ser Pro Gln
            165                 170                 175

Glu Glu Ser Phe Ser Pro Thr Ala Met Asp Ala Ile Phe Gly Ser Leu
        180                 185                 190

Ser Asp Glu Gly Ser Gly Ser Gln Glu Lys Glu Gly Pro Ser Thr Ser
    195                 200                 205

```
Pro Asp Leu Ile Asp Pro Glu Ser Phe Ser Gln Asp Ile Leu His Asp
    210                 215                 220

Lys Ile Ile Asp Leu Val His Leu Leu Arg Lys Tyr Arg Val Lys
225                 230                 235                 240

Gly Leu Ile Thr Lys Ala Glu Met Leu Gly Ser Val Ile Lys Asn Tyr
                245                 250                 255

Glu Asp Tyr Phe Pro Glu Ile Phe Arg Glu Ala Ser Val Cys Met Gln
                260                 265                 270

Leu Leu Phe Gly Ile Asp Val Lys Glu Val Asp Pro Thr Ser His Ser
            275                 280                 285

Tyr Val Leu Val Thr Ser Leu Asn Leu Ser Tyr Asp Gly Ile Gln Cys
    290                 295                 300

Asn Glu Gln Ser Met Pro Lys Ser Gly Leu Leu Ile Ile Val Leu Gly
305                 310                 315                 320

Val Ile Phe Met Glu Gly Asn Cys Ile Pro Glu Val Met Trp Glu
                325                 330                 335

Val Leu Ser Ile Met Gly Val Tyr Ala Gly Arg Glu His Phe Leu Phe
            340                 345                 350

Gly Glu Pro Lys Arg Leu Leu Thr Gln Asn Trp Val Gln Glu Lys Tyr
                355                 360                 365

Leu Val Tyr Arg Gln Val Pro Gly Thr Asp Pro Ala Cys Tyr Glu Phe
    370                 375                 380

Leu Trp Gly Pro Arg Ala His Ala Glu Thr Ser Lys Met Lys Val Leu
385                 390                 395                 400

Glu Tyr Ile Ala Asn Ala Asn Gly Arg Asp Pro Thr Ser Tyr Pro Ser
                405                 410                 415

Leu Tyr Glu Asp Ala Leu Arg Glu Glu Gly Glu Gly Val
            420                 425

<210> SEQ ID NO 150
<211> LENGTH: 509
<212> TYPE: PRT
<213> ORGANISM: Artificial Sequence
<220> FEATURE:
<223> OTHER INFORMATION: PRAME antigen

<400> SEQUENCE: 150

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
    115                 120                 125

His Gln Asp Phe Trp Thr Val Trp Ser Gly Asn Arg Ala Ser Leu Tyr
            130                 135                 140
```

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
            165                 170                 175

Val Leu Val Asp Leu Phe Leu Lys Glu Gly Ala Cys Asp Glu Leu Phe
        180                 185                 190

Ser Tyr Leu Ile Glu Lys Val Lys Arg Lys Asn Val Leu Arg Leu
    195                 200                 205

Cys Cys Lys Lys Leu Lys Ile Phe Ala Met Pro Met Gln Asp Ile Lys
210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
            245                 250                 255

Gly Gln Met Ile Asn Leu Arg Arg Leu Leu Ser His Ile His Ala
            260                 265                 270

Ser Ser Tyr Ile Ser Pro Glu Lys Glu Glu Tyr Ile Ala Gln Phe
    275                 280                 285

Thr Ser Gln Phe Leu Ser Leu Gln Cys Leu Gln Ala Leu Tyr Val Asp
290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
            370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 151
<211> LENGTH: 315
<212> TYPE: PRT
<213> ORGANISM: Artificial Sequence
<220> FEATURE:
<223> OTHER INFORMATION: MAGE-A9 antigen

<400> SEQUENCE: 151

Met Ser Leu Glu Gln Arg Ser Pro His Cys Lys Pro Asp Glu Asp Leu
1               5                   10                  15

Glu Ala Gln Gly Glu Asp Leu Gly Leu Met Gly Ala Gln Glu Pro Thr
            20                  25                  30

Gly Glu Glu Glu Glu Thr Thr Ser Ser Ser Asp Ser Lys Glu Glu
        35                  40                  45

Val Ser Ala Ala Gly Ser Ser Ser Pro Pro Gln Ser Pro Gln Gly Gly
    50                  55                  60

Ala Ser Ser Ser Ile Ser Val Tyr Tyr Thr Leu Trp Ser Gln Phe Asp
65                  70                  75                  80

Glu Gly Ser Ser Ser Gln Glu Glu Glu Pro Ser Ser Ser Val Asp
            85                  90                  95

Pro Ala Gln Leu Glu Phe Met Phe Gln Glu Ala Leu Lys Leu Lys Val
            100                 105                 110

Ala Glu Leu Val His Phe Leu Leu His Lys Tyr Arg Val Lys Glu Pro
            115                 120                 125

Val Thr Lys Ala Glu Met Leu Glu Ser Val Ile Lys Asn Tyr Lys Arg
            130                 135                 140

Tyr Phe Pro Val Ile Phe Gly Lys Ala Ser Glu Phe Met Gln Val Ile
145                 150                 155                 160

Phe Gly Thr Asp Val Lys Glu Val Asp Pro Ala Gly His Ser Tyr Ile
                165                 170                 175

Leu Val Thr Ala Leu Gly Leu Ser Cys Asp Ser Met Leu Gly Asp Gly
            180                 185                 190

His Ser Met Pro Lys Ala Ala Leu Leu Ile Ile Val Leu Gly Val Ile
            195                 200                 205

Leu Thr Lys Asp Asn Cys Ala Pro Glu Glu Val Ile Trp Glu Ala Leu
210                 215                 220

Ser Val Met Gly Val Tyr Val Gly Lys Glu His Met Phe Tyr Gly Glu
225                 230                 235                 240

Pro Arg Lys Leu Leu Thr Gln Asp Trp Val Gln Glu Asn Tyr Leu Glu
            245                 250                 255

Tyr Arg Gln Val Pro Gly Ser Asp Pro Ala His Tyr Glu Phe Leu Trp
            260                 265                 270

Gly Ser Lys Ala His Ala Glu Thr Ser Tyr Glu Lys Val Ile Asn Tyr
            275                 280                 285

Leu Val Met Leu Asn Ala Arg Glu Pro Ile Cys Tyr Pro Ser Leu Tyr
            290                 295                 300

Glu Glu Val Leu Gly Glu Glu Gln Glu Gly Val
305                 310                 315

<210> SEQ ID NO 152
<211> LENGTH: 313
<212> TYPE: PRT
<213> ORGANISM: Artificial Sequence
<220> FEATURE:
<223> OTHER INFORMATION: HOME-TES-85

<400> SEQUENCE: 152

Met Ala Ser Phe Arg Lys Leu Thr Leu Ser Glu Lys Val Pro Pro Asn
1               5                   10                  15

His Pro Ser Arg Lys Lys Val Asn Phe Leu Asp Met Ser Leu Asp Asp
            20                  25                  30

Ile Ile Ile Tyr Lys Glu Leu Glu Gly Thr Asn Ala Glu Glu Glu Lys
            35                  40                  45

```
Asn Lys Arg Gln Asn His Ser Lys Lys Glu Ser Pro Ser Arg Gln Gln
    50                  55                  60

Ser Lys Ala His Arg His Arg His Arg Gly Tyr Ser Arg Cys Arg
65                  70                  75                  80

Ser Asn Ser Glu Glu Gly Asn His Asp Lys Lys Pro Ser Gln Lys Pro
                85                  90                  95

Ser Gly Phe Lys Ser Gly Gln His Pro Leu Asn Gly Gln Pro Leu Ile
                100                 105                 110

Glu Gln Glu Lys Cys Ser Asp Asn Tyr Glu Ala Gln Ala Glu Lys Asn
            115                 120                 125

Gln Gly Gln Ser Glu Gly Asn Gln His Gln Ser Glu Gly Asn Pro Asp
    130                 135                 140

Lys Ser Glu Glu Ser Gln Gly Gln Pro Glu Glu Asn His His Ser Glu
145                 150                 155                 160

Arg Ser Arg Asn His Leu Glu Arg Ser Leu Ser Gln Ser Asp Arg Ser
                165                 170                 175

Gln Gly Gln Leu Lys Arg His His Pro Gln Tyr Glu Arg Ser His Gly
                180                 185                 190

Gln Tyr Lys Arg Ser His Gly Gln Ser Glu Arg Ser His Gly His Ser
            195                 200                 205

Glu Arg Ser His Gly His Ser Glu Arg Ser His Gly His Ser Glu Arg
    210                 215                 220

Ser His Gly His Ser Lys Arg Ser Arg Ser Gln Gly Asp Leu Val Asp
225                 230                 235                 240

Thr Gln Ser Asp Leu Ile Ala Thr Gln Arg Asp Leu Ile Ala Thr Gln
                245                 250                 255

Lys Asp Leu Ile Ala Thr Gln Arg Asp Leu Ile Ala Thr Gln Arg Asp
                260                 265                 270

Leu Ile Val Thr Gln Arg Asp Leu Val Ala Thr Glu Arg Asp Leu Ile
            275                 280                 285

Asn Gln Ser Gly Arg Ser His Gly Gln Ser Glu Arg His Gln Arg Tyr
    290                 295                 300

Ser Thr Gly Lys Asn Thr Ile Thr Thr
305                 310

<210> SEQ ID NO 153
<211> LENGTH: 385
<212> TYPE: PRT
<213> ORGANISM: Artificial Sequence
<220> FEATURE:
<223> OTHER INFORMATION: TSP50 antigen

<400> SEQUENCE: 153

Met Gly Arg Trp Cys Gln Thr Val Ala Arg Gly Gln Arg Pro Arg Thr
1               5                   10                  15

Ser Ala Pro Ser Arg Ala Gly Ala Leu Leu Leu Leu Leu Leu Leu Leu
                20                  25                  30

Arg Ser Ala Gly Cys Trp Gly Ala Gly Glu Ala Pro Gly Ala Leu Ser
            35                  40                  45

Thr Ala Asp Pro Ala Asp Gln Ser Val Gln Cys Val Pro Lys Ala Thr
    50                  55                  60

Cys Pro Ser Ser Arg Pro Arg Leu Leu Trp Gln Thr Pro Thr Thr Gln
65                  70                  75                  80

Thr Leu Pro Ser Thr Thr Met Glu Thr Gln Phe Pro Val Ser Glu Gly
                85                  90                  95
```

-continued

Lys Val Asp Pro Tyr Arg Ser Cys Gly Phe Ser Tyr Glu Gln Asp Pro
            100                 105                 110

Thr Leu Arg Asp Pro Glu Ala Val Ala Arg Arg Trp Pro Trp Met Val
            115                 120                 125

Ser Val Arg Ala Asn Gly Thr His Ile Cys Ala Gly Thr Ile Ile Ala
        130                 135                 140

Ser Gln Trp Val Leu Thr Val Ala His Cys Leu Ile Trp Arg Asp Val
145                 150                 155                 160

Ile Tyr Ser Val Arg Val Gly Ser Pro Trp Ile Asp Gln Met Thr Gln
                165                 170                 175

Thr Ala Ser Asp Val Pro Val Leu Gln Val Ile Met His Ser Arg Tyr
            180                 185                 190

Arg Ala Gln Arg Phe Trp Ser Trp Val Gly Gln Ala Asn Asp Ile Gly
        195                 200                 205

Leu Leu Lys Leu Lys Gln Glu Leu Lys Tyr Ser Asn Tyr Val Arg Pro
210                 215                 220

Ile Cys Leu Pro Gly Thr Asp Tyr Val Leu Lys Asp His Ser Arg Cys
225                 230                 235                 240

Thr Val Thr Gly Trp Gly Leu Ser Lys Ala Asp Gly Met Trp Pro Gln
                245                 250                 255

Phe Arg Thr Ile Gln Glu Lys Glu Val Ile Ile Leu Asn Asn Lys Glu
            260                 265                 270

Cys Asp Asn Phe Tyr His Asn Phe Thr Lys Ile Pro Thr Leu Val Gln
        275                 280                 285

Ile Ile Lys Ser Gln Met Met Cys Ala Glu Asp Thr His Arg Glu Lys
290                 295                 300

Phe Cys Tyr Glu Leu Thr Gly Glu Pro Leu Val Cys Ser Met Glu Gly
305                 310                 315                 320

Thr Trp Tyr Leu Val Gly Leu Val Ser Trp Gly Ala Gly Cys Gln Lys
                325                 330                 335

Ser Glu Ala Pro Pro Ile Tyr Leu Gln Val Ser Ser Tyr Gln His Trp
            340                 345                 350

Ile Trp Asp Cys Leu Asn Gly Gln Ala Leu Ala Leu Pro Ala Pro Ser
        355                 360                 365

Arg Thr Leu Leu Leu Ala Leu Pro Leu Pro Leu Ser Leu Leu Ala Ala
    370                 375                 380

Leu
385

<210> SEQ ID NO 154
<211> LENGTH: 314
<212> TYPE: PRT
<213> ORGANISM: Artificial Sequence
<220> FEATURE:
<223> OTHER INFORMATION: EpCAM antigen

<400> SEQUENCE: 154

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

```
Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
                 85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
            275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 155
<211> LENGTH: 777
<212> TYPE: PRT
<213> ORGANISM: Artificial Sequence
<220> FEATURE:
<223> OTHER INFORMATION: CAGE1 antigen

<400> SEQUENCE: 155

Met Asn Lys Asp Tyr Gln Lys Phe Trp Ser Ser Pro Ser Asp Pro Val
 1                5                   10                  15

His Phe Glu Val Asp Thr Ser His Glu Lys Val Glu Ser Met Ser Glu
                 20                  25                  30

Ser Asp Thr Met Asn Val Ser Asn Leu Ser Gln Gly Val Met Leu Ser
            35                  40                  45

His Ser Pro Ile Cys Met Glu Thr Thr Gly Thr Thr Cys Asp Leu Pro
        50                  55                  60

Gln Asn Glu Ile Lys Asn Phe Glu Arg Glu Asn Glu Tyr Glu Ser Thr
 65                  70                  75                  80

Leu Cys Glu Asp Ala Tyr Gly Thr Leu Asp Asn Leu Leu Asn Asp Asn
                 85                  90                  95

Asn Ile Glu Asn Tyr Ser Thr Asn Ala Leu Ile Gln Pro Val Asp Thr
            100                 105                 110
```

-continued

```
Ile Ser Ile Ser Ser Leu Arg Gln Phe Glu Thr Val Cys Lys Phe His
            115                 120                 125
Trp Val Glu Ala Phe Asp Asp Glu Met Thr Glu Lys Pro Glu Phe Gln
130                 135                 140
Ser Gln Val Tyr Asn Tyr Ala Lys Asp Asn Asn Ile Lys Gln Asp Ser
145                 150                 155                 160
Phe Lys Glu Glu Asn Pro Met Glu Thr Ser Val Ser Ala Asn Thr Asp
                165                 170                 175
Gln Leu Gly Asn Glu Tyr Phe Arg Gln Pro Pro Arg Ser Pro Pro
            180                 185                 190
Leu Ile His Cys Ser Gly Glu Met Leu Lys Phe Thr Glu Lys Ser Leu
            195                 200                 205
Ala Lys Ser Ile Ala Lys Glu Ser Ala Leu Asn Pro Ser Gln Pro Pro
210                 215                 220
Ser Phe Leu Cys Lys Thr Ala Val Pro Ser Lys Glu Ile Gln Asn Tyr
225                 230                 235                 240
Gly Glu Ile Pro Glu Met Ser Val Ser Tyr Glu Lys Glu Val Thr Ala
                245                 250                 255
Glu Gly Val Glu Arg Pro Glu Ile Val Ser Thr Trp Ser Ser Ala Gly
            260                 265                 270
Ile Ser Trp Arg Ser Glu Ala Cys Arg Glu Asn Cys Glu Met Pro Asp
            275                 280                 285
Trp Glu Gln Ser Ala Glu Ser Leu Gln Pro Val Gln Glu Asp Met Ala
290                 295                 300
Leu Asn Glu Val Leu Gln Lys Leu Lys His Thr Asn Arg Lys Gln Glu
305                 310                 315                 320
Val Arg Ile Gln Glu Leu Gln Cys Ser Asn Leu Tyr Leu Glu Lys Arg
                325                 330                 335
Val Lys Glu Leu Gln Met Lys Ile Thr Lys Gln Gln Val Phe Ile Asp
            340                 345                 350
Val Ile Asn Lys Leu Lys Glu Asn Val Glu Glu Leu Ile Glu Asp Lys
            355                 360                 365
Tyr Lys Ile Ile Leu Glu Lys Asn Asp Thr Lys Lys Thr Leu Gln Asn
370                 375                 380
Leu Glu Glu Val Leu Ala Asn Thr Gln Lys His Leu Gln Glu Ser Arg
385                 390                 395                 400
Asn Asp Lys Glu Met Leu Gln Leu Gln Phe Lys Lys Ile Lys Ala Asn
                405                 410                 415
Tyr Val Cys Leu Gln Glu Arg Tyr Met Thr Glu Met Gln Gln Lys Asn
            420                 425                 430
Lys Ser Val Ser Gln Tyr Leu Glu Met Asp Lys Thr Leu Ser Lys Lys
            435                 440                 445
Glu Glu Glu Val Glu Arg Leu Gln Gln Leu Lys Glu Leu Glu Lys
450                 455                 460
Ala Thr Ala Ser Ala Leu Asp Leu Leu Lys Arg Glu Lys Glu Ala Gln
465                 470                 475                 480
Glu Gln Glu Phe Leu Ser Leu Gln Glu Phe Gln Lys Leu Glu Lys
                485                 490                 495
Glu Asn Leu Glu Arg Gln Lys Lys Ser Arg Leu Glu Lys Leu
            500                 505                 510
Leu Thr Gln Val Arg Asn Leu Gln Phe Met Ser Glu Asn Glu Arg Thr
            515                 520                 525
Lys Asn Ile Lys Leu Gln Gln Gln Ile Asn Glu Val Lys Asn Glu Asn
```

```
                     530              535              540
Ala Lys Leu Lys Gln Gln Val Ala Arg Ser Glu Glu Gln Asn Tyr Val
545                 550              555              560

Pro Lys Phe Glu Thr Ala Gln Leu Lys Asp Gln Leu Glu Glu Val Leu
                565              570              575

Lys Ser Asp Ile Thr Lys Asp Thr Lys Thr Thr His Ser Asn Leu Leu
            580              585              590

Pro Asp Cys Ser Pro Cys Glu Glu Arg Leu Asn Pro Ala Asp Ile Lys
        595              600              605

Arg Ala Ser Gln Leu Ala Ser Lys Met His Ser Leu Leu Ala Leu Met
    610              615              620

Val Gly Leu Leu Thr Cys Gln Asp Ile Ile Asn Ser Asp Ala Glu His
625              630              635              640

Phe Lys Glu Ser Glu Lys Val Ser Asp Ile Met Leu Gln Lys Leu Lys
                645              650              655

Ser Leu His Leu Lys Lys Lys Thr Leu Asp Lys Glu Val Ile Asp Cys
                660              665              670

Asp Ser Asp Glu Ala Lys Ser Ile Arg Asp Val Pro Thr Leu Leu Gly
            675              680              685

Ala Lys Leu Asp Lys Tyr His Ser Leu Asn Glu Glu Leu Asp Phe Leu
        690              695              700

Val Thr Ser Tyr Glu Glu Ile Ile Glu Cys Ala Asp Gln Arg Leu Ala
705              710              715              720

Ile Ser His Ser Gln Ile Ala His Leu Glu Glu Arg Asn Lys His Leu
                725              730              735

Glu Asp Leu Ile Arg Lys Pro Arg Glu Lys Ala Arg Lys Pro Arg Ser
                740              745              750

Lys Ser Leu Glu Asn His Pro Lys Ser Met Thr Met Met Pro Ala Leu
                755              760              765

Phe Lys Glu Asn Arg Asn Asp Leu Asp
                770              775

<210> SEQ ID NO 156
<211> LENGTH: 442
<212> TYPE: PRT
<213> ORGANISM: Artificial Sequence
<220> FEATURE:
<223> OTHER INFORMATION: FBXO39 antigen

<400> SEQUENCE: 156

Met Asp Glu Glu Ser Glu Leu Ile Gln Pro Gln Asp Gln Ser Cys Trp
1               5                  10                  15

Ala Phe Leu Pro Asp Leu Cys Leu Cys Arg Val Phe Trp Trp Leu Gly
            20                  25                  30

Asp Arg Asp Arg Ser Arg Ala Ala Leu Val Cys Arg Lys Trp Asn Gln
        35                  40                  45

Met Met Tyr Ser Ala Glu Leu Trp Arg Tyr Arg Thr Ile Thr Phe Ser
    50                  55                  60

Gly Arg Pro Ser Arg Val His Ala Ser Glu Val Glu Ser Ala Val Trp
65                  70                  75                  80

Tyr Val Lys Lys Phe Gly Arg Tyr Leu Glu His Leu Glu Val Lys Phe
                85                  90                  95

Met Asn Pro Tyr Asn Ala Val Leu Thr Lys Lys Phe Gln Val Thr Met
            100                 105                 110

Arg Gly Leu Leu Ser Cys Leu Ser Lys Ser Asn Asn Arg Leu Lys Ser
```

115                 120                 125
Leu Ser Ile Gln Tyr Leu Glu Leu Asp Arg Leu Val Trp Arg Asn Ser
130                 135                 140
Ile Arg Ser Ser Phe Ile Ser Ser Leu Ser Phe Phe Leu Lys Lys Met
145                 150                 155                 160
Gly Lys Arg Leu Asp Tyr Leu Asn Leu Lys Gly Ala Arg Leu Thr Val
                165                 170                 175
Glu Gln Gly Cys Gln Ile Leu Asp Ser Leu Ser Tyr Met Arg Asn Glu
            180                 185                 190
Asn Val Ile Ser Glu Leu Asn Ile Glu Asp Tyr Phe Ser His His Leu
        195                 200                 205
Ala Val Tyr Asn Ser Pro Gln Phe Lys Lys Thr Met Ser Thr Phe His
210                 215                 220
Asn Leu Val Ser Leu Asn Leu Asn Tyr Asn Cys Ile Ser Asp Glu Leu
225                 230                 235                 240
Leu Glu Asn Leu Cys Glu Asn Ala Ser Thr Leu Arg Thr Ile Asn Ile
                245                 250                 255
Lys Cys His Val His Asp Pro His Gly Gln Val Ile Trp Gly Met Ser
            260                 265                 270
Trp Ala Lys Leu Ala Arg Gln Ala Thr Asn Leu Lys Val Asn Phe Phe
        275                 280                 285
Phe Glu Arg Ile Met Lys Tyr Glu Arg Leu Ala Arg Ile Leu Leu Gln
290                 295                 300
Glu Ile Pro Ile Arg Ser Ile Ser Leu Arg Ser Cys Tyr Phe Ser Asp
305                 310                 315                 320
Pro Asp Cys Ser Met Arg Pro Thr Leu Ile Asp Leu Leu Pro Thr Phe
                325                 330                 335
Arg His Thr Leu Gln Lys Leu Thr Cys Glu Phe Asn Asn Asn His Glu
            340                 345                 350
Ser Leu Asp Glu Glu Leu His Leu Leu Ile Ile Ser Cys Arg Lys Leu
        355                 360                 365
Phe Tyr Phe Lys Ile Trp Ala Phe Leu Asp Val Ser Phe Val Glu Arg
370                 375                 380
Ile Leu Lys Ser Gln Lys Glu Arg Gln Cys Ala Leu Arg Val Phe Lys
385                 390                 395                 400
Ala Arg Ile Tyr Thr Asn Arg Tyr Glu Thr Asn Glu Glu Asp Lys Thr
                405                 410                 415
Leu Gln Glu Ile Tyr Arg Lys Tyr Arg Lys Leu Ile Glu Ser Glu Leu
            420                 425                 430
Ser Tyr Phe Val Ile Val Tyr Ser Val Met
        435                 440

<210> SEQ ID NO 157
<211> LENGTH: 318
<212> TYPE: PRT
<213> ORGANISM: Artificial Sequence
<220> FEATURE:
<223> OTHER INFORMATION: MAGE-A8

<400> SEQUENCE: 157

Met Leu Leu Gly Gln Lys Ser Gln Arg Tyr Lys Ala Glu Glu Gly Leu
1               5                   10                  15
Gln Ala Gln Gly Glu Ala Pro Gly Leu Met Asp Val Gln Ile Pro Thr
            20                  25                  30
Ala Glu Glu Gln Lys Ala Ala Ser Ser Ser Ser Thr Leu Ile Met Gly

```
            35                  40                  45
Thr Leu Glu Glu Val Thr Asp Ser Gly Ser Pro Ser Pro Gln Ser
     50                  55                  60

Pro Glu Gly Ala Ser Ser Leu Thr Val Thr Asp Ser Thr Leu Trp
 65                  70                  75                  80

Ser Gln Ser Asp Glu Gly Ser Ser Asn Glu Glu Gly Pro Ser
                 85                  90                  95

Thr Ser Pro Asp Pro Ala His Leu Glu Ser Leu Phe Arg Glu Ala Leu
             100                 105                 110

Asp Glu Lys Val Ala Glu Leu Val Arg Phe Leu Leu Arg Lys Tyr Gln
             115                 120                 125

Ile Lys Glu Pro Val Thr Lys Ala Glu Met Leu Glu Ser Val Ile Lys
         130                 135                 140

Asn Tyr Lys Asn His Phe Pro Asp Ile Phe Ser Lys Ala Ser Glu Cys
145                 150                 155                 160

Met Gln Val Ile Phe Gly Ile Asp Val Lys Glu Val Asp Pro Ala Gly
                 165                 170                 175

His Ser Tyr Ile Leu Val Thr Cys Leu Gly Leu Ser Tyr Asp Gly Leu
             180                 185                 190

Leu Gly Asp Asp Gln Ser Thr Pro Lys Thr Gly Leu Leu Ile Ile Val
         195                 200                 205

Leu Gly Met Ile Leu Met Glu Gly Ser Arg Ala Pro Glu Glu Ala Ile
     210                 215                 220

Trp Glu Ala Leu Ser Val Met Gly Leu Tyr Asp Gly Arg Glu His Ser
225                 230                 235                 240

Val Tyr Trp Lys Leu Arg Lys Leu Leu Thr Gln Glu Trp Val Gln Glu
                 245                 250                 255

Asn Tyr Leu Glu Tyr Arg Gln Ala Pro Gly Ser Asp Pro Val Arg Tyr
             260                 265                 270

Glu Phe Leu Trp Gly Pro Arg Ala Leu Ala Glu Thr Ser Tyr Val Lys
         275                 280                 285

Val Leu Glu His Val Val Arg Val Asn Ala Arg Val Arg Ile Ser Tyr
     290                 295                 300

Pro Ser Leu His Glu Glu Ala Leu Gly Glu Glu Lys Gly Val
305                 310                 315

<210> SEQ ID NO 158
<211> LENGTH: 314
<212> TYPE: PRT
<213> ORGANISM: Artificial Sequence
<220> FEATURE:
<223> OTHER INFORMATION: MAGE-A6 antigen

<400> SEQUENCE: 158

Met Pro Leu Glu Gln Arg Ser Gln His Cys Lys Pro Glu Glu Gly Leu
 1               5                  10                  15

Glu Ala Arg Gly Glu Ala Leu Gly Leu Val Gly Ala Gln Ala Pro Ala
             20                  25                  30

Thr Glu Glu Gln Glu Ala Ala Ser Ser Ser Thr Leu Val Glu Val
         35                  40                  45

Thr Leu Gly Glu Val Pro Ala Ala Glu Ser Pro Asp Pro Pro Gln Ser
     50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
```

```
                    85                  90                  95
Thr Phe Pro Asp Leu Glu Ser Glu Phe Gln Ala Ala Leu Ser Arg Lys
                100                 105                 110

Val Ala Lys Leu Val His Phe Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Asp Ser Leu Gln Leu
145                 150                 155                 160

Val Phe Gly Ile Glu Leu Met Glu Val Asp Pro Ile Gly His Val Tyr
                165                 170                 175

Ile Phe Ala Thr Cys Leu Gly Leu Ser Tyr Asp Gly Leu Leu Gly Asp
                180                 185                 190

Asn Gln Ile Met Pro Lys Thr Gly Phe Leu Ile Ile Leu Ala Ile
            195                 200                 205

Ile Ala Lys Glu Gly Asp Cys Ala Pro Glu Gly Lys Ile Trp Glu Glu
        210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Ile Glu Thr Ser Tyr Val Lys Val Leu His
            275                 280                 285

His Met Val Lys Ile Ser Gly Gly Pro Arg Ile Ser Tyr Pro Leu Leu
        290                 295                 300

His Glu Trp Ala Leu Arg Glu Gly Glu Glu
305                 310

<210> SEQ ID NO 159
<211> LENGTH: 16
<212> TYPE: PRT
<213> ORGANISM: Artificial Sequence
<220> FEATURE:
<223> OTHER INFORMATION: additional peptide 1

<400> SEQUENCE: 159

Met Met Asn Leu Met Gln Pro Lys Thr Gln Gln Thr Tyr Thr Tyr Asp
1               5                   10                  15

<210> SEQ ID NO 160
<211> LENGTH: 21
<212> TYPE: PRT
<213> ORGANISM: Artificial Sequence
<220> FEATURE:
<223> OTHER INFORMATION: additional peptide 2

<400> SEQUENCE: 160

Gly Arg Gly Ser Thr Thr Thr Asn Tyr Leu Leu Asp Arg Asp Asp Tyr
1               5                   10                  15

Arg Asn Thr Ser Asp
            20

<210> SEQ ID NO 161
<211> LENGTH: 22
<212> TYPE: PRT
<213> ORGANISM: Artificial Sequence
<220> FEATURE:
```

<223> OTHER INFORMATION: additional peptide 3

<400> SEQUENCE: 161

Leu Lys Lys Gly Ala Ala Asp Gly Gly Lys Leu Asp Gly Asn Ala Lys
1               5                   10                  15

Leu Asn Arg Ser Leu Lys
            20

<210> SEQ ID NO 162
<211> LENGTH: 22
<212> TYPE: PRT
<213> ORGANISM: Artificial Sequence
<220> FEATURE:
<223> OTHER INFORMATION: additional peptide 4

<400> SEQUENCE: 162

Phe Pro Pro Lys Asp Asp His Thr Leu Lys Phe Leu Tyr Asp Asp Asn
1               5                   10                  15

Gln Arg Pro Tyr Pro Pro
            20

<210> SEQ ID NO 163
<211> LENGTH: 21
<212> TYPE: PRT
<213> ORGANISM: Artificial Sequence
<220> FEATURE:
<223> OTHER INFORMATION: additional peptide 5

<400> SEQUENCE: 163

Arg Tyr Arg Lys Pro Asp Tyr Thr Leu Asp Asp Gly His Gly Leu Leu
1               5                   10                  15

Arg Phe Lys Ser Thr
            20

<210> SEQ ID NO 164
<211> LENGTH: 18
<212> TYPE: PRT
<213> ORGANISM: Artificial Sequence
<220> FEATURE:
<223> OTHER INFORMATION: additional peptide 6

<400> SEQUENCE: 164

Gln Arg Pro Pro Phe Ser Gln Leu His Arg Phe Leu Ala Asp Ala Leu
1               5                   10                  15

Asn Thr

<210> SEQ ID NO 165
<211> LENGTH: 25
<212> TYPE: PRT
<213> ORGANISM: Artificial Sequence
<220> FEATURE:
<223> OTHER INFORMATION: additional peptide 7

<400> SEQUENCE: 165

Ala Leu Asp Gln Cys Lys Thr Ser Cys Ala Leu Met Gln Gln His Tyr
1               5                   10                  15

Asp Gln Thr Ser Cys Phe Ser Ser Pro
            20                  25

<210> SEQ ID NO 166
<211> LENGTH: 25
<212> TYPE: PRT
<213> ORGANISM: Artificial Sequence
<220> FEATURE:

<223> OTHER INFORMATION: additional peptide 8

<400> SEQUENCE: 166

Ser Thr Ala Pro Pro Ala His Gly Val Thr Ser Ala Pro Asp Thr Arg
1               5                   10                  15

Pro Ala Pro Gly Ser Thr Ala Pro Pro
            20                  25

<210> SEQ ID NO 167
<211> LENGTH: 9
<212> TYPE: PRT
<213> ORGANISM: Artificial Sequence
<220> FEATURE:
<223> OTHER INFORMATION: additional peptide 9

<400> SEQUENCE: 167

Tyr Leu Glu Pro Gly Pro Val Thr Ala
1               5

<210> SEQ ID NO 168
<211> LENGTH: 21
<212> TYPE: PRT
<213> ORGANISM: Artificial Sequence
<220> FEATURE:
<223> OTHER INFORMATION: additional peptide 10

<400> SEQUENCE: 168

Met Thr Pro Gly Thr Gln Ser Pro Phe Phe Leu Leu Leu Leu Leu Thr
1               5                   10                  15

Val Leu Thr Val Val
            20

<210> SEQ ID NO 169
<211> LENGTH: 9
<212> TYPE: PRT
<213> ORGANISM: Artificial Sequence
<220> FEATURE:
<223> OTHER INFORMATION: additional peptide 11

<400> SEQUENCE: 169

Ser Ser Lys Ala Leu Gln Arg Pro Val
1               5

<210> SEQ ID NO 170
<211> LENGTH: 9
<212> TYPE: PRT
<213> ORGANISM: Artificial Sequence
<220> FEATURE:
<223> OTHER INFORMATION: additional peptide 12

<400> SEQUENCE: 170

Arg Met Phe Pro Asn Ala Pro Tyr Leu
1               5

<210> SEQ ID NO 171
<211> LENGTH: 9
<212> TYPE: PRT
<213> ORGANISM: Artificial Sequence
<220> FEATURE:
<223> OTHER INFORMATION: additional peptide 13

<400> SEQUENCE: 171

Arg Met Phe Pro Asn Ala Pro Tyr Leu
1               5

```
<210> SEQ ID NO 172
<211> LENGTH: 9
<212> TYPE: PRT
<213> ORGANISM: Artificial Sequence
<220> FEATURE:
<223> OTHER INFORMATION: 9mer T cell epitope 41

<400> SEQUENCE: 172

Phe Val Ala Ser Ile Asn Leu Thr Leu
1               5

<210> SEQ ID NO 173
<211> LENGTH: 9
<212> TYPE: PRT
<213> ORGANISM: Artificial Sequence
<220> FEATURE:
<223> OTHER INFORMATION: 9mer T cell epitope 42

<400> SEQUENCE: 173

Phe Tyr Asp Pro Thr Ser Ala Met Val
1               5

<210> SEQ ID NO 174
<211> LENGTH: 9
<212> TYPE: PRT
<213> ORGANISM: Artificial Sequence
<220> FEATURE:
<223> OTHER INFORMATION: 9mer T cell epitope 43

<400> SEQUENCE: 174

Arg Thr Tyr Trp Ile Ile Ile Glu Leu
1               5

<210> SEQ ID NO 175
<211> LENGTH: 9
<212> TYPE: PRT
<213> ORGANISM: Artificial Sequence
<220> FEATURE:
<223> OTHER INFORMATION: 9mer T cell epitope 45

<400> SEQUENCE: 175

His Ala Phe Asp Gly Thr Ile Leu Phe
1               5

<210> SEQ ID NO 176
<211> LENGTH: 9
<212> TYPE: PRT
<213> ORGANISM: Artificial Sequence
<220> FEATURE:
<223> OTHER INFORMATION: 9mer T cell epitope 46

<400> SEQUENCE: 176

Phe Gln Met Pro His Gln Glu Ile Val
1               5

<210> SEQ ID NO 177
<211> LENGTH: 9
<212> TYPE: PRT
<213> ORGANISM: Artificial Sequence
<220> FEATURE:
<223> OTHER INFORMATION: 9mer T cell epitope 47

<400> SEQUENCE: 177

Leu Gln Tyr Glu Asn Ser Ile Met Leu
1               5

<210> SEQ ID NO 178
```

```
<211> LENGTH: 9
<212> TYPE: PRT
<213> ORGANISM: Artificial Sequence
<220> FEATURE:
<223> OTHER INFORMATION: 9mer T cell epitope 48

<400> SEQUENCE: 178

Tyr Thr Leu Asp Asp Leu Tyr Pro Met
1               5

<210> SEQ ID NO 179
<211> LENGTH: 9
<212> TYPE: PRT
<213> ORGANISM: Artificial Sequence
<220> FEATURE:
<223> OTHER INFORMATION: 9mer T cell epitope 49

<400> SEQUENCE: 179

Asn Ala Tyr His Met Ser Ser Thr Met
1               5

<210> SEQ ID NO 180
<211> LENGTH: 9
<212> TYPE: PRT
<213> ORGANISM: Artificial Sequence
<220> FEATURE:
<223> OTHER INFORMATION: 9mer T cell epitope 50

<400> SEQUENCE: 180

Val Gln Phe Glu Lys Val Ser Ala Leu
1               5

<210> SEQ ID NO 181
<211> LENGTH: 9
<212> TYPE: PRT
<213> ORGANISM: Artificial Sequence
<220> FEATURE:
<223> OTHER INFORMATION: 9mer T cell epitope 51

<400> SEQUENCE: 181

Arg Thr Ser Tyr Leu His Ser Pro Phe
1               5

<210> SEQ ID NO 182
<211> LENGTH: 9
<212> TYPE: PRT
<213> ORGANISM: Artificial Sequence
<220> FEATURE:
<223> OTHER INFORMATION: 9mer T cell epitope 52

<400> SEQUENCE: 182

Phe Gln Trp Arg Ile Thr His Ser Phe
1               5

<210> SEQ ID NO 183
<211> LENGTH: 9
<212> TYPE: PRT
<213> ORGANISM: Artificial Sequence
<220> FEATURE:
<223> OTHER INFORMATION: 9mer T cell epitope 53

<400> SEQUENCE: 183

Phe Ala Ala Ala Tyr Phe Glu Ser Leu
1               5

<210> SEQ ID NO 184
<211> LENGTH: 9
```

```
<212> TYPE: PRT
<213> ORGANISM: Artificial Sequence
<220> FEATURE:
<223> OTHER INFORMATION: 9mer T cell epitope 54

<400> SEQUENCE: 184

Tyr Val Asn Arg Leu Ser Ser Leu Val
1               5

<210> SEQ ID NO 185
<211> LENGTH: 9
<212> TYPE: PRT
<213> ORGANISM: Artificial Sequence
<220> FEATURE:
<223> OTHER INFORMATION: 9mer T cell epitope 55

<400> SEQUENCE: 185

Arg Leu Leu Ser Ser Thr Leu Ser Leu
1               5

<210> SEQ ID NO 186
<211> LENGTH: 9
<212> TYPE: PRT
<213> ORGANISM: Artificial Sequence
<220> FEATURE:
<223> OTHER INFORMATION: 9mer T cell epitope 56

<400> SEQUENCE: 186

Tyr Thr Phe Glu Gly Ala Arg Tyr Tyr
1               5

<210> SEQ ID NO 187
<211> LENGTH: 9
<212> TYPE: PRT
<213> ORGANISM: Artificial Sequence
<220> FEATURE:
<223> OTHER INFORMATION: 9mer T cell epitope 57

<400> SEQUENCE: 187

Lys Ala Met Ala Arg Leu Gln Glu Leu
1               5

<210> SEQ ID NO 188
<211> LENGTH: 10
<212> TYPE: PRT
<213> ORGANISM: Artificial Sequence
<220> FEATURE:
<223> OTHER INFORMATION: 9mer T cell epitope 58

<400> SEQUENCE: 188

Phe Val Ala Ser Ile Asn Glu Gly Met Thr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: 9mer T cell epitope 59

<400> SEQUENCE: 189

Tyr Ala Val His Pro Met Ser Pro Val
1               5

<210> SEQ ID NO 190
<211> LENGTH: 9
<212> TYPE: PRT
```

<213> ORGANISM: Artificial Sequence
<220> FEATURE:
<223> OTHER INFORMATION: 9mer T cell epitope 60

<400> SEQUENCE: 190

Met Gln Met Phe Gly Leu Gly Ala Ile
1               5

<210> SEQ ID NO 191
<211> LENGTH: 9
<212> TYPE: PRT
<213> ORGANISM: Artificial Sequence
<220> FEATURE:
<223> OTHER INFORMATION: 9mer T cell epitope 61

<400> SEQUENCE: 191

Tyr Val Asp Glu Lys Ala Pro Glu Phe
1               5

<210> SEQ ID NO 192
<211> LENGTH: 9
<212> TYPE: PRT
<213> ORGANISM: Artificial Sequence
<220> FEATURE:
<223> OTHER INFORMATION: 9mer T cell epitope 62

<400> SEQUENCE: 192

His Ser Tyr Val Leu Val Thr Ser Leu
1               5

<210> SEQ ID NO 193
<211> LENGTH: 9
<212> TYPE: PRT
<213> ORGANISM: Artificial Sequence
<220> FEATURE:
<223> OTHER INFORMATION: 9mer T cell epitope 63

<400> SEQUENCE: 193

Arg Leu Leu Glu Phe Tyr Leu Ala Met
1               5

<210> SEQ ID NO 194
<211> LENGTH: 9
<212> TYPE: PRT
<213> ORGANISM: Artificial Sequence
<220> FEATURE:
<223> OTHER INFORMATION: 9mer T cell epitope 64

<400> SEQUENCE: 194

Leu Ala Met Pro Phe Ala Thr Pro Met
1               5

<210> SEQ ID NO 195
<211> LENGTH: 15
<212> TYPE: PRT
<213> ORGANISM: Artificial Sequence
<220> FEATURE:
<223> OTHER INFORMATION: 15mer T cell epitope 41

<400> SEQUENCE: 195

Phe Val Ala Ser Ile Asn Leu Thr Leu Thr Lys Trp Tyr Ser Arg
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: 15mer T cell epitope 42

<400> SEQUENCE: 196

Arg Asn Phe Tyr Asp Pro Thr Ser Ala Met Val Leu Gln Gln His
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: 15mer T cell epitope 43

<400> SEQUENCE: 197

Val Asn Ile Asp Tyr Leu Met Asn Arg Pro Gln Asn Leu Arg Leu
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: 15mer T cell epitope 44

<400> SEQUENCE: 198

Arg Thr Tyr Trp Ile Ile Ile Glu Leu Lys His Lys Ala Arg Glu
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: 15mer T cell epitope 46

<400> SEQUENCE: 199

Val Cys Met Phe Thr Ser Ser Arg Met Ser Ser Phe Asn Arg His
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: 15mer T cell epitope 47

<400> SEQUENCE: 200

His Ala Phe Asp Gly Thr Ile Leu Phe Leu Pro Lys Arg Leu Gln
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: 15mer T cell epitope 48

<400> SEQUENCE: 201

Ser Asp Leu Gln Lys Tyr Ala Leu Gly Phe Gln His Ala Leu Ser
1               5                   10                  15

<210> SEQ ID NO 202
<211> LENGTH: 15
<212> TYPE: PRT
<213> ORGANISM: Artificial Sequence
<220> FEATURE:

<223> OTHER INFORMATION: 15mer T cell epitope 49

<400> SEQUENCE: 202

Lys Leu Gly Phe Ser Phe Val Arg Ile Thr Ala Leu Met Val Ser
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: 15mer T cell epitope 50

<400> SEQUENCE: 203

Tyr Ser Arg Val Val Phe Gln Met Pro His Gln Glu Ile Val Asp
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: 15mer T cell epitope 51

<400> SEQUENCE: 204

Gly Phe Thr Thr Ser Ile Leu Gln Tyr Glu Asn Ser Ile Met Leu
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: 15mer T cell epitope 52

<400> SEQUENCE: 205

Leu Arg Tyr Arg Tyr Thr Leu Asp Asp Leu Tyr Pro Met Met Asn
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: 15mer T cell epitope 53

<400> SEQUENCE: 206

Tyr Ser Ser Asn Ala Tyr His Met Ser Ser Thr Met Lys Pro Asn
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: 15mer T cell epitope 54

<400> SEQUENCE: 207

Leu Gln Lys Val Gln Phe Glu Lys Val Ser Ala Leu Ala Asp Leu
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: 15mer T cell epitope 55

```
<400> SEQUENCE: 208

Asn Arg Thr Ser Tyr Leu His Ser Pro Phe Ser Thr Gly Arg Ser
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: 15mer T cell epitope 56

<400> SEQUENCE: 209

Leu Asp Ser Phe Thr Val Cys Asn Ser His Val Leu Cys Ile Ala
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: 15mer T cell epitope 57

<400> SEQUENCE: 210

Asn Ser Pro Leu Pro Phe Gln Trp Arg Ile Thr His Ser Phe Arg
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: 15mer T cell epitope 58

<400> SEQUENCE: 211

Ala Phe Ala Ala Ala Tyr Phe Glu Ser Leu Leu Glu Lys Arg Glu
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: 15mer T cell epitope 59

<400> SEQUENCE: 212

Asp Leu Ser Phe Tyr Val Asn Arg Leu Ser Ser Leu Val Ile Gln
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: 15mer T cell epitope 60

<400> SEQUENCE: 213

Gln Asp Gly Arg Leu Leu Ser Ser Thr Leu Ser Leu Ser Ser Asn
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: 15mer T cell epitope 61
```

```
<400> SEQUENCE: 214

Trp Glu Glu Ala Tyr Thr Phe Glu Gly Ala Arg Tyr Tyr Ile Asn
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: 15mer T cell epitope 62

<400> SEQUENCE: 215

Glu Lys Ala Met Ala Arg Leu Gln Glu Leu Leu Thr Val Ser Glu
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: 15mer T cell epitope 63

<400> SEQUENCE: 216

Arg Ser Ile Ala Gly Phe Val Ala Ser Ile Asn Glu Gly Met Thr
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: 15mer T cell epitope 64

<400> SEQUENCE: 217

Ser Asp Tyr Ala Val His Pro Met Ser Pro Val Gly Arg Thr Ser
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: 15mer T cell epitope 65

<400> SEQUENCE: 218

Met Met Gln Met Phe Gly Leu Gly Ala Ile Ser Leu Ile Leu Val
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: 15mer T cell epitope 66

<400> SEQUENCE: 219

Leu Arg His Lys Cys Cys Phe Ser Ser Ser Gly Thr Thr Ser Phe
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: 15mer T cell epitope 67

<400> SEQUENCE: 220
```

Arg Phe Thr Gln Ser Gly Thr Met Lys Ile His Ile Leu Gln Lys
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: 15mer T cell epitope 68

<400> SEQUENCE: 221

Gln Thr Leu Ile Tyr Tyr Val Asp Glu Lys Ala Pro Glu Phe Ser
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: 15mer T cell epitope 69

<400> SEQUENCE: 222

Phe Val Leu Ala Asn Gly His Ile Leu Pro Asn Ser Glu Asn Ala
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: 15mer T cell epitope 70

<400> SEQUENCE: 223

Ser Ser Tyr Phe Val Leu Ala Asn Gly His Ile Leu Pro Asn Ser
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: 15mer T cell epitope 71

<400> SEQUENCE: 224

Phe Met Phe Gln Glu Ala Leu Lys Leu Lys Val Ala Glu Leu Val
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: 15mer T cell epitope 72

<400> SEQUENCE: 225

His Ser Gln Thr Leu Lys Ala Met Val Gln Ala Trp Pro Phe Thr
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: 15mer T cell epitope 73

<400> SEQUENCE: 226

Gln Thr Leu Lys Ala Met Val Gln Ala Trp Pro Phe Thr Cys Leu
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: 15mer T cell epitope 74

<400> SEQUENCE: 227

Ser His Ser Tyr Val Leu Val Thr Ser Leu Asn Leu Ser Tyr Asp
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: 15mer T cell epitope 75

<400> SEQUENCE: 228

Thr Ser His Ser Tyr Val Leu Val Thr Ser Leu Asn Leu Ser Tyr
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: 15mer T cell epitope 76

<400> SEQUENCE: 229

Ala Met Asp Ala Ile Phe Gly Ser Leu Ser Asp Glu Gly Ser Gly
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: 15mer T cell epitope 77

<400> SEQUENCE: 230

Glu Ser Phe Ser Pro Thr Ala Met Asp Ala Ile Phe Gly Ser Leu
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: 15mer T cell epitope 78

<400> SEQUENCE: 231

Lys Pro Ser Ala Phe Glu Pro Ala Thr Glu Met Gln Lys Ser Val
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: 15mer T cell epitope 79

<400> SEQUENCE: 232

Ser Arg Leu Leu Glu Phe Tyr Leu Ala Met Pro Phe Ala Thr Pro

```
1               5                  10                 15
```

<210> SEQ ID NO 233
<211> LENGTH: 15
<212> TYPE: PRT
<213> ORGANISM: Artificial Sequence
<220> FEATURE:
<223> OTHER INFORMATION: 15mer T cell epitope 80

<400> SEQUENCE: 233

```
Phe Tyr Leu Ala Met Pro Phe Ala Thr Pro Met Glu Ala Glu Leu
1               5                   10                  15
```

<210> SEQ ID NO 234
<211> LENGTH: 9
<212> TYPE: PRT
<213> ORGANISM: Artificial Sequence
<220> FEATURE:
<223> OTHER INFORMATION: 9mer T cell epitope 65

<400> SEQUENCE: 234

```
Cys Ser Met Glu Gly Thr Trp Tyr Leu
1               5
```

<210> SEQ ID NO 235
<211> LENGTH: 9
<212> TYPE: PRT
<213> ORGANISM: Artificial Sequence
<220> FEATURE:
<223> OTHER INFORMATION: 9mer T cell epitope 66

<400> SEQUENCE: 235

```
Leu Leu Ala Ala Ala Thr Ala Thr Phe
1               5
```

<210> SEQ ID NO 236
<211> LENGTH: 9
<212> TYPE: PRT
<213> ORGANISM: Artificial Sequence
<220> FEATURE:
<223> OTHER INFORMATION: 9mer T cell epitope 67

<400> SEQUENCE: 236

```
Phe Thr Val Cys Asn Ser His Val Leu
1               5
```

<210> SEQ ID NO 237
<211> LENGTH: 9
<212> TYPE: PRT
<213> ORGANISM: Artificial Sequence
<220> FEATURE:
<223> OTHER INFORMATION: 9mer T cell epitope 68

<400> SEQUENCE: 237

```
Leu Ala Leu Pro Leu Pro Leu Ser Leu
1               5
```

<210> SEQ ID NO 238
<211> LENGTH: 9
<212> TYPE: PRT
<213> ORGANISM: Artificial Sequence
<220> FEATURE:
<223> OTHER INFORMATION: 9mer T cell epitope 69

<400> SEQUENCE: 238

```
Arg Thr Leu Leu Leu Ala Leu Pro Leu
1               5
```

```
<210> SEQ ID NO 239
<211> LENGTH: 9
<212> TYPE: PRT
<213> ORGANISM: Artificial Sequence
<220> FEATURE:
<223> OTHER INFORMATION: 9mer T cell epitope 70

<400> SEQUENCE: 239

Phe Ile Ile Val Val Phe Val Tyr Leu
1               5

<210> SEQ ID NO 240
<211> LENGTH: 9
<212> TYPE: PRT
<213> ORGANISM: Artificial Sequence
<220> FEATURE:
<223> OTHER INFORMATION: 9mer T cell epitope 71

<400> SEQUENCE: 240

Leu Ala Ser Lys Met His Ser Leu Leu
1               5

<210> SEQ ID NO 241
<211> LENGTH: 9
<212> TYPE: PRT
<213> ORGANISM: Artificial Sequence
<220> FEATURE:
<223> OTHER INFORMATION: 9mer T cell epitope 72

<400> SEQUENCE: 241

Ser Ser Phe Ile Ser Ser Leu Ser Phe
1               5

<210> SEQ ID NO 242
<211> LENGTH: 9
<212> TYPE: PRT
<213> ORGANISM: Artificial Sequence
<220> FEATURE:
<223> OTHER INFORMATION: 9mer T cell epitope 73

<400> SEQUENCE: 242

Ser Thr Asn Ala Leu Ile Gln Pro Val
1               5

<210> SEQ ID NO 243
<211> LENGTH: 9
<212> TYPE: PRT
<213> ORGANISM: Artificial Sequence
<220> FEATURE:
<223> OTHER INFORMATION: 9mer T cell epitope 74

<400> SEQUENCE: 243

Thr Leu Pro Pro Ala Trp Gln Pro Phe
1               5

<210> SEQ ID NO 244
<211> LENGTH: 9
<212> TYPE: PRT
<213> ORGANISM: Artificial Sequence
<220> FEATURE:
<223> OTHER INFORMATION: 9mer T cell episode 75

<400> SEQUENCE: 244

Arg Gln Phe Glu Thr Val Cys Lys Phe
1               5
```

<210> SEQ ID NO 245
<211> LENGTH: 9
<212> TYPE: PRT
<213> ORGANISM: Artificial Sequence
<220> FEATURE:
<223> OTHER INFORMATION: 9mer T cell epitope 76

<400> SEQUENCE: 245

Phe Ala Thr Cys Leu Gly Leu Ser Tyr
1               5

<210> SEQ ID NO 246
<211> LENGTH: 9
<212> TYPE: PRT
<213> ORGANISM: Artificial Sequence
<220> FEATURE:
<223> OTHER INFORMATION: 9mer T cell epitope 77

<400> SEQUENCE: 246

Phe Val Gln Glu Asn Tyr Leu Glu Tyr
1               5

<210> SEQ ID NO 247
<211> LENGTH: 9
<212> TYPE: PRT
<213> ORGANISM: Artificial Sequence
<220> FEATURE:
<223> OTHER INFORMATION: 9mer T cell epitope 78

<400> SEQUENCE: 247

Ala Ser Ser Ser Ser Thr Leu Ile Met
1               5

<210> SEQ ID NO 248
<211> LENGTH: 9
<212> TYPE: PRT
<213> ORGANISM: Artificial Sequence
<220> FEATURE:
<223> OTHER INFORMATION: 9mer T cell epitope 79

<400> SEQUENCE: 248

Tyr Ile Phe Ala Thr Cys Leu Gly Leu
1               5

<210> SEQ ID NO 249
<211> LENGTH: 9
<212> TYPE: PRT
<213> ORGANISM: Artificial Sequence
<220> FEATURE:
<223> OTHER INFORMATION: 9mer T cell epitope 80

<400> SEQUENCE: 249

Leu Pro Pro Ala Trp Gln Pro Phe Leu
1               5

<210> SEQ ID NO 250
<211> LENGTH: 9
<212> TYPE: PRT
<213> ORGANISM: Artificial Sequence
<220> FEATURE:
<223> OTHER INFORMATION: 9mer T cell epitope 81

<400> SEQUENCE: 250

Ile Ser Thr Phe Lys Asn Trp Pro Phe
1               5

<210> SEQ ID NO 251
<211> LENGTH: 15
<212> TYPE: PRT
<213> ORGANISM: Artificial Sequence
<220> FEATURE:
<223> OTHER INFORMATION: 15mer T cell epitope 81

<400> SEQUENCE: 251

Val Cys Ser Met Glu Gly Thr Trp Tyr Leu Val Gly Leu Val Ser
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: 15mer T cell epitope 82

<400> SEQUENCE: 252

Gly Phe Ser Tyr Glu Gln Asp Pro Thr Leu Arg Asp Pro Glu Ala
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: 15mer T cell epitope 83

<400> SEQUENCE: 253

Tyr Arg Ser Cys Gly Phe Ser Tyr Glu Gln Asp Pro Thr Leu Arg
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: 15mer T cell epitope 84

<400> SEQUENCE: 254

Leu Leu Ala Ala Ala Thr Ala Thr Phe Ala Ala Ala Gln Glu Glu
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: 15mer T cell epitope 85

<400> SEQUENCE: 255

Lys Leu Gly Phe Ser Phe Val Arg Ile Thr Ala Leu Met Val Ser
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: 15mer T cell epitope 86

<400> SEQUENCE: 256

Leu Pro Ser Thr Thr Met Glu Thr Gln Phe Pro Val Ser Glu Gly
1               5                   10                  15

<210> SEQ ID NO 257

```
<211> LENGTH: 15
<212> TYPE: PRT
<213> ORGANISM: Artificial Sequence
<220> FEATURE:
<223> OTHER INFORMATION: 15mer T cell epitope 87

<400> SEQUENCE: 257

Leu Asp Ser Phe Thr Val Cys Asn Ser His Val Leu Cys Ile Ala
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: 15mer T cell epitope 88

<400> SEQUENCE: 258

Gly Asn Ile Leu Asp Ser Phe Thr Val Cys Asn Ser His Val Leu
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: 15mer T cell epitope 89

<400> SEQUENCE: 259

Gln Thr Leu Ile Tyr Tyr Val Asp Glu Lys Ala Pro Glu Phe Ser
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: 15mer T cell epitope 90

<400> SEQUENCE: 260

Ser Arg Thr Leu Leu Leu Ala Leu Pro Leu Pro Leu Ser Leu Leu
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: 15mer T cell epitope 91

<400> SEQUENCE: 261

Phe Ile Ile Val Val Phe Val Tyr Leu Thr Val Glu Asn Lys Ser
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: 15mer T cell epitope 92

<400> SEQUENCE: 262

Arg Asn Ser Ile Arg Ser Ser Phe Ile Ser Ser Leu Ser Phe Phe
1               5                   10                  15

<210> SEQ ID NO 263
<211> LENGTH: 15
```

```
<212> TYPE: PRT
<213> ORGANISM: Artificial Sequence
<220> FEATURE:
<223> OTHER INFORMATION: 15mer T cell epitope 93

<400> SEQUENCE: 263

Asn Ile Glu Asn Tyr Ser Thr Asn Ala Leu Ile Gln Pro Val Asp
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: 15mer T cell epitope 94

<400> SEQUENCE: 264

Met Gly Ala Pro Thr Leu Pro Pro Ala Trp Gln Pro Phe Leu Lys
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: 15mer T cell epitope 95

<400> SEQUENCE: 265

Arg Gln Phe Glu Thr Val Cys Lys Phe His Trp Val Glu Ala Phe
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: 15mer T cell epitope 96

<400> SEQUENCE: 266

Pro Glu Glu Ala Ile Trp Glu Ala Leu Ser Val Met Gly Leu Tyr
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: 15mer T cell epitope 97

<400> SEQUENCE: 267

Glu Lys Val Ala Glu Leu Val Arg Phe Leu Leu Arg Lys Tyr Gln
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: 15mer T cell epitioe 98

<400> SEQUENCE: 268

Lys Leu Leu Thr Gln Tyr Phe Val Gln Glu Asn Tyr Leu Glu Tyr
1               5                   10                  15

<210> SEQ ID NO 269
<211> LENGTH: 15
<212> TYPE: PRT
```

-continued

```
<213> ORGANISM: Artificial Sequence
<220> FEATURE:
<223> OTHER INFORMATION: 15mer T cell epitope 99

<400> SEQUENCE: 269

Ile Gly His Leu Tyr Ile Phe Ala Thr Cys Leu Gly Leu Ser Tyr
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: 15mer T cell epitope 100

<400> SEQUENCE: 270

Lys Leu Leu Thr Gln His Phe Val Gln Glu Asn Tyr Leu Glu Tyr
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: 15mer T cell epitope 101

<400> SEQUENCE: 271

Ala Ser Ser Ser Ser Thr Leu Ile Met Gly Thr Leu Glu Glu Val
1               5                   10                  15

<210> SEQ ID NO 272
<211> LENGTH: 9
<212> TYPE: PRT
<213> ORGANISM: Artificial Sequence
<220> FEATURE:
<223> OTHER INFORMATION: 9mer T cell epitope 82

<400> SEQUENCE: 272

Met Met Met Ser Ile Ala Thr Lys Ile
1               5

<210> SEQ ID NO 273
<211> LENGTH: 9
<212> TYPE: PRT
<213> ORGANISM: Artificial Sequence
<220> FEATURE:
<223> OTHER INFORMATION: 9mer T cell epitope 83

<400> SEQUENCE: 273

Lys Ala Phe Asp Gly Ala Ile Leu Phe
1               5

<210> SEQ ID NO 274
<211> LENGTH: 9
<212> TYPE: PRT
<213> ORGANISM: Artificial Sequence
<220> FEATURE:
<223> OTHER INFORMATION: 9mer T cell epitope 84

<400> SEQUENCE: 274

Arg Met Phe Pro Asn Ala Pro Tyr Leu
1               5

<210> SEQ ID NO 275
<211> LENGTH: 9
<212> TYPE: PRT
<213> ORGANISM: Artificial Sequence
```

```
<220> FEATURE:
<223> OTHER INFORMATION: 9mer T cell epitope 85

<400> SEQUENCE: 275

Arg Thr Tyr Trp Ile Ile Ile Glu Leu
1               5

<210> SEQ ID NO 276
<211> LENGTH: 9
<212> TYPE: PRT
<213> ORGANISM: Artificial Sequence
<220> FEATURE:
<223> OTHER INFORMATION: 9mer T cell epitope 86

<400> SEQUENCE: 276

Phe Thr Ser Ser Arg Met Ser Ser Phe
1               5

<210> SEQ ID NO 277
<211> LENGTH: 9
<212> TYPE: PRT
<213> ORGANISM: Artificial Sequence
<220> FEATURE:
<223> OTHER INFORMATION: 9mer T cell epitope 87

<400> SEQUENCE: 277

Tyr Leu Met Asn Arg Pro Gln Asn Leu
1               5

<210> SEQ ID NO 278
<211> LENGTH: 9
<212> TYPE: PRT
<213> ORGANISM: Artificial Sequence
<220> FEATURE:
<223> OTHER INFORMATION: 9mer T cell epitope 88

<400> SEQUENCE: 278

Met Ile Met Glu Asn Ile Gln Glu Leu
1               5

<210> SEQ ID NO 279
<211> LENGTH: 9
<212> TYPE: PRT
<213> ORGANISM: Artificial Sequence
<220> FEATURE:
<223> OTHER INFORMATION: 9mer T cell epitope 89

<400> SEQUENCE: 279

Met Met Ala Tyr Ser Asp Thr Thr Met
1               5

<210> SEQ ID NO 280
<211> LENGTH: 9
<212> TYPE: PRT
<213> ORGANISM: Artificial Sequence
<220> FEATURE:
<223> OTHER INFORMATION: 9mer T cell epitope 90

<400> SEQUENCE: 280

Phe Ala Ala Ala Tyr Phe Glu Ser Leu
1               5

<210> SEQ ID NO 281
<211> LENGTH: 9
<212> TYPE: PRT
<213> ORGANISM: Artificial Sequence
<220> FEATURE:
```

```
<223> OTHER INFORMATION: 9mer T cell epitope 91

<400> SEQUENCE: 281

Tyr Val Asp Pro Asp Val Gln Leu Val
1               5

<210> SEQ ID NO 282
<211> LENGTH: 9
<212> TYPE: PRT
<213> ORGANISM: Artificial Sequence
<220> FEATURE:
<223> OTHER INFORMATION: 9mer T cell epitope 92

<400> SEQUENCE: 282

Phe Val Ala Ser Ile Asn Leu Thr Leu
1               5

<210> SEQ ID NO 283
<211> LENGTH: 9
<212> TYPE: PRT
<213> ORGANISM: Artificial Sequence
<220> FEATURE:
<223> OTHER INFORMATION: 9mer T cell epitope 93

<400> SEQUENCE: 283

Tyr Ala Leu Gly Phe Gln His Ala Leu
1               5

<210> SEQ ID NO 284
<211> LENGTH: 9
<212> TYPE: PRT
<213> ORGANISM: Artificial Sequence
<220> FEATURE:
<223> OTHER INFORMATION: 9mer T cell epitope 94

<400> SEQUENCE: 284

Leu Gln Tyr Glu Asn Ser Ile Thr Leu
1               5

<210> SEQ ID NO 285
<211> LENGTH: 9
<212> TYPE: PRT
<213> ORGANISM: Artificial Sequence
<220> FEATURE:
<223> OTHER INFORMATION: 9mer T cell epitope 95

<400> SEQUENCE: 285

Lys Met Ser Ser Leu Leu Pro Thr Met
1               5

<210> SEQ ID NO 286
<211> LENGTH: 9
<212> TYPE: PRT
<213> ORGANISM: Artificial Sequence
<220> FEATURE:
<223> OTHER INFORMATION: 9mer T cell epitope 96

<400> SEQUENCE: 286

His Leu Gln Ser Val Thr Ala Pro Met
1               5

<210> SEQ ID NO 287
<211> LENGTH: 9
<212> TYPE: PRT
<213> ORGANISM: Artificial Sequence
<220> FEATURE:
<223> OTHER INFORMATION: 9mer T cell epitope 97
```

```
<400> SEQUENCE: 287

Phe Val Ala Ser Thr Asn Ala Glu Leu
1               5

<210> SEQ ID NO 288
<211> LENGTH: 9
<212> TYPE: PRT
<213> ORGANISM: Artificial Sequence
<220> FEATURE:
<223> OTHER INFORMATION: 9mer T cell epitope 98

<400> SEQUENCE: 288

Phe Tyr Asp Pro Thr Ser Ala Met Val
1               5

<210> SEQ ID NO 289
<211> LENGTH: 9
<212> TYPE: PRT
<213> ORGANISM: Artificial Sequence
<220> FEATURE:
<223> OTHER INFORMATION: 9mer T cell epitope 99

<400> SEQUENCE: 289

Met Ala Phe Val Thr Ser Gly Glu Leu
1               5

<210> SEQ ID NO 290
<211> LENGTH: 9
<212> TYPE: PRT
<213> ORGANISM: Artificial Sequence
<220> FEATURE:
<223> OTHER INFORMATION: 9mer T cell epitope 100

<400> SEQUENCE: 290

Tyr Val Asn Arg Leu Ser Ser Leu Val
1               5

<210> SEQ ID NO 291
<211> LENGTH: 9
<212> TYPE: PRT
<213> ORGANISM: Artificial Sequence
<220> FEATURE:
<223> OTHER INFORMATION: 9mer T cell epitope 101

<400> SEQUENCE: 291

Tyr Leu His Ala Arg Leu Arg Glu Leu
1               5

<210> SEQ ID NO 292
<211> LENGTH: 9
<212> TYPE: PRT
<213> ORGANISM: Artificial Sequence
<220> FEATURE:
<223> OTHER INFORMATION: 9mer T cell epitope 102

<400> SEQUENCE: 292

Phe Thr Gln Ser Gly Thr Met Lys Ile
1               5

<210> SEQ ID NO 293
<211> LENGTH: 9
<212> TYPE: PRT
<213> ORGANISM: Artificial Sequence
<220> FEATURE:
<223> OTHER INFORMATION: 9mer T cell epitope 103
```

```
<400> SEQUENCE: 293

His Ala Phe Asp Gly Thr Ile Leu Phe
1               5

<210> SEQ ID NO 294
<211> LENGTH: 9
<212> TYPE: PRT
<213> ORGANISM: Artificial Sequence
<220> FEATURE:
<223> OTHER INFORMATION: 9mer T cell epitope 104

<400> SEQUENCE: 294

Tyr Val Asp Glu Lys Ala Pro Glu Phe
1               5

<210> SEQ ID NO 295
<211> LENGTH: 9
<212> TYPE: PRT
<213> ORGANISM: Artificial Sequence
<220> FEATURE:
<223> OTHER INFORMATION: 9mer T cell epitope 105

<400> SEQUENCE: 295

Val Met Ser Glu Arg Val Ser Gly Leu
1               5

<210> SEQ ID NO 296
<211> LENGTH: 9
<212> TYPE: PRT
<213> ORGANISM: Artificial Sequence
<220> FEATURE:
<223> OTHER INFORMATION: 9mer T cell epitope 106

<400> SEQUENCE: 296

Leu Gln Tyr Glu Asn Ser Ile Met Leu
1               5

<210> SEQ ID NO 297
<211> LENGTH: 9
<212> TYPE: PRT
<213> ORGANISM: Artificial Sequence
<220> FEATURE:
<223> OTHER INFORMATION: 9mer T cell epitope 107

<400> SEQUENCE: 297

Phe Gln Met Pro His Gln Glu Ile Val
1               5

<210> SEQ ID NO 298
<211> LENGTH: 9
<212> TYPE: PRT
<213> ORGANISM: Artificial Sequence
<220> FEATURE:
<223> OTHER INFORMATION: 9mer T cell epitope 108

<400> SEQUENCE: 298

Lys Ala Met Val Gln Ala Trp Pro Phe
1               5

<210> SEQ ID NO 299
<211> LENGTH: 9
<212> TYPE: PRT
<213> ORGANISM: Artificial Sequence
<220> FEATURE:
<223> OTHER INFORMATION: 9mer T cell epitope 109

<400> SEQUENCE: 299
```

```
Arg Ala Ile Glu Gln Leu Ala Ala Met
1               5

<210> SEQ ID NO 300
<211> LENGTH: 9
<212> TYPE: PRT
<213> ORGANISM: Artificial Sequence
<220> FEATURE:
<223> OTHER INFORMATION: 9mer T cell epitope 110

<400> SEQUENCE: 300

Arg Ser Asp Glu Ile Val Leu Thr Val
1               5

<210> SEQ ID NO 301
<211> LENGTH: 9
<212> TYPE: PRT
<213> ORGANISM: Artificial Sequence
<220> FEATURE:
<223> OTHER INFORMATION: 9mer T cell epitope 111

<400> SEQUENCE: 301

Tyr Ser Ser Asp Asn Leu Tyr Gln Met
1               5

<210> SEQ ID NO 302
<211> LENGTH: 15
<212> TYPE: PRT
<213> ORGANISM: Artificial Sequence
<220> FEATURE:
<223> OTHER INFORMATION: 15mer T cell epitope 102

<400> SEQUENCE: 302

Gln Gly Met Met Met Ser Ile Ala Thr Lys Ile Ala Met Gln Met
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: 15mer T cell epitope 103

<400> SEQUENCE: 303

Lys Ala Lys Ala Phe Asp Gly Ala Ile Leu Phe Leu Ser Gln Lys
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: 15mer T cell epitope 104

<400> SEQUENCE: 304

Ser Ser Gly Gln Ala Arg Met Phe Pro Asn Ala Pro Tyr Leu Pro
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: 15mer T cell epitope 105

<400> SEQUENCE: 305
```

```
Arg Thr Tyr Trp Ile Ile Ile Glu Leu Lys His Lys Ala Arg Glu
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: 15mer T cell epitope 106

<400> SEQUENCE: 306

Met Phe Thr Ser Ser Arg Met Ser Ser Phe Asn Arg His Met Lys
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: 15mer T cell epitope 107

<400> SEQUENCE: 307

Gln Val Asn Ile Asp Tyr Leu Met Asn Arg Pro Gln Asn Leu Arg
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: 15mer T cell epitope 108

<400> SEQUENCE: 308

Ser Thr Pro Met Ile Met Glu Asn Ile Gln Glu Leu Ile Arg Ser
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: 15mer T cell epitope 109

<400> SEQUENCE: 309

Met Met Ala Tyr Ser Asp Thr Thr Met Met Ser Asp Asp Ile Asp
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: 15mer T cell epitope 110

<400> SEQUENCE: 310

Ala Phe Ala Ala Ala Tyr Phe Glu Ser Leu Leu Glu Lys Arg Glu
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: 15mer T cell epitope 111

<400> SEQUENCE: 311

Arg Ala Ile Gln Gln Tyr Val Asp Pro Asp Val Gln Leu Val Met
```

<210> SEQ ID NO 312
<211> LENGTH: 15
<212> TYPE: PRT
<213> ORGANISM: Artificial Sequence
<220> FEATURE:
<223> OTHER INFORMATION: 15mer T cell epitope 112

<400> SEQUENCE: 312

Gly Phe Val Ala Ser Ile Asn Leu Thr Leu Thr Lys Trp Tyr Ser
1               5                   10                  15

<210> SEQ ID NO 313
<211> LENGTH: 15
<212> TYPE: PRT
<213> ORGANISM: Artificial Sequence
<220> FEATURE:
<223> OTHER INFORMATION: 15mer T cell epitope 113

<400> SEQUENCE: 313

Asp Leu Gln Lys Tyr Ala Leu Gly Phe Gln His Ala Leu Ser Pro
1               5                   10                  15

<210> SEQ ID NO 314
<211> LENGTH: 15
<212> TYPE: PRT
<213> ORGANISM: Artificial Sequence
<220> FEATURE:
<223> OTHER INFORMATION: 15mer T cell epitope 114

<400> SEQUENCE: 314

Gly Tyr Val Thr Ser Val Leu Gln Tyr Glu Asn Ser Ile Thr Leu
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: 15mer T cell epitope 115

<400> SEQUENCE: 315

Val Arg Glu Glu Ala Gln Lys Met Ser Ser Leu Leu Pro Thr Met
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: 15mer T cell epitope 116

<400> SEQUENCE: 316

Met Ser Leu Lys Gly His Leu Gln Ser Val Thr Ala Pro Met Gly
1               5                   10                  15

<210> SEQ ID NO 317
<211> LENGTH: 15
<212> TYPE: PRT
<213> ORGANISM: Artificial Sequence
<220> FEATURE:
<223> OTHER INFORMATION: 15mer T cell epitope 117

<400> SEQUENCE: 317

Gln Lys Ser Ile Ala Gly Phe Val Ala Ser Thr Asn Ala Glu Leu
1               5                   10                  15

```
<210> SEQ ID NO 318
<211> LENGTH: 15
<212> TYPE: PRT
<213> ORGANISM: Artificial Sequence
<220> FEATURE:
<223> OTHER INFORMATION: 15mer T cell epitope 118

<400> SEQUENCE: 318

Arg Asn Phe Tyr Asp Pro Thr Ser Ala Met Val Leu Gln Gln His
1               5                   10                  15

<210> SEQ ID NO 319
<211> LENGTH: 15
<212> TYPE: PRT
<213> ORGANISM: Artificial Sequence
<220> FEATURE:
<223> OTHER INFORMATION: 15mer T cell epitope 119

<400> SEQUENCE: 319

Asn Met Ala Phe Val Thr Ser Gly Glu Leu Val Arg His Arg Arg
1               5                   10                  15

<210> SEQ ID NO 320
<211> LENGTH: 15
<212> TYPE: PRT
<213> ORGANISM: Artificial Sequence
<220> FEATURE:
<223> OTHER INFORMATION: 15mer T cell epitope 120

<400> SEQUENCE: 320

Leu Ser Phe Tyr Val Asn Arg Leu Ser Ser Leu Val Ile Gln Met
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: 15mer T cell epitope 121

<400> SEQUENCE: 321

Leu Glu Arg Leu Ala Tyr Leu His Ala Arg Leu Arg Glu Leu Leu
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: 15mer T cell epitope 122

<400> SEQUENCE: 322

Arg Phe Thr Gln Ser Gly Thr Met Lys Ile His Ile Leu Gln Lys
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: 15mer T cell epitope 123

<400> SEQUENCE: 323

His Ala Phe Asp Gly Thr Ile Leu Phe Leu Pro Lys Arg Leu Gln
1               5                   10                  15
```

<210> SEQ ID NO 324
<211> LENGTH: 15
<212> TYPE: PRT
<213> ORGANISM: Artificial Sequence
<220> FEATURE:
<223> OTHER INFORMATION: 15mer T cell epitope 124

<400> SEQUENCE: 324

Tyr Val Asp Glu Lys Ala Pro Glu Phe Ser Met Gln Gly Leu Lys
1               5                   10                  15

<210> SEQ ID NO 325
<211> LENGTH: 15
<212> TYPE: PRT
<213> ORGANISM: Artificial Sequence
<220> FEATURE:
<223> OTHER INFORMATION: 15mer T cell epitope 125

<400> SEQUENCE: 325

Ser Gly Ala Val Met Ser Glu Arg Val Ser Gly Leu Ala Gly Ser
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: 15mer T cell epitope 126

<400> SEQUENCE: 326

Gly Phe Thr Thr Ser Ile Leu Gln Tyr Glu Asn Ser Ile Met Leu
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: 15mer T cell epitope 127

<400> SEQUENCE: 327

Tyr Ser Arg Val Val Phe Gln Met Pro His Gln Glu Ile Val Asp
1               5                   10                  15

<210> SEQ ID NO 328
<211> LENGTH: 15
<212> TYPE: PRT
<213> ORGANISM: Artificial Sequence
<220> FEATURE:
<223> OTHER INFORMATION: 15mer T cell epitope 128

<400> SEQUENCE: 328

Arg His Ser Gln Thr Leu Lys Ala Met Val Gln Ala Trp Pro Phe
1               5                   10                  15

<210> SEQ ID NO 329
<211> LENGTH: 15
<212> TYPE: PRT
<213> ORGANISM: Artificial Sequence
<220> FEATURE:
<223> OTHER INFORMATION: 15mer T cell epitope 129

<400> SEQUENCE: 329

Ala Lys Lys Val Arg Arg Ala Ile Glu Gln Leu Ala Ala Met Asp
1               5                   10                  15

-continued

```
<210> SEQ ID NO 330
<211> LENGTH: 15
<212> TYPE: PRT
<213> ORGANISM: Artificial Sequence
<220> FEATURE:
<223> OTHER INFORMATION: 15mer T cell epitope 130

<400> SEQUENCE: 330

Glu Arg Ser Asp Glu Ile Val Leu Thr Val Ser Asn Ser Asn Val
1               5                  10                  15

<210> SEQ ID NO 331
<211> LENGTH: 15
<212> TYPE: PRT
<213> ORGANISM: Artificial Sequence
<220> FEATURE:
<223> OTHER INFORMATION: 15mer T cell epitope 131

<400> SEQUENCE: 331

Arg Thr Pro Tyr Ser Ser Asp Asn Leu Tyr Gln Met Thr Ser Gln
1               5                  10                  15

<210> SEQ ID NO 332
<211> LENGTH: 30
<212> TYPE: PRT
<213> ORGANISM: Artificial Sequence
<220> FEATURE:
<223> OTHER INFORMATION: ovarian pep 1

<400> SEQUENCE: 332

Ser Thr Pro Met Ile Met Glu Asn Ile Gln Glu Leu Ile Arg Ser Gln
1               5                  10                  15

Gly Met Met Met Ser Ile Ala Thr Lys Ile Ala Met Gln Met
            20                  25                  30

<210> SEQ ID NO 333
<211> LENGTH: 30
<212> TYPE: PRT
<213> ORGANISM: Artificial Sequence
<220> FEATURE:
<223> OTHER INFORMATION: ovarian pep 2

<400> SEQUENCE: 333

Arg Asn Phe Tyr Asp Pro Thr Ser Ala Met Val Leu Gln Gln His Lys
1               5                  10                  15

Ala Lys Ala Phe Asp Gly Ala Ile Leu Phe Leu Ser Gln Lys
            20                  25                  30

<210> SEQ ID NO 334
<211> LENGTH: 30
<212> TYPE: PRT
<213> ORGANISM: Artificial Sequence
<220> FEATURE:
<223> OTHER INFORMATION: ovarian pep 3

<400> SEQUENCE: 334

Asn Met Ala Phe Val Thr Ser Gly Glu Leu Val Arg His Arg Arg Met
1               5                  10                  15

Met Ala Tyr Ser Asp Thr Thr Met Met Ser Asp Asp Ile Asp
            20                  25                  30

<210> SEQ ID NO 335
<211> LENGTH: 30
<212> TYPE: PRT
<213> ORGANISM: Artificial Sequence
<220> FEATURE:
```

<223> OTHER INFORMATION: ovarian pep 4

<400> SEQUENCE: 335

Ser Ser Gly Gln Ala Arg Met Phe Pro Asn Ala Pro Tyr Leu Pro Arg
1               5                   10                  15

Thr Pro Tyr Ser Ser Asp Asn Leu Tyr Gln Met Thr Ser Gln
            20                  25                  30

<210> SEQ ID NO 336
<211> LENGTH: 30
<212> TYPE: PRT
<213> ORGANISM: Artificial Sequence
<220> FEATURE:
<223> OTHER INFORMATION: ovarian pep 5

<400> SEQUENCE: 336

Met Phe Thr Ser Ser Arg Met Ser Phe Asn Arg His Met Lys His
1               5                   10                  15

Ala Phe Asp Gly Thr Ile Leu Phe Leu Pro Lys Arg Leu Gln
            20                  25                  30

<210> SEQ ID NO 337
<211> LENGTH: 30
<212> TYPE: PRT
<213> ORGANISM: Artificial Sequence
<220> FEATURE:
<223> OTHER INFORMATION: ovarian pep 6

<400> SEQUENCE: 337

Tyr Ser Arg Val Val Phe Gln Met Pro His Gln Glu Ile Val Asp Arg
1               5                   10                  15

Thr Tyr Trp Ile Ile Ile Glu Leu Lys His Lys Ala Arg Glu
            20                  25                  30

<210> SEQ ID NO 338
<211> LENGTH: 30
<212> TYPE: PRT
<213> ORGANISM: Artificial Sequence
<220> FEATURE:
<223> OTHER INFORMATION: ovarian pep 7

<400> SEQUENCE: 338

Leu Ser Phe Tyr Val Asn Arg Leu Ser Ser Leu Val Ile Gln Met Arg
1               5                   10                  15

Ala Ile Gln Gln Tyr Val Asp Pro Asp Val Gln Leu Val Met
            20                  25                  30

<210> SEQ ID NO 339
<211> LENGTH: 30
<212> TYPE: PRT
<213> ORGANISM: Artificial Sequence
<220> FEATURE:
<223> OTHER INFORMATION: ovarian pep 8

<400> SEQUENCE: 339

Gln Val Asn Ile Asp Tyr Leu Met Asn Arg Pro Gln Asn Leu Arg Ala
1               5                   10                  15

Phe Ala Ala Ala Tyr Phe Glu Ser Leu Leu Glu Lys Arg Glu
            20                  25                  30

<210> SEQ ID NO 340
<211> LENGTH: 30
<212> TYPE: PRT
<213> ORGANISM: Artificial Sequence

```
<220> FEATURE:
<223> OTHER INFORMATION: ovarian pep 9

<400> SEQUENCE: 340

Gly Tyr Val Thr Ser Val Leu Gln Tyr Glu Asn Ser Ile Thr Leu Gln
1               5                   10                  15

Lys Ser Ile Ala Gly Phe Val Ala Ser Thr Asn Ala Glu Leu
            20                  25                  30

<210> SEQ ID NO 341
<211> LENGTH: 30
<212> TYPE: PRT
<213> ORGANISM: Artificial Sequence
<220> FEATURE:
<223> OTHER INFORMATION: ovarian pep 10

<400> SEQUENCE: 341

Val Arg Glu Glu Ala Gln Lys Met Ser Ser Leu Leu Pro Thr Met Arg
1               5                   10                  15

Phe Thr Gln Ser Gly Thr Met Lys Ile His Ile Leu Gln Lys
            20                  25                  30

<210> SEQ ID NO 342
<211> LENGTH: 30
<212> TYPE: PRT
<213> ORGANISM: Artificial Sequence
<220> FEATURE:
<223> OTHER INFORMATION: ovarian pep 11

<400> SEQUENCE: 342

Gly Phe Val Ala Ser Ile Asn Leu Thr Leu Thr Lys Trp Tyr Ser Tyr
1               5                   10                  15

Val Asp Glu Lys Ala Pro Glu Phe Ser Met Gln Gly Leu Lys
            20                  25                  30

<210> SEQ ID NO 343
<211> LENGTH: 30
<212> TYPE: PRT
<213> ORGANISM: Artificial Sequence
<220> FEATURE:
<223> OTHER INFORMATION: ovarian pep 12

<400> SEQUENCE: 343

Met Ser Leu Lys Gly His Leu Gln Ser Val Thr Ala Pro Met Gly Ser
1               5                   10                  15

Gly Ala Val Met Ser Glu Arg Val Ser Gly Leu Ala Gly Ser
            20                  25                  30

<210> SEQ ID NO 344
<211> LENGTH: 30
<212> TYPE: PRT
<213> ORGANISM: Artificial Sequence
<220> FEATURE:
<223> OTHER INFORMATION: ovarian pep 13

<400> SEQUENCE: 344

Asp Leu Gln Lys Tyr Ala Leu Gly Phe Gln His Ala Leu Ser Pro Leu
1               5                   10                  15

Glu Arg Leu Ala Tyr Leu His Ala Arg Leu Arg Glu Leu Leu
            20                  25                  30

<210> SEQ ID NO 345
<211> LENGTH: 30
<212> TYPE: PRT
```

```
<213> ORGANISM: Artificial Sequence
<220> FEATURE:
<223> OTHER INFORMATION: ovarian pep 14

<400> SEQUENCE: 345

Gly Phe Thr Thr Ser Ile Leu Gln Tyr Glu Asn Ser Ile Met Leu Glu
1               5                   10                  15

Arg Ser Asp Glu Ile Val Leu Thr Val Ser Asn Ser Asn Val
            20                  25                  30

<210> SEQ ID NO 346
<211> LENGTH: 30
<212> TYPE: PRT
<213> ORGANISM: Artificial Sequence
<220> FEATURE:
<223> OTHER INFORMATION: ovarian pep 15

<400> SEQUENCE: 346

Arg His Ser Gln Thr Leu Lys Ala Met Val Gln Ala Trp Pro Phe Ala
1               5                   10                  15

Lys Lys Val Arg Arg Ala Ile Glu Gln Leu Ala Ala Met Asp
            20                  25                  30

<210> SEQ ID NO 347
<211> LENGTH: 314
<212> TYPE: PRT
<213> ORGANISM: Artificial Sequence
<220> FEATURE:
<223> OTHER INFORMATION: MAGE-A3

<400> SEQUENCE: 347

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220
```

-continued

```
Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Pro His Ile Ser Tyr Pro Pro Leu
    290                 295                 300

His Glu Trp Val Leu Arg Glu Gly Glu Glu
305                 310
```

<210> SEQ ID NO 348
<211> LENGTH: 181
<212> TYPE: PRT
<213> ORGANISM: Artificial Sequence
<220> FEATURE:
<223> OTHER INFORMATION: LEMD1

<400> SEQUENCE: 348

```
Met Val Asp Val Lys Cys Leu Ser Asp Cys Lys Leu Gln Asn Gln Leu
1               5                   10                  15

Glu Lys Leu Gly Phe Ser Pro Gly Pro Ile Leu Pro Ser Thr Arg Lys
                20                  25                  30

Leu Tyr Glu Lys Lys Leu Val Gln Leu Leu Val Ser Pro Pro Cys Ala
            35                  40                  45

Pro Pro Val Met Asn Gly Pro Arg Glu Leu Asp Gly Ala Gln Asp Ser
        50                  55                  60

Asp Asp Ser Glu Glu Leu Asn Ile Ile Leu Gln Gly Asn Ile Ile Leu
65                  70                  75                  80

Ser Thr Glu Lys Ser Lys Lys Leu Lys Lys Trp Pro Glu Ala Ser Thr
                85                  90                  95

Thr Lys Arg Lys Ala Val Asp Thr Tyr Cys Leu Asp Tyr Lys Pro Ser
            100                 105                 110

Lys Gly Arg Arg Trp Ala Ala Arg Ala Pro Ser Thr Arg Ile Thr Tyr
        115                 120                 125

Gly Thr Ile Thr Lys Glu Arg Asp Tyr Cys Ala Glu Asp Gln Thr Ile
    130                 135                 140

Glu Ser Trp Arg Glu Glu Gly Phe Pro Val Gly Leu Lys Leu Ala Val
145                 150                 155                 160

Leu Gly Ile Phe Ile Ile Val Val Phe Val Tyr Leu Thr Val Glu Asn
                165                 170                 175

Lys Ser Leu Phe Gly
            180
```

<210> SEQ ID NO 349
<211> LENGTH: 973
<212> TYPE: PRT
<213> ORGANISM: Artificial Sequence
<220> FEATURE:
<223> OTHER INFORMATION: PIWIL-2

<400> SEQUENCE: 349

```
Met Asp Pro Phe Arg Pro Ser Phe Arg Gly Gln Ser Pro Ile His Pro
1               5                   10                  15

Ser Gln Cys Gln Ala Val Arg Met Pro Gly Cys Trp Pro Gln Ala Ser
```

```
                20                  25                  30
Lys Pro Leu Asp Pro Ala Leu Gly Arg Gly Ala Pro Gly Arg Gly
            35                  40                  45
His Val Phe Gly Lys Pro Glu Glu Pro Ser Thr Gln Arg Gly Pro Ala
        50                  55                  60
Gln Arg Glu Ser Val Gly Leu Val Ser Met Phe Arg Gly Leu Gly Ile
65                  70                  75                  80
Glu Thr Val Ser Lys Thr Pro Leu Lys Arg Glu Met Leu Pro Ser Gly
                85                  90                  95
Arg Gly Ile Leu Gly Arg Gly Leu Ser Ala Asn Leu Val Arg Lys Asp
            100                 105                 110
Arg Glu Glu Leu Ser Pro Thr Phe Trp Asp Pro Lys Val Leu Ala Ala
            115                 120                 125
Gly Asp Ser Lys Met Ala Glu Thr Ser Val Gly Trp Ser Arg Thr Leu
        130                 135                 140
Gly Arg Gly Ser Ser Asp Ala Ser Leu Leu Pro Leu Gly Arg Ala Ala
145                 150                 155                 160
Gly Gly Ile Ser Arg Glu Val Asp Lys Pro Pro Cys Thr Phe Ser Thr
                165                 170                 175
Pro Ser Arg Gly Pro Pro Gln Leu Ser Ser Pro Pro Ala Leu Pro Gln
            180                 185                 190
Ser Pro Leu His Ser Pro Asp Arg Pro Leu Val Leu Thr Val Glu His
            195                 200                 205
Lys Glu Lys Glu Leu Ile Val Lys Gln Gly Ser Lys Gly Thr Pro Gln
        210                 215                 220
Ser Leu Gly Leu Asn Leu Val Lys Ile Gln Cys His Asn Glu Ala Val
225                 230                 235                 240
Tyr Gln Tyr His Val Thr Phe Ser Pro Asn Val Glu Cys Lys Ser Met
                245                 250                 255
Arg Phe Gly Met Leu Lys Asp His Gln Ala Val Thr Gly Asn Val Thr
            260                 265                 270
Ala Phe Asp Gly Ser Ile Leu Tyr Leu Pro Val Lys Leu Gln Gln Val
            275                 280                 285
Leu Glu Leu Lys Ser Gln Arg Lys Thr Asp Ser Ala Glu Ile Ser Ile
        290                 295                 300
Lys Ile Gln Met Thr Lys Ile Leu Glu Pro Cys Ser Asp Leu Cys Ile
305                 310                 315                 320
Pro Phe Tyr Asn Val Val Phe Arg Arg Val Met Lys Leu Leu Asp Met
                325                 330                 335
Lys Leu Val Gly Arg Asn Phe Tyr Asp Pro Thr Ser Ala Met Val Leu
            340                 345                 350
Gln Gln His Arg Leu Gln Ile Trp Pro Gly Tyr Ala Ala Ser Ile Arg
        355                 360                 365
Arg Thr Asp Gly Gly Leu Phe Leu Leu Ala Asp Val Ser His Lys Val
        370                 375                 380
Ile Arg Asn Asp Cys Val Leu Asp Val Met His Ala Ile Tyr Gln Gln
385                 390                 395                 400
Asn Lys Glu His Phe Gln Asp Glu Cys Thr Lys Leu Leu Val Gly Asn
                405                 410                 415
Ile Val Ile Thr Arg Tyr Asn Asn Arg Thr Tyr Arg Ile Asp Asp Val
            420                 425                 430
Asp Trp Asn Lys Thr Pro Lys Asp Ser Phe Thr Met Ser Asp Gly Lys
            435                 440                 445
```

-continued

```
Glu Ile Thr Phe Leu Glu Tyr Tyr Ser Lys Asn Tyr Gly Ile Thr Val
    450                 455                 460
Lys Glu Glu Asp Gln Pro Leu Leu Ile His Arg Pro Ser Glu Arg Gln
465                 470                 475                 480
Asp Asn His Gly Met Leu Leu Lys Gly Glu Ile Leu Leu Pro Glu
                485                 490                 495
Leu Ser Phe Met Thr Gly Ile Pro Glu Lys Met Lys Lys Asp Phe Arg
                500                 505                 510
Ala Met Lys Asp Leu Ala Gln Gln Ile Asn Leu Ser Pro Lys Gln His
        515                 520                 525
His Ser Ala Leu Glu Cys Leu Leu Gln Arg Ile Ala Lys Asn Glu Ala
    530                 535                 540
Ala Thr Asn Glu Leu Met Arg Trp Gly Leu Arg Leu Gln Lys Asp Val
545                 550                 555                 560
His Lys Ile Glu Gly Arg Val Leu Pro Met Glu Arg Ile Asn Leu Lys
                565                 570                 575
Asn Thr Ser Phe Ile Thr Ser Gln Glu Leu Asn Trp Val Lys Glu Val
                580                 585                 590
Thr Arg Asp Pro Ser Ile Leu Thr Ile Pro Met His Phe Trp Ala Leu
        595                 600                 605
Phe Tyr Pro Lys Arg Ala Met Asp Gln Ala Arg Glu Leu Val Asn Met
    610                 615                 620
Leu Glu Lys Ile Ala Gly Pro Ile Gly Met Arg Met Ser Pro Ala
625                 630                 635                 640
Trp Val Glu Leu Lys Asp Asp Arg Ile Glu Thr Tyr Val Arg Thr Ile
                645                 650                 655
Gln Ser Thr Leu Gly Ala Glu Gly Lys Ile Gln Met Val Cys Ile
                660                 665                 670
Ile Met Gly Pro Arg Asp Asp Leu Tyr Gly Ala Ile Lys Lys Leu Cys
        675                 680                 685
Cys Val Gln Ser Pro Val Pro Ser Gln Val Val Asn Val Arg Thr Ile
    690                 695                 700
Gly Gln Pro Thr Arg Leu Arg Ser Val Ala Gln Lys Ile Leu Leu Gln
705                 710                 715                 720
Ile Asn Cys Lys Leu Gly Gly Glu Leu Trp Gly Val Asp Ile Pro Leu
                725                 730                 735
Lys Gln Leu Met Val Ile Gly Met Asp Val Tyr His Asp Pro Ser Arg
                740                 745                 750
Gly Met Arg Ser Val Val Gly Phe Val Ala Ser Ile Asn Leu Thr Leu
        755                 760                 765
Thr Lys Trp Tyr Ser Arg Val Val Phe Gln Met Pro His Gln Glu Ile
    770                 775                 780
Val Asp Ser Leu Lys Leu Cys Leu Val Gly Ser Leu Lys Lys Phe Tyr
785                 790                 795                 800
Glu Val Asn His Cys Leu Pro Glu Lys Ile Val Val Tyr Arg Asp Gly
                805                 810                 815
Val Ser Asp Gly Gln Leu Lys Thr Val Ala Asn Tyr Glu Ile Pro Gln
                820                 825                 830
Leu Gln Lys Cys Phe Glu Ala Phe Glu Asn Tyr Gln Pro Lys Met Val
        835                 840                 845
Val Phe Val Val Gln Lys Lys Ile Ser Thr Asn Leu Tyr Leu Ala Ala
    850                 855                 860
```

Pro Gln Asn Phe Val Thr Pro Thr Pro Gly Thr Val Val Asp His Thr
865                 870                 875                 880

Ile Thr Ser Cys Glu Trp Val Asp Phe Tyr Leu Leu Ala His His Val
                885                 890                 895

Arg Gln Gly Cys Gly Ile Pro Thr His Tyr Val Cys Val Leu Asn Thr
            900                 905                 910

Ala Asn Leu Ser Pro Asp His Met Gln Arg Leu Thr Phe Lys Leu Cys
        915                 920                 925

His Met Tyr Trp Asn Trp Pro Gly Thr Ile Arg Val Pro Ala Pro Cys
    930                 935                 940

Lys Tyr Ala His Lys Leu Ala Phe Leu Ser Gly His Ile Leu His His
945                 950                 955                 960

Glu Pro Ala Ile Gln Leu Cys Glu Asn Leu Phe Phe Leu
                965                 970

<210> SEQ ID NO 350
<211> LENGTH: 861
<212> TYPE: PRT
<213> ORGANISM: Artificial Sequence
<220> FEATURE:
<223> OTHER INFORMATION: HIWI

<400> SEQUENCE: 350

Met Thr Gly Arg Ala Arg Ala Arg Ala Arg Gly Arg Ala Arg Gly Gln
1               5                   10                  15

Glu Thr Ala Gln Leu Val Gly Ser Thr Ala Ser Gln Gln Pro Gly Tyr
            20                  25                  30

Ile Gln Pro Arg Pro Gln Pro Pro Ala Glu Gly Glu Leu Phe Gly
        35                  40                  45

Arg Gly Arg Gln Arg Gly Thr Ala Gly Gly Thr Ala Lys Ser Gln Gly
    50                  55                  60

Leu Gln Ile Ser Ala Gly Phe Gln Glu Leu Ser Leu Ala Glu Arg Gly
65                  70                  75                  80

Gly Arg Arg Arg Asp Phe His Asp Leu Gly Val Asn Thr Arg Gln Asn
                85                  90                  95

Leu Asp His Val Lys Glu Ser Lys Thr Gly Ser Ser Gly Ile Ile Val
            100                 105                 110

Arg Leu Ser Thr Asn His Phe Arg Leu Thr Ser Arg Pro Gln Trp Ala
        115                 120                 125

Leu Tyr Gln Tyr His Ile Asp Tyr Asn Pro Leu Met Glu Ala Arg Arg
    130                 135                 140

Leu Arg Ser Ala Leu Leu Phe Gln His Glu Asp Leu Ile Gly Lys Cys
145                 150                 155                 160

His Ala Phe Asp Gly Thr Ile Leu Phe Leu Pro Lys Arg Leu Gln Gln
                165                 170                 175

Lys Val Thr Glu Val Phe Ser Lys Thr Arg Asn Gly Glu Asp Val Arg
            180                 185                 190

Ile Thr Ile Thr Leu Thr Asn Glu Leu Pro Pro Thr Ser Pro Thr Cys
        195                 200                 205

Leu Gln Phe Tyr Asn Ile Ile Phe Arg Arg Leu Leu Lys Ile Met Asn
    210                 215                 220

Leu Gln Gln Ile Gly Arg Asn Tyr Tyr Asn Pro Asn Asp Pro Ile Asp
225                 230                 235                 240

Ile Pro Ser His Arg Leu Val Ile Trp Pro Gly Phe Thr Thr Ser Ile
                245                 250                 255

-continued

```
Leu Gln Tyr Glu Asn Ser Ile Met Leu Cys Thr Asp Val Ser His Lys
                260                 265                 270

Val Leu Arg Ser Glu Thr Val Leu Asp Phe Met Phe Asn Phe Tyr His
            275                 280                 285

Gln Thr Glu Glu His Lys Phe Gln Glu Gln Val Ser Lys Glu Leu Ile
        290                 295                 300

Gly Leu Val Val Leu Thr Lys Tyr Asn Asn Lys Thr Tyr Arg Val Asp
305                 310                 315                 320

Asp Ile Asp Trp Asp Gln Asn Pro Lys Ser Thr Phe Lys Ala Asp
                325                 330                 335

Gly Ser Glu Val Ser Phe Leu Glu Tyr Tyr Arg Lys Gln Tyr Asn Gln
            340                 345                 350

Glu Ile Thr Asp Leu Lys Gln Pro Val Leu Val Ser Gln Pro Lys Arg
        355                 360                 365

Arg Arg Gly Pro Gly Gly Thr Leu Pro Gly Pro Ala Met Leu Ile Pro
370                 375                 380

Glu Leu Cys Tyr Leu Thr Gly Leu Thr Asp Lys Met Arg Asn Asp Phe
385                 390                 395                 400

Asn Val Met Lys Asp Leu Ala Val His Thr Arg Leu Thr Pro Glu Gln
                405                 410                 415

Arg Gln Arg Glu Val Gly Arg Leu Ile Asp Tyr Ile His Lys Asn Asp
            420                 425                 430

Asn Val Gln Arg Glu Leu Arg Asp Trp Gly Leu Ser Phe Asp Ser Asn
        435                 440                 445

Leu Leu Ser Phe Ser Gly Arg Ile Leu Gln Thr Glu Lys Ile His Gln
450                 455                 460

Gly Gly Lys Thr Phe Asp Tyr Asn Pro Gln Phe Ala Asp Trp Ser Lys
465                 470                 475                 480

Glu Thr Arg Gly Ala Pro Leu Ile Ser Val Lys Pro Leu Asp Asn Trp
            485                 490                 495

Leu Leu Ile Tyr Thr Arg Arg Asn Tyr Glu Ala Ala Asn Ser Leu Ile
        500                 505                 510

Gln Asn Leu Phe Lys Val Thr Pro Ala Met Gly Met Gln Met Arg Lys
    515                 520                 525

Ala Ile Met Ile Glu Val Asp Asp Arg Thr Glu Ala Tyr Leu Arg Val
530                 535                 540

Leu Gln Gln Lys Val Thr Ala Asp Thr Gln Ile Val Val Cys Leu Leu
545                 550                 555                 560

Ser Ser Asn Arg Lys Asp Lys Tyr Asp Ala Ile Lys Lys Tyr Leu Cys
                565                 570                 575

Thr Asp Cys Pro Thr Pro Ser Gln Cys Val Val Ala Arg Thr Leu Gly
            580                 585                 590

Lys Gln Gln Thr Val Met Ala Ile Ala Thr Lys Ile Ala Leu Gln Met
        595                 600                 605

Asn Cys Lys Met Gly Gly Glu Leu Trp Arg Val Asp Ile Pro Leu Lys
    610                 615                 620

Leu Val Met Ile Val Gly Ile Asp Cys Tyr His Asp Met Thr Ala Gly
625                 630                 635                 640

Arg Arg Ser Ile Ala Gly Phe Val Ala Ser Ile Asn Glu Gly Met Thr
                645                 650                 655

Arg Trp Phe Ser Arg Cys Ile Phe Gln Asp Arg Gly Gln Glu Leu Val
            660                 665                 670

Asp Gly Leu Lys Val Cys Leu Gln Ala Ala Leu Arg Ala Trp Asn Ser
```

```
                        675                 680                 685
Cys Asn Glu Tyr Met Pro Ser Arg Ile Ile Val Tyr Arg Asp Gly Val
    690                 695                 700

Gly Asp Gly Gln Leu Lys Thr Leu Val Asn Tyr Glu Val Pro Gln Phe
705                 710                 715                 720

Leu Asp Cys Leu Lys Ser Ile Gly Arg Gly Tyr Asn Pro Arg Leu Thr
                    725                 730                 735

Val Ile Val Val Lys Lys Arg Val Asn Thr Arg Phe Phe Ala Gln Ser
                740                 745                 750

Gly Gly Arg Leu Gln Asn Pro Leu Pro Gly Thr Val Ile Asp Val Glu
            755                 760                 765

Val Thr Arg Pro Glu Trp Tyr Asp Phe Phe Ile Val Ser Gln Ala Val
770                 775                 780

Arg Ser Gly Ser Val Ser Pro Thr His Tyr Asn Val Ile Tyr Asp Asn
785                 790                 795                 800

Ser Gly Leu Lys Pro Asp His Ile Gln Arg Leu Thr Tyr Lys Leu Cys
                    805                 810                 815

His Ile Tyr Tyr Asn Trp Pro Gly Val Ile Arg Val Pro Ala Pro Cys
                820                 825                 830

Gln Tyr Ala His Lys Leu Ala Phe Leu Val Gly Gln Ser Ile His Arg
            835                 840                 845

Glu Pro Asn Leu Ser Leu Ser Asn Arg Leu Tyr Tyr Leu
        850                 855                 860

<210> SEQ ID NO 351
<211> LENGTH: 1544
<212> TYPE: PRT
<213> ORGANISM: Artificial Sequence
<220> FEATURE:
<223> OTHER INFORMATION: PLU-1

<400> SEQUENCE: 351

Met Glu Ala Ala Thr Thr Leu His Pro Gly Pro Arg Pro Ala Leu Pro
1               5                   10                  15

Leu Gly Gly Pro Gly Pro Leu Gly Glu Phe Leu Pro Pro Glu Cys
                20                  25                  30

Pro Val Phe Glu Pro Ser Trp Glu Glu Phe Ala Asp Pro Phe Ala Phe
            35                  40                  45

Ile His Lys Ile Arg Pro Ile Ala Glu Gln Thr Gly Ile Cys Lys Val
        50                  55                  60

Arg Pro Pro Pro Asp Trp Gln Pro Pro Phe Ala Cys Asp Val Asp Lys
65                  70                  75                  80

Leu His Phe Thr Pro Arg Ile Gln Arg Leu Asn Glu Leu Glu Ala Gln
                85                  90                  95

Thr Arg Val Lys Leu Asn Phe Leu Asp Gln Ile Ala Lys Tyr Trp Glu
            100                 105                 110

Leu Gln Gly Ser Thr Leu Lys Ile Pro His Val Glu Arg Lys Ile Leu
        115                 120                 125

Asp Leu Phe Gln Leu Asn Lys Leu Val Ala Glu Glu Gly Gly Phe Ala
    130                 135                 140

Val Val Cys Lys Asp Arg Lys Trp Thr Lys Ile Ala Thr Lys Met Gly
145                 150                 155                 160

Phe Ala Pro Gly Lys Ala Val Gly Ser His Ile Arg Gly His Tyr Glu
                165                 170                 175

Arg Ile Leu Asn Pro Tyr Asn Leu Phe Leu Ser Gly Asp Ser Leu Arg
```

```
            180                 185                 190
Cys Leu Gln Lys Pro Asn Leu Thr Thr Asp Thr Lys Asp Lys Glu Tyr
            195                 200                 205
Lys Pro His Asp Ile Pro Gln Arg Gln Ser Val Gln Pro Ser Glu Thr
            210                 215                 220
Cys Pro Pro Ala Arg Ala Lys Arg Met Arg Ala Glu Ala Met Asn
225                 230                 235                 240
Ile Lys Ile Glu Pro Glu Thr Thr Glu Ala Arg Thr His Asn Leu
                245                 250                 255
Arg Arg Arg Met Gly Cys Pro Thr Pro Lys Cys Glu Asn Glu Lys Glu
                260                 265                 270
Met Lys Ser Ser Ile Lys Gln Glu Pro Ile Glu Arg Lys Asp Tyr Ile
                275                 280                 285
Val Glu Asn Glu Lys Glu Lys Pro Lys Ser Arg Ser Lys Lys Ala Thr
                290                 295                 300
Asn Ala Val Asp Leu Tyr Val Cys Leu Leu Cys Gly Ser Gly Asn Asp
305                 310                 315                 320
Glu Asp Arg Leu Leu Leu Cys Asp Gly Cys Asp Asp Ser Tyr His Thr
                325                 330                 335
Phe Cys Leu Ile Pro Pro Leu His Asp Val Pro Lys Gly Asp Trp Arg
                340                 345                 350
Cys Pro Lys Cys Leu Ala Gln Glu Cys Ser Lys Pro Gln Glu Ala Phe
                355                 360                 365
Gly Phe Glu Gln Ala Ala Arg Asp Tyr Thr Leu Arg Thr Phe Gly Glu
                370                 375                 380
Met Ala Asp Ala Phe Lys Ser Asp Tyr Phe Asn Met Pro Val His Met
385                 390                 395                 400
Val Pro Thr Glu Leu Val Glu Lys Glu Phe Trp Arg Leu Val Ser Thr
                405                 410                 415
Ile Glu Glu Asp Val Thr Val Glu Tyr Gly Ala Asp Ile Ala Ser Lys
                420                 425                 430
Glu Phe Gly Ser Gly Phe Pro Val Arg Asp Gly Lys Ile Lys Leu Ser
                435                 440                 445
Pro Glu Glu Glu Tyr Leu Asp Ser Gly Trp Asn Leu Asn Asn Met
450                 455                 460
Pro Val Met Glu Gln Ser Val Leu Ala His Ile Thr Ala Asp Ile Cys
465                 470                 475                 480
Gly Met Lys Leu Pro Trp Leu Tyr Val Gly Met Cys Phe Ser Ser Phe
                485                 490                 495
Cys Trp His Ile Glu Asp His Trp Ser Tyr Ser Ile Asn Tyr Leu His
                500                 505                 510
Trp Gly Glu Pro Lys Thr Trp Tyr Gly Val Pro Gly Tyr Ala Ala Glu
                515                 520                 525
Gln Leu Glu Asn Val Met Lys Lys Leu Ala Pro Glu Leu Phe Val Ser
                530                 535                 540
Gln Pro Asp Leu Leu His Gln Leu Val Thr Ile Met Asn Pro Asn Thr
545                 550                 555                 560
Leu Met Thr His Glu Val Pro Val Tyr Arg Thr Asn Gln Cys Ala Gly
                565                 570                 575
Glu Phe Val Ile Thr Phe Pro Arg Ala Tyr His Ser Gly Phe Asn Gln
                580                 585                 590
Gly Phe Asn Phe Ala Glu Ala Val Asn Phe Cys Thr Val Asp Trp Leu
                595                 600                 605
```

-continued

```
Pro Leu Gly Arg Gln Cys Val Glu His Tyr Arg Leu Leu His Arg Tyr
    610                 615                 620

Cys Val Phe Ser His Asp Glu Met Ile Cys Lys Met Ala Ser Lys Ala
625                 630                 635                 640

Asp Val Leu Asp Val Val Ala Ser Thr Val Gln Lys Asp Met Ala
                645                 650                 655

Ile Met Ile Glu Asp Glu Lys Ala Leu Arg Glu Thr Val Arg Lys Leu
            660                 665                 670

Gly Val Ile Asp Ser Glu Arg Met Asp Phe Glu Leu Leu Pro Asp Asp
        675                 680                 685

Glu Arg Gln Cys Val Lys Cys Lys Thr Thr Cys Phe Met Ser Ala Ile
    690                 695                 700

Ser Cys Ser Cys Lys Pro Gly Leu Leu Val Cys Leu His His Val Lys
705                 710                 715                 720

Glu Leu Cys Ser Cys Pro Pro Tyr Lys Tyr Lys Leu Arg Tyr Arg Tyr
                725                 730                 735

Thr Leu Asp Asp Leu Tyr Pro Met Met Asn Ala Leu Lys Leu Arg Ala
            740                 745                 750

Glu Ser Tyr Asn Glu Trp Ala Leu Asn Val Asn Glu Ala Leu Glu Ala
        755                 760                 765

Lys Ile Asn Lys Lys Lys Ser Leu Val Ser Phe Lys Ala Leu Ile Glu
    770                 775                 780

Glu Ser Glu Met Lys Lys Phe Pro Asp Asn Asp Leu Leu Arg His Leu
785                 790                 795                 800

Arg Leu Val Thr Gln Asp Ala Glu Lys Cys Ala Ser Val Ala Gln Gln
                805                 810                 815

Leu Leu Asn Gly Lys Arg Gln Thr Arg Tyr Arg Ser Gly Gly Gly Lys
            820                 825                 830

Ser Gln Asn Gln Leu Thr Val Asn Glu Leu Arg Gln Phe Val Thr Gln
        835                 840                 845

Leu Tyr Ala Leu Pro Cys Val Leu Ser Gln Thr Pro Leu Leu Lys Asp
    850                 855                 860

Leu Leu Asn Arg Val Glu Asp Phe Gln Gln His Ser Gln Lys Leu Leu
865                 870                 875                 880

Ser Glu Glu Thr Pro Ser Ala Ala Glu Leu Gln Asp Leu Leu Asp Val
                885                 890                 895

Ser Phe Glu Phe Asp Val Glu Leu Pro Gln Leu Ala Glu Met Arg Ile
            900                 905                 910

Arg Leu Glu Gln Ala Arg Trp Leu Glu Glu Val Gln Gln Ala Cys Leu
    915                 920                 925

Asp Pro Ser Ser Leu Thr Leu Asp Asp Met Arg Arg Leu Ile Asp Leu
930                 935                 940

Gly Val Gly Leu Ala Pro Tyr Ser Ala Val Glu Lys Ala Met Ala Arg
945                 950                 955                 960

Leu Gln Glu Leu Leu Thr Val Ser Glu His Trp Asp Asp Lys Ala Lys
                965                 970                 975

Ser Leu Leu Lys Ala Arg Pro Arg His Ser Leu Asn Ser Leu Ala Thr
            980                 985                 990

Ala Val Lys Glu Ile Glu Glu Ile Pro Ala Tyr Leu Pro Asn Gly Ala
        995                 1000                1005

Ala Leu Lys Asp Ser Val Gln Arg Ala Arg Asp Trp Leu Gln Asp
    1010                1015                1020
```

Val Glu Gly Leu Gln Ala Gly Gly Arg Val Pro Val Leu Asp Thr
1025             1030                 1035

Leu Ile Glu Leu Val Thr Arg Gly Arg Ser Ile Pro Val His Leu
1040             1045                 1050

Asn Ser Leu Pro Arg Leu Glu Thr Leu Val Ala Glu Val Gln Ala
1055             1060                 1065

Trp Lys Glu Cys Ala Val Asn Thr Phe Leu Thr Glu Asn Ser Pro
1070             1075                 1080

Tyr Ser Leu Leu Glu Val Leu Cys Pro Arg Cys Asp Ile Gly Leu
1085             1090                 1095

Leu Gly Leu Lys Arg Lys Gln Arg Lys Leu Lys Glu Pro Leu Pro
1100             1105                 1110

Asn Gly Lys Lys Lys Ser Thr Lys Leu Glu Ser Leu Ser Asp Leu
1115             1120                 1125

Glu Arg Ala Leu Thr Glu Ser Lys Glu Thr Ala Ser Ala Met Ala
1130             1135                 1140

Thr Leu Gly Glu Ala Arg Leu Arg Glu Met Glu Ala Leu Gln Ser
1145             1150                 1155

Leu Arg Leu Ala Asn Glu Gly Lys Leu Leu Ser Pro Leu Gln Asp
1160             1165                 1170

Val Asp Ile Lys Ile Cys Leu Cys Gln Lys Ala Pro Ala Ala Pro
1175             1180                 1185

Met Ile Gln Cys Glu Leu Cys Arg Asp Ala Phe His Thr Ser Cys
1190             1195                 1200

Val Ala Val Pro Ser Ile Ser Gln Gly Leu Arg Ile Trp Leu Cys
1205             1210                 1215

Pro His Cys Arg Arg Ser Glu Lys Pro Pro Leu Glu Lys Ile Leu
1220             1225                 1230

Pro Leu Leu Ala Ser Leu Gln Arg Ile Arg Val Arg Leu Pro Glu
1235             1240                 1245

Gly Asp Ala Leu Arg Tyr Met Ile Glu Arg Thr Val Asn Trp Gln
1250             1255                 1260

His Arg Ala Gln Gln Leu Leu Ser Ser Gly Asn Leu Lys Phe Val
1265             1270                 1275

Gln Asp Arg Val Gly Ser Gly Leu Leu Tyr Ser Arg Trp Gln Ala
1280             1285                 1290

Ser Ala Gly Gln Val Ser Asp Thr Asn Lys Val Ser Gln Pro Pro
1295             1300                 1305

Gly Thr Thr Ser Phe Ser Leu Pro Asp Asp Trp Asp Asn Arg Thr
1310             1315                 1320

Ser Tyr Leu His Ser Pro Phe Ser Thr Gly Arg Ser Cys Ile Pro
1325             1330                 1335

Leu His Gly Val Ser Pro Glu Val Asn Glu Leu Leu Met Glu Ala
1340             1345                 1350

Gln Leu Leu Gln Val Ser Leu Pro Glu Ile Gln Glu Leu Tyr Gln
1355             1360                 1365

Thr Leu Leu Ala Lys Pro Ser Pro Ala Gln Gln Thr Asp Arg Ser
1370             1375                 1380

Ser Pro Val Arg Pro Ser Ser Glu Lys Asn Asp Cys Cys Arg Gly
1385             1390                 1395

Lys Arg Asp Gly Ile Asn Ser Leu Glu Arg Lys Leu Lys Arg Arg
1400             1405                 1410

Leu Glu Arg Glu Gly Leu Ser Ser Glu Arg Trp Glu Arg Val Lys

```
                1415                1420                1425

Lys  Met  Arg  Thr  Pro  Lys  Lys  Lys  Ile  Lys  Leu  Ser  His  Pro
         1430                1435                1440

Lys  Asp  Met  Asn  Asn  Phe  Lys  Leu  Glu  Arg  Glu  Arg  Ser  Tyr  Glu
         1445                1450                1455

Leu  Val  Arg  Ser  Ala  Glu  Thr  His  Ser  Leu  Pro  Ser  Asp  Thr  Ser
         1460                1465                1470

Tyr  Ser  Glu  Gln  Glu  Asp  Ser  Glu  Asp  Glu  Asp  Ala  Ile  Cys  Pro
         1475                1480                1485

Ala  Val  Ser  Cys  Leu  Gln  Pro  Glu  Gly  Asp  Glu  Val  Asp  Trp  Val
         1490                1495                1500

Gln  Cys  Asp  Gly  Ser  Cys  Asn  Gln  Trp  Phe  His  Gln  Val  Cys  Val
         1505                1510                1515

Gly  Val  Ser  Pro  Glu  Met  Ala  Glu  Lys  Glu  Asp  Tyr  Ile  Cys  Val
         1520                1525                1530

Arg  Cys  Thr  Val  Lys  Asp  Ala  Pro  Ser  Arg  Lys
         1535                1540

<210> SEQ ID NO 352
<211> LENGTH: 698
<212> TYPE: PRT
<213> ORGANISM: Artificial Sequence
<220> FEATURE:
<223> OTHER INFORMATION: TSGA10

<400> SEQUENCE: 352

Met  Met  Arg  Ser  Arg  Ser  Lys  Ser  Pro  Arg  Arg  Pro  Ser  Pro  Thr  Ala
1                    5                    10                   15

Arg  Gly  Ala  Asn  Cys  Asp  Val  Glu  Leu  Leu  Lys  Thr  Thr  Thr  Arg  Asp
              20                   25                   30

Arg  Glu  Glu  Leu  Lys  Cys  Met  Leu  Glu  Lys  Tyr  Glu  Arg  His  Leu  Ala
         35                   40                   45

Glu  Ile  Gln  Gly  Asn  Val  Lys  Val  Leu  Lys  Ser  Glu  Arg  Asp  Lys  Ile
    50                   55                   60

Phe  Leu  Leu  Tyr  Glu  Gln  Ala  Gln  Glu  Glu  Ile  Thr  Arg  Leu  Arg  Arg
65                   70                   75                   80

Glu  Met  Met  Lys  Ser  Cys  Lys  Ser  Pro  Lys  Ser  Thr  Thr  Ala  His  Ala
                  85                   90                   95

Ile  Leu  Arg  Arg  Val  Glu  Thr  Glu  Arg  Asp  Val  Ala  Phe  Thr  Asp  Leu
             100                  105                  110

Arg  Arg  Met  Thr  Thr  Glu  Arg  Asp  Ser  Leu  Arg  Glu  Arg  Leu  Lys  Ile
         115                  120                  125

Ala  Gln  Glu  Thr  Ala  Phe  Asn  Glu  Lys  Ala  His  Leu  Glu  Gln  Arg  Ile
    130                  135                  140

Glu  Glu  Leu  Glu  Cys  Thr  Val  His  Asn  Leu  Asp  Asp  Glu  Arg  Met  Glu
145                  150                  155                  160

Gln  Met  Ser  Asn  Met  Thr  Leu  Met  Lys  Glu  Thr  Ile  Ser  Thr  Val  Glu
                 165                  170                  175

Lys  Glu  Met  Lys  Ser  Leu  Ala  Arg  Lys  Ala  Met  Asp  Thr  Glu  Ser  Glu
             180                  185                  190

Leu  Gly  Arg  Gln  Lys  Ala  Glu  Asn  Asn  Ser  Leu  Arg  Leu  Leu  Tyr  Glu
         195                  200                  205

Asn  Thr  Glu  Lys  Asp  Leu  Ser  Asp  Thr  Gln  Arg  His  Leu  Ala  Lys  Lys
    210                  215                  220

Lys  Tyr  Glu  Leu  Gln  Leu  Thr  Gln  Glu  Lys  Ile  Met  Cys  Leu  Asp  Glu
```

```
                225                 230                 235                 240
Lys Ile Asp Asn Phe Thr Arg Gln Asn Ile Ala Gln Arg Glu Glu Ile
                245                 250                 255

Ser Ile Leu Gly Gly Thr Leu Asn Asp Leu Ala Lys Glu Lys Glu Cys
                260                 265                 270

Leu Gln Ala Cys Leu Asp Lys Lys Ser Glu Asn Ile Ala Ser Leu Gly
                275                 280                 285

Glu Ser Leu Ala Met Lys Glu Lys Thr Ile Ser Gly Met Lys Asn Ile
                290                 295                 300

Ile Ala Glu Met Glu Gln Ala Ser Arg Gln Cys Thr Glu Ala Leu Ile
305                 310                 315                 320

Val Cys Glu Gln Asp Val Ser Arg Met Arg Arg Gln Leu Asp Glu Thr
                325                 330                 335

Asn Asp Glu Leu Ala Gln Ile Ala Arg Glu Arg Asp Ile Leu Ala His
                340                 345                 350

Asp Asn Asp Asn Leu Gln Glu Gln Phe Ala Lys Ala Lys Gln Glu Asn
                355                 360                 365

Gln Ala Leu Ser Lys Lys Leu Asn Asp Thr His Asn Glu Leu Asn Asp
                370                 375                 380

Ile Lys Gln Lys Val Gln Asp Thr Asn Leu Glu Val Asn Lys Leu Lys
385                 390                 395                 400

Asn Ile Leu Lys Ser Glu Glu Ser Glu Asn Arg Gln Met Met Glu Gln
                405                 410                 415

Leu Arg Lys Ala Asn Glu Asp Ala Glu Asn Trp Glu Asn Lys Ala Arg
                420                 425                 430

Gln Ser Glu Ala Asp Asn Asn Thr Leu Lys Leu Glu Leu Ile Thr Ala
                435                 440                 445

Glu Ala Glu Gly Asn Arg Leu Lys Glu Lys Val Asp Ser Leu Asn Arg
                450                 455                 460

Glu Val Glu Gln His Leu Asn Ala Glu Arg Ser Tyr Lys Ser Gln Ile
465                 470                 475                 480

Ser Thr Leu His Lys Ser Val Val Lys Met Glu Glu Glu Leu Gln Lys
                485                 490                 495

Val Gln Phe Glu Lys Val Ser Ala Leu Ala Asp Leu Ser Ser Thr Arg
                500                 505                 510

Glu Leu Cys Ile Lys Leu Asp Ser Ser Lys Glu Leu Leu Asn Arg Gln
                515                 520                 525

Leu Val Ala Lys Asp Gln Glu Ile Glu Met Arg Glu Asn Glu Leu Asp
                530                 535                 540

Ser Ala His Ser Glu Ile Glu Leu Leu Arg Ser Gln Met Ala Asn Glu
545                 550                 555                 560

Arg Ile Ser Met Gln Asn Leu Glu Ala Leu Val Ala Asn Arg Asp
                565                 570                 575

Lys Glu Tyr Gln Ser Gln Ile Ala Leu Gln Glu Lys Glu Ser Glu Ile
                580                 585                 590

Gln Leu Leu Lys Glu His Leu Cys Leu Ala Glu Asn Lys Met Ala Ile
                595                 600                 605

Gln Ser Arg Asp Val Ala Gln Phe Arg Asn Val Thr Gln Leu Glu
                610                 615                 620

Ala Asp Leu Asp Ile Thr Lys Arg Gln Leu Gly Thr Glu Arg Phe Glu
625                 630                 635                 640

Arg Glu Arg Ala Val Gln Glu Leu Arg Arg Gln Asn Tyr Ser Ser Asn
                645                 650                 655
```

```
Ala Tyr His Met Ser Ser Thr Met Lys Pro Asn Thr Lys Cys His Ser
            660                 665                 670

Pro Glu Arg Ala His His Arg Ser Pro Asp Arg Gly Leu Asp Arg Ser
            675                 680                 685

Leu Glu Glu Asn Leu Cys Tyr Arg Asp Phe
            690                 695
```

<210> SEQ ID NO 353
<211> LENGTH: 257
<212> TYPE: PRT
<213> ORGANISM: Artificial Sequence
<220> FEATURE:
<223> OTHER INFORMATION: ODF-4

<400> SEQUENCE: 353

```
Met Asp Ala Glu Tyr Ser Gly Asn Glu Phe Pro Arg Ser Glu Gly Glu
1               5                   10                  15

Arg Asp Gln His Gln Arg Pro Gly Lys Glu Arg Lys Ser Gly Glu Ala
            20                  25                  30

Gly Trp Gly Thr Gly Glu Leu Gly Gln Asp Gly Arg Leu Leu Ser Ser
            35                  40                  45

Thr Leu Ser Leu Ser Ser Asn Arg Ser Leu Gly Gln Arg Gln Asn Ser
50                  55                  60

Pro Leu Pro Phe Gln Trp Arg Ile Thr His Ser Phe Arg Trp Met Ala
65                  70                  75                  80

Gln Val Leu Ala Ser Glu Leu Ser Leu Val Ala Phe Ile Leu Leu Leu
                85                  90                  95

Val Val Ala Phe Ser Lys Lys Trp Leu Asp Leu Ser Arg Ser Leu Phe
            100                 105                 110

Tyr Gln Arg Trp Pro Val Asp Val Ser Asn Arg Ile His Thr Ser Ala
            115                 120                 125

His Val Met Ser Met Gly Leu Leu His Phe Tyr Lys Ser Arg Ser Cys
        130                 135                 140

Ser Asp Leu Glu Asn Gly Lys Val Thr Phe Ile Phe Ser Thr Leu Met
145                 150                 155                 160

Leu Phe Pro Ile Asn Ile Trp Ile Phe Glu Leu Glu Arg Asn Val Ser
                165                 170                 175

Ile Pro Ile Gly Trp Ser Tyr Phe Ile Gly Trp Leu Val Leu Ile Leu
            180                 185                 190

Tyr Phe Thr Cys Ala Ile Leu Cys Tyr Phe Asn His Lys Ser Phe Trp
            195                 200                 205

Ser Leu Ile Leu Ser His Pro Ser Gly Ala Val Ser Cys Ser Ser Ser
        210                 215                 220

Phe Gly Ser Val Glu Glu Ser Pro Arg Ala Gln Thr Ile Thr Asp Thr
225                 230                 235                 240

Pro Ile Thr Gln Glu Gly Val Leu Asp Pro Glu Gln Lys Asp Thr His
                245                 250                 255

Val
```

<210> SEQ ID NO 354
<211> LENGTH: 151
<212> TYPE: PRT
<213> ORGANISM: Artificial Sequence
<220> FEATURE:
<223> OTHER INFORMATION: SP17

<400> SEQUENCE: 354

```
Met Ser Ile Pro Phe Ser Asn Thr His Tyr Arg Ile Pro Gln Gly Phe
1               5                   10                  15

Gly Asn Leu Leu Glu Gly Leu Thr Arg Glu Ile Leu Arg Glu Gln Pro
                20                  25                  30

Asp Asn Ile Pro Ala Phe Ala Ala Tyr Phe Glu Ser Leu Leu Glu
            35                  40                  45

Lys Arg Glu Lys Thr Asn Phe Asp Pro Ala Glu Trp Gly Ser Lys Val
50                  55                  60

Glu Asp Arg Phe Tyr Asn Asn His Ala Phe Glu Gln Glu Pro Pro
65                  70                  75                  80

Glu Lys Ser Asp Pro Lys Gln Glu Glu Ser Gln Ile Ser Gly Lys Glu
                85                  90                  95

Glu Glu Thr Ser Val Thr Ile Leu Asp Ser Ser Glu Glu Asp Lys Glu
                100                 105                 110

Lys Glu Glu Val Ala Ala Val Lys Ile Gln Ala Ala Phe Arg Gly His
            115                 120                 125

Ile Ala Arg Glu Glu Ala Lys Lys Met Lys Thr Asn Ser Leu Gln Asn
        130                 135                 140

Glu Glu Lys Glu Glu Asn Lys
145                 150

<210> SEQ ID NO 355
<211> LENGTH: 1116
<212> TYPE: PRT
<213> ORGANISM: Artificial Sequence
<220> FEATURE:
<223> OTHER INFORMATION: RHOXF-2

<400> SEQUENCE: 355

Met Ala Ala Asp Leu Asn Leu Glu Trp Ile Ser Leu Pro Arg Ser Trp
1               5                   10                  15

Thr Tyr Gly Ile Thr Arg Gly Gly Arg Val Phe Phe Ile Asn Glu Glu
                20                  25                  30

Ala Lys Ser Thr Thr Trp Leu His Pro Val Thr Gly Glu Ala Val Val
            35                  40                  45

Thr Gly His Arg Arg Gln Ser Thr Asp Leu Pro Thr Gly Trp Glu Glu
50                  55                  60

Ala Tyr Thr Phe Glu Gly Ala Arg Tyr Tyr Ile Asn His Asn Glu Arg
65                  70                  75                  80

Lys Val Thr Cys Lys His Pro Val Thr Gly Gln Pro Ser Gln Asp Asn
                85                  90                  95

Cys Ile Phe Val Val Asn Glu Gln Thr Val Ala Thr Met Thr Ser Glu
                100                 105                 110

Glu Lys Lys Glu Arg Pro Ile Ser Met Ile Asn Glu Ala Ser Asn Tyr
            115                 120                 125

Asn Val Thr Ser Asp Tyr Ala Val His Pro Met Ser Pro Val Gly Arg
        130                 135                 140

Thr Ser Arg Ala Ser Lys Lys Val His Asn Phe Gly Lys Arg Ser Asn
145                 150                 155                 160

Ser Ile Lys Arg Asn Pro Asn Ala Pro Val Val Arg Arg Gly Trp Leu
                165                 170                 175

Tyr Lys Gln Asp Ser Thr Gly Met Lys Leu Trp Lys Lys Arg Trp Phe
                180                 185                 190

Val Leu Ser Asp Leu Cys Leu Phe Tyr Tyr Arg Asp Glu Lys Glu Glu
            195                 200                 205
```

```
Gly Ile Leu Gly Ser Ile Leu Leu Pro Ser Phe Gln Ile Ala Leu Leu
    210                 215                 220

Thr Ser Glu Asp His Ile Asn Arg Lys Tyr Ala Phe Lys Ala Ala His
225                 230                 235                 240

Pro Asn Met Arg Thr Tyr Tyr Phe Cys Thr Asp Thr Gly Lys Glu Met
                245                 250                 255

Glu Leu Trp Met Lys Ala Met Leu Asp Ala Ala Leu Val Gln Thr Glu
            260                 265                 270

Pro Val Lys Arg Val Asp Lys Ile Thr Ser Glu Asn Ala Pro Thr Lys
        275                 280                 285

Glu Thr Asn Asn Ile Pro Asn His Arg Val Leu Ile Lys Pro Glu Ile
    290                 295                 300

Gln Asn Asn Gln Lys Asn Lys Glu Met Ser Lys Ile Glu Glu Lys Lys
305                 310                 315                 320

Ala Leu Glu Ala Glu Lys Tyr Gly Phe Gln Lys Asp Gly Gln Asp Arg
                325                 330                 335

Pro Leu Thr Lys Ile Asn Ser Val Lys Leu Asn Ser Leu Pro Ser Glu
            340                 345                 350

Tyr Glu Ser Gly Ser Ala Cys Pro Ala Gln Thr Val His Tyr Arg Pro
        355                 360                 365

Ile Asn Leu Ser Ser Ser Glu Asn Lys Ile Val Asn Val Ser Leu Ala
    370                 375                 380

Asp Leu Arg Gly Gly Asn Arg Pro Asn Thr Gly Pro Leu Tyr Thr Glu
385                 390                 395                 400

Ala Asp Arg Val Ile Gln Arg Thr Asn Ser Met Gln Gln Leu Glu Gln
                405                 410                 415

Trp Ile Lys Ile Gln Lys Gly Arg Gly His Glu Glu Gly Thr Arg Gly
            420                 425                 430

Val Ile Ser Tyr Gln Thr Leu Pro Arg Asn Met Pro Ser His Arg Ala
        435                 440                 445

Gln Ile Met Ala Arg Tyr Pro Glu Gly Tyr Arg Thr Leu Pro Arg Asn
    450                 455                 460

Ser Lys Thr Arg Pro Glu Ser Ile Cys Ser Val Thr Pro Ser Thr His
465                 470                 475                 480

Asp Lys Thr Leu Gly Pro Gly Ala Glu Glu Lys Arg Arg Ser Met Arg
                485                 490                 495

Asp Asp Thr Met Trp Gln Leu Tyr Glu Trp Gln Gln Arg Gln Phe Tyr
            500                 505                 510

Asn Lys Gln Ser Thr Leu Pro Arg His Ser Thr Leu Ser Ser Pro Lys
        515                 520                 525

Thr Met Val Asn Ile Ser Asp Gln Thr Met His Ser Ile Pro Thr Ser
    530                 535                 540

Pro Ser His Gly Ser Ile Ala Ala Tyr Gln Gly Tyr Ser Pro Gln Arg
545                 550                 555                 560

Thr Tyr Arg Ser Glu Val Ser Ser Pro Ile Gln Arg Gly Asp Val Thr
                565                 570                 575

Ile Asp Arg Arg His Arg Ala His His Pro Lys His Val Tyr Val Pro
            580                 585                 590

Asp Arg Arg Ser Val Pro Ala Gly Leu Thr Leu Gln Ser Val Ser Pro
        595                 600                 605

Gln Ser Leu Gln Gly Lys Thr Leu Ser Gln Asp Glu Gly Arg Gly Thr
    610                 615                 620
```

-continued

Leu Tyr Lys Tyr Arg Pro Glu Glu Val Asp Ile Asp Ala Lys Leu Ser
625                 630                 635                 640

Arg Leu Cys Glu Gln Asp Lys Val Val His Ala Leu Glu Glu Lys Leu
            645                 650                 655

Gln Gln Leu His Lys Glu Lys Tyr Thr Leu Glu Gln Ala Leu Leu Ser
        660                 665                 670

Ala Ser Gln Glu Ile Glu Met His Ala Asp Asn Pro Ala Ala Ile Gln
    675                 680                 685

Thr Val Val Leu Gln Arg Asp Asp Leu Gln Asn Gly Leu Leu Ser Thr
690                 695                 700

Cys Arg Glu Leu Ser Arg Ala Thr Ala Glu Leu Glu Arg Ala Trp Arg
705                 710                 715                 720

Glu Tyr Asp Lys Leu Glu Tyr Asp Val Thr Val Thr Arg Asn Gln Met
            725                 730                 735

Gln Glu Gln Leu Asp His Leu Gly Glu Val Gln Thr Glu Ser Ala Gly
        740                 745                 750

Ile Gln Arg Ala Gln Ile Gln Lys Glu Leu Trp Arg Ile Gln Asp Val
    755                 760                 765

Met Glu Gly Leu Ser Lys His Lys Gln Gln Arg Gly Thr Thr Glu Ile
770                 775                 780

Gly Met Ile Gly Ser Lys Pro Phe Ser Thr Val Lys Tyr Lys Asn Glu
785                 790                 795                 800

Gly Pro Asp Tyr Arg Leu Tyr Lys Ser Glu Pro Glu Leu Thr Thr Val
            805                 810                 815

Ala Glu Val Asp Glu Ser Asn Gly Glu Glu Lys Ser Glu Pro Val Ser
        820                 825                 830

Glu Ile Glu Thr Ser Val Val Lys Gly Ser His Phe Pro Val Gly Val
    835                 840                 845

Val Pro Pro Arg Ala Lys Ser Pro Thr Pro Glu Ser Ser Thr Ile Ala
850                 855                 860

Ser Tyr Val Thr Leu Arg Lys Thr Lys Lys Met Met Asp Leu Arg Thr
865                 870                 875                 880

Glu Arg Pro Arg Ser Ala Val Glu Gln Leu Cys Leu Ala Glu Ser Thr
            885                 890                 895

Arg Pro Arg Met Thr Val Glu Glu Gln Met Glu Arg Ile Arg Arg His
        900                 905                 910

Gln Gln Ala Cys Leu Arg Glu Lys Lys Lys Gly Leu Asn Val Ile Gly
    915                 920                 925

Ala Ser Asp Gln Ser Pro Leu Gln Ser Pro Ser Asn Leu Arg Asp Asn
930                 935                 940

Pro Phe Arg Thr Thr Gln Thr Arg Arg Arg Asp Asp Lys Glu Leu Asp
945                 950                 955                 960

Thr Ala Ile Arg Glu Asn Asp Val Lys Pro Asp His Glu Thr Pro Ala
            965                 970                 975

Thr Glu Ile Val Gln Leu Lys Glu Thr Glu Pro Gln Asn Val Asp Phe
        980                 985                 990

Ser Lys Glu Leu Lys Lys Thr Glu Asn Ile Ser Tyr Glu Met Leu Phe
    995                 1000                1005

Glu Pro Glu Pro Asn Gly Val Asn Ser Val Glu Met Met Asp Lys
    1010                1015                1020

Glu Arg Asn Lys Asp Lys Met Pro Glu Asp Val Thr Phe Ser Pro
    1025                1030                1035

Gln Asp Glu Thr Gln Thr Ala Asn His Lys Pro Glu Glu His Pro

```
                    1040                1045                1050

Glu Glu Asn Thr Lys Asn Ser Val Asp Glu Gln Glu Glu Thr Val
        1055                1060                1065

Ile Ser Tyr Glu Ser Thr Pro Glu Val Ser Arg Gly Asn Gln Thr
        1070                1075                1080

Met Ala Val Lys Ser Leu Ser Pro Ser Pro Glu Ser Ser Ala Ser
        1085                1090                1095

Pro Val Pro Ser Thr Gln Pro Gln Leu Thr Glu Gly Ser His Phe
        1100                1105                1110

Met Cys Val
        1115

<210> SEQ ID NO 356
<211> LENGTH: 180
<212> TYPE: PRT
<213> ORGANISM: Artificial Sequence
<220> FEATURE:
<223> OTHER INFORMATION: NY-ESO-1

<400> SEQUENCE: 356

Met Gln Ala Glu Gly Arg Gly Thr Gly Gly Ser Thr Gly Asp Ala
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 357
<211> LENGTH: 852
<212> TYPE: PRT
<213> ORGANISM: Artificial Sequence
<220> FEATURE:
<223> OTHER INFORMATION: PIWIL-4

<400> SEQUENCE: 357

Met Ser Gly Arg Ala Arg Val Lys Ala Arg Gly Ile Ala Arg Ser Pro
1               5                   10                  15

Ser Ala Thr Glu Val Gly Arg Ile Gln Ala Ser Pro Leu Pro Arg Ser
            20                  25                  30
```

-continued

```
Val Asp Leu Ser Asn Asn Glu Ala Ser Ser Asn Gly Phe Leu Gly
         35                  40                  45

Thr Ser Arg Ile Ser Thr Asn Asp Lys Tyr Gly Ile Ser Ser Gly Asp
 50                  55                  60

Ala Gly Ser Thr Phe Met Glu Arg Gly Val Lys Asn Lys Gln Asp Phe
 65                  70                  75                  80

Met Asp Leu Ser Ile Cys Thr Arg Glu Lys Leu Ala His Val Arg Asn
                 85                  90                  95

Cys Lys Thr Gly Ser Ser Gly Ile Pro Val Lys Leu Val Thr Asn Leu
             100                 105                 110

Phe Asn Leu Asp Phe Pro Gln Asp Trp Gln Leu Tyr Gln Tyr His Val
             115                 120                 125

Thr Tyr Ile Pro Asp Leu Ala Ser Arg Arg Leu Arg Ile Ala Leu Leu
         130                 135                 140

Tyr Ser His Ser Glu Leu Ser Asn Lys Ala Lys Ala Phe Asp Gly Ala
145                 150                 155                 160

Ile Leu Phe Leu Ser Gln Lys Leu Glu Glu Lys Val Thr Glu Leu Ser
                 165                 170                 175

Ser Glu Thr Gln Arg Gly Glu Thr Ile Lys Met Thr Ile Thr Leu Lys
             180                 185                 190

Arg Glu Leu Pro Ser Ser Ser Pro Val Cys Ile Gln Val Phe Asn Ile
         195                 200                 205

Ile Phe Arg Lys Ile Leu Lys Lys Leu Ser Met Tyr Gln Ile Gly Arg
         210                 215                 220

Asn Phe Tyr Asn Pro Ser Glu Pro Met Glu Ile Pro Gln His Lys Leu
225                 230                 235                 240

Ser Leu Trp Pro Gly Phe Ala Ile Ser Val Ser Tyr Phe Glu Arg Lys
                 245                 250                 255

Leu Leu Phe Ser Ala Asp Val Ser Tyr Lys Val Leu Arg Asn Glu Thr
             260                 265                 270

Val Leu Glu Phe Met Thr Ala Leu Cys Gln Arg Thr Gly Leu Ser Cys
         275                 280                 285

Phe Thr Gln Thr Cys Glu Lys Gln Leu Ile Gly Leu Ile Val Leu Thr
290                 295                 300

Arg Tyr Asn Asn Arg Thr Tyr Ser Ile Asp Asp Ile Asp Trp Ser Val
305                 310                 315                 320

Lys Pro Thr His Thr Phe Gln Lys Arg Asp Gly Thr Glu Ile Thr Tyr
                 325                 330                 335

Val Asp Tyr Tyr Lys Gln Gln Tyr Asp Ile Thr Val Ser Asp Leu Asn
             340                 345                 350

Gln Pro Met Leu Val Ser Leu Leu Lys Lys Arg Asn Asp Asn Ser
         355                 360                 365

Glu Ala Gln Leu Ala His Leu Ile Pro Glu Leu Cys Phe Leu Thr Gly
     370                 375                 380

Leu Thr Asp Gln Ala Thr Ser Asp Phe Gln Leu Met Lys Ala Val Ala
385                 390                 395                 400

Glu Lys Thr Arg Leu Ser Pro Ser Gly Arg Gln Gln Arg Leu Ala Arg
                 405                 410                 415

Leu Val Asp Asn Ile Gln Arg Asn Thr Asn Ala Arg Phe Glu Leu Glu
             420                 425                 430

Thr Trp Gly Leu His Phe Gly Ser Gln Ile Ser Leu Thr Gly Arg Ile
         435                 440                 445

Val Pro Ser Glu Lys Ile Leu Met Gln Asp His Ile Cys Gln Pro Val
```

```
            450                 455                 460
Ser Ala Ala Asp Trp Ser Lys Asp Ile Arg Thr Cys Lys Ile Leu Asn
465                 470                 475                 480

Ala Gln Ser Leu Asn Thr Trp Leu Ile Leu Cys Ser Asp Arg Thr Glu
                485                 490                 495

Tyr Val Ala Glu Ser Phe Leu Asn Cys Leu Arg Arg Val Ala Gly Ser
                500                 505                 510

Met Gly Phe Asn Val Asp Tyr Pro Lys Ile Ile Lys Val Gln Glu Asn
            515                 520                 525

Pro Ala Ala Phe Val Arg Ala Ile Gln Gln Tyr Val Asp Pro Asp Val
        530                 535                 540

Gln Leu Val Met Cys Ile Leu Pro Ser Asn Gln Lys Thr Tyr Tyr Asp
545                 550                 555                 560

Ser Ile Lys Lys Tyr Leu Ser Ser Asp Cys Pro Val Pro Ser Gln Cys
                565                 570                 575

Val Leu Ala Arg Thr Leu Asn Lys Gln Gly Met Met Met Ser Ile Ala
            580                 585                 590

Thr Lys Ile Ala Met Gln Met Thr Cys Lys Leu Gly Gly Glu Leu Trp
        595                 600                 605

Ala Val Glu Ile Pro Leu Lys Ser Leu Met Val Val Gly Ile Asp Val
            610                 615                 620

Cys Lys Asp Ala Leu Ser Lys Asp Val Met Val Val Gly Cys Val Ala
625                 630                 635                 640

Ser Val Asn Pro Arg Ile Thr Arg Trp Phe Ser Arg Cys Ile Leu Gln
                645                 650                 655

Arg Thr Met Thr Asp Val Ala Asp Cys Leu Lys Val Phe Met Thr Gly
            660                 665                 670

Ala Leu Asn Lys Trp Tyr Lys Tyr Asn His Asp Leu Pro Ala Arg Ile
        675                 680                 685

Ile Val Tyr Arg Ala Gly Val Gly Asp Gly Gln Leu Lys Thr Leu Ile
            690                 695                 700

Glu Tyr Glu Val Pro Gln Leu Leu Ser Ser Val Ala Glu Ser Ser Ser
705                 710                 715                 720

Asn Thr Ser Ser Arg Leu Ser Val Ile Val Val Arg Lys Lys Cys Met
                725                 730                 735

Pro Arg Phe Phe Thr Glu Met Asn Arg Thr Val Gln Asn Pro Pro Leu
            740                 745                 750

Gly Thr Val Val Asp Ser Glu Ala Thr Arg Asn Glu Trp Tyr Asp Phe
        755                 760                 765

Tyr Leu Ile Ser Gln Val Ala Cys Arg Gly Thr Val Ser Pro Thr Tyr
    770                 775                 780

Tyr Asn Val Ile Tyr Asp Asp Asn Gly Leu Lys Pro Asp His Met Gln
785                 790                 795                 800

Arg Leu Thr Phe Lys Leu Cys His Leu Tyr Tyr Asn Trp Pro Gly Ile
                805                 810                 815

Val Ser Val Pro Ala Pro Cys Gln Tyr Ala His Lys Leu Thr Phe Leu
            820                 825                 830

Val Ala Gln Ser Ile His Lys Glu Pro Ser Leu Glu Leu Ala Asn His
        835                 840                 845

Leu Phe Tyr Leu
    850

<210> SEQ ID NO 358
```

```
<211> LENGTH: 449
<212> TYPE: PRT
<213> ORGANISM: Artificial Sequence
<220> FEATURE:
<223> OTHER INFORMATION: WT1

<400> SEQUENCE: 358

Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380
```

```
Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 359
<211> LENGTH: 543
<212> TYPE: PRT
<213> ORGANISM: Artificial Sequence
<220> FEATURE:
<223> OTHER INFORMATION: OY-TES-1

<400> SEQUENCE: 359

Met Arg Lys Pro Ala Ala Gly Phe Leu Pro Ser Leu Leu Lys Val Leu
1               5                   10                  15

Leu Leu Pro Leu Ala Pro Ala Ala Gln Asp Ser Thr Gln Ala Ser
            20                  25                  30

Thr Pro Gly Ser Pro Leu Ser Pro Thr Glu Tyr Glu Arg Phe Phe Ala
            35                  40                  45

Leu Leu Thr Pro Thr Trp Lys Ala Glu Thr Thr Cys Arg Leu Arg Ala
50                  55                  60

Thr His Gly Cys Arg Asn Pro Thr Leu Val Gln Leu Asp Gln Tyr Glu
65                  70                  75                  80

Asn His Gly Leu Val Pro Asp Gly Ala Val Cys Ser Asn Leu Pro Tyr
                85                  90                  95

Ala Ser Trp Phe Glu Ser Phe Cys Gln Phe Thr His Tyr Arg Cys Ser
            100                 105                 110

Asn His Val Tyr Tyr Ala Lys Arg Val Leu Cys Ser Gln Pro Val Ser
        115                 120                 125

Ile Leu Ser Pro Asn Thr Leu Lys Glu Ile Glu Ala Ser Ala Glu Val
130                 135                 140

Ser Pro Thr Thr Met Thr Ser Pro Ile Ser Pro His Phe Thr Val Thr
145                 150                 155                 160

Glu Arg Gln Thr Phe Gln Pro Trp Pro Glu Arg Leu Ser Asn Asn Val
                165                 170                 175

Glu Glu Leu Leu Gln Ser Ser Leu Ser Leu Gly Gly Gln Glu Gln Ala
            180                 185                 190

Pro Glu His Lys Gln Glu Gln Gly Val Glu His Arg Gln Glu Pro Thr
        195                 200                 205

Gln Glu His Lys Gln Glu Glu Gly Gln Lys Gln Glu Glu Gln Glu Glu
210                 215                 220

Glu Gln Glu Glu Glu Gly Lys Gln Glu Glu Gln Glu Gly Thr Lys Glu
225                 230                 235                 240

Gly Arg Glu Ala Val Ser Gln Leu Gln Thr Asp Ser Glu Pro Lys Phe
                245                 250                 255

His Ser Glu Ser Leu Ser Ser Asn Pro Ser Ser Phe Ala Pro Arg Val
            260                 265                 270

Arg Glu Val Glu Ser Thr Pro Met Ile Met Glu Asn Ile Gln Glu Leu
        275                 280                 285
```

-continued

Ile Arg Ser Ala Gln Glu Ile Asp Glu Met Asn Glu Ile Tyr Asp Glu
290                 295                 300

Asn Ser Tyr Trp Arg Asn Gln Asn Pro Gly Ser Leu Leu Gln Leu Pro
305                 310                 315                 320

His Thr Glu Ala Leu Leu Val Leu Cys Tyr Ser Ile Val Glu Asn Thr
            325                 330                 335

Cys Ile Ile Thr Pro Thr Ala Lys Ala Trp Lys Tyr Met Glu Glu Glu
            340                 345                 350

Ile Leu Gly Phe Gly Lys Ser Val Cys Asp Ser Leu Gly Arg Arg His
            355                 360                 365

Met Ser Thr Cys Ala Leu Cys Asp Phe Cys Ser Leu Lys Leu Glu Gln
370                 375                 380

Cys His Ser Glu Ala Ser Leu Gln Arg Gln Cys Asp Thr Ser His
385                 390                 395                 400

Lys Thr Pro Phe Val Ser Pro Leu Leu Ala Ser Gln Ser Leu Ser Ile
            405                 410                 415

Gly Asn Gln Val Gly Ser Pro Glu Ser Gly Arg Phe Tyr Gly Leu Asp
            420                 425                 430

Leu Tyr Gly Gly Leu His Met Asp Phe Trp Cys Ala Arg Leu Ala Thr
            435                 440                 445

Lys Gly Cys Glu Asp Val Arg Val Ser Gly Trp Leu Gln Thr Glu Phe
450                 455                 460

Leu Ser Phe Gln Asp Gly Asp Phe Pro Thr Lys Ile Cys Asp Thr Asp
465                 470                 475                 480

Tyr Ile Gln Tyr Pro Asn Tyr Cys Ser Phe Lys Ser Gln Gln Cys Leu
            485                 490                 495

Met Arg Asn Arg Asn Arg Lys Val Ser Arg Met Arg Cys Leu Gln Asn
            500                 505                 510

Glu Thr Tyr Ser Ala Leu Ser Pro Gly Lys Ser Glu Asp Val Val Leu
            515                 520                 525

Arg Trp Ser Gln Glu Phe Ser Thr Leu Thr Leu Gly Gln Phe Gly
530                 535                 540

<210> SEQ ID NO 360
<211> LENGTH: 882
<212> TYPE: PRT
<213> ORGANISM: Artificial Sequence
<220> FEATURE:
<223> OTHER INFORMATION: PIWIL-3

<400> SEQUENCE: 360

Met Pro Gly Arg Ala Arg Thr Arg Ala Arg Gly Arg Ala Arg Arg
1               5                   10                  15

Glu Ser Tyr Gln Gln Glu Ala Pro Gly Gly Pro Arg Ala Pro Gly Ser
            20                  25                  30

Ala Thr Thr Gln Glu Pro Pro Gln Leu Gln Ser Thr Pro Arg Pro Leu
            35                  40                  45

Gln Glu Glu Val Pro Val Val Arg Pro Leu Gln Pro Arg Ala Ala Arg
    50                  55                  60

Gly Gly Ala Gly Gly Gly Ala Gln Ser Gln Gly Val Lys Glu Pro Gly
65                  70                  75                  80

Pro Glu Ala Gly Leu His Thr Ala Pro Leu Gln Glu Arg Arg Ile Gly
                85                  90                  95

Gly Val Phe Gln Asp Leu Val Val Asn Thr Arg Gln Asp Met Lys His
            100                 105                 110

```
Val Lys Asp Ser Lys Thr Gly Ser Glu Gly Thr Val Gln Leu Leu
            115                 120                 125

Ala Asn His Phe Arg Val Ile Ser Arg Pro Gln Trp Val Ala Tyr Lys
130                 135                 140

Tyr Asn Val Asp Tyr Lys Pro Asp Ile Glu Asp Gly Asn Leu Arg Thr
145                 150                 155                 160

Ile Leu Leu Asp Gln His Arg Arg Lys Phe Gly Arg His Ile Phe
                165                 170                 175

Asp Gly Asn Ser Leu Leu Leu Ser Arg Pro Leu Lys Glu Arg Arg Val
                180                 185                 190

Glu Trp Leu Ser Thr Thr Lys Asp Lys Asn Ile Val Lys Ile Thr Val
            195                 200                 205

Glu Phe Ser Lys Glu Leu Thr Pro Thr Ser Pro Asp Cys Leu Arg Tyr
            210                 215                 220

Tyr Asn Ile Leu Phe Arg Arg Thr Phe Lys Leu Leu Asp Phe Glu Gln
225                 230                 235                 240

Val Gly Arg Asn Tyr Tyr Thr Lys Lys Ala Ile Gln Leu Tyr Arg
                245                 250                 255

His Gly Thr Ser Leu Glu Ile Trp Leu Gly Tyr Val Thr Ser Val Leu
                260                 265                 270

Gln Tyr Glu Asn Ser Ile Thr Leu Cys Ala Asp Val Ser His Lys Leu
            275                 280                 285

Leu Arg Ile Glu Thr Ala Tyr Asp Phe Ile Lys Arg Thr Ser Ala Gln
            290                 295                 300

Ala Gln Thr Gly Asn Ile Arg Glu Glu Val Thr Asn Lys Leu Ile Gly
305                 310                 315                 320

Ser Ile Val Leu Thr Lys Tyr Asn Asn Lys Thr Tyr Arg Val Asp Asp
                325                 330                 335

Ile Asp Trp Lys Gln Asn Pro Glu Asp Thr Phe Asn Lys Ser Asp Gly
                340                 345                 350

Ser Lys Ile Thr Tyr Ile Asp Tyr Tyr Arg Gln Gln His Lys Glu Ile
            355                 360                 365

Val Thr Val Lys Lys Gln Pro Leu Leu Val Ser Gln Gly Arg Trp Lys
370                 375                 380

Lys Gly Leu Thr Gly Thr Gln Arg Glu Pro Ile Leu Leu Ile Pro Gln
385                 390                 395                 400

Leu Cys His Met Thr Gly Leu Thr Asp Glu Ile Cys Lys Asp Tyr Ser
                405                 410                 415

Ile Val Lys Glu Leu Ala Lys His Thr Arg Leu Ser Pro Arg Arg Arg
            420                 425                 430

His His Thr Leu Lys Glu Phe Ile Asn Thr Leu Gln Asp Asn Lys Lys
            435                 440                 445

Val Arg Glu Leu Leu Gln Leu Trp Asp Leu Lys Phe Asp Thr Asn Phe
450                 455                 460

Leu Ser Val Pro Gly Arg Val Leu Lys Asn Ala Asn Ile Val Gln Gly
465                 470                 475                 480

Arg Arg Met Val Lys Ala Asn Ser Gln Gly Asp Trp Ser Arg Glu Ile
                485                 490                 495

Arg Glu Leu Pro Leu Leu Asn Ala Met Pro Leu His Ser Trp Leu Ile
            500                 505                 510

Leu Tyr Ser Arg Ser Ser His Arg Glu Ala Met Ser Leu Lys Gly His
            515                 520                 525

Leu Gln Ser Val Thr Ala Pro Met Gly Ile Thr Met Lys Pro Ala Glu
```

```
                530             535             540
Met Ile Glu Val Asp Gly Asp Ala Asn Ser Tyr Ile Asp Thr Leu Arg
545                 550                 555                 560

Lys Tyr Thr Arg Pro Thr Leu Gln Met Gly Met Ser Cys Leu Leu Val
                565                 570                 575

Phe Lys Val Ile Cys Ile Leu Pro Asn Asp Asp Lys Arg Arg Tyr Asp
            580                 585                 590

Ser Ile Lys Arg Tyr Leu Cys Thr Lys Cys Pro Ile Pro Ser Gln Cys
        595                 600                 605

Val Val Lys Lys Thr Leu Glu Lys Val Gln Ala Arg Thr Ile Val Thr
    610                 615                 620

Lys Ile Ala Gln Gln Met Asn Cys Lys Met Gly Gly Ala Leu Trp Lys
625                 630                 635                 640

Val Glu Thr Asp Val Gln Arg Thr Met Phe Val Gly Ile Asp Cys Phe
                645                 650                 655

His Asp Ile Val Asn Arg Gln Lys Ser Ile Ala Gly Phe Val Ala Ser
            660                 665                 670

Thr Asn Ala Glu Leu Thr Lys Trp Tyr Ser Gln Cys Val Ile Gln Lys
        675                 680                 685

Thr Gly Glu Glu Leu Val Lys Glu Leu Glu Ile Cys Leu Lys Ala Ala
    690                 695                 700

Leu Asp Val Trp Cys Lys Asn Glu Ser Ser Met Pro His Ser Val Ile
705                 710                 715                 720

Val Tyr Arg Asp Gly Val Gly Asp Gly Gln Leu Gln Ala Leu Leu Asp
                725                 730                 735

His Glu Ala Lys Lys Met Ser Thr Tyr Leu Lys Thr Ile Ser Pro Asn
            740                 745                 750

Asn Phe Thr Leu Ala Phe Ile Val Lys Lys Arg Ile Asn Thr Arg
        755                 760                 765

Phe Phe Leu Lys His Gly Ser Asn Phe Gln Asn Pro Pro Gly Thr
    770                 775                 780

Val Ile Asp Val Glu Leu Thr Arg Asn Glu Trp Tyr Asp Phe Phe Ile
785                 790                 795                 800

Val Ser Gln Ser Val Gln Asp Gly Thr Val Thr Pro Thr His Tyr Asn
                805                 810                 815

Val Ile Tyr Asp Thr Ile Gly Leu Ser Pro Asp Thr Val Gln Arg Leu
            820                 825                 830

Thr Tyr Cys Leu Cys His Met Tyr Tyr Asn Leu Pro Gly Ile Ile Arg
        835                 840                 845

Val Pro Ala Pro Cys His Tyr Ala His Lys Leu Ala Tyr Leu Val Gly
    850                 855                 860

Gln Ser Ile His Gln Glu Pro Asn Arg Ser Leu Ser Thr Arg Leu Phe
865                 870                 875                 880

Tyr Leu

<210> SEQ ID NO 361
<211> LENGTH: 853
<212> TYPE: PRT
<213> ORGANISM: Artificial Sequence
<220> FEATURE:
<223> OTHER INFORMATION: AKAP3

<400> SEQUENCE: 361

Met Ser Glu Lys Val Asp Trp Leu Gln Ser Gln Asn Gly Val Cys Lys
1               5                   10                  15
```

```
Val Asp Val Tyr Ser Pro Gly Asp Asn Gln Ala Gln Asp Trp Lys Met
            20                  25                  30

Asp Thr Ser Thr Asp Pro Val Arg Val Leu Ser Trp Leu Arg Arg Asp
        35                  40                  45

Leu Glu Lys Ser Thr Ala Glu Phe Gln Asp Val Arg Phe Lys Pro Gly
 50                  55                  60

Glu Ser Phe Gly Gly Thr Ser Asn Ser Gly Asp Pro His Lys Gly
65                   70                  75                  80

Phe Ser Val Asp Tyr Tyr Asn Thr Thr Lys Gly Thr Pro Glu Arg
                85                  90                  95

Leu His Phe Glu Met Thr His Lys Glu Ile Pro Cys Gln Gly Pro Arg
                100                 105                 110

Ala Gln Leu Gly Asn Gly Ser Ser Val Asp Glu Val Ser Phe Tyr Ala
            115                 120                 125

Asn Arg Leu Thr Asn Leu Val Ile Ala Met Ala Arg Lys Glu Ile Asn
130                 135                 140

Glu Lys Ile Asp Gly Ser Glu Asn Lys Cys Val Tyr Gln Ser Leu Tyr
145                 150                 155                 160

Met Gly Asn Glu Pro Thr Pro Thr Lys Ser Leu Ser Lys Ile Ala Ser
                165                 170                 175

Glu Leu Val Asn Glu Thr Val Ser Ala Cys Ser Arg Asn Ala Ala Pro
            180                 185                 190

Asp Lys Ala Pro Gly Ser Gly Asp Arg Val Ser Gly Ser Ser Gln Ser
        195                 200                 205

Pro Pro Asn Leu Lys Tyr Lys Ser Thr Leu Lys Ile Lys Glu Ser Thr
    210                 215                 220

Lys Glu Arg Gln Gly Pro Asp Asp Lys Pro Pro Ser Lys Lys Ser Phe
225                 230                 235                 240

Phe Tyr Lys Glu Val Phe Glu Ser Arg Asn Gly Asp Tyr Ala Arg Glu
                245                 250                 255

Gly Gly Arg Phe Phe Pro Arg Glu Arg Lys Arg Phe Arg Gly Gln Glu
            260                 265                 270

Arg Pro Asp Asp Phe Thr Ala Ser Val Ser Glu Gly Ile Met Thr Tyr
        275                 280                 285

Ala Asn Ser Val Val Ser Asp Met Met Val Ser Ile Met Lys Thr Leu
    290                 295                 300

Lys Ile Gln Val Lys Asp Thr Thr Ile Ala Thr Ile Leu Leu Lys Lys
305                 310                 315                 320

Val Leu Leu Lys His Ala Lys Glu Val Val Ser Asp Leu Ile Asp Ser
                325                 330                 335

Phe Leu Arg Asn Leu His Ser Val Thr Gly Thr Leu Met Thr Asp Thr
            340                 345                 350

Gln Phe Val Ser Ala Val Lys Arg Thr Val Phe Ser His Gly Ser Gln
        355                 360                 365

Lys Ala Thr Asp Ile Met Asp Ala Met Leu Arg Lys Leu Tyr Asn Val
    370                 375                 380

Met Phe Ala Lys Lys Val Pro Glu His Val Arg Lys Ala Gln Asp Lys
385                 390                 395                 400

Ala Glu Ser Tyr Ser Leu Ile Ser Met Lys Gly Met Gly Asp Pro Lys
                405                 410                 415

Asn Arg Asn Val Asn Phe Ala Met Lys Ser Glu Thr Lys Leu Arg Glu
            420                 425                 430
```

-continued

Lys Met Tyr Ser Glu Pro Lys Ser Glu Glu Thr Cys Ala Lys Thr
            435                 440                 445

Leu Gly Glu His Ile Ile Lys Glu Gly Leu Thr Leu Trp His Lys Thr
    450                 455                 460

Gln Gln Lys Glu Cys Lys Ser Leu Gly Phe Gln His Ala Ala Phe Glu
465             470                 475                     480

Ala Pro Asn Thr Gln Arg Lys Pro Ala Ser Asp Ile Ser Phe Glu Tyr
                485                 490                 495

Pro Glu Asp Ile Gly Asn Leu Ser Pro Pro Tyr Pro Pro Glu Lys
                500             505                 510

Pro Glu Asn Phe Met Tyr Asp Ser Asp Ser Trp Ala Glu Asp Leu Ile
                515             520                 525

Val Ser Ala Leu Leu Leu Ile Gln Tyr His Leu Ala Gln Gly Gly Arg
    530                 535                 540

Arg Asp Ala Arg Ser Phe Val Glu Ala Ala Gly Thr Thr Asn Phe Pro
545             550                 555                     560

Ala Asn Glu Pro Pro Val Ala Pro Asp Glu Ser Cys Leu Lys Ser Ala
                565                 570                 575

Pro Ile Val Gly Asp Gln Glu Gln Ala Glu Lys Lys Asp Leu Arg Ser
            580                 585                 590

Val Phe Phe Asn Phe Ile Arg Asn Leu Leu Ser Glu Thr Ile Phe Lys
    595                 600                 605

Arg Asp Gln Ser Pro Glu Pro Lys Val Pro Glu Gln Pro Val Lys Glu
        610                 615                 620

Asp Arg Lys Leu Cys Glu Arg Pro Leu Ala Ser Ser Pro Pro Arg Leu
625             630                 635                     640

Tyr Glu Asp Asp Glu Thr Pro Gly Ala Leu Ser Gly Leu Thr Lys Met
                645                 650                 655

Ala Val Ser Gln Ile Asp Gly His Met Ser Gly Gln Met Val Glu His
                660                 665                 670

Leu Met Asn Ser Val Met Lys Leu Cys Val Ile Ile Ala Lys Ser Cys
            675                 680                 685

Asp Ala Ser Leu Ala Glu Leu Gly Asp Asp Lys Ser Gly Asp Ala Ser
690                 695                 700

Arg Leu Thr Ser Ala Phe Pro Asp Ser Leu Tyr Glu Cys Leu Pro Ala
705                 710                 715                 720

Lys Gly Thr Gly Ser Ala Glu Ala Val Leu Gln Asn Ala Tyr Gln Ala
                725                 730                 735

Ile His Asn Glu Met Arg Gly Thr Ser Gly Gln Pro Pro Glu Gly Cys
            740                 745                 750

Ala Ala Pro Thr Val Ile Val Ser Asn His Asn Leu Thr Asp Thr Val
                755                 760                 765

Gln Asn Lys Gln Leu Gln Ala Val Leu Gln Trp Val Ala Ala Ser Glu
            770                 775                 780

Leu Asn Val Pro Ile Leu Tyr Phe Ala Gly Asp Asp Glu Gly Ile Gln
785                 790                 795                 800

Glu Lys Leu Leu Gln Leu Ser Ala Ala Val Asp Lys Gly Cys Ser
                805                 810                 815

Val Gly Glu Val Leu Gln Ser Val Leu Arg Tyr Glu Lys Glu Arg Gln
            820                 825                 830

Leu Asn Glu Ala Val Gly Asn Val Thr Pro Leu Gln Leu Leu Asp Trp
835                 840                 845

Leu Met Val Asn Leu

-continued

850

<210> SEQ ID NO 362
<211> LENGTH: 20
<212> TYPE: PRT
<213> ORGANISM: Artificial Sequence
<220> FEATURE:
<223> OTHER INFORMATION: XYZ 1

<400> SEQUENCE: 362

Asn Ser Leu Gln Lys Gln Leu Gln Ala Val Leu Gln Trp Ile Ala Ala
1               5                   10                  15

Ser Gln Phe Asn
            20

<210> SEQ ID NO 363
<211> LENGTH: 20
<212> TYPE: PRT
<213> ORGANISM: Artificial Sequence
<220> FEATURE:
<223> OTHER INFORMATION: XYZ 2

<400> SEQUENCE: 363

Ser Gly Asp Glu Arg Ser Asp Glu Ile Val Leu Thr Val Ser Asn Ser
1               5                   10                  15

Asn Val Glu Glu
            20

<210> SEQ ID NO 364
<211> LENGTH: 20
<212> TYPE: PRT
<213> ORGANISM: Artificial Sequence
<220> FEATURE:
<223> OTHER INFORMATION: XYZ 3

<400> SEQUENCE: 364

Val Gln Lys Glu Asp Gly Arg Val Gln Ala Phe Gly Trp Ser Leu Pro
1               5                   10                  15

Gln Lys Tyr Lys
            20

<210> SEQ ID NO 365
<211> LENGTH: 20
<212> TYPE: PRT
<213> ORGANISM: Artificial Sequence
<220> FEATURE:
<223> OTHER INFORMATION: XYZ 4

<400> SEQUENCE: 365

Glu Val Glu Ser Thr Pro Met Ile Met Glu Asn Ile Gln Glu Leu Ile
1               5                   10                  15

Arg Ser Ala Gln
            20

<210> SEQ ID NO 366
<211> LENGTH: 20
<212> TYPE: PRT
<213> ORGANISM: Artificial Sequence
<220> FEATURE:
<223> OTHER INFORMATION: XYZ 5

<400> SEQUENCE: 366

Ala Tyr Phe Glu Ser Leu Leu Glu Lys Arg Glu Lys Thr Asn Phe Asp
1               5                   10                  15

```
Pro Ala Glu Trp
            20

<210> SEQ ID NO 367
<211> LENGTH: 20
<212> TYPE: PRT
<213> ORGANISM: Artificial Sequence
<220> FEATURE:
<223> OTHER INFORMATION: XYZ 6

<400> SEQUENCE: 367

Pro Ser Gln Ala Ser Ser Gly Gln Ala Arg Met Phe Pro Asn Ala Pro
1               5                   10                  15

Tyr Leu Pro Ser
            20

<210> SEQ ID NO 368
<211> LENGTH: 20
<212> TYPE: PRT
<213> ORGANISM: Artificial Sequence
<220> FEATURE:
<223> OTHER INFORMATION: XYZ 7

<400> SEQUENCE: 368

Arg Arg Ser Ile Ala Gly Phe Val Ala Ser Ile Asn Glu Gly Met Thr
1               5                   10                  15

Arg Trp Phe Ser
            20

<210> SEQ ID NO 369
<211> LENGTH: 20
<212> TYPE: PRT
<213> ORGANISM: Artificial Sequence
<220> FEATURE:
<223> OTHER INFORMATION: XYZ 8

<400> SEQUENCE: 369

Met Gln Asp Ile Lys Met Ile Leu Lys Met Val Gln Leu Asp Ser Ile
1               5                   10                  15

Glu Asp Leu Glu
            20

<210> SEQ ID NO 370
<211> LENGTH: 20
<212> TYPE: PRT
<213> ORGANISM: Artificial Sequence
<220> FEATURE:
<223> OTHER INFORMATION: XYZ 9

<400> SEQUENCE: 370

Ala Asn Ser Val Val Ser Asp Met Met Val Ser Ile Met Lys Thr Leu
1               5                   10                  15

Lys Ile Gln Val
            20

<210> SEQ ID NO 371
<211> LENGTH: 20
<212> TYPE: PRT
<213> ORGANISM: Artificial Sequence
<220> FEATURE:
<223> OTHER INFORMATION: XYZ 10

<400> SEQUENCE: 371

Arg Glu Ala Leu Ser Asn Lys Val Asp Glu Leu Ala His Phe Leu Leu
1               5                   10                  15
```

```
Arg Lys Tyr Arg
            20

<210> SEQ ID NO 372
<211> LENGTH: 20
<212> TYPE: PRT
<213> ORGANISM: Artificial Sequence
<220> FEATURE:
<223> OTHER INFORMATION: XYZ 11

<400> SEQUENCE: 372

Glu Thr Ser Tyr Glu Lys Val Ile Asn Tyr Leu Val Met Leu Asn Ala
1               5                   10                  15

Arg Glu Pro Ile
            20

<210> SEQ ID NO 373
<211> LENGTH: 20
<212> TYPE: PRT
<213> ORGANISM: Artificial Sequence
<220> FEATURE:
<223> OTHER INFORMATION: XYZ 12

<400> SEQUENCE: 373

Asp Val Lys Glu Val Asp Pro Thr Gly His Ser Phe Val Leu Val Thr
1               5                   10                  15

Ser Leu Gly Leu
            20

<210> SEQ ID NO 374
<211> LENGTH: 20
<212> TYPE: PRT
<213> ORGANISM: Artificial Sequence
<220> FEATURE:
<223> OTHER INFORMATION: XYZ 13

<400> SEQUENCE: 374

Ser Ala Gln Leu Leu Gln Ala Arg Leu Met Lys Glu Glu Ser Pro Val
1               5                   10                  15

Val Ser Trp Arg
            20

<210> SEQ ID NO 375
<211> LENGTH: 20
<212> TYPE: PRT
<213> ORGANISM: Artificial Sequence
<220> FEATURE:
<223> OTHER INFORMATION: ABC 1

<400> SEQUENCE: 375

Ile Ser Asp Thr Lys Asp Tyr Phe Met Ser Lys Thr Leu Gly Ile Gly
1               5                   10                  15

Arg Leu Lys Arg
            20

<210> SEQ ID NO 376
<211> LENGTH: 20
<212> TYPE: PRT
<213> ORGANISM: Artificial Sequence
<220> FEATURE:
<223> OTHER INFORMATION: ABC 2

<400> SEQUENCE: 376

Phe Asp Arg Asn Thr Glu Ser Leu Phe Glu Glu Leu Ser Ser Ala Gly
```

```
1               5                   10                  15

Ser Gly Leu Ile
            20

<210> SEQ ID NO 377
<211> LENGTH: 20
<212> TYPE: PRT
<213> ORGANISM: Artificial Sequence
<220> FEATURE:
<223> OTHER INFORMATION: ABC 3

<400> SEQUENCE: 377

Ser Gln Lys Met Asp Met Ser Asn Ile Val Leu Met Leu Ile Gln Lys
1               5                   10                  15

Leu Leu Asn Glu
            20

<210> SEQ ID NO 378
<211> LENGTH: 20
<212> TYPE: PRT
<213> ORGANISM: Artificial Sequence
<220> FEATURE:
<223> OTHER INFORMATION: ABC 4

<400> SEQUENCE: 378

Ser Ala Val Phe His Glu Arg Tyr Ala Leu Ile Gln His Gln Lys Thr
1               5                   10                  15

His Lys Asn Glu
            20

<210> SEQ ID NO 379
<211> LENGTH: 20
<212> TYPE: PRT
<213> ORGANISM: Artificial Sequence
<220> FEATURE:
<223> OTHER INFORMATION: ABC 5

<400> SEQUENCE: 379

Asp Val Lys Glu Val Asp Pro Thr Ser His Ser Tyr Val Leu Val Thr
1               5                   10                  15

Ser Leu Asn Leu
            20

<210> SEQ ID NO 380
<211> LENGTH: 20
<212> TYPE: PRT
<213> ORGANISM: Artificial Sequence
<220> FEATURE:
<223> OTHER INFORMATION: ABC 6

<400> SEQUENCE: 380

Glu Asn Ala His Gly Gln Ser Leu Glu Glu Asp Ser Ala Leu Glu Ala
1               5                   10                  15

Leu Leu Asn Phe
            20

<210> SEQ ID NO 381
<211> LENGTH: 20
<212> TYPE: PRT
<213> ORGANISM: Artificial Sequence
<220> FEATURE:
<223> OTHER INFORMATION: ABC 7

<400> SEQUENCE: 381
```

```
Met Ala Ser Phe Arg Lys Leu Thr Leu Ser Glu Lys Val Pro Pro Asn
1               5                   10                  15

His Pro Ser Arg
            20

<210> SEQ ID NO 382
<211> LENGTH: 20
<212> TYPE: PRT
<213> ORGANISM: Artificial Sequence
<220> FEATURE:
<223> OTHER INFORMATION: ABC 8

<400> SEQUENCE: 382

Lys Arg Ala Ser Gln Tyr Ser Gly Gln Leu Lys Val Leu Ile Ala Glu
1               5                   10                  15

Asn Thr Met Leu
            20

<210> SEQ ID NO 383
<211> LENGTH: 20
<212> TYPE: PRT
<213> ORGANISM: Artificial Sequence
<220> FEATURE:
<223> OTHER INFORMATION: ABC 9

<400> SEQUENCE: 383

Val Asp Pro Ala Gln Leu Glu Phe Met Phe Gln Glu Ala Leu Lys Leu
1               5                   10                  15

Lys Val Ala Glu
            20

<210> SEQ ID NO 384
<211> LENGTH: 20
<212> TYPE: PRT
<213> ORGANISM: Artificial Sequence
<220> FEATURE:
<223> OTHER INFORMATION: ABC 10

<400> SEQUENCE: 384

Glu Tyr Glu Arg Glu Glu Thr Arg Gln Val Tyr Met Asp Leu Asn Asn
1               5                   10                  15

Asn Ile Glu Lys
            20

<210> SEQ ID NO 385
<211> LENGTH: 20
<212> TYPE: PRT
<213> ORGANISM: Artificial Sequence
<220> FEATURE:
<223> OTHER INFORMATION: ABC 11

<400> SEQUENCE: 385

Pro Glu Ile Phe Gly Lys Ala Ser Glu Ser Leu Gln Leu Val Phe Gly
1               5                   10                  15

Ile Asp Val Lys
            20

<210> SEQ ID NO 386
<211> LENGTH: 20
<212> TYPE: PRT
<213> ORGANISM: Artificial Sequence
<220> FEATURE:
<223> OTHER INFORMATION: ABC 12

<400> SEQUENCE: 386
```

Asp Ser Glu Ser Ser Phe Thr Tyr Thr Leu Asp Glu Lys Val Ala Glu
1               5                   10                  15

Leu Val Glu Phe
            20

<210> SEQ ID NO 387
<211> LENGTH: 9
<212> TYPE: PRT
<213> ORGANISM: Artificial Sequence
<220> FEATURE:
<223> OTHER INFORMATION: CRC-P1 1

<400> SEQUENCE: 387

Gln Phe Pro Val Ser Glu Gly Lys Ser
1               5

<210> SEQ ID NO 388
<211> LENGTH: 9
<212> TYPE: PRT
<213> ORGANISM: Artificial Sequence
<220> FEATURE:
<223> OTHER INFORMATION: CRC-P1 2

<400> SEQUENCE: 388

Phe Pro Val Ser Glu Gly Lys Ser Arg
1               5

<210> SEQ ID NO 389
<211> LENGTH: 9
<212> TYPE: PRT
<213> ORGANISM: Artificial Sequence
<220> FEATURE:
<223> OTHER INFORMATION: CRC-P1 3

<400> SEQUENCE: 389

Pro Val Ser Glu Gly Lys Ser Arg Tyr
1               5

<210> SEQ ID NO 390
<211> LENGTH: 9
<212> TYPE: PRT
<213> ORGANISM: Artificial Sequence
<220> FEATURE:
<223> OTHER INFORMATION: CRC-P1 4

<400> SEQUENCE: 390

Val Ser Glu Gly Lys Ser Arg Tyr Arg
1               5

<210> SEQ ID NO 391
<211> LENGTH: 9
<212> TYPE: PRT
<213> ORGANISM: Artificial Sequence
<220> FEATURE:
<223> OTHER INFORMATION: CRC-P1 5

<400> SEQUENCE: 391

Ser Glu Gly Lys Ser Arg Tyr Arg Ala
1               5

<210> SEQ ID NO 392
<211> LENGTH: 9
<212> TYPE: PRT
<213> ORGANISM: Artificial Sequence
<220> FEATURE:
<223> OTHER INFORMATION: CRC-P1 6

<400> SEQUENCE: 392

Glu Gly Lys Ser Arg Tyr Arg Ala Gln
1               5

<210> SEQ ID NO 393
<211> LENGTH: 9
<212> TYPE: PRT
<213> ORGANISM: Artificial Sequence
<220> FEATURE:
<223> OTHER INFORMATION: CRC-P1 7

<400> SEQUENCE: 393

Gly Lys Ser Arg Tyr Arg Ala Gln Arg
1               5

<210> SEQ ID NO 394
<211> LENGTH: 9
<212> TYPE: PRT
<213> ORGANISM: Artificial Sequence
<220> FEATURE:
<223> OTHER INFORMATION: CRC-P1 8

<400> SEQUENCE: 394

Lys Ser Arg Tyr Arg Ala Gln Arg Phe
1               5

<210> SEQ ID NO 395
<211> LENGTH: 9
<212> TYPE: PRT
<213> ORGANISM: Artificial Sequence
<220> FEATURE:
<223> OTHER INFORMATION: CRC-P2 1

<400> SEQUENCE: 395

Ile Glu Leu Lys His Lys Ala Arg Thr
1               5

<210> SEQ ID NO 396
<211> LENGTH: 9
<212> TYPE: PRT
<213> ORGANISM: Artificial Sequence
<220> FEATURE:
<223> OTHER INFORMATION: CRC-P2 2

<400> SEQUENCE: 396

Glu Leu Lys His Lys Ala Arg Thr Ala
1               5

<210> SEQ ID NO 397
<211> LENGTH: 9
<212> TYPE: PRT
<213> ORGANISM: Artificial Sequence
<220> FEATURE:
<223> OTHER INFORMATION: CRC-P2 3

<400> SEQUENCE: 397

Leu Lys His Lys Ala Arg Thr Ala Lys
1               5

<210> SEQ ID NO 398
<211> LENGTH: 9
<212> TYPE: PRT
<213> ORGANISM: Artificial Sequence
<220> FEATURE:
<223> OTHER INFORMATION: CRC-P2 4

```
<400> SEQUENCE: 398

Lys His Lys Ala Arg Thr Ala Lys Lys
1               5

<210> SEQ ID NO 399
<211> LENGTH: 9
<212> TYPE: PRT
<213> ORGANISM: Artificial Sequence
<220> FEATURE:
<223> OTHER INFORMATION: CRC-P2 5

<400> SEQUENCE: 399

His Lys Ala Arg Thr Ala Lys Lys Val
1               5

<210> SEQ ID NO 400
<211> LENGTH: 9
<212> TYPE: PRT
<213> ORGANISM: Artificial Sequence
<220> FEATURE:
<223> OTHER INFORMATION: CRC-P2 6

<400> SEQUENCE: 400

Lys Ala Arg Thr Ala Lys Lys Val Arg
1               5

<210> SEQ ID NO 401
<211> LENGTH: 9
<212> TYPE: PRT
<213> ORGANISM: Artificial Sequence
<220> FEATURE:
<223> OTHER INFORMATION: CRC-P2 7

<400> SEQUENCE: 401

Ala Arg Thr Ala Lys Lys Val Arg Arg
1               5

<210> SEQ ID NO 402
<211> LENGTH: 9
<212> TYPE: PRT
<213> ORGANISM: Artificial Sequence
<220> FEATURE:
<223> OTHER INFORMATION: CRC-P2 8

<400> SEQUENCE: 402

Arg Thr Ala Lys Lys Val Arg Arg Ala
1               5

<210> SEQ ID NO 403
<211> LENGTH: 9
<212> TYPE: PRT
<213> ORGANISM: Artificial Sequence
<220> FEATURE:
<223> OTHER INFORMATION: CRC-P3 1

<400> SEQUENCE: 403

Glu Phe Ser Met Gln Gly Leu Lys Asp
1               5

<210> SEQ ID NO 404
<211> LENGTH: 9
<212> TYPE: PRT
<213> ORGANISM: Artificial Sequence
<220> FEATURE:
<223> OTHER INFORMATION: CRC-P3 2

<400> SEQUENCE: 404
```

```
Phe Ser Met Gln Gly Leu Lys Asp Glu
1               5
```

<210> SEQ ID NO 405
<211> LENGTH: 9
<212> TYPE: PRT
<213> ORGANISM: Artificial Sequence
<220> FEATURE:
<223> OTHER INFORMATION: SMQGLKDEK

<400> SEQUENCE: 405

```
Ser Met Gln Gly Leu Lys Asp Glu Lys
1               5
```

<210> SEQ ID NO 406
<211> LENGTH: 9
<212> TYPE: PRT
<213> ORGANISM: Artificial Sequence
<220> FEATURE:
<223> OTHER INFORMATION: CRC-P3 4

<400> SEQUENCE: 406

```
Met Gln Gly Leu Lys Asp Glu Lys Val
1               5
```

<210> SEQ ID NO 407
<211> LENGTH: 9
<212> TYPE: PRT
<213> ORGANISM: Artificial Sequence
<220> FEATURE:
<223> OTHER INFORMATION: CRC-P3 5

<400> SEQUENCE: 407

```
Gln Gly Leu Lys Asp Glu Lys Val Ala
1               5
```

<210> SEQ ID NO 408
<211> LENGTH: 9
<212> TYPE: PRT
<213> ORGANISM: Artificial Sequence
<220> FEATURE:
<223> OTHER INFORMATION: CRC-P3 6

<400> SEQUENCE: 408

```
Gly Leu Lys Asp Glu Lys Val Ala Glu
1               5
```

<210> SEQ ID NO 409
<211> LENGTH: 9
<212> TYPE: PRT
<213> ORGANISM: Artificial Sequence
<220> FEATURE:
<223> OTHER INFORMATION: CRC-P3 7

<400> SEQUENCE: 409

```
Leu Lys Asp Glu Lys Val Ala Glu Leu
1               5
```

<210> SEQ ID NO 410
<211> LENGTH: 9
<212> TYPE: PRT
<213> ORGANISM: Artificial Sequence
<220> FEATURE:
<223> OTHER INFORMATION: CRC-P3 8

<400> SEQUENCE: 410

Lys Asp Glu Lys Val Ala Glu Leu Val
1               5

<210> SEQ ID NO 411
<211> LENGTH: 9
<212> TYPE: PRT
<213> ORGANISM: Artificial Sequence
<220> FEATURE:
<223> OTHER INFORMATION: CRC-P6 1

<400> SEQUENCE: 411

Leu Leu Ala Leu Met Val Gly Leu Lys
1               5

<210> SEQ ID NO 412
<211> LENGTH: 9
<212> TYPE: PRT
<213> ORGANISM: Artificial Sequence
<220> FEATURE:
<223> OTHER INFORMATION: CRC-P6 2

<400> SEQUENCE: 412

Leu Ala Leu Met Val Gly Leu Lys Asp
1               5

<210> SEQ ID NO 413
<211> LENGTH: 9
<212> TYPE: PRT
<213> ORGANISM: Artificial Sequence
<220> FEATURE:
<223> OTHER INFORMATION: CRC-P6 3

<400> SEQUENCE: 413

Ala Leu Met Val Gly Leu Lys Asp His
1               5

<210> SEQ ID NO 414
<211> LENGTH: 9
<212> TYPE: PRT
<213> ORGANISM: Artificial Sequence
<220> FEATURE:
<223> OTHER INFORMATION: CRC-P6 4

<400> SEQUENCE: 414

Leu Met Val Gly Leu Lys Asp His Arg
1               5

<210> SEQ ID NO 415
<211> LENGTH: 9
<212> TYPE: PRT
<213> ORGANISM: Artificial Sequence
<220> FEATURE:
<223> OTHER INFORMATION: CRC-P6 5

<400> SEQUENCE: 415

Met Val Gly Leu Lys Asp His Arg Ile
1               5

<210> SEQ ID NO 416
<211> LENGTH: 9
<212> TYPE: PRT
<213> ORGANISM: Artificial Sequence
<220> FEATURE:
<223> OTHER INFORMATION: CRC-P6 6

<400> SEQUENCE: 416

Val Gly Leu Lys Asp His Arg Ile Ser

```
<210> SEQ ID NO 417
<211> LENGTH: 9
<212> TYPE: PRT
<213> ORGANISM: Artificial Sequence
<220> FEATURE:
<223> OTHER INFORMATION: CRC-P6 7

<400> SEQUENCE: 417

Gly Leu Lys Asp His Arg Ile Ser Thr
1               5

<210> SEQ ID NO 418
<211> LENGTH: 9
<212> TYPE: PRT
<213> ORGANISM: Artificial Sequence
<220> FEATURE:
<223> OTHER INFORMATION: CRC-P6 8

<400> SEQUENCE: 418

Leu Lys Asp His Arg Ile Ser Thr Phe
1               5

<210> SEQ ID NO 419
<211> LENGTH: 9
<212> TYPE: PRT
<213> ORGANISM: Artificial Sequence
<220> FEATURE:
<223> OTHER INFORMATION: CRC-P7 1

<400> SEQUENCE: 419

Pro Ala Leu Phe Lys Glu Asn Arg Ser
1               5

<210> SEQ ID NO 420
<211> LENGTH: 9
<212> TYPE: PRT
<213> ORGANISM: Artificial Sequence
<220> FEATURE:
<223> OTHER INFORMATION: CRC-P7 2

<400> SEQUENCE: 420

Ala Leu Phe Lys Glu Asn Arg Ser Gly
1               5

<210> SEQ ID NO 421
<211> LENGTH: 9
<212> TYPE: PRT
<213> ORGANISM: Artificial Sequence
<220> FEATURE:
<223> OTHER INFORMATION: CRC-P7 3

<400> SEQUENCE: 421

Leu Phe Lys Glu Asn Arg Ser Gly Ala
1               5

<210> SEQ ID NO 422
<211> LENGTH: 9
<212> TYPE: PRT
<213> ORGANISM: Artificial Sequence
<220> FEATURE:
<223> OTHER INFORMATION: CRC-P7 4

<400> SEQUENCE: 422

Phe Lys Glu Asn Arg Ser Gly Ala Val
1               5
```

```
<210> SEQ ID NO 423
<211> LENGTH: 9
<212> TYPE: PRT
<213> ORGANISM: Artificial Sequence
<220> FEATURE:
<223> OTHER INFORMATION: CRC-P7 5

<400> SEQUENCE: 423

Lys Glu Asn Arg Ser Gly Ala Val Met
1               5

<210> SEQ ID NO 424
<211> LENGTH: 9
<212> TYPE: PRT
<213> ORGANISM: Artificial Sequence
<220> FEATURE:
<223> OTHER INFORMATION: CRC-P7 6

<400> SEQUENCE: 424

Glu Asn Arg Ser Gly Ala Val Met Ser
1               5

<210> SEQ ID NO 425
<211> LENGTH: 9
<212> TYPE: PRT
<213> ORGANISM: Artificial Sequence
<220> FEATURE:
<223> OTHER INFORMATION: CRC-P7 7

<400> SEQUENCE: 425

Asn Arg Ser Gly Ala Val Met Ser Glu
1               5

<210> SEQ ID NO 426
<211> LENGTH: 9
<212> TYPE: PRT
<213> ORGANISM: Artificial Sequence
<220> FEATURE:
<223> OTHER INFORMATION: CRC-P7 8

<400> SEQUENCE: 426

Arg Ser Gly Ala Val Met Ser Glu Arg
1               5

<210> SEQ ID NO 427
<211> LENGTH: 9
<212> TYPE: PRT
<213> ORGANISM: Artificial Sequence
<220> FEATURE:
<223> OTHER INFORMATION: CRC-P8 1

<400> SEQUENCE: 427

Ala Val Leu Thr Lys Lys Phe Gln Lys
1               5

<210> SEQ ID NO 428
<211> LENGTH: 9
<212> TYPE: PRT
<213> ORGANISM: Artificial Sequence
<220> FEATURE:
<223> OTHER INFORMATION: CRC-P8 2

<400> SEQUENCE: 428

Val Leu Thr Lys Lys Phe Gln Lys Val
1               5
```

```
<210> SEQ ID NO 429
<211> LENGTH: 9
<212> TYPE: PRT
<213> ORGANISM: Artificial Sequence
<220> FEATURE:
<223> OTHER INFORMATION: CRC-P8 3

<400> SEQUENCE: 429

Leu Thr Lys Lys Phe Gln Lys Val Asn
1               5

<210> SEQ ID NO 430
<211> LENGTH: 9
<212> TYPE: PRT
<213> ORGANISM: Artificial Sequence
<220> FEATURE:
<223> OTHER INFORMATION: CRC-P8 4

<400> SEQUENCE: 430

Thr Lys Lys Phe Gln Lys Val Asn Phe
1               5

<210> SEQ ID NO 431
<211> LENGTH: 9
<212> TYPE: PRT
<213> ORGANISM: Artificial Sequence
<220> FEATURE:
<223> OTHER INFORMATION: CRC-P8 5

<400> SEQUENCE: 431

Lys Lys Phe Gln Lys Val Asn Phe Phe
1               5

<210> SEQ ID NO 432
<211> LENGTH: 9
<212> TYPE: PRT
<213> ORGANISM: Artificial Sequence
<220> FEATURE:
<223> OTHER INFORMATION: CRC-P8 6

<400> SEQUENCE: 432

Lys Phe Gln Lys Val Asn Phe Phe Phe
1               5

<210> SEQ ID NO 433
<211> LENGTH: 9
<212> TYPE: PRT
<213> ORGANISM: Artificial Sequence
<220> FEATURE:
<223> OTHER INFORMATION: CRC-P8 7

<400> SEQUENCE: 433

Phe Gln Lys Val Asn Phe Phe Phe Glu
1               5

<210> SEQ ID NO 434
<211> LENGTH: 9
<212> TYPE: PRT
<213> ORGANISM: Artificial Sequence
<220> FEATURE:
<223> OTHER INFORMATION: CRC-P8 8

<400> SEQUENCE: 434

Gln Lys Val Asn Phe Phe Phe Glu Arg
1               5
```

```
<210> SEQ ID NO 435
<211> LENGTH: 30
<212> TYPE: PRT
<213> ORGANISM: Artificial Sequence
<220> FEATURE:
<223> OTHER INFORMATION: BCV900-6-1

<400> SEQUENCE: 435

Tyr Ser Ser Asn Ala Tyr His Met Ser Thr Met Lys Pro Asn Phe
1               5                   10                  15

Val Ala Ser Ile Asn Leu Thr Leu Thr Lys Trp Tyr Ser Arg
                20                  25                  30

<210> SEQ ID NO 436
<211> LENGTH: 30
<212> TYPE: PRT
<213> ORGANISM: Artificial Sequence
<220> FEATURE:
<223> OTHER INFORMATION: BCV900-6-2

<400> SEQUENCE: 436

Arg Asn Phe Tyr Asp Pro Thr Ser Ala Met Val Leu Gln Gln His Met
1               5                   10                  15

Met Ala Tyr Ser Asp Thr Thr Met Met Ser Asp Asp Ile Asp
                20                  25                  30

<210> SEQ ID NO 437
<211> LENGTH: 30
<212> TYPE: PRT
<213> ORGANISM: Artificial Sequence
<220> FEATURE:
<223> OTHER INFORMATION: BCV900-6-3

<400> SEQUENCE: 437

Leu Arg Tyr Arg Tyr Thr Leu Asp Asp Leu Tyr Pro Met Met Asn Ser
1               5                   10                  15

Asp Tyr Ala Val His Pro Met Ser Pro Val Gly Arg Thr Ser
                20                  25                  30

<210> SEQ ID NO 438
<211> LENGTH: 30
<212> TYPE: PRT
<213> ORGANISM: Artificial Sequence
<220> FEATURE:
<223> OTHER INFORMATION: BCV900-6-4

<400> SEQUENCE: 438

Ser Gly Ala Val Met Ser Glu Arg Val Ser Gly Leu Ala Gly Ser Arg
1               5                   10                  15

Thr Tyr Trp Ile Ile Ile Glu Leu Lys His Lys Ala Arg Glu
                20                  25                  30

<210> SEQ ID NO 439
<211> LENGTH: 30
<212> TYPE: PRT
<213> ORGANISM: Artificial Sequence
<220> FEATURE:
<223> OTHER INFORMATION: BCV900-6-5

<400> SEQUENCE: 439

Asp Leu Ser Phe Tyr Val Asn Arg Leu Ser Ser Leu Val Ile Gln Asn
1               5                   10                  15

Arg Thr Ser Tyr Leu His Ser Pro Phe Ser Thr Gly Arg Ser
                20                  25                  30
```

<210> SEQ ID NO 440
<211> LENGTH: 30
<212> TYPE: PRT
<213> ORGANISM: Artificial Sequence
<220> FEATURE:
<223> OTHER INFORMATION: BCV900-6-6

<400> SEQUENCE: 440

Val Asn Ile Asp Tyr Leu Met Asn Arg Pro Gln Asn Leu Arg Leu His
1               5                   10                  15

Ala Phe Asp Gly Thr Ile Leu Phe Leu Pro Lys Arg Leu Gln
            20                  25                  30

<210> SEQ ID NO 441
<211> LENGTH: 30
<212> TYPE: PRT
<213> ORGANISM: Artificial Sequence
<220> FEATURE:
<223> OTHER INFORMATION: BCV900-6-7

<400> SEQUENCE: 441

Ser Asp Leu Gln Lys Tyr Ala Leu Gly Phe Gln His Ala Leu Ser Glu
1               5                   10                  15

Lys Ala Met Ala Arg Leu Gln Glu Leu Leu Thr Val Ser Glu
            20                  25                  30

<210> SEQ ID NO 442
<211> LENGTH: 30
<212> TYPE: PRT
<213> ORGANISM: Artificial Sequence
<220> FEATURE:
<223> OTHER INFORMATION: BCV900-6-8

<400> SEQUENCE: 442

Gly Phe Thr Thr Ser Ile Leu Gln Tyr Glu Asn Ser Ile Met Leu Gln
1               5                   10                  15

Asp Gly Arg Leu Leu Ser Ser Thr Leu Ser Leu Ser Ser Asn
            20                  25                  30

<210> SEQ ID NO 443
<211> LENGTH: 30
<212> TYPE: PRT
<213> ORGANISM: Artificial Sequence
<220> FEATURE:
<223> OTHER INFORMATION: BCV900-6-9

<400> SEQUENCE: 443

Tyr Ser Arg Val Val Phe Gln Met Pro His Gln Glu Ile Val Asp Asn
1               5                   10                  15

Met Ala Phe Val Thr Ser Gly Glu Leu Val Arg His Arg Arg
            20                  25                  30

<210> SEQ ID NO 444
<211> LENGTH: 30
<212> TYPE: PRT
<213> ORGANISM: Artificial Sequence
<220> FEATURE:
<223> OTHER INFORMATION: BCV900-6-10

<400> SEQUENCE: 444

Ala Phe Ala Ala Ala Tyr Phe Glu Ser Leu Leu Glu Lys Arg Glu Met
1               5                   10                  15

Phe Thr Ser Ser Arg Met Ser Ser Phe Asn Arg His Met Lys
            20                  25                  30

<210> SEQ ID NO 445
<211> LENGTH: 30
<212> TYPE: PRT
<213> ORGANISM: Artificial Sequence
<220> FEATURE:
<223> OTHER INFORMATION: BCV900-6-11

<400> SEQUENCE: 445

Asn Ser Pro Leu Pro Phe Gln Trp Arg Ile Thr His Ser Phe Arg Arg
1               5                   10                  15
Ser Ile Ala Gly Phe Val Ala Ser Ile Asn Glu Gly Met Thr
            20                  25                  30

<210> SEQ ID NO 446
<211> LENGTH: 30
<212> TYPE: PRT
<213> ORGANISM: Artificial Sequence
<220> FEATURE:
<223> OTHER INFORMATION: BCV900-6-12

<400> SEQUENCE: 446

Ser Ser Tyr Phe Val Leu Ala Asn Gly His Ile Leu Pro Asn Ser Trp
1               5                   10                  15
Glu Glu Ala Tyr Thr Phe Glu Gly Ala Arg Tyr Tyr Ile Asn
            20                  25                  30

<210> SEQ ID NO 447
<211> LENGTH: 30
<212> TYPE: PRT
<213> ORGANISM: Artificial Sequence
<220> FEATURE:
<223> OTHER INFORMATION: BCV900-6-13

<400> SEQUENCE: 447

Leu Gln Lys Val Gln Phe Glu Lys Val Ser Ala Leu Ala Asp Leu Leu
1               5                   10                  15
Glu Arg Leu Ala Tyr Leu His Ala Arg Leu Arg Glu Leu Leu
            20                  25                  30

<210> SEQ ID NO 448
<211> LENGTH: 30
<212> TYPE: PRT
<213> ORGANISM: Artificial Sequence
<220> FEATURE:
<223> OTHER INFORMATION: BCV900-6-14

<400> SEQUENCE: 448

Ser His Ser Tyr Val Leu Val Thr Ser Leu Asn Leu Ser Tyr Asp Phe
1               5                   10                  15
Met Phe Gln Glu Ala Leu Lys Leu Lys Val Ala Glu Leu Val
            20                  25                  30

<210> SEQ ID NO 449
<211> LENGTH: 30
<212> TYPE: PRT
<213> ORGANISM: Artificial Sequence
<220> FEATURE:
<223> OTHER INFORMATION: BCV900-6-15

```
<400> SEQUENCE: 449

Arg Phe Thr Gln Ser Gly Thr Met Lys Ile His Ile Leu Gln Lys Gln
1               5                   10                  15

Thr Leu Ile Tyr Tyr Val Asp Glu Lys Ala Pro Glu Phe Ser
            20                  25                  30
```